US005719306A

United States Patent [19]
Chandrakumar et al.

[11] Patent Number: 5,719,306
[45] Date of Patent: Feb. 17, 1998

[54] LTA₄ HYDROLASE INHIBITORS

[75] Inventors: Nizal Samuel Chandrakumar, Vernon Hills; Barbara Baosheng Chen, Glenview; Michael Clare, Skokie; Bipinchandra Nanubhai Desai, Vernon Hills, all of Ill.; Stevan Wakefield Djuric, Malvern, Pa.; Stephen Hermann Docter, Mt. Prospect, Ill.; Alan Frank Gasiecki, Vernon Hills, Ill.; Richard Arthur Haack, Chicago, Ill.; Chi-Dean Liang, Glenview, Ill.; Julie Marion Miyashiro, Chicago, Ill.; Thomas Dale Penning, Elmhurst, Ill.; Mark Andrew Russell, Gurnee, Ill.; Stella Siu-tzyy Yu, Morton Grove, Ill.

[73] Assignee: G.D. Searle & Co., Chicago, Ill.

[21] Appl. No.: 466,010

[22] Filed: Jun. 6, 1995

Related U.S. Application Data

[63] Continuation of Ser. No. 321,183, Oct. 11, 1994, Pat. No. 5,585,492.

[51] Int. Cl.⁶ .................. C07C 205/06; C07C 229/18; C07C 229/40
[52] U.S. Cl. .................. 560/19; 560/20; 560/21; 560/22; 560/23; 560/29; 562/433; 562/434; 562/435; 562/442; 562/443; 562/444; 562/449
[58] Field of Search .................. 562/433, 434, 562/435, 442, 443, 444, 449; 560/29, 30, 31

[56] References Cited

U.S. PATENT DOCUMENTS

| | | | |
|---|---|---|---|
| 2,831,859 | 4/1958 | Kindler et al. | 260/247.1 |
| 4,010,272 | 3/1977 | Loewe et al. | 424/273 |
| 4,038,319 | 7/1977 | Pinhas | 260/570 |
| 4,339,576 | 7/1982 | Zenitz | 544/130 |
| 4,417,052 | 11/1983 | Zenitz | 546/246 |
| 4,803,227 | 2/1989 | Brandes et al. | 514/651 |
| 4,829,068 | 5/1989 | Brandes et al. | 514/239.2 |
| 5,192,786 | 3/1993 | Press et al. | |
| 5,432,168 | 7/1995 | Brandes . | |

FOREIGN PATENT DOCUMENTS

| | | | |
|---|---|---|---|
| 831514 | 11/1975 | Belgium . | |
| 0005541 | 11/1979 | European Pat. Off. | C07D 295/06 |
| 0052311 | 5/1982 | European Pat. Off. | C07D 211/26 |
| 0115700 | 8/1984 | European Pat. Off. | C07D 211/14 |
| 0153160 | 8/1985 | European Pat. Off. | C07D 93/06 |
| 0360246 | 3/1990 | European Pat. Off. | |
| 527714 | 6/1931 | Germany . | |
| 06239815 | 8/1994 | Japan . | |
| 1134290 | 11/1968 | United Kingdom . | |
| 1508456 | 4/1978 | United Kingdom . | |
| WO 92/11035 | 9/1992 | WIPO . | |
| 9320807 | 10/1993 | WIPO . | |
| 9418961 | 9/1994 | WIPO . | |

OTHER PUBLICATIONS

J. Evans et al., Prostaglandins, Leukotrienes and Medicine, vol. 23, 1986, pp. 167–171.
R. Kikumoto et al., J. Med. Chem., vol. 24, No. 2, 1981, pp. 145–148.
Chemical Abstracts, vol. 122, No. 15 Abst. No. 18759b (Apr. 10, 1995).
L.J. Brandes et al., Biochem. Biophys. Res. Commun., vol. 179, No. 3, pp. 1297–1304 (Sep. 30, 1991).
M. Poirot et al., Biochem. Pharmacol., vol. 40, No. 3, pp. 425–429A (Aug. 1, 1990).
C. Chailleux et al., Mol. Pharmacol., vol. 44, No. 2, pp. 324–327 (Aug. 2, 1993).
L.J. Brandes et al., J. Clin. Oncol., vol. 12, No. 6 pp. 1281–1290 (Jun. 6, 1994).
L. Brandes et al. Chem. Abstr. 115:64790h, "Treatment of ulcer disorders of the gastrointestinal tract with diphenylmethane derivatives" (1991).
A. Fargin et al. Chem.–Biol. Interactions, 66, 101–109 (1988), "Further Evidence For a Biological Role of Anti–Estrogen–Binding Sites in Mediating the Growth Inhibitory Action of Diphenylmethane Derivatives".
K. Kindler et al. Ann die Chemie (617), 25–54 (1958), "Katalytisch–Specifische Kondensationen Mit Dihalogeniden, I".
R. Labaudinière et al. J. Med. Chem., 35:3170–3179 (1992), "ω-[(ω-Arylalkyl)thienyl]alkanoic Acids: From Specific LTA₄ Hydrolase Inhibitors to LTB₄ Receptor Antagonists".
R. Labaudinière et al. J. Med. Chem., 35, 3156–3169 (1992), "ω[(ω-Arylalkyl)aryl]alkanoic Acids: A New Class of Specific LTA₄ Hydrolase Inhibitors".
F. Lakhdar–Ghazal et al. Biochemical Pharmacology 42 (11), 2099–2105 (1991), "Interactions Between Trypanocidal Drugs and Membrane Phospholipids".
D. Nardi et al. Il Farmaco–Ed. Sc.—vol. 20(8) 557–565 (1965), "Nuovi Sali Ammonici Quaternari Ad Attivita Ganglioplegica E. Ipotensiva".
A. Oda et al. Chem. Abstr. 119:88896f, "Phenoxyethylamines as bactericides for crops" (1993).

(List continued on next page.)

Primary Examiner—Alan L. Rotman
Attorney, Agent, or Firm—Fitzpatrick, Cella, Harper & Scinto

[57] ABSTRACT

The present invention provides compounds of the formula Ar¹—Q—Ar²—Y—R—Z and pharmaceutically acceptable salts thereof wherein Ar¹ and Ar² are optionally substituted aryl moieties, Z is an optionally substituted nitrogen-containing moiety which may be an acyclic, cyclic or bicyclic amine or an optionally substituted monocyclic or bicyclic nitrogen-containing heteroaromatic moiety; Q is a linking group capable of linking two aryl groups; R is an alkylene moiety; Y is a linking moiety capable of linking an aryl group to an alkylene moiety and wherein Z is bonded to R through a nitrogen atom. The compounds and pharmaceutical compositions of the present invention are useful in the treatment of inflammatory diseases which are mediated by LTB₄ production, such as psoriasis, ulcerative colitis, IBD and asthma.

9 Claims, No Drawings

OTHER PUBLICATIONS

M. Protiva et al. *Chem. listech* 43, 254–257 (1949) "Antihistaminové látky XIV.*) Basické ethery odvozené od 2–a 4–hydroxydifenylsulfidu, 2–hydroxydifenyletheru a 2–hydroxydifenylaminu".

W. Yuan et al. *J. Med. Chem.*, 36, 211–220 (1993), "Development of Selective Tight–Binding Inhibitors of Leukotriene $A_4$ Hydrolase".

W. Yuan et al. *J. Am. Chem. Soc.* 114, 6552–6553 (1992), "Novel Tight–Binding Inhibitors of Leukotriene $A_4$ Hydrolase".

LTA₄ HYDROLASE INHIBITORS

This is a continuation Application of application Ser. No. 08/321,183 filed on Oct. 11, 1994, now U.S. Pat. No. 5,585,492.

FIELD OF THE INVENTION

This invention relates generally to anti-inflammatory compounds and pharmaceutical compositions, and more particularly to anti-inflammatory compounds and compositions which are capable of inhibiting leukotriene A₄ hydrolase.

LTA₄ hydrolase is a requisite enzyme in the biosynthetic pathway leading to LTB₄ formation. LTB₄ is a proinflammatory compound. R. Lewis, et al., *N. Engl. J. Med.* 323, 645–655 (1990) have demonstrated that LTB₄ is a potent granulocyte agonist inducing chemotaxis, aggregation, degranulation, adherence and priming of inflammatory cells for induction by other agonists. Binding of LTB₄ to receptors is stereospecific with two distinct classes of binding sites. A. Lin, et al., *Prostaglandins* 28, 837–849 (1984). A high affinity site [4–5×10⁻¹⁰M] mediates chemotaxis and chemokinesis while lower affinity sites [0.6–5×10⁻⁷M] stimulate granular secretion and oxidative burst. The LTB₄ receptor is associated with a GTP-binding protein that regulates affinity and transduces signals. T. Schepers, et al., *J. Biol. Chem.* 267, 159–165 (1992). Elevated LTB₄ levels have been reported for many diseases. Most prominently, elevated LTB₄ levels have been correlated to the pathology of inflammatory bowel disease (IBD) including Crohn's disease and ulcerative colitis and in psoriasis. P. Sharon, et al., *Gastroent.* 86, 453–460; K. Lauritsen, et al., *Gastroent.* 95, 11–17 (1989); S. Brain, et al., *Br. J. Pharm.*, 83, 313–317 (1984). Other properties of LTB₄ which may contribute to disease processes are: stimulation of mucus secretion; stimulation of cytokine production; and the ability to act synergistically with other inflammatory mediators such as prostaglandins and cysteinyl leukotrienes thereby amplifying the inflammatory process.

B. Samuelsson, et al., *J. Biol Chem.*, 264, 19469–19472 (1989) have shown that LTB₄ biosynthesis from arachidonic acid involves the action of 2 enzymes, 5-lipoxygenase [5-LO] and LTA₄ hydrolase. 5-LO transforms arachidonic acid to 5-HPETE and subsequent formation of LTA₄, which is an unstable allylic epoxide intermediate which is enzymatically hydrolyzed by LTA₄ hydrolase to form the dihydroxy acid LTB₄.

LTA₄ hydrolase is distinct from cytosolic and microsomal epoxide hydrolases based on strict substrate requirements, product formation [5(S),12(R) vs. 5(S),6(R) for mouse liver cytosolic epoxide hydrolase, and lack of inhibition by inhibitors of cytosolic epoxide hydrolase. LTA₄ hydrolase appears to be ubiquitously distributed in mammalian tissues even in cell types that do not express 5-LO, suggesting the importance of transcellular metabolism of LTA₄. While peptidomimetic compounds such as bestatin and captopril have been shown to exhibit LTA₄ hydrolase inhibitory activity, they are not able to satisfy the requirement of a small organic compound which is capable of cellular penetration. It would therefore be very advantageous to be able to provide low molecular weight inhibitors of LTB₄ biosynthesis which preferably exhibit oral activity in vivo at desirably low concentrations.

SUMMARY OF THE INVENTION

Applicants have now discovered that compounds of the formula I

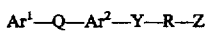   (I)

and pharmaceutically acceptable salts and stereoisomers thereof possess LTA₄ hydrolase inhibitor activity, wherein:

Ar¹ is an aryl moiety selected from the group consisting of:
(i) phenyl, mono-, di-, or tri-substituted phenyl with the substituents selected from the group consisting of Cl, Br, F, CF₃, lower alkyl, lower alkoxy, NH₂, NO₂ and OH;
(ii) 2-, 4- or 5-thiazolyl,
(iii) 2-, 3- or 4-pyridinyl,
(iv) 2- or 3-thienyl, and
(v) 2- or 3-furyl;

Ar² is an aryl moiety selected from the group consisting of:

(i) 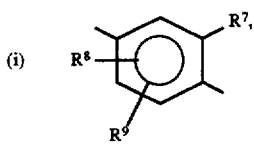

(ii) 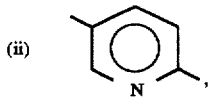

(iii) 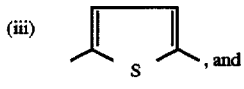, and (iv) 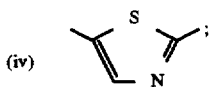;

Q is selected from the group consisting of:
(i) —O—,
(ii) —CH₂—,
(iii) —OCH₂—,
(iv) —CH₂O—,
(v) —NH—;
(vi) —NHCH₂—,
(vii) —CH₂NH—,
(viii) —CF₂—,
(ix) —CH=CH—,
(x) —CH₂CH₂—, and
(xi) carbon-carbon single bond;

Y is selected from the group consisting of
(i) —O—,
(ii) —S—,
(iii) —NH—,
(iv) —S(O)—, and
(v) —S(O₂)—;

R is selected from the group consisting of:
(i) linear or branched C₂–C₆ alkylene; or
(ii) C(R¹⁰)(R¹¹)—(CH₂)ₘ; and Z is selected from the group consisting of:

(i) 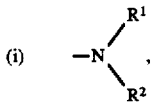,

-continued (ii) 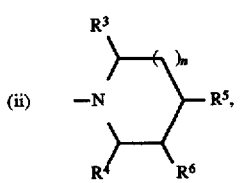

(iii) 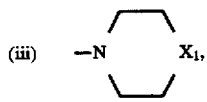

(iv) 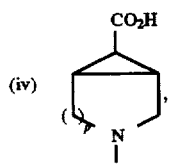

(v) 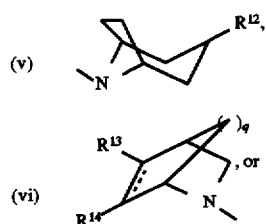

(vi) 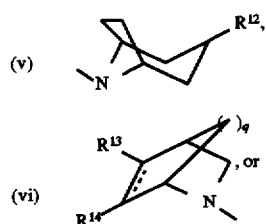

(vii) a monocyclic or bicyclic heteroaromatic moiety having at least one heteroatom, wherein the heteroatom is nitrogen, and wherein the monocyclic heteroaromatic moiety comprises a 5- or 6-membered ring and the bicyclic heteroaromatic moiety comprises a fused 9- or 10-membered ring;

wherein $R^1$ and $R^2$ are independently selected from the group consisting of:

(i) H, (ii) lower alkyl or allyl, (iii) benzyl, (iv) —$(CH_2)_a COR^{15}$, (v) 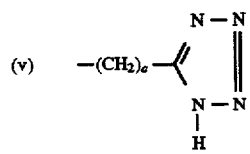

(vi) —$(CH_2)_a OH$ $R^3$ and $R^4$ are independently H or lower alkyl;

$R^5$ and $R^6$ are independently selected from the group consisting of:

(i)  H, (ii)  —OH or =O, (iii)  —$(CH_2)_a COR^{15}$, (iv)  —$(CH_2)_a CONH(CH_2)_b CO_2 R^{16}$, -continued (v) —$NHR^{17}$, (vi) 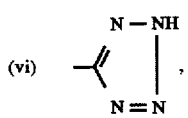

(vii) 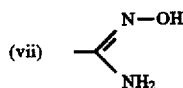

(viii) 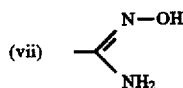

(ix) 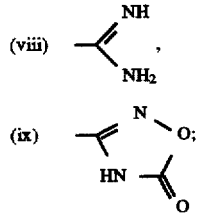

$R^7$ is H, halogen, lower alkyl, lower alkoxy, nitro, hydroxy, or $R^7$ taken together with $R^{10}$ is an alkylene group having one or two carbon atoms;

$R^8$ and $R^9$ are independently H, halogen, lower alkyl, lower alkoxy, $NH_2$, $NO_2$ or OH;

$R^{10}$ is H, lower alkyl, or $R^{10}$ taken together with $R^7$ is an alkylene group having one or two carbon atoms;

$R^{11}$ is H or lower alkyl;

$R^{12}$ is selected from the group consisting of:

(i) H, (ii) —OH or =O, (iii) —$(CH_2)_a COR^{15}$, (iv) —$(CH_2)_a CONH(CH_2)_b CO_2 R^{16}$, (v) —$NHR^{17}$;

$R^{13}$ and $R^{14}$ are independently hydrogen, —$(CH_2)_a COR^{15}$, provided that at least one of $R^{13}$ and $R^{14}$ is hydrogen;

$R^{15}$ is —$OR^{16}$, —$NHR^{16}$ or —$NHNH_2$;

$R^{16}$ is H, lower alkyl or benzyl;

$R^{17}$ is H, lower alkyl, benzyl, —$COR^{16}$ or —$CONH_2$;

$X^1$ is

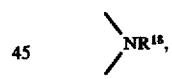

—S—, or —O—, wherein $R^{18}$ is H, lower alkyl, —$CONH_2$, $CSNH_2$, —$COCH_3$ or —$SO_2CH_3$;

a and b are independently integers of from 0 to 5;

m is 1, 2 or 3;

n is 0, 1, 2 or 3;

p is 1 or 2; and q is 1, 2 or 3;

provided however that where R is $C(R^{10})(R^{11})$—$(CH_2)_m$, and $R^{10}$ taken together with $R^7$ forms an alkylene group having one or two carbon atoms, then —$Ar^2$—Y—R is

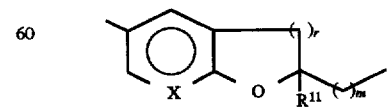

wherein X is —CH— or —N—, and r is 1 or 2, further provided that wherein $R^1$, $R^2$ or both $R^1$ and $R^2$ are —$(CH_2)_a COR^{15}$, then a is not 0.

DETAILED DESCRIPTION OF THE INVENTION

In one of its embodiments, the present invention entails compounds of the formula I

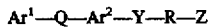    (I)

and pharmaceutically acceptable salts and stereoisomers thereof, wherein:

$Ar^1$ is an aryl moiety selected from the group consisting of:
(i) phenyl, mono-, di-, or tri-substituted phenyl with the substituents selected from the group consisting of Cl, Br, F, $CF_3$, lower alkyl, lower alkoxy, $NH_2$, $NO_2$ and OH;
(ii) 2-, 4- or 5-thiazolyl,
(iii) 2-, 3- or 4-pyridinyl,
(iv) 2- or 3-thienyl, and
(v) 2- or 3-furyl;

$Ar^2$ is an aryl moiety selected from the group consisting of:

(i) 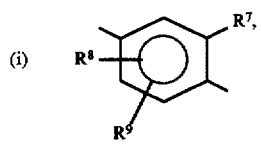

(ii) 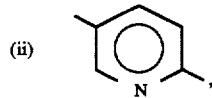

(iii) 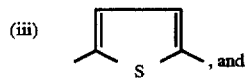, and (iv) 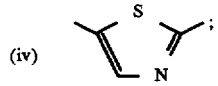;

Q is selected from the group consisting of:
(i) —O—,
(ii) —$CH_2$—,
(iii) —$OCH_2$—,
(iv) —$CH_2O$—,
(v) —NH—;
(vi) —$NHCH_2$—,
(vii) —$CH_2NH$—,
(viii) —$CF_2$—,
(ix) —CH=CH—,
(x) —$CH_2CH_2$—, and
(xi) carbon-carbon single bond;

Y is selected from the group consisting of
(i) —O—,
(ii) —S—,
(iii) —NH—,
(iv) —S(O)—, and
(v) —$S(O_2)$—;

R is selected from the group consisting of:
(i) linear or branched $C_2$-$C_6$ alkylene; or
(ii) $C(R^{10})(R^{11})$—$(CH_2)_m$; and Z is selected from the group consisting of:

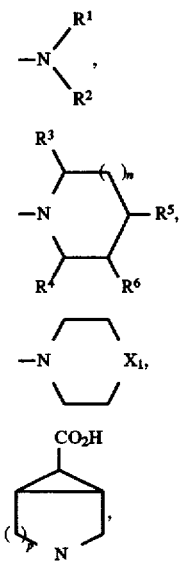

(vii) a monocyclic or bicyclic heteroaromatic moiety having at least one heteroatom, wherein the heteroatom is nitrogen, and wherein the monocyclic heteroaromatic moiety comprises a 5- or 6-membered ring and the bicyclic heteroaromatic moiety comprises a fused 9- or 10-membered ring;

wherein
$R^1$ and $R^2$ are independently selected from the group consisting of:
(i) H,
(ii) lower alkyl or allyl,
(iii) benzyl,
(iv) —$(CH_2)_a COR^{15}$, (v) 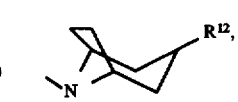

(vi) —$(CH_2)_a OH$ $R^3$ and $R^4$ are independently H or lower alkyl;
$R^5$ and $R^6$ are independently selected from the group consisting of:

(i) H, (ii) —OH, =O, or —$(CH_2)_a OH$ (iii) —(CH₂)ₐCOR¹⁵, (iv) —(CH₂)ₐCONH(CH₂)ᵦCO₂R¹⁶, (v) —NHR¹⁷, (vi) 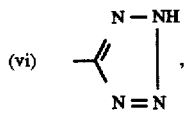

(vii) 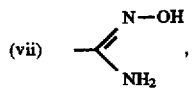

(viii) 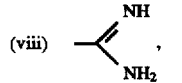

(ix) 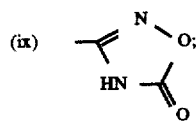

R⁷ is H, halogen, lower alkyl, lower alkoxy, nitro, hydroxy, or R⁷ taken together with R¹⁰ is an alkylenyl group having one or two carbon atoms;

R⁸ and R⁹ are independently H, halogen, lower alkyl, lower alkoxy, NH₂, NO₂ or OH;

R¹⁰ is H, lower alkyl, or R¹⁰ taken together with R⁷ is an alkylenyl group having one or two carbon atoms;

R¹¹ is H or lower alkyl;

R¹² is selected from the group consisting of:

(i) H, (ii) —OH or =O, (iii) —(CH₂)ₐCOR¹⁵, (iv) —(CH₂)ₐCONH(CH₂)ᵦCO₂R¹⁶, (v) —NHR¹⁷;

R¹³ and R¹⁴ are independently hydrogen, —(CH₂)ₐCOR¹⁵, provided that at least one of R¹³ and R¹⁴ is hydrogen;

R¹⁵ is —OR¹⁶, —NHR¹⁶ or —NHNH₂;

R¹⁶ is H, lower alkyl or benzyl;

R¹⁷ is H, lower alkyl, benzyl, —COR¹⁶ or —CONH₂;

X¹ is

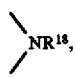

—S—, or —O—, wherein R¹⁸ is H, lower alkyl, —CONH₂, CSNH₂, —COCH₃ or —SO₂CH₃;

a and b are independently integers of from 0 to 5;

m is 1, 2 or 3;

n is 0, 1, 2 or 3;

p is 1 or 2; and q is 1, 2 or 3;

provided however that where R is C(R¹⁰)(R¹¹)—(CH₂)ₘ, and R¹⁰ taken together with R⁷ forms an alkylenyl group having one or two carbon atoms, then —Ar²—Y—R— is

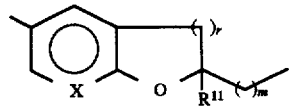

wherein X is —CH— or —N—, and r is 1 or 2, further provided that wherein Z is

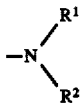

and R¹ and/or R² is —(CH₂)ₐCOR¹⁵, then a is not 0.

In one of its embodiments the present invention entails compounds of formula I Ar¹—Q—Ar²—Y—R—Z, wherein Z is an amine moiety of the formula

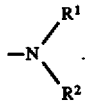

In another of its embodiments the present invention includes compounds of formula I Ar¹—Q—Ar²—Y—R—Z, wherein Z is

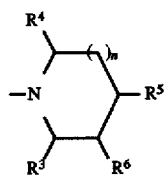

wherein R³, R⁴, R⁵ and R⁶ are defined as set forth hereinbefore.

In another of its embodiments the present invention entails compounds of the formula Ar¹—Q—Ar²—Y—R—Z wherein when Ar¹—Q—Ar²—Y is

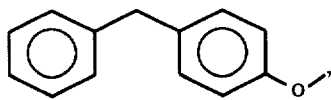

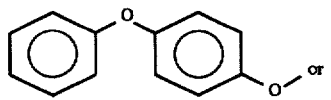

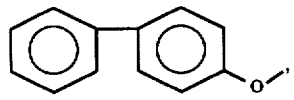

then (A) R¹ and R² are not simultaneously H or lower alkyl; or (B) R³, R⁴, R⁵ and R⁶ are not simultaneously H.

The compounds of the present invention, in several embodiments, may comprise a carboxylic acid or ester moiety. It will be appreciated by the art-skilled that a compound of the present invention comprising an ester moiety is readily converted, in vivo, especially when administered orally, into its corresponding carboxylic acid form. The ester-containing compounds of the present invention are therefore prodrugs of their carboxylic acid form.

In another of its embodiments the present invention concerns compounds of formula I Ar¹—Q—Ar²—Y—R—

Z, wherein Z is a monocyclic or bicyclic heteroaromatic moiety having at least one heteroatom, the at least one heteroatom being nitrogen, wherein the monocyclic heteroaromatic moiety comprises a 5- or 6-membered ring and the bicyclic heteroaromatic moiety comprises a fused 9- or 10-membered ring.

In another of its aspects the invention entails pharmaceutical composition comprising a pharmacologically effective amount of a compound of formula I and a pharmaceutically acceptable carrier.

In still another of its embodiments the present invention involves a method for treating a mammal exhibiting an $LTB_4$ mediated inflammatory condition comprising administering to the mammal a pharmacologically effective amount of a compound of formula I.

The term "lower alkyl" means straight or branched chain alkyl having 1 to 6 carbon atoms such as methyl, ethyl, propyl, butyl, pentyl, hexyl and the branched chain isomers thereof.

The term "lower alkoxy" means straight or branched chain alkoxy having 1 to 6 carbon atoms such as methoxy, ethoxy, propoxy, butoxy, pentoxy, hexoxy and the branched chain isomers thereof.

The term "allyl" as used herein means the 1-propenyl radical, $—CH_2—CH_2=CH_2$.

The term "halo" means fluoro, cloro, bromo, or iodo.

The phrase "monocyclic or bicyclic heteroaromatic moiety" having at least one heteroatom which is nitrogen, includes but is not limited to imidazole, triazole, benzimidazole, imidazopyridine, triazolopyridine, thiazole, purine and the like. Such monocyclic and bicyclic heteroaromatic moieties having at least two nitrogen atoms may be bonded, in a compound of the present invention, through any of the nitrogen atoms, as will be appreciated by the person of ordinary skill in the art, to provide two or more conformational isomers.

Such monocyclic heteroaromatic and bicyclic heteroaromatic compounds are included in the group of compounds referred to herein as "ZH", which group also includes non-aromatic compounds. Non-aromatic compounds which are contemplated by reference to "ZH" include acyclic amines, monocyclic amines, and bicyclic amines as defined herein. A compound of formula I, which comprises a "Z moiety" may be readily formed by reacting a compound of the formula $Ar^1—Q—Ar^2—R—Cl$ or $Ar^1—Q—Ar^2—R—OTs$ with an amine or heteroaromatic compound, ZH.

Included within the classes and subclasses of compounds embraced by Formula I are isomeric forms of the described compounds including diastereoisomers, enantiomers and tautomeric forms of the described compounds. Pharmaceutically acceptable salts of such compounds are also included as well as pharmaceutically acceptable salts of such isomers and tautomers.

In the structures herein a bond drawn across a bond in a ring indicates that the bond can be to any available atom of the ring structure.

The expression "pharmaceutically acceptable salts" is intended to include those salts capable of being formed with the compounds of the present invention without materially altering the chemical structure or pharmacological properties thereof. Such salts include inorganic and organic cations or acid addition salts, such as sodium, potassium, calcium, ammonium, alkylammonium, quaternary ammonium, triethanolamine, lysine, hydrochloride, hydrobromide, etc. well known to those skilled in the art. The foregoing salts are prepared in the conventional manner by neutralization of the compounds of formula I with the desired base or acid.

The compounds of the present invention can be administered to a patient in such oral dosage forms as tablets, capsules, pills, powders, granules, elixirs or syrups, as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex and medical condition of the patient; the severity of the condition to be ameliorated; and the route of administration. A physician of ordinary skill can readily determine and prescribe a "pharmaceutically effective amount" of a compound of Formula I, that is, the effective amount of the compound required to prevent, treat or arrest the progress of the condition. Dosages of the compounds of the present invention will range generally between 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses three to four times daily.

As used herein the phrase "$LTA_4$ hydrolase inhibitor" means a compound which is capable of exhibiting an $IC_{50}$ of less than 1 mM in an in vitro assay employing 10 µg/ml of $LTA_4$ hydrolase enzyme (specific activity 600 nMoles $LTB_4$/min/mg of enzyme) in the presence of 25 µM substrate ($LTA_4$) in a total reaction volume of 100 µl.

In the pharmaceutical compositions and methods of the present invention, at least one of the active compounds of formula I or a pharmaceutically acceptable salt thereof will typically be administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintigrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Lubricants for use in these dosage forms include boric acid, sodium benzoate, sodium acetate, sodium chloride and the like. Disintigrators include, without limitation, starch, methylcellulose, agar, bentonite, guar gum and the like.

By virtue of their activity as $LTA_4$ hydrolase inhibitors, the compounds of Formula I are useful in treating inflammatory conditions mediated by $LTB_4$ production in mammals such as psoriasis, contact and atropic dermatitis, Crohn's disease, ulcerative colitis, inflammatory bowel disease, multiple sclerosis, ankylosing spondylitis arthritis, asthma and the like. Similarly, the compounds of Formula I can be used in preventing recurring inflammatory attacks. A physician or veterinarian of ordinary skill can readily determine whether a subject exhibits the inflammatory condition. A preferred utility relates to treatment of ulcerative colitis.

Among the compounds of the present invention which possess LTA$_4$ hydrolase inhibiting activity are the following:

1-[2-(4-phenoxyphenoxy)ethyl]pyrrolidine;
1-[2-(4-phenylmethyl)phenoxyethyl]pyrrolidine;
1-[2-[4-(2-phenylethenyl)phenoxy]ethyl]pyrrolidine;
1-[2-[4-(4-fluorophenoxy)phenoxy]ethyl]pyrrolidine;
4-[[4-[2-(1-pyrrolidinyl)ethoxy]phenyl]methyl]thiazole;
1-[2-[4-(phenylmethoxy)phenoxy]ethyl]pyrrolidine;
4-[4-[2-(1-pyrrolidinyl)ethoxy]phenyl]benzoic acid;
4-[4-[2-(1-pyrrolidinyl)ethoxy]phenoxy]benzoic acid;
5-phenoxy-2-[2-(1-pyrrolidinyl)ethoxy]pyridine;
1-[2-[4-(2-phenylethyl)phenoxy]ethyl]pyrrolidine;
1-[2-[4-[(difluoro)phenylmethyl]phenoxy]ethyl]pyrrolidine;
1-[2-[4-(phenylmethyl)phenylthio]ethyl]pyrrolidine, monohydrochloride;
1-[2-[4-(phenylmethyl)phenylsulfinyl]ethyl]pyrrolidine, monohydrochloride;
N-[[4-[2-(1-pyrrolidinyl)ethoxy]phenyl]methyl]-3-pyridinamine;
N-(4-phenoxyphenyl)-1-pyrrolidine ethanamine, monohydrochloride;
5-(phenylmethyl)-2-[2-(1-pyrrolidinyl)ethoxy]thiazole;
1-[2-[2-fluoro-4-(phenylmethyl)phenoxy]ethyl]pyrrolidine;
1-[2-[3-fluoro-4-(phenylmethyl)phenoxy]ethyl]pyrrolidine;
1-[2-[2-methyl-4-(phenylmethyl)phenoxy]ethyl]pyrrolidine;
1-[2-[2,6-difluoro-4-(phenylmethyl)phenoxy]ethyl]pyrrolidine;
2-[4-[2-(1-pyrrolidinyl)ethoxy]phenylmethyl]thiazole;
5-[[4-[2-(1-pyrrolidinyl)ethoxy]phenyl]methyl]thiazole;
methyl 5-(phenylmethyl)-2-[2-(1-pyrrolidinyl)ethoxy]benzoate;
3-[4-[2-(1-pyrrolidinyl)ethoxy]phenylmethyl]pyridine;
4-[4-[2-(1-pyrrolidinyl)ethoxy]phenylmethyl]pyridine;
1-[2-[4-[(3-methoxyphenyl)methyl]phenoxy]ethyl]pyrrolidine;
1-[2-[4-[4-(methoxyphenyl)methyl]phenoxy]ethyl]pyrrolidine;
1-[2-[4-[(2-methoxyphenyl)methyl]phenoxy]ethyl]pyrrolidine;
1-[2-[4-[(1,3-benzodioxol-5-yl)methyl]phenoxy]ethyl]pyrrolidine;
2-[4-[2-(1-pyrrolidinyl)ethoxy]phenylmethyl]quinoline;
3-[4-[2-(1-pyrrolidinyl)ethoxy]phenylmethyl]quinoline;
1-[2-[4-[(2-thiophenyl)methyl]phenoxy]ethyl]pyrrolidine;
1-[2-[4-[(3-thiophenyl)methyl]phenoxy]ethyl]pyrrolidine;
1-[2-[4-[(2-furanyl)methyl]phenoxy]ethyl]pyrrolidine;
1-[2-[4-[(3-furanyl)methyl]phenoxy]ethyl]pyrrolidine;
2-[[4-[2-(1-pyrrolidinyl)ethoxy]phenyl]methyl]pyridine;
1-[2-[4-[(4-fluorophenyl)methyl]phenoxy]ethyl]pyrrolidine;
1-[2-[4-[(4-chlorophenyl)methyl]phenoxy]ethyl]pyrrolidine;
1-[2-[4-[(2-fluorophenyl)methyl]phenoxy]ethyl]pyrrolidine;
1-[2-[4-[(3-fluorophenyl)methyl]phenoxy]ethyl]pyrrolidine;
1-[2-[4-[(3-chlorophenyl)methyl]phenoxy]ethyl]pyrrolidine;
1-[2-[[5-(phenylmethyl)pyridin-2-yl]oxy]ethyl]-4-piperidine-carboxamide;
1-[2-[4-(2-naphthalenyl)methoxy]phenoxyethyl]pyrrolidine;
3-[4-[2-(1-pyrrolidinyl)ethoxy]phenoxymethyl]quinoline;
2-methyl-4-[[4-[2-(1-pyrrolidinyl)ethoxy]phenoxy]methyl]thiazole;
1-[2-[4-[(4-bromophenyl)methoxy]phenoxy]ethyl]pyrrolidine;
1-[2-[4-[(2,6-dichlorophenyl)methoxy]phenoxy]ethyl]pyrrolidine;
1-[2-[4-[(4-fluorophenyl)methoxy]phenoxy]ethyl]pyrrolidine;
1-[2-[4-[(3-chlorophenyl)methoxy]phenoxy]ethyl]pyrrolidine;
1-[2-[4-[(2-fluorophenyl)methoxy]phenoxy]ethyl]pyrrolidine;
1-[2-[4-[(2-chlorophenyl)methoxy]phenoxy]ethyl]pyrrolidine;
1-[2-[4-[[(3-trifluoromethyl)phenyl]methoxy]phenoxy]ethyl]-pyrrolidine;
1-[2-[4-[(2-methylphenyl)methoxy]phenoxy]ethyl]pyrrolidine;
1-[2-[4-[(3-fluorophenyl)methoxy]phenoxy]ethyl]pyrrolidine;
1-[2-[4-[(4-methylphenyl)methoxy]phenoxy]ethyl]pyrrolidine;
1-[2-[4-[(4-methoxyphenyl)methoxy]phenoxy]ethyl]pyrrolidine;
1-[2-[4-[(1-naphthyl)methoxy]phenoxy]ethyl]pyrrolidine;
1-[2-[4-[(2-thiophenyl)methoxy]phenoxy]ethyl]pyrrolidine;
methyl-1-[2-[4-(phenylmethyl)phenoxy]ethyl]-2S-pyrrolidine-2-carboxylate, monohydrochloride, hydrate;
1-[3-[4-(phenylmethyl)phenoxy]propyl]-4-piperidine-carboxamide;
N-[1-[2-[4-(phenylmethyl)phenoxy)ethyl]pyrrolidin-3-yl]acetamide, monohydrochloride;
phenylmethyl 1-[3-[4-(phenylmethyl)phenoxy]propyl]-L-prolinate;
1-[2-[4-[(2-thiophenyl)methyl]phenoxy]ethyl-4-piperidine-carboxamide;
1-[2-[4-[(3-thiophenyl)methyl]phenoxy]ethyl]-4-piperidine-carboxamide;
1-[2-[4-[(2-thiazolyl)methyl]phenoxy]ethyl]-4-piperidine-carboxamide;
1-[2-[4-[(4-methoxyphenyl)methyl]phenoxy]ethyl]-4-piperidine-carboxamide;
1-[2-[4-[(4-fluorophenyl)methyl]phenoxy]ethyl]-4-piperidine-carboxamide;
N-[1-[2-[4-(phenylmethyl)phenoxy]ethyl]piperidin-4-yl]-acetamide;

N-[2-[4-(phenylmethyl)phenoxy]ethyl]cyclohexanamine, monohydrochloride;

N-[2-[4-(phenylmethyl)phenoxy]ethyl]cyclopentanamine, monohydrochloride;

1-[2-[4-(phenylmethyl)phenoxy]ethyl]piperidine-4-carboxamide;

1-[2-[4-(phenylmethyl)phenoxy]ethyl]-3-piperidinecarboxamide;

1-[3-[4-(phenylmethyl)phenoxy]propyl]-3-piperidinecarboxamide;

ethyl-1-[2-[4-(phenylmethyl)phenoxy]ethyl]-4-piperidine-carboxylate, monohydrochloride;

8-[2-[4-(phenylmethyl)phenoxy]ethyl]-1,4-dioxa-8-azaspiro[4.5]-decane, monohydrochloride;

1-[2-[4-(phenylmethyl)phenoxy]ethyl]-4-piperidinol, monohydrochloride;

N-[1-[2-[4-(phenylmethyl)phenoxy]ethyl]piperidin-4-yl]-2-benzo[b]furancarboxamide;

ethyl 3-[[[1-[2-[4-(phenylmethyl)phenoxy]ethyl]piperidine-4-yl]-carbonyl]amino]propanoate;

1-[3-(4-phenoxyphenoxy)propyl]-3-piperidinecarboxamide;

1-[3-(4-phenoxyphenoxy)propyl]-4-piperidinecarboxamide;

1-[2-(4-phenoxyphenoxy)ethyl]-4-piperidinecarboxamide;

1-[2-(4-phenoxyphenoxy)ethyl]-3-piperidinecarboxamide;

ethyl 1-[2-(4-phenoxyphenoxy)ethyl]-4-piperidinecarboxylate, monohydrochloride;

N-methyl-1-[2-(4-phenoxyphenoxy)ethyl]-4-piperidinecarboxamide;

4-[2-[4-(phenylmethyl)phenoxy]ethyl]morpholine, monohydrochloride;

1-[3-[4-(phenylmethyl)phenoxy]propyl]pyrrolidine;

1,1-dimethylethyl 1-[3-[4-(phenylmethyl)phenoxy]propyl]-L-prolinate;

phenylmethyl 3-[[3-[4-(phenylmethyl)phenoxy]propyl]amino]propanoate;

methyl 4-oxo-1-[3-[4-(phenylmethyl)phenoxy]propyl]piperidine-3-carboxylate;

1,1-dimethylethyl 1-[3-[4-(phenylmethyl)phenoxy]propyl]piperidine-4-carboxylate;

ethyl N-[3-[4-(phenylmethyl)phenoxy]propyl]glycinate;

ethyl 3-[[3-[4-(phenylmethyl)phenoxy]propyl]amino]propanoate;

phenylmethyl 3-[[2-[4-(phenylmethyl)phenoxy]ethyl]amino]propanoate;

methyl 3-[[3-[4-(phenylmethyl)phenoxy]propyl]amino]propanoate;

1,1-dimethylethyl 3-[[3-[4-(phenylmethyl)phenoxy]propyl]amino]propanoate;

ethyl 1-[3-[4-(phenylmethyl)phenoxy]propyl]piperidine-3-carboxylate;

ethyl 1-[2-[4-(phenylmethyl)phenoxy]ethyl]-3-piperidine carboxylate;

ethyl beta-[[2-[4-(phenylmethyl)phenoxy]ethyl]amino]-3-pyridinepropanoate;

ethyl 3-[4-[4-(phenylmethyl)phenoxy]butylamino]propanoate;

phenylmethyl 3-[[4-[4-(phenylmethyl)phenoxy]butyl]amino]-propanoate;

ethyl 3-[[5-[4-(phenylmethyl)phenoxy]pentyl]amino]propanoate;

methyl 1-[2-[4-(phenylmethyl)phenoxy]ethyl]-3-pyrrolidineacetate;

methyl 1-[2-[4-(phenylmethyl)phenoxy]ethyl]-3-pyrrolidinecarboxylate;

1-[hexahydro-4-[2-[4-(phenylmethyl)phenoxy]ethyl]pyrazin-1-yl]-ethanone, monohydrochloride;

1-[2-[4-(phenylmethyl)phenoxy]ethyl]-4-piperidinecarbonitrile, monohydrochloride;

1-[[2,3-dihydro-5-(phenylmethyl)benzofuran-2-yl]methyl]-4-piperidinecarboxamide;

ethyl 1-[[2,3-dihydro-5-(phenylmethyl)benzo[b]furan-2-yl]methyl]-4-piperidine carboxylate, monohydrochloride;

(+)-1-[[2,3-dihydro-2-methyl-5-(phenylmethyl)benzo[b]furan-2-yl]methyl]pyrrolidine, monohydrochloride;

(+)-1-[[2,3-dihydro-3-methyl-5-(phenylmethyl)benzo[b]furan-2-yl]methyl]-4-piperidinecarboxamide;

2,3-dihydro-5-(phenylmethyl)-2-(1-pyrrolidinylmethyl)furo[2,3-b]-pyridine, dihydrochloride;

(+)-1-[[5-(phenylmethyl)furo[2,3-b]pyridin-2-yl]methyl]-4-piperidine carboxamide;

1-[[2,3-dihydro-5-phenoxybenzo[b]furan-2-yl]methyl]pyrrolidine, monohydrochloride;

1-[[2,3-dihydro-5-phenoxybenzo[b]furan-2-yl]methyl-4-piperidinecarboxamide;

ethyl 1-[(2,3-dihydro-5-phenoxybenzo[b]furan-2-yl)methyl]-4-piperidinecarboxylate, monohydrochloride;

(+)-1-[[3,4-dihydro-6-(phenylmethyl)-2H-benzopyran-2-yl]methyl]-4-piperidine, monohydrochloride carboxamide;

1-[[2,3-dihydro-5-(phenylmethyl)benzo[b]furan-2-yl]-methyl]-N-methyl-4-piperidine carboxamide;

1-[(2,3-dihydro-5-phenoxybenzo[b]furan-2-yl]methyl]-N-methyl-4-piperidinecarboxamide;

2S-alpha-methyl-1-[2-[4-(phenylmethyl)phenoxy]-ethyl]-4-alpha-pyridinecarboxamide;

N-methyl-1-[2-[4-(phenylmethyl)phenoxy]ethyl]-4-piperidinecarboxamide;

[[2,3-dihydro-5-(phenylmethyl)benzofuran-2-yl]methyl]-1-pyrazinecarboxamide;

4-[2-[4-(phenylmethyl)phenoxy]ethyl]-4H-imidazo[4,5-b]pyridine;

1-[2-[4-(phenylmethyl)phenoxy]ethyl]-1H-imidazo[4,5-b]pyridine;

3-[2-[4-(phenylmethyl)phenoxy]ethyl]-3H-imidazo[4,5-b]pyridine;

1-[2-[4-(phenylmethyl)phenoxy]ethyl]-1H-benzimidazole;

5-[2-[4-(phenylmethyl)phenoxy]ethyl]-5H-imidazo[4,5-c]pyridine, hydrate;

1-[2-[4-(phenylmethyl)phenoxy]ethyl]-1H-imidazo[4,5-c]pyridine;

3-[2-[4-(phenylmethyl)phenoxy]ethyl]-3H-imidazo[4,5-c]pyridine;

3-[3-[4-(phenylmethyl)phenoxy]propyl]-3H-imidazo[4,5-b]pyridine;

1-[3-[4-(phenylmethyl)phenoxy]propyl]-1H-imidazo[4,5-b]pyridine;

1-[2-[4-(phenylmethyl)phenoxy]ethyl]-1H-pyrrolol[3,2-b]pyridine;

1-[3-(4-phenoxyphenoxy)propyl]-1H-benzimidazole;

1-[2-(4-phenoxyphenoxy)ethyl]-1H-benzimidazole;

1-[2-[4-(phenylmethoxy)phenoxy]ethyl]-1H-benzimidazole;

3-[2-[4-(phenylmethoxy)phenoxy]ethyl]-3H-imidazo[4,5-b]pyridine;

1-[2-[4-(phenylmethoxy)phenoxy]ethyl]-1H-imidazo[4,5-b]pyridine;

4-[2-[4-(phenylmethoxy)phenoxy]ethyl]-4H-imidazo[4,5-b]pyridine;

3-[2-[4-(phenylmethoxy)phenoxy]ethyl]-3H-imidazo[4,5-c]pyridine;

1-[2-[4-(phenylmethoxy)phenoxy]ethyl]-1H-imidazo[4,5-c]pyridine;

5-[2-[4-(phenylmethoxy)phenoxy]ethyl]-5H-imidazo[4,5-c]pyridine;

3-[2-(4-phenoxyphenoxy)ethyl]-3H-imidazo[4,5-b]pyridine;

1-[2-(4-phenoxyphenoxy)ethyl]-1H-imidazo[4,5-b]pyridine;

4-[2-(4-phenoxyphenoxy)ethyl]-4H-imidazo[4,5-b]pyridine;

5-[2-(4-phenoxyphenoxy)ethyl]-5H-imidazo[4,5-c]pyridine;

1-[2-(4-phenoxyphenoxy)ethyl]-1H-imidazo[4,5-c]pyridine;

3-[2-(4-phenoxyphenoxy)ethyl]-3H-imidazo[4,5-c]pyridine;

3-[3-(4-phenoxyphenoxy)propyl]-3H-imidazo[4,5-b]pyridine;

1-[3-(4-phenoxyphenoxy)propyl]-1H-imidazo[4,5-b]pyridine;

4-[3-(4-phenoxyphenoxy)propyl]-4H-imidazo[4,5-b]pyridine;

3-[3-(4-phenoxyphenoxy)propyl]-3H-imidazo[4,5-c]pyridine;

1-[3-(4-phenoxyphenoxy)propyl]-1H-imidazo[4,5-c]pyridine;

5-[3-(4-phenoxyphenoxy)propyl]-5H-imidazo[4,5-c]pyridine;

1-[2-[4-(phenylmethyl)phenoxy]ethyl]-1H-imidazole, monohydrochloride;

2,3,6,7-tetrahydro-1,3-dimethyl-7-[2-[4-(phenylmethyl)phenoxy]ethyl]-1H-purine-2,6-dione;

3-[2-[4-(4-fluorophenoxy)phenoxy]ethyl]-3H-imidazo[4,5-b]pyridine;

1-[2-[4-(4-fluorophenoxy)phenoxy]ethyl]-1H-imidazo[4,5-b]pyridine;

3-[2-[4-(4-fluorophenoxy)phenoxy]ethyl]-3H-imidazo[4,5-c]pyridine;

1-[2-[4-(4-fluorophenoxy)phenoxy]ethyl]-1H-imidazo[4,5-c]pyridine;

5-[2-[4-(4-fluorophenoxy)phenoxy]ethyl]-5H-imidazo[4,5-c]pyridine;

3-[3-[4-(phenylmethyl)phenoxy]propyl]-3H-imidazo[4,5-c]pyridine;

1-[3-[4-(phenylmethyl)phenoxy]propyl]-1H-imidazo[4,5-c]pyridine;

5-[3-[4-(phenylmethyl)phenoxy]propyl]-5H-imidazo[4,5-c]pyridine;

7-[2-[4-(phenylmethyl)phenoxy]ethyl]-7H-purine;

9-[2-[4-(phenylmethyl)phenoxy]ethyl]-9H-purine;

1-[2-[4-(phenylmethyl)phenoxy]ethyl]-1H-purine;

3-[2-[4-(phenylmethyl)phenoxy]ethyl]-3H-purine, monohydrochloride;

3-[[2,3-dihydro-5-(phenylmethyl)benzo[b]furan-2-yl]methyl]-3H-imidazo [4,5-b]pyridine, monohydrochloride;

1-[[2,3-dihydro-5-(phenylmethyl)benzo[b]furan-2-yl]methyl]-1H-imidazo [4,5-b]pyridine;

4-[[2,3-dihydro-5-(phenylmethyl)benzo[b]furan-2-yl]methyl]-4H-imidazo [4,5-b]pyridine, hydrochloride;

3-[[2,3-dihydro-5-(phenylmethyl)benzo[b]furan-2-yl]methyl]-3H-1,2,3-triazolo[4,5-b]pyridine;

2-[[2,3-dihydro-5-(phenylmethyl)benzo[b]furan-2-yl]methyl]-2H-1,2,3-triazolo[4,5-b]pyridine;

1-[[2,3-dihydro-5-(phenylmethyl)benzo[b]furan-2-yl]methyl-1H-1,2,3-triazolo[4,5-b]pyridine;

2-[[2,3-dihydro-5-(phenylmethyl)benzo[b]furan-2-yl]methyl]-2H-1,2,3-triazolo[4,5-c]pyridine, monohydrochloride;

1-[[2,3-dihydro-5-(phenylmethyl)benzo[b]furan-2-yl]methyl]-1H-1,2,3-triazolo[4,5-c]pyridine, monohydrochloride;

1-[2-[4-(phenylmethyl)phenoxy]ethyl]-1H-benzimidazole-5-amine;

1-[2-[4-(phenylmethyl)phenoxy]ethyl]-1H-benzimidazole-6-amine;

1-[2-[4-(phenylmethyl)phenoxy]ethyl]-1H-imidazo[4,5-b]pyridinium 4-oxide;

3-[2-[4-(phenylmethyl)phenoxy]ethyl]-3H-imidazo[4,5-c]pyridinium, 5-oxide;

1-[2-[4-(phenylmethyl)phenoxy]ethyl]-1H-imidazo[4,5-c]pyridinium, 5-oxide;

1-[2-[4-(phenylmethyl)phenoxy]ethyl]-2-pyrrolidinemethanol, monohydrochloride;

1-[2-[4-(phenylmethyl)phenoxy]ethyl]-3-pyrrolidinol;

hexahydro-1-[2-[4-(phenylmethyl)phenoxy]ethyl]-1H-azepine, monohydrochloride;

1-[2-[4-(phenylmethyl)phenoxy]ethyl]azocine, monohydrochloride;

2,5-dimethyl-1-[2-[4-(phenylmethyl)phenoxy]ethyl]pyrrolidine, monohydrochloride;

2S-(methoxymethyl)-1-[2-[4-(phenylmethyl)phenoxy]ethyl]pyrrolidine, monohydrochloride;

1-[2-[4-(phenylmethyl)phenoxy]ethyl]piperidine, monohydrochloride;

2,6-dimethyl-1-[2-[4-(phenylmethyl)phenoxy]ethyl]piperidine, monohydrochloride;

1-[2-[4-(phenylmethyl)phenoxy]propyl]piperidine, monohydrochloride;

hexahydro-1-[2-[4-(phenylmethyl)phenoxy]propyl]-1H-azepine, monohydrochloride;

[2-[4-(phenylmethyl)phenoxy]butyl]pyrrolidine, monohydrochloride;

2-[4-(phenylmethyl)phenoxy]ethyl]-1-[2-phenylmethyl]pyrrolidine, monohydrochloride;

ethyl beta-[[3-[4-(phenylmethyl)phenoxy]propyl]amino]-4-pentynoate;

ethyl beta-[[2-[4-(phenylmethyl)phenoxy]ethyl]amino]-4-pentynoate;

phenylmethyl 3-[[3-[4-(phenylmethyl)henoxy]propyl](2-propenyl)amino]propanoate;

ethyl [[4-[4-(phenylmethyl)phenoxy]butyl]-(2-propenyl) amino]propanoate;

ethyl 3-[methyl-[3-[4-(phenylmethyl)phenoxy]propyl] amino]propanoate;

methyl 3-[methyl[3-[4-(phenylmethyl)phenoxy]propyl] amino]propanoate, hydrate;

ethyl 3-[[3-[4-(phenylmethyl)phenoxy]propyl] (pyridin-3-ylmethyl)amino]propanoate;

ethyl [methyl[4-[4-(phenylmethyl)phenoxy]butyl]amino] propanoate, triethylamine salt;

1,1-dimethyl-3-[[3-[4-(phenylmethyl)phenoxy]propyl] amino]propanol;

phenylmethyl 2,2-dimethyl-3-[methyl[3-[4-(phenylmethyl) phenoxy]propyl]amino]propanoate;

1-[2-[4-(phenylmethyl)phenoxy]ethyl]-4-piperidine-carboxylic acid hydrazide;

N-[2-(aminocarbonyl)ethyl]-1-[2-[4-(phenylmethyl)-phenoxy]ethyl]-4-piperidinecarboxamide;

N-methyl-3-[[3-[4-(phenylmethyl)phenoxy]propyl] amino]propanamide;

3-[[3-[4-(phenylmethyl)phenoxy]propyl]amino] propanamide;

1-(4-morpholinyl)-3-[[3-[4-(phenylmethyl)phenoxy] propyl]amino]-1-propanone;

1-[2-[4-(phenylmethyl)phenoxy]ethyl]-3-pyrrolidine-carboxamide;

1-[2-[4-(phenylmethyl)phenoxy]ethyl]-3-pyrrolidine-acetamide;

[1-[2-[4-(phenylmethyl)phenoxy]ethyl]-2S-pyrrolidin-2-yl]methyl N-phenylcarbamate;

1-[2-[4-(phenylmethyl)phenoxy]ethyl]-4-piperidine-carboxylic acid, monohydrochloride, hydrate;

1-[3-[4-(phenylmethyl)phenoxy]propyl]-2S-pyrrolidine-2-carboxylic acid;

3-[[3-[4-(phenylmethyl)phenoxy]propyl]amino] propanoic acid;

2-methyl-3-[methyl[3-[4-(phenylmethyl]propyl]amino] propanoic acid;

3-[[4-[4-(phenylmethyl)phenoxy]butyl]amino]propanoic acid;

3-[methyl[3-[4-(phenylmethyl)phenoxy]propyl]amino] propanoic acid;

1-[2-[4-(phenylmethyl)phenoxy]ethyl]-3-pyrrolidinamine, dihydrochloride;

N-[1-[2-[4-(phenylmethyl)phenoxy]ethyl]pyrrolidin-3-yl] urea;

alpha-chloro-N-[1-[2-[4-(phenylmethyl)phenoxy]ethyl] pyrrolidin-3-yl]acetamide, monohydrochloride;

1-[2-[4-(phenylmethyl)phenoxy]ethyl]-4-piperidinamine;

N-[1-[2-[4-(phenylmethyl)phenoxy]ethyl]piperidin-4-yl] urea;

hexahydro-1-[2-[4-(phenylmethyl)phenoxy]ethyl] pyrazine, dihydrochloride;

hexahydro-4-[2-[4-(phenylmethyl)phenoxy]ethyl]-1-pyrazinethioamide;

hexahydro-4-[2-[4-(phenylmethyl)phenoxy]ethyl]-1-pyrazinecarboxamide;

hexahydro-1-methylsulfonyl-4-[2-[4-(phenylmethyl) phenoxy]ethyl]pyrazine;

N-[2-alpha-methyl-1-[2-[4-(phenylmethyl)phenoxy] ethyl]piperidin-4-beta-yl]acetamide;

4-hydroxy-cis-2-methyl-1-[2-[4-(phenylmethyl)phenoxy] ethyl]piperidine, monohydrochloride;

2-[4-(phenylmethyl)phenoxy]ethanamine, monohydrochloride;

(±)ethyl 2-methyl-1-[2-[4-(phenylmethyl)phenoxy]ethyl] piperidine-4-carboxylate;

phenylmethyl 3-[[3-(4-phenoxyphenoxy)propyl]amino] propanoate;

phenylmethyl 3-[methyl[3-(4-phenoxyphenoxy)propyl] amino]propanoate;

methyl 8-[2-[4-(phenylmethyl)phenoxy]ethyl]-8-azabicyclo[3.2.1]octane-3-carboxylate;

3-[[3-(4-phenoxyphenoxy)propyl]amino]propanoic acid;

ethyl 1-[2-(4-phenoxyphenoxy)ethyl]piperidine-4-acetate, monohydrochloride;

ethyl 1-[2-[[5-(phenylmethyl)thien-2-yl]oxy]ethyl] piperidine-4-carboxylate;

3-[methyl[3-(4-phenoxyphenoxy)propyl]amino] propanoic acid;

phenylmethyl 3-[[4-(4-phenoxyphenoxy)butyl]amino] propanoate;

5-[1-[2-[4-(phenylmethyl)phenoxy]ethyl]piperidin-4-yl]-1H-tetrazole;

(cis)-2R,6-dimethyl-1-[2-[4-(phenylmethyl)phenoxy] ethyl]piperidine-4-carboxamide;

3-[[4-(4-phenoxyphenoxy)butyl]amino]propanoic acid;

ethyl 1-[2-[4-[[3-fluorophenyl)methyl]phenoxy]ethyl] piperidine-4-carboxylate;

ethyl 1-[2-[4-(2-thienylmethyl)phenoxy]ethyl]piperidine-4-carboxylate;

3-[[3-[4-[(4-fluorophenyl)methyl]phenoxy]propyl] methylamino]propanoic acid, monohydrochloride;

methyl 3-[methyl[3-[4-(2-thienylmethyl)phenoxy] propyl]amino]propanoate;

3-[methyl[3-[4-(2-thienylmethyl)phenoxy]propyl]amino] propanoic acid, monohydrochloride;

1-[2-(4-phenoxyphenoxy)ethyl]piperidine-4-carboxylic acid, monohydrochloride;

methyl 3-[3-[4-[(4-fluorophenyl)methyl]phenoxy]propyl] methylamino]propanoate;

ethyl 1-[2-[4-[(4-fluorophenyl)methyl]phenoxy]ethyl] piperidine-4-carboxylate;

ethyl 1-[2-[4-(3-thienylmethyl)phenoxy]ethyl]piperidine-4-carboxylate;

methyl 3-[methyl[3-[4-(3-thienylmethyl)phenoxy] propyl]amino]propanoate;

5-[2-methyl-1-[2-[4-(phenylmethyl)phenoxy]ethyl] piperidin-4-yl]-1H-tetrazole, monohydrate;

methyl 3-[[3-[4-(4-fluorophenoxy)phenoxy]propyl] methylamino]propanoate;

1-[2-[4-[(4-fluorophenyl)methyl]phenoxy]ethyl] piperidine-4-carboxylic acid, monohydrochloride;

1-[2-[4-(3-thienylmethyl)phenoxy]ethyl]piperidine-4-carboxylic acid, monohydrochloride;

3-[methyl[3-[4-(3-thienylmethyl)phenoxy]propyl]amino] propanoic acid, monohydrochloride;

ethyl 1-[2-[4-(4-fluorophenoxy)phenoxy]ethyl] piperidine-4-carboxylate, monohydrochloride;

1-[2-[4-(4-fluorophenoxy)phenoxy]ethyl]piperidine-4-carboxylic acid, monohydrochloride;

1-[2-[4-[(3-fluorophenyl)methyl]phenoxy]ethyl]-4-carboxylic acid, monohydrochloride;

5-phenylmethyl-2-[2-(1-pyrrolidinyl)ethoxy]pyridine;

methyl(cis)-2R,6-dimethyl-1-[2-[4-(phenylmethyl)phenoxy]ethyl]piperidine-4-carboxylate;

ethyl 3-[[4-[4-phenoxyphenoxy]butyl]amino]propanoate;

1-[2-[4-(2-thienylmethyl)phenoxy]ethyl]piperidine-4-carboxylic acid, monohydrochloride.

The compounds of the invention are prepared from readily available starting materials by any of the following alternate processes in a conventional manner. The following reaction schemes describe methods which can be employed for preparing the compounds of formula I, including starting materials, intermediates and reaction conditions. The following terms, as used herein, have the definitions which are given in the table below.

| DEFINITIONS | |
|---|---|
| NMMO | N-methylmorpholine-N-oxide |
| Me | methyl |
| SitBuMe$_2$ | t-butyldimethylsilyl |
| nBuLi | n-butyllithium |
| THF | tetrahydrofuran |
| Et$_2$O | diethyl ether |
| EtOH | ethyl alcohol |
| Pd/C | palladium on carbon |
| TFA | trifluoroacetic acid |
| Et$_3$SiH | triethylsilane |
| TBAF | tetrabutylammonium fluoride |
| DMF | dimethylformamide |
| nBu$_4$NBr | tetra-n-butylammonium bromide |
| TSCl | tosylchloride or p-toluenesulfonyl chloride |
| TsO | tosylate or p-toluenesulfonate |
| MeOH | methyl alcohol |
| AcOH | acetic acid |
| Bn | benzyl |
| DEAD | diethylazodicarboxylate |
| Ph$_3$P | triphenylphosphine |
| MCPBA | metachloroperbenzoic acid |
| LAH | lithium aluminum hydride |
| TsOH | tosic acid or p-toluenesulfonic acid |
| LDA | lithium diisopropylamide |
| DSC | disuccinylcarbonate |
| nBuOH | n-butyl alcohol |
| TFAA | trifluoroacetic anhydride |
| Me$_3$SnN$_3$ | trimethyl-tin azide |
| TMS | trimethyl silyl |
| Ac$_2$O | acetic anhydride |
| Ac | acetate |
| EtOAc | ethyl acetate |
| Hep | heptane |

Preparation of the compounds of formula I may be accomplished via one or more of the synthetic schemes which are set forth hereinafter.

Schemes 1–4 depict various methods for preparing substituted phenols of the formula Ar$^1$—Q—Ar$^2$—OH, wherein Ar$^1$ and Ar$^2$ are independently phenyl, substituted phenyl, pyridyl or thienyl moieties.

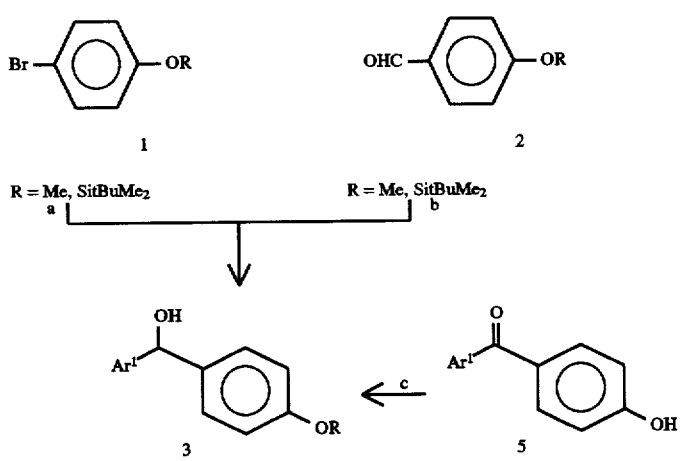

Scheme 1

-continued
Scheme 1

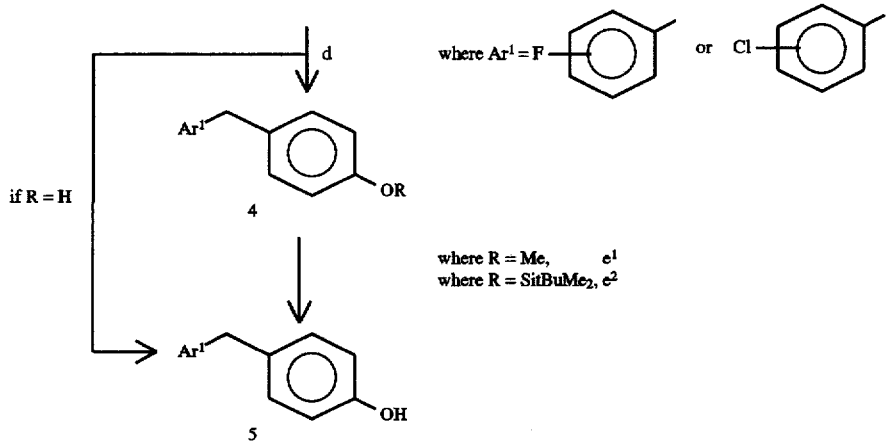

a) nBuLi, THF, −78° C.; Ar¹CHO.
b) Ar¹Li or Ar¹MgBr, Et₂O, −78° C.
c) EtOH, NaBH₄.
d) EtOH, 4% Pd/C, H₂ or CH₂Cl₂, TFA, Et₃SiH.
e¹) BBr₃, CH₂Cl₂, −78° C.
e²) THF, TBAF.

Scheme 1 shows methods for producing compounds of the formula Ar¹—CH₂—Ar²—OH wherein Ar² is a phenyl moiety. Scheme 1 shows two related precursor compounds (1, 2) which may be employed as a starting material. Compound 1 is an alkylated or silylated derivative of p-bromophenol. A convenient starting material 1 is 1-bromo, 4-methoxyphenol (i.e., R is methyl). On the other hand, compound 1 may be readily provided by silylation of p-bromophenol with t-butyldiphenylsilyl chloride or other silylating agents (see, Example 2). In either event, compound 1 may be reacted with tert-butyl lithium in an ethereal solvent at low temperature, such as in THF at −78° C., and quenched with an arylaldehyde (Ar¹CHO) to yield compound 3. Similarly, starting from compound 2, a p-methoxybenzaldehyde or a silylated derivative of p-hydroxybenzaldehyde (see, Example 1) may be employed. Compound 2 may be reacted with an aryl lithium (Ar¹Li) or aryl magnesium bromide (Ar¹MgBr) to yield compound 3. Regardless of which route is chosen, compound 3 is reduced, e.g., by hydrogenation over palladium on carbon or with triethylsilane, to provide compound 4. Compound 4 is readily deprotected using TBAF in THF (desilylation) or using BBr₃ in methylene chloride at −78° C. (dealkylation) to provide compound 5.

Compounds 5 of the formula Ar¹—CH₂—Ar²—OH, wherein Ar¹ is a para-halogen-substituted phenyl moiety, such compounds are preferably provided by sodium borohydride reduction of a compound 6 to provide compound 3, followed by hydrogenation as described above to afford compound 5.

Scheme 2

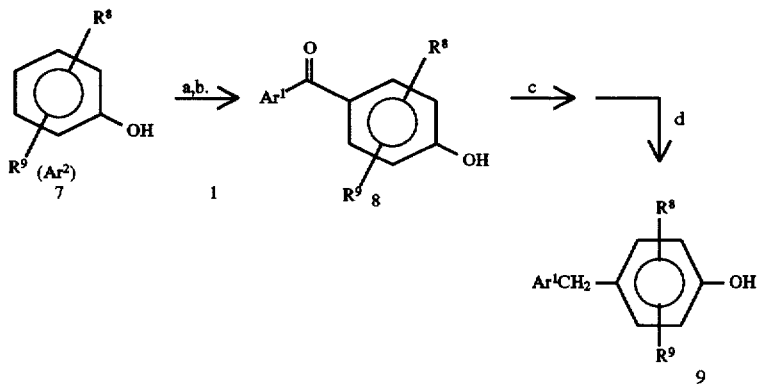

a) Ar¹COCl, CH₂Cl₂, Pyridine.
b) AlCl₃, 160° C., 5 min.
c) NaBH₄/EtOH.
d) TFA, CH₂Cl₂, Et₃SiH.

Scheme 2 depicts the preparation of compounds of formula Ar¹—CH₂—Ar²—OH wherein —Ar²—OH is a substituted phenol R⁸(R⁹)PhOH and R⁸ and R⁹ are as defined hereinbefore. In this reaction sequence, the substituted phenol 7 is reacted with a suitable aryloyl chloride to give the intermediate aryloyl ester (not shown) which is heated to a temperature of about 160° C. in the presence of AlCl₃ to promote Fries rearrangement which affords the desired compound 8, having the specifically substituted Ar² moiety. Compound 8 may be reduced utilizing the two-step reduction sequence (Scheme 1, steps (c) and (d)) to provide compound 9.

Scheme 3

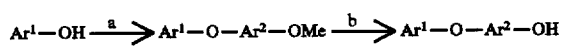

a) KOH, I—Ar²—OMe, Cu°, 160° C.
b) CH₂Cl₂,BBr₃,–78° C.

Scheme 3 shows a general method for the preparation of phenols of the formula Ar¹—O—Ar²—OH wherein Ar¹ is a substituted phenol. Ar¹ may be any substituted arylphenol which is capable of reacting with 4-iodoanisole in an Ullman coupling reaction. See, A. Moroz, et al., *Russ. Chem. Rev.* 43, 679 (1974). The Ullman reaction is carried out conventionally in the presence of activated copper or copper iodide at a temperature of about 150° C. to 200° C. A particularly preferred substituted phenol for providing compounds of the present invention having a substituted Ar¹ moiety is 4-fluorophenol.

Scheme 4

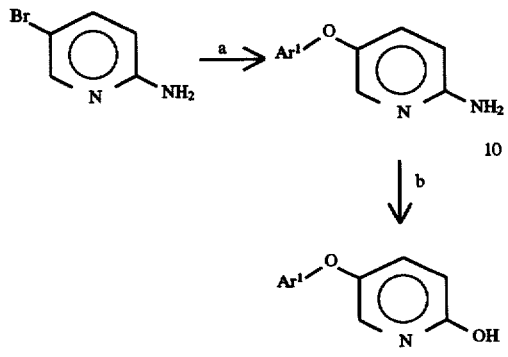

a) Ar¹OH, CuI, K₂CO₃.
b) 4N—H₂SO₄, NaNO₂.

Scheme 4 shows a synthesis for making compounds of the formula Ar¹—O-pyridyl-OH (i.e., Ar² is pyridyl). In the reaction, 2-amino-5-bromopyridine is combined with an excess of a suitable phenol (Ar¹OH) and coupled utilizing the Ullman reaction, essentially as described with reference to Scheme 3, to provide the aminopyridine derivative 10. Compound 10 is diazotized with sodium nitrite/H₂SO₄/H₂O and decomposed to afford compound 11.

Scheme 5

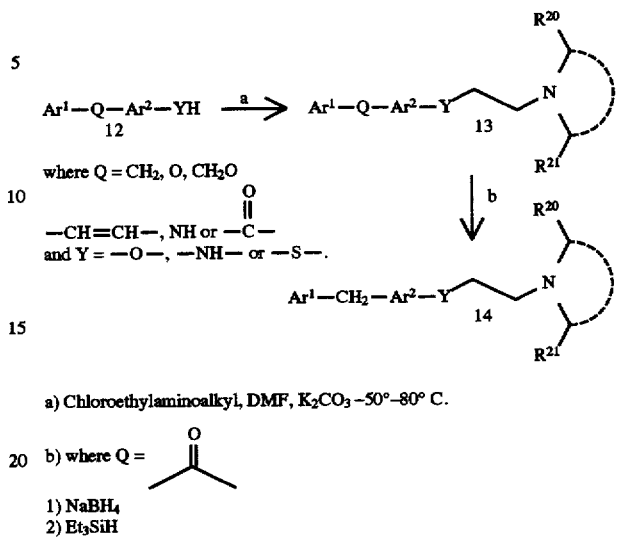

a) Chloroethylaminoalkyl, DMF, K₂CO₃ –50°–80° C.

b) where Q = $\overset{O}{\underset{\|}{C}}$

1) NaBH₄
2) Et₃SiH

Scheme 5 shows the preparation of compounds of the general formula Ar¹—Q—Ar²—Y—R—Z (Formula I) from compounds of the formula Ar¹—Q—Ar²—YH (12) (wherein R ethylene, Y is —O—, —NH— or —S—, R²⁰ and R²¹ are independently hydrogen or lower alkyl, and wherein Ar¹, Q, Ar², and Z are previously defined). Compounds of the formula Ar¹—Q—Ar²—YH may be made in accordance with Schemes 1–4 or may be obtained commercially, including 4-hydroxydiphenylmethane, 4-hydroxybenzophenone, 4-benzyloxyphenol, etc.

A compound of the formula Ar¹—Q—Ar²—YH (12) may be converted into a compound of the present invention via alkylation with any of a variety of chloroethylaminoalkyl analogs, wherein the aminoalkyl moiety may be cyclic or acyclic. Where Q is carbonyl, the carbonyl moiety of compound 13 is reduced to —CH₂— as depicted in steps (c) and (d) of Scheme 1 to afford compound 14.

Scheme 6

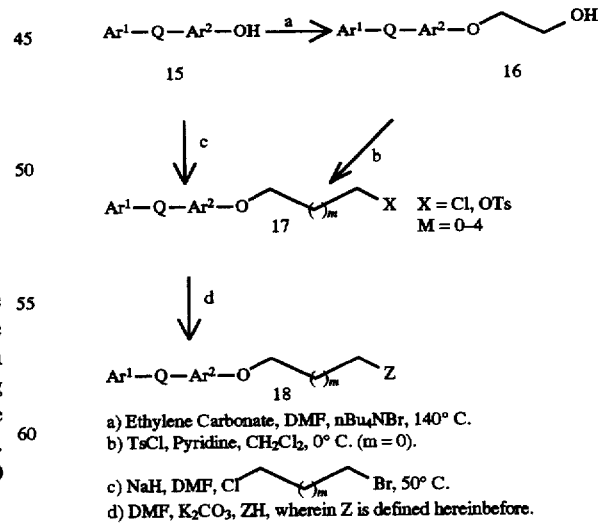

a) Ethylene Carbonate, DMF, nBu₄NBr, 140° C.
b) TsCl, Pyridine, CH₂Cl₂, 0° C. (m = 0).

c) NaH, DMF, Cl~~~~Br, 50° C.
d) DMF, K₂CO₃, ZH, wherein Z is defined hereinbefore.

Scheme 6 shows a presently preferred method for preparing compounds of the formula $Ar^1$—Q—$Ar^2$—O—R—Z, wherein R is a linear alkylene moiety. Scheme 6 depicts alternate reaction pathways for adding an alkylene linker moiety, R (as defined in formula I) to the phenolic hydroxyl group of compound 15, which alkylene linker terminates in a reactive halogen or tosylate group. In the pathway which provides compound 17 wherein R is ethylene (i.e., R provides a 2 carbon linker) compound 15 is reacted with ethylene carbonate in DMF in the presence of $nBu_4NBr$ to give compound 16 which is subsequently reacted with tosylchloride in dichloromethane and pyridine to provide compound 17 wherein X is —OTs.

Where R is a $C_3$–$C_6$ alkylene moiety, compound 15 is reacted with $CH_2Cl$—$(CH_2)_m$—$CH_2Br$ (wherein m is 1–4) in the presence of DMF and NaH to provide compound 17 wherein X is Cl.

Compound 17 is reacted with a nitrogen containing compound of the formula ZH in DMF at 60° in the presence of $K_2CO_3$, to give compound 18, wherein Z is an acyclic amine moiety, a monocyclic or bicyclic amine moiety or a monocyclic or bicyclic heteroaromatic moiety as defined hereinbefore with reference to compounds of Formula I.

pentanediol and 1,6 hexanediol. The reaction is carried in the presence of copper (II) oxide in the diol as solvent at 120° C. to afford compound 19. Compound 19 is lithiated on the thiophene ring with nBuLi (2 equivalents) in THF at –78° C. to produce the corresponding 5-lithio anion of compound 19 which is then quenched with a suitable arylmethylbromide ($Ar^1CH_2Br$), for example, benzylbromide, to afford compound 20, which may be converted into compound of Formula I via tosylation followed by displacement as described in Scheme 6 (20→21→22).

Scheme 8

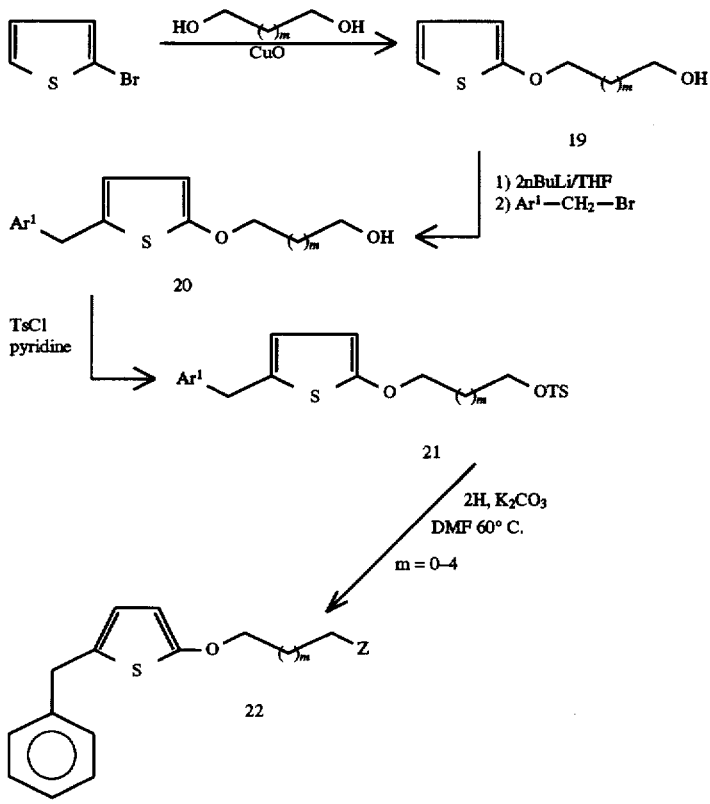

Scheme 7

Scheme 7 describes a method for making compounds of the Formula I wherein $Ar^2$ is thiophene. The synthesis entails reaction of 2-bromothiophene or 2-iodothiophene with a terminally substituted diol of the formula $CH_2OH$—$(CH_2)_m$—$CH_2OH$ wherein m=0–4. Such diols include ethylene glycol, 1,3 propanediol, 1,4 butanediol and 1,5

-continued
Scheme 8

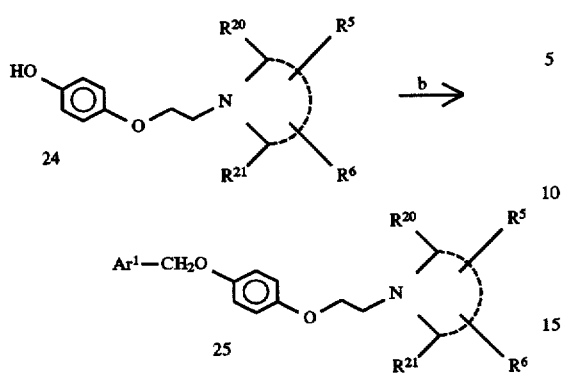

a) H₂/4% Pd/C, EtOH.
b) NaH, DMF, Ar¹—CH₂Br.

Scheme 8 describes the synthesis of compounds of Formula I wherein —Q—Ar²— is "—CH₂O-phenyl-" and Ar¹ may be any of a variety of aryl moieities (see, for example, Table 13). The synthesis starts with a compound of Formula I wherein Ar¹—Q— is Ph—CH₂—O— (23), and debenzylates the compound, employing H₂, 4% Pd/C, EtOH, to afford intermediate phenol 24 which is alkylated in the presence of NaH in DMF with any of a variety of arylmethybromides to afford compound 25. Suitable arylmethylbromides include, but are not limited to the arylmethylbromides enumerated with reference to Scheme 7.

Scheme 9

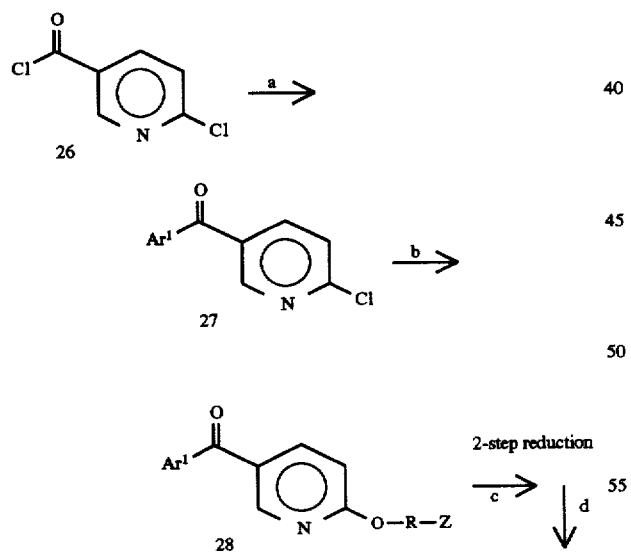

-continued
Scheme 9

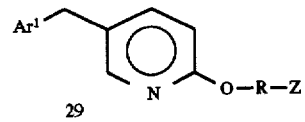

a) Ar¹, AlCl₃, Benzene. 70° C.
b) HO—R—Z, Benzene, NaH.
c) EtOH, NaBH₄.
d) 4% Pd/C, MeOH/40%AcOH.

Scheme 9 generally depicts methods for preparing compounds of Formula I wherein Ar² is a 2,5-disubstituted pyridinyl moiety. Such compounds of the present invention may be prepared starting from the acid chloride of 2-chloro-5-pyridine-carboxylic acid. The acid chloride 26 is combined with a suitable aryl compound (Ar¹) and reacted under Friedel-Crafts acylation conditions to provide the chloropyridinyl containing ketone 27, which is reacted with a suitable hydroxyalkylamine of the formula HO—R—Z, wherein R and Z are as defined hereinbefore, to yield compound 28 which is subject to a 2-step reduction (shown in steps (c) and (d) of Scheme 1) to provide compound 29 which is a compound of Formula I.

Scheme 10

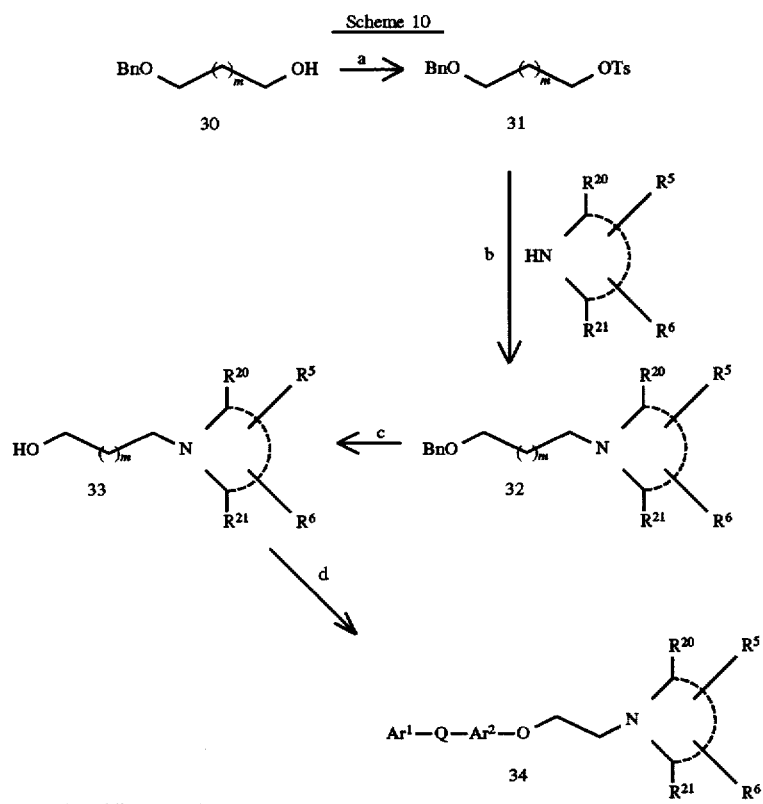

a) TsCl, Pyridine, CH$_2$Cl$_2$
b) DMF, K$_2$SO$_3$
c) H$_2$/Pd, EtOH
d) Ar$^1$—Q—Ar$^2$—OH, DEAD, Ph$_3$P, THF.

Scheme 10 describes preparation of a variety of compounds of the formula HO—R—Z 33 wherein R is alkylene and Z is defined hereinbefore. These compounds may be employed in the methods described in Scheme 9, step b. In Scheme 10, a benzyloxyalcohol 30 is converted into the corresponding tosylate 31 by reaction with tosylchloride in the presence of pyridine and methylene chloride at 0° C. which is reacted with a secondary amine of the formula

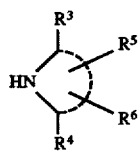

in DMF at 60° C., in the presence of K$_2$CO$_3$ to provide compound 32. Compound 32 is hydrogenated [H$_2$/Pd, ethanol] to afford compounds of the formula HO—R—Z (33), wherein R is alkylene, and coupled to compounds of the formula Ar$^1$—Q—Ar$^2$—OH (see schemes 1–4) in the presence of diethylazodicarboxylate (DEAD) and triphenylphosphine in THF (O. Mitsunoba, *Synthesis*, 1, (1981)) to provide compound 34 which is a compound of Formula I.

In another of its embodiments the present invention entails the compound of the formula

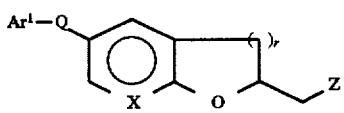

wherein r is 1 or 2, and Ar$^1$, Q, X and Z are as defined hereinbefore. In this embodiment of the invention the compounds are rotationally constrained by fusion of a portion of the linker group R to the Ar$^2$ moiety through a 5- or 6-membered fused ring (i.e., dihydrobenzofuran or tetrahydrobenzopyran).

Scheme 11

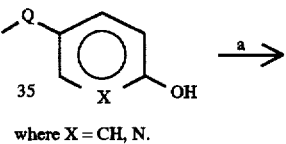

where X = CH, N.

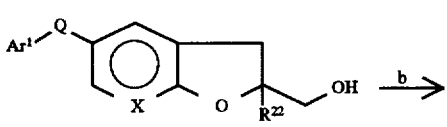

5,719,306

31

-continued
Scheme 11

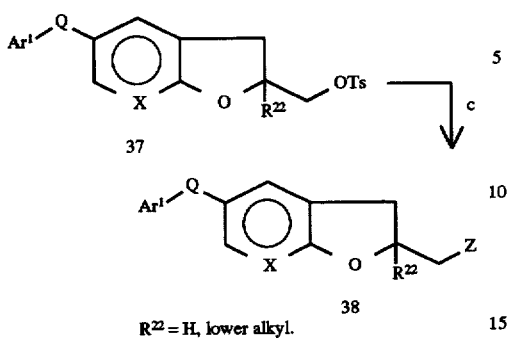

R²² = H, lower alkyl.

a. (1) ![](R²² /=\ Br), NaH, DMF.
(2) Δ 230° C.
(3) CHCl₃ mCPBA.
b. TsCl pyridine, CH₂Cl₂, 0° C.
c. ZH, DMF, K₂CO₃.

With reference to Scheme 11, compound 35 is alkylated in DMF in the presence of sodium hydride with allylbromide or a 2-methyl substituted allylbromide to afford the corresponding O-allyl ether (not shown), which is heated to 230° C. in a Claisen rearrangement reaction, followed by oxidative cyclization with metachloroperbenzoic acid (mCPBA) in chloroform to yield the alcohol 36. Alcohol 36 is reacted with tosyl chloride in pyridine/methylene chloride mixture at 0° C. to afford the corresponding tosylate 37, which is then condensed (in DMF in the presence of potassium carbonate) with a primary or secondary amine, ZH, or an aromatic nitrogen containing heterocycle, ZH, wherein Z is define hereinbefore to afford compound 38 which is a compound of formula I.

Scheme 12

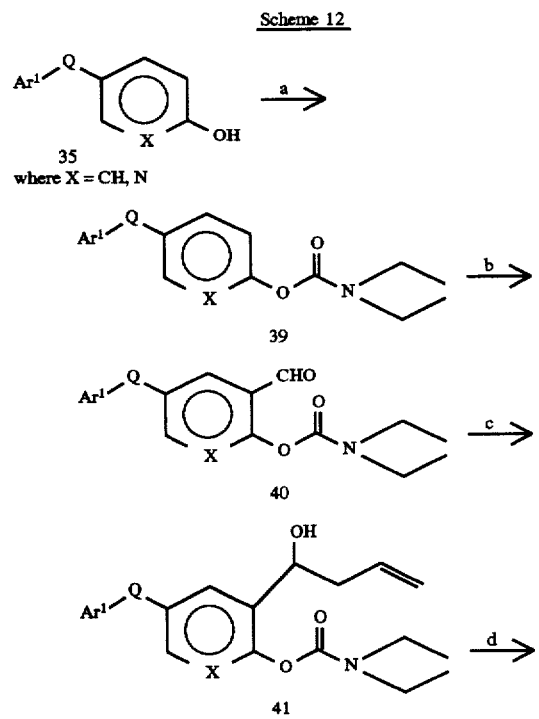

where X = CH, N

32

-continued
Scheme 12

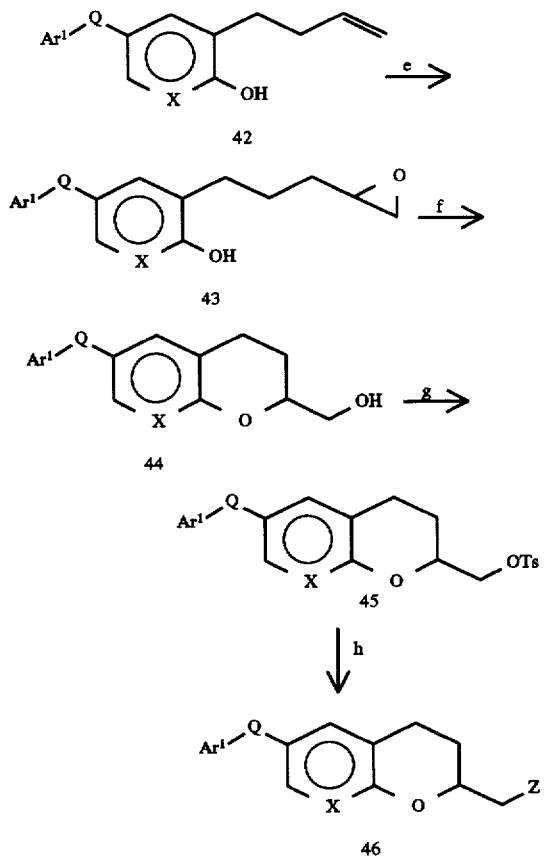

a. Cl–C(=O)–N(piperidine), KH, THF.
b. (1) Sec BuLi, Et₂O, TMEDA;
(2) DMF.
c. , Et₂O
d. (1) SO₃/pyridine, THF;
(2) LAH.
e. mCPBA, CH₂Cl₂, 0° C.
f. TsOH, CHCl₃.
g. TsCl, pyridine, CH₂Cl₂, 0° C.
h. ZH, K₂CO₃, DMF.

Scheme 12 shows a method for preparing compounds of the present invention from phenols of the formula 35. Phenol 35 can be transformed into tetrahydrobenzopyran analogs via the following six-step (steps (a)–(f)) procedure. In step (a), the phenol 35 is converted into its corresponding diethylcarbamate 39 employing diethylcarbamoylchloride, KH, and DMF. In step (b), the diethylcarbamate compound 39 is then ortho-lithiated (sec.butyllithium, Et₂O, TMEDA) and quenched with DMF to afford aldehyde 40. The aldehyde 40 is reacted with allylmagnesium bromide in step (c) and the resulting alcohol 41 is reduced and deprotected in step (d) utilizing sulphur-trioxide/pyridine in THF, followed by addition of lithium aluminum hydride to afford phenol 42, which is substituted with but-3-ene in the position ortho to the phenolic hydroxyl. Phenol 42 is oxidatively cyclized in two steps, via epoxide 43 utilizing mCPBA in CHCl₂, followed by acid-catalyzed epoxide ring opening with tosic acid in CHCl₃ in step (f) to afford the tetrahydrobenzopyran containing alcohol 44. Alcohol 44 may be further converted into compounds of the formula I, via formation of the corresponding tosylate 45, followed by displacement with compounds of the formula ZH, as described in Scheme 6.

Scheme 13

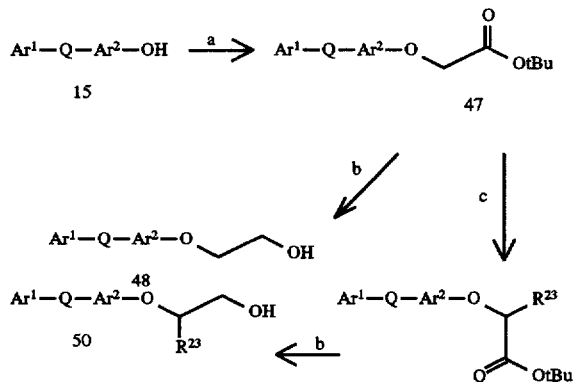

a) THF, NaH, tButylbromoacetate.
b) THF, LAH.
c) THF, LDA, −78° C.; R²³X, wherein
R²³ is lower alkyl or benzyl and
X is Br or I.

Scheme 13 represents an alternative procedure to that shown in Scheme 6 for attaching an hydoxyethylene moiety to phenols of the formula Ar¹—Q—Ar²—OH (15). In the methods depicted in Scheme 13, phenol 15 is alkylated with t-butylbromoacetate in THF in the presence of sodium hydride to yield t-butyl ester 47, which is then reduced with LAH in THF to afford the hydroxyethylene substituted analogs, Ar¹—Q—Ar²—O—CH₂CH₂—OH 48.

In an analogous reaction sequence, t-butyl ester 47 may be alpha-alkylated via reaction with LDA in THF at −78° C., followed by quenching with an alkylhalide (R²²X) at −78° C. The resulting alpha-substituted ester 49 is reduced (LAH in THF) to afford compound 50 having a branched alkylene moiety.

The synthetic route described in Scheme 13 provides compounds which may be employed in steps (c) and (d) of Scheme 6 to provide compounds of Formula I having a linear or branched alkylene moiety.

Scheme 14

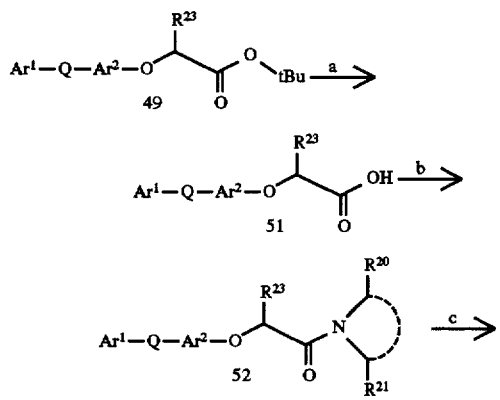

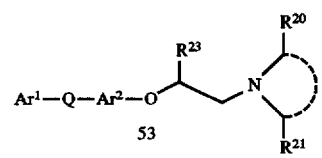

R = H, CH₃, CH₂CH₃ or benzyl
a) TFA, CH₂Cl₂, MeOH.

b) Disuccinylcarbonate, DMF, Pyridine, HN
c) THF, LAH.

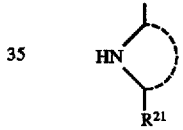

wherein HN   does not contain functionality reactive towards LAH reduction.

Scheme 14 describes yet another synthetic pathway utilizing t-butyl ester 49 as a starting material for the preparation of compounds of Formula I. Here, the t-butyl ester is deprotected with trifluoroacetic acid in methylene chloride to afford the corresponding acid 51 which is then coupled to an amine compound of the formula using DSC in pyridine and DMF to yield amide 52. As depicted, R²⁰ and R²¹ are independently hydrogen or alkyl and optionally the defined amine may be a cyclic amine. Amide 52 may be reduced with lithium aluminum hydride in THF to give compound 53, provided that neither R²⁰ nor R²¹ is (nor comprises) a functional moiety, such as an amide, ester, nitrile or the like, which is reactive toward LAH. Compound 53 is a compound of formula I.

Scheme 15

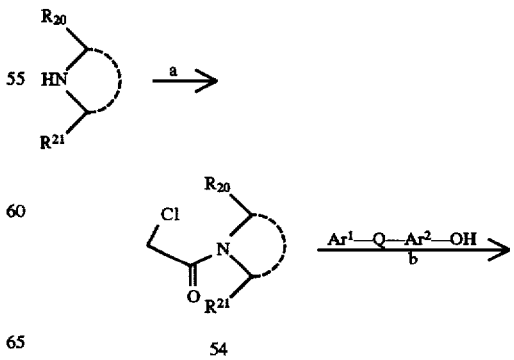

-continued
Scheme 15

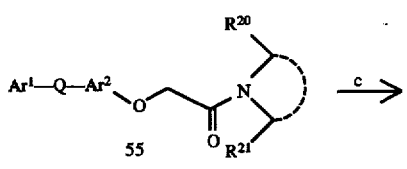
55 c →

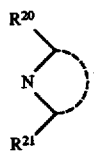
56 a) Chloroacetylchloride, CH$_2$Cl$_2$/Pyridine, 0°C.
b) DMF, NaH.
c) LAH, THF.

wherein does not contain functionality reactive towards LAH reduction.

Scheme 15 depicts a preferred method for preparing compounds of Formula I which comprise sterically hindered amines such as 2,6-dimethylpiperidine, 2,5-dimethylpyrrolidine and the like. In this method, the sterically hindered amine is acylated with chloroacetylchloride in methylene chloride/pyridine at 0° C. to afford α-chloroamide 54. Alkylation of a phenol of the formula Ar$^1$—Q—Ar$^2$—OH with the α-chloroamide 54 [DMF,NaH] affords amide 55. Provided that the amide group of compound 55 is the only moiety which is reactive toward LAH, reduction of compound 55 with LAH in THF provides a compound 56 which is a compound of Formula I.

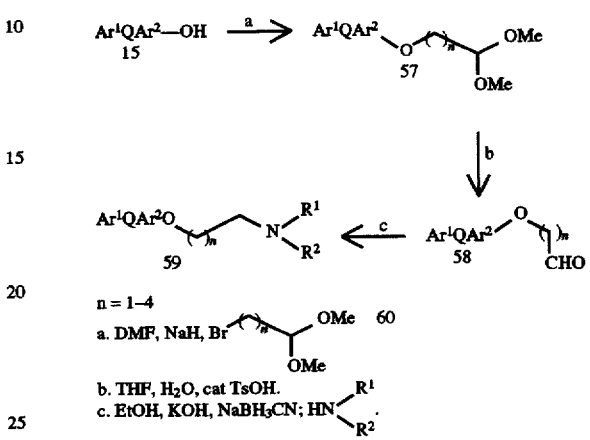

Scheme 16 describes yet another method for preparation of compounds of Formula I in which compound 15 is alkylated with a bromodimethyl acetal (60) in DMF in the presence of NaH to afford acetal 57. Subsequent deprotection with toluene-4-sulfonic acid in THF/H$_2$O affords intermediate aldehyde 58 which is reductively aminated [EtOH, KOH, NaBH$_3$CN] with an amine of the formula HNR$^1$R$^2$ to afford compound 59 which is a compound of Formula I.

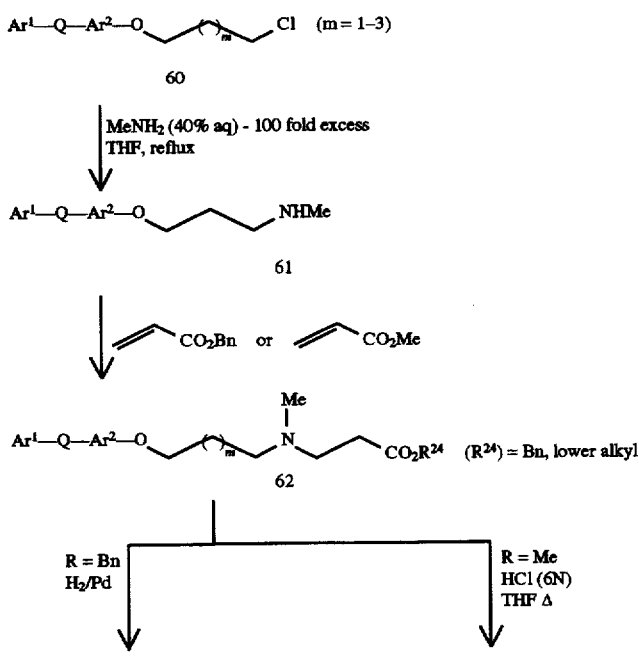

Scheme 17

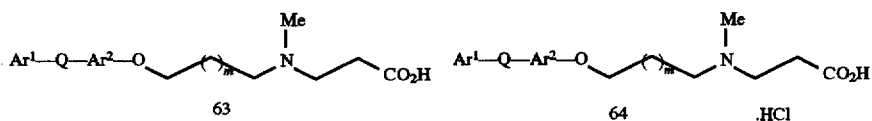

Scheme 17 shows a preferred method for preparing compounds 63 and 64 employing an intermediate chloride 60 as an alternative to using the corresponding tosylate. Compound 60 is aminated with a 100-fold excess of methylamine in acetonitrile at 60° C.–70° C. to afford secondary amine 61. While compound 61 is a compound of Formula I, compound 61 may be further elaborated by reaction with a benzylacrylate ester or a methylacrylate ester to provide compound 62 which is also a compound of Formula I. Where the ester 62 is a benzyl ester, it may be converted into its corresponding acid 63 by hydrogenation ($H_2$/Pd/EtOH at 2 psi); and where ester 62 is alkyl ester, it may be converted into its corresponding acid as the hydrochloride salt 64 via hydrolysis with 6N HCl in THF at 60° C.

Among the preferred compounds of the present invention are those in which the nitrogen-containing moiety (i.e., Z, as defined herein) comprises at least one polar moiety, such as a carboxylic acid or ester moiety or a carboxamide, acylhydrazide, alkylamide or alanineamide moiety or the like.

Scheme 18

Ar$^1$—Q—Ar$^2$—O—R—N(H)—CH$_2$CH$_2$—CO$_2$R$^{24}$  →  $R^{25}$CHO·NaCNBH$_3$

65

Ar$^1$—Q—Ar$^2$—O—R—N(CH$_2$R$^{25}$)—CH$_2$CH$_2$—CO$_2$R$^{24}$  →  MeMgBr / Et$_2$O, 0°C.

66

Ar$^1$—Q—Ar$^2$—O—R—N(H)—...—OH $R^{25}$ = alkyl, branched alkyl, aryl.

Scheme 18 illustrates further modification of a compound 65 which is also referred to herein as a β-alanine-based compound of Formula I. Compound 65, which is representative, is reductively aminated with a $C_1$–$C_4$ aldehyde or ketone included but not limited to formaldehyde, acetaldehyde, 1-propanal, acetone, methyl-ethyl ketone and the like to provide compound 66 which is a compound of Formula I. Compound 66 may optionally be converted tertiary alcohol 67 (also a compound of Formula I) by reaction with methylmagnesium bromide in ether at 0° C.

Scheme 19

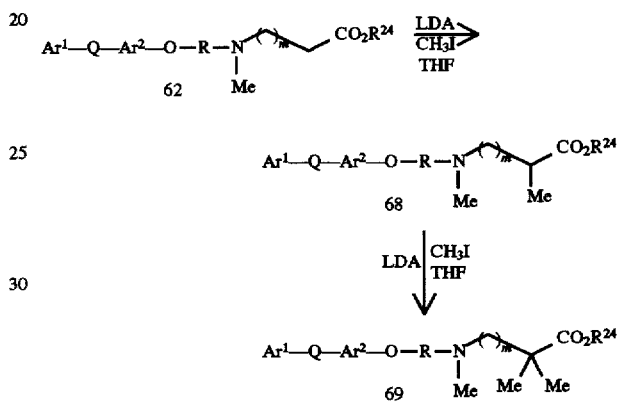

MeI = CH$_3$I

Scheme 19 illustrates a method for introducing one or two methyl substitution(s) into the backbone of the β-alanine moiety of compound 62. Compound 62 may be sequentially alpha-methylated by reaction with LDA in THF at –78° C. followed by quenching with methyliodide to afford compound 68 or compound 69.

Schemes 20 and 21 show modification of a compound 70 comprising an ester-containing Z group to produce compound 71 or compound 72 possessing a variety of polar substitutions.

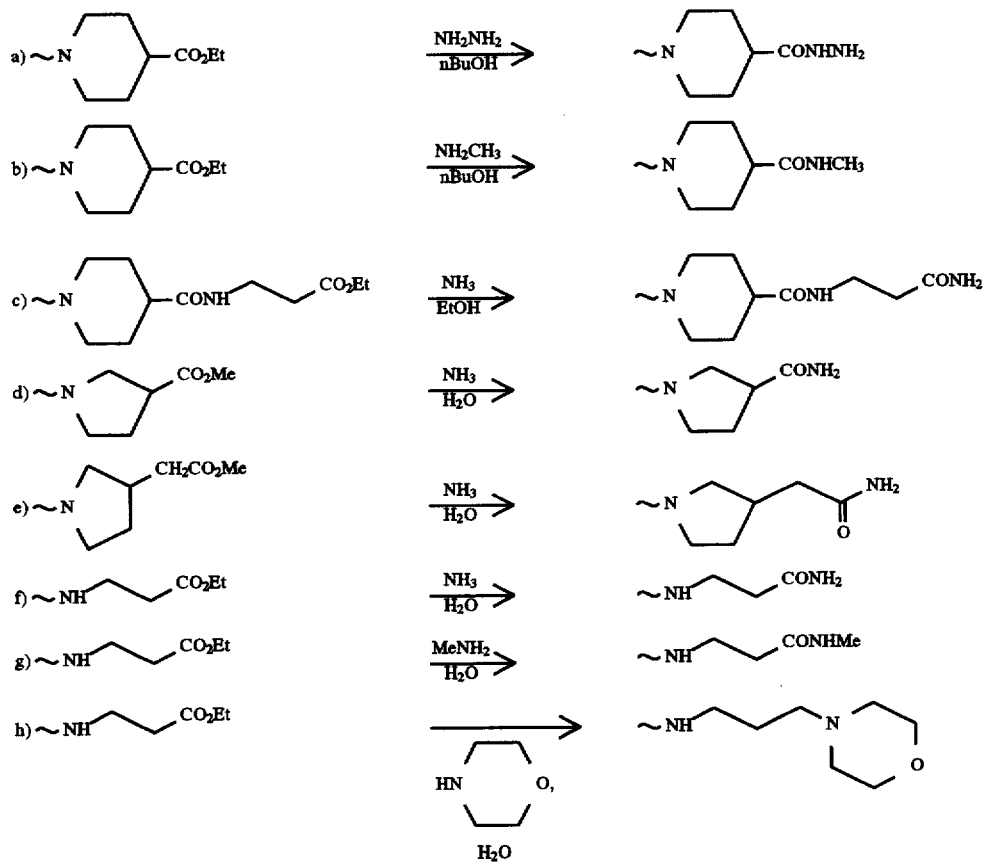
Scheme 20 depicts the modification of a compound 70 which comprises an ester moiety in which the ester is modified by the addition of a nucleophile such as an amine or hydrazine to provide compound 71 as shown in the "Exemplified Reactions" set forth in equations (a)–(h) of Scheme 20.

Scheme 21

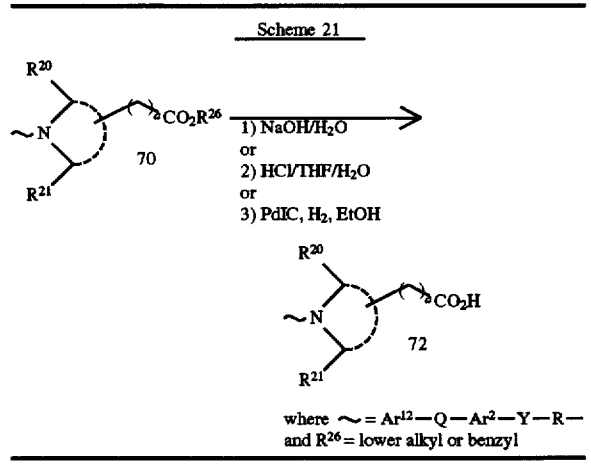

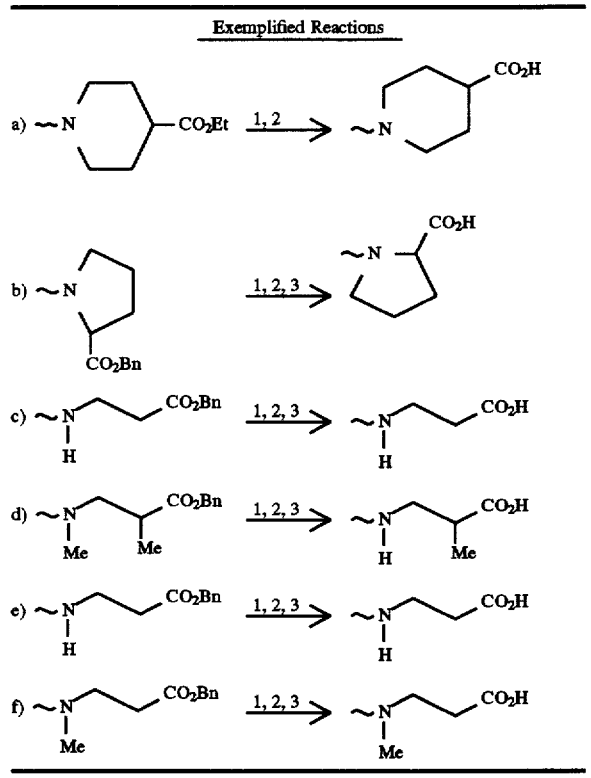

Scheme 21 shows the conversion of compound 70 which comprises an ester moiety to corresponding acid 72 via one of three reactions: (1) basic hydrolysis; (2) acidic hydrolysis, which is preferred where R is a lower alkyl or benzyl; or (3) hydrogenolysis over palladium on carbon in EtOH, which is especially preferred where R is benzyl.

Schemes 22 and 23 show alternative methods for preparing a nitrile containing compound 74 which is a compound of Formula I and which conveniently may be employed as an intermediate in the preparation of various compounds of the present invention described in Scheme 24 below.

Scheme 22

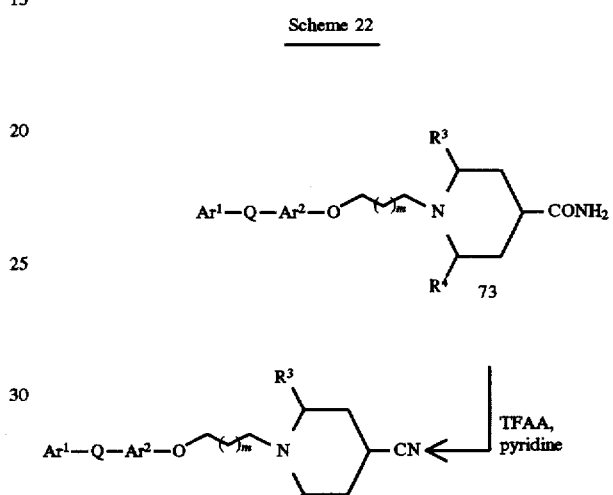

In Scheme 22 dehydration of a carboxamide containing compound 73 with trifluoroacetic anhydride in pyridine/THF at 0° C. affords the corresponding nitrile containing compound 74.

Scheme 23

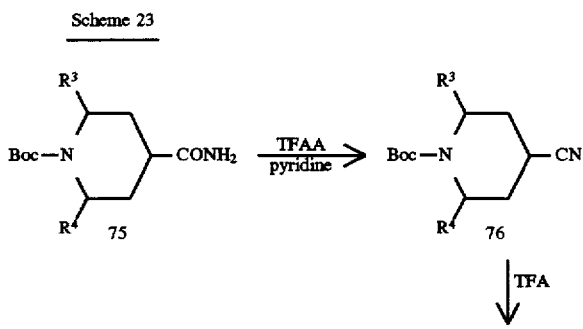

-continued
Scheme 23

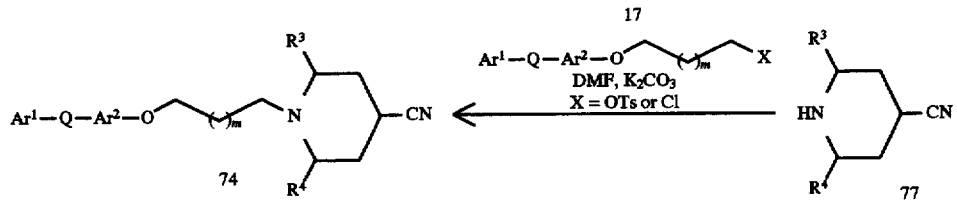

Scheme 23 shows a synthetic route to compound 74 which is analogous to Scheme 22. In Scheme 23, the t-butoxycarbonyl-protected (i.e., BOC-protected) piperidine amide 75 is dehydrated using the conditions described in Scheme 22 (TFAA/pyridine) to afford protected nitrile 76. Deprotection of nitrile 76 with trifluoroacetic acid in methylene chloride at 0° C. affords the corresponding secondary amine 77 which may be coupled to compound 17 essentially as described in Scheme 6 (step d) to afford nitrile-containing compounds of the present invention, which may be utilized as described in Scheme 24.

hydroxylamine in an alcoholic solvent such as ethanol, propanol, butanol, or the like to afford the corresponding hydroxyamidine 79 which is a compound of the present invention as well as an intermediate for step (b) of this Scheme. Thus, in step (b), hydroxyamidine 79 may be hydrogenated in ethanol over palladium on carbon to afford the corresponding amidine 80 which is a compound of the present invention. Alternatively, hydroxyamidine 79 may be cyclized with phosgene in toluene at 60° C. to yield 81 which is a compound of the present invention. Scheme 21

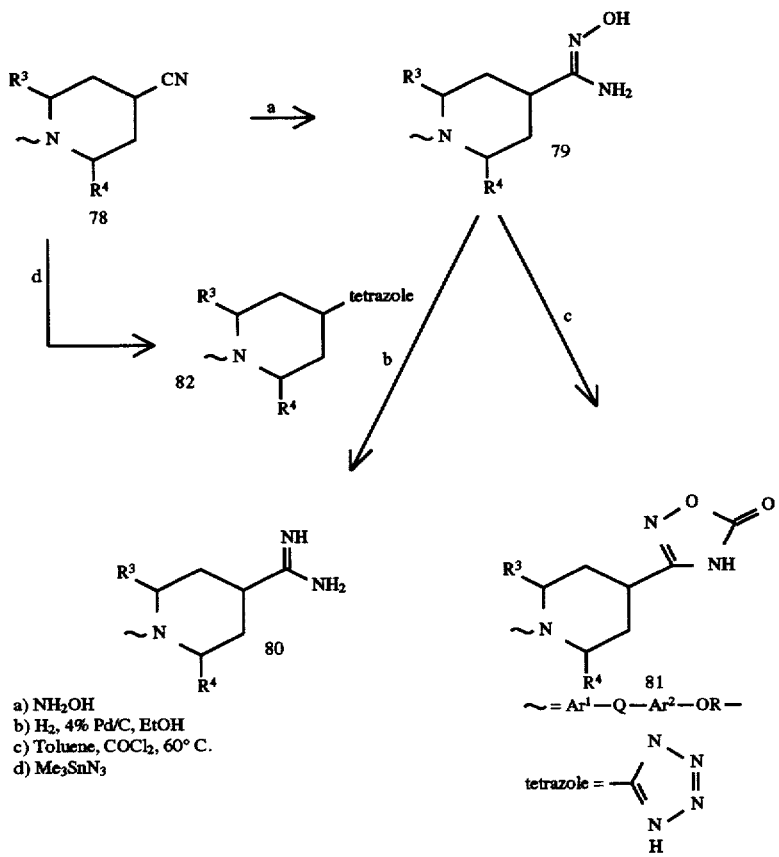

Scheme 24 shows several reaction pathways which may be used to modify the nitrile moiety of compound 78 to afford a variety of compounds of the present inventions. In step (a) the nitrile moiety of compound 78 is condensed with furthers shows, in step d, reacting nitrile 78 with trimethyltin azide in xylene at 130° C. to afford the corresponding tetrazole containing compound 82 which is a compound of the present invention.

Scheme 25

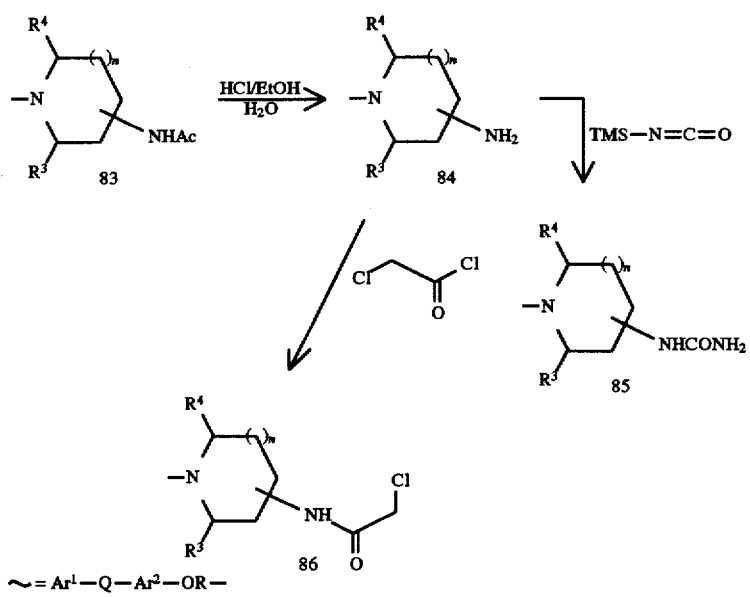

Scheme 25 illustrates modification of compounds having a cyclic amine moiety derivatized with an acetamide group (compound 83) to convert the acetamide moiety to a primary amine (HCl/EtOH/H$_2$O 80°–100° C.) to provide compound 84 which, in turn, may be modified to a urea moiety (TMS-NCO) to provide compound 85 or to an alpha-chloroamide moiety to provide compound 86. Compounds 84, 85 and 86 are compounds of the present invention.

Compounds of the present invention containing a piperazine moiety, compound 87, may be derivatized in essentially the same manner as described in Scheme 24 to yield derivatized piperazine compounds which include methylsulfonamide-containing compound 88, thiourea-containing compound 89 or urea-containing compound 90, as illustrated in Scheme 26.

Scheme 26

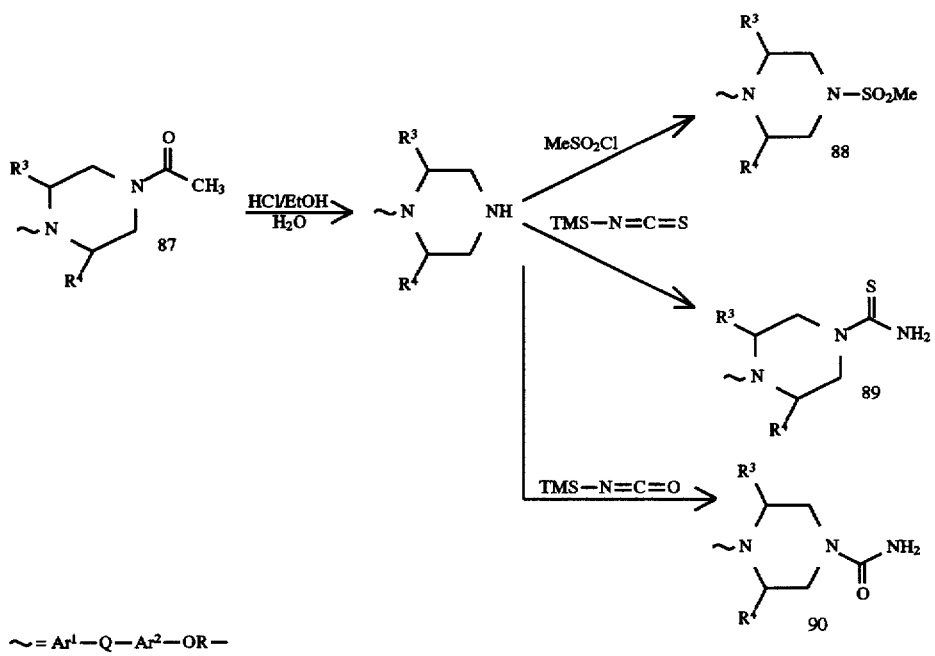

Scheme 27

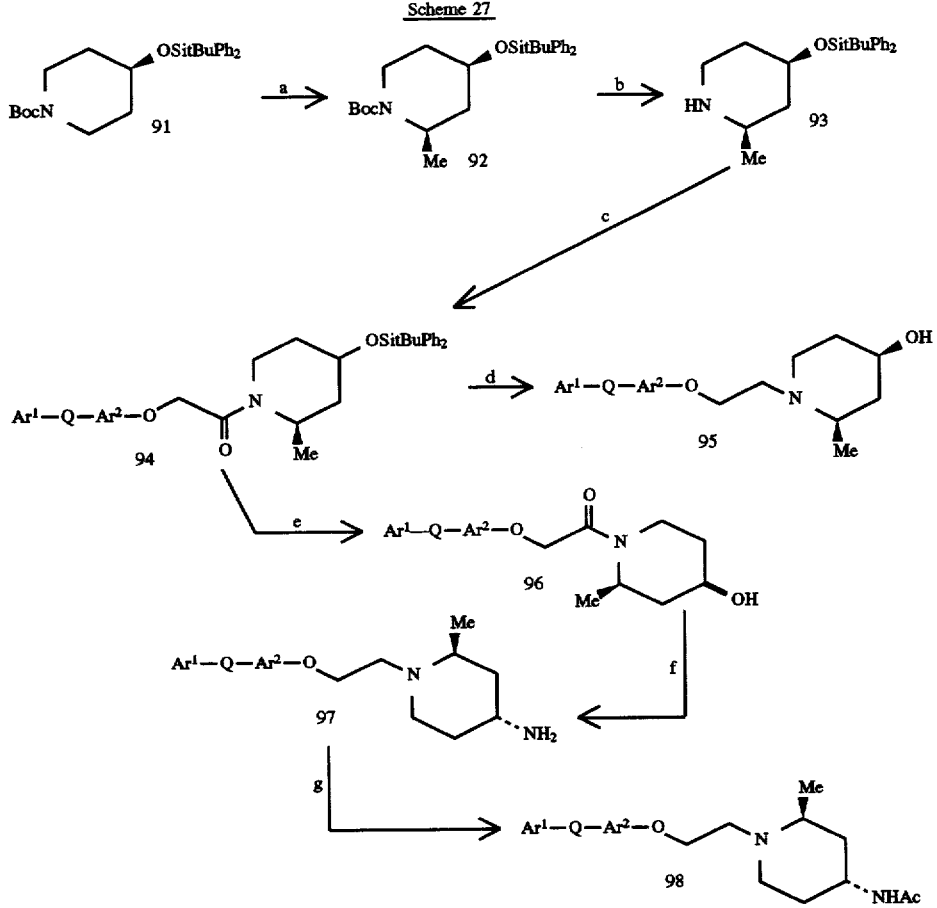

a) Sec. BuLi, TMEDA, MeI
b) TFA, CH$_2$Cl$_2$, 0° C.
c) DSC, pyridine, Ar$^1$—Q—Ar$^2$—O$\diagdown$$\diagup$$\overset{\displaystyle\|}{\underset{\displaystyle O}{C}}$—OH d) LAH, THF
e) TBAF
f) 1) TsCl/CH$_2$Cl$_2$/Pyridine 0° C.
   2) NaN$_3$, DMF, 60–80
   3) Pd/C, H$_2$, MeOH
   4) LAH
g) Ac$_2$O, pyridine, CH$_2$Cl$_2$ Scheme 27 shows methods for preparing compounds of the invention having a 4-substituted 2-methyl piperadine moiety. In Scheme 27, di-protected 4-piperadol 91 is methylated in the 2-position using the method of P. Beak, et al., *J. Org. Chem.* 58, 1109 (1993). The 2-methyl derivative 92 is deprotected using trifluoracetic acid in methylene chloride at 0° C. to yield the secondary amine 93 which, in turn, is coupled to a compound of the formula Ar$^1$—Q—Ar$^2$—CH$_2$CO$_2$H (compound 51, wherein R is hydrogen) using the method described in Scheme 14, step (b). The resulting amide 94 may be reduced and desilylated in one step with LAH in THF at room temperature to afford the trans di-substituted piperadine 95 which is a compound of the present invention.

Alternatively, amide 94 may be desilylated (TBAF) to afford alcohol 96 which is subjected to a four-step reaction sequence (steps (f)(1)–(f)(4)) to afford cis 2-methyl, 4-amino piperadine 97.

The four-step reaction scheme consists of reacting the alcohol 96 with TsCl in methylene chloride/pyridine at 0° C. to give the corresponding tosylate which is displaced with sodium azide in DMF (60°–80° C.) to afford the corresponding azide having inverted stereochemistry (i.e., trans→cis). The azide is hydrogenated at atmospheric pressure in methanol over 4% palladium on carbon to afford the corresponding amine of the formula

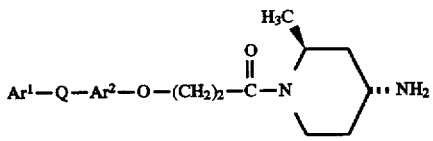

the amide function of which is reduced with LAH in THF at room temperature to afford compound 97. Optional acylation of the 4-amino moiety of compound 97 affords compound 98.

Scheme 28

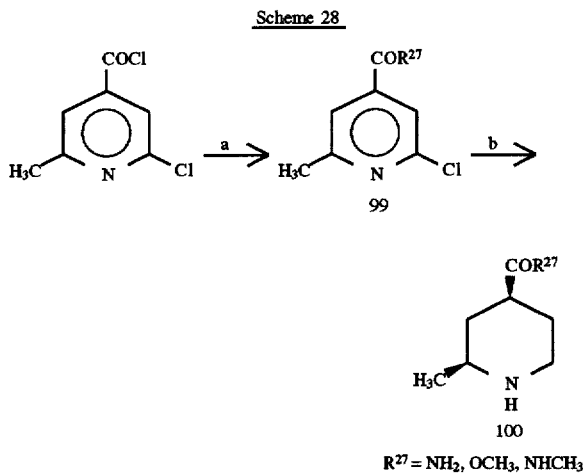

$R^{27}$ = $NH_2$, $OCH_3$, $NHCH_3$ a) (1) $NH_4OH$
     $CH_2Cl_2$
   or
   (2) MeOH
   or
   (3) $CH_2Cl_2$/MeNH$_2$
b) $H_2$, Ru, 60 psi, 140° C.

Scheme 28 shows methods for making cis 2-methyl, 4-substituted piperidines, 100, (which are compounds encompassed within "ZH" as used herein) which compounds can be coupled in a coupling reaction as described in Scheme 6 to afford compounds of formula I. Scheme 28 starts with commercially available 2-chloro-6-methyl pyridine-4-carbonylchloride (Maybridge Chem.) which is reacted with one of the following: (1) ammonium hydroxide; (2) methanol; or (3) methylamine. The reactions each may be carried out in methylene chloride at 0° C. to afford a substituted pyridine of the formula 99 wherein R is (1) $NH_2$; (2) $OCH_3$; or (3) $NHCH_3$, respectively. Compound 99 is hydrogenated over ruthenium catalyst (e.g. 5% ruthenium on charcoal) at 140° C. at 60 psi to afford a cis 2-methyl,4-substituted piperidine 100.

Scheme 29 shows methods for preparing cis 2,6 dimethyl, 4-substituted piperidines 103 and 105 (which compounds are also encompassed within "ZH" as defined herein) which may be coupled in a coupling reaction as described in Scheme 6 to afford compounds of the present invention. Scheme 29 starts from 2,6-dimethyl-4-cyanopyridine 101 which is prepared in accordance with the method of Feely, et al., JACS 81, 4004 (1959). Compound 101 is hydrolyzed using basic hydrogen peroxide in ethanol to afford primary amide 102 which, in turn, is hydrogenated under the conditions described in Scheme 28 to afford the corresponding tri-substituted piperidine 103.

Alternatively, primary amide 102 may be esterified using HCl(g) in methanol to afford the corresponding methylester 104 which, in turn, may be hydrogenated as described in Scheme 28 to afford the corresponding tri-substituted piperidine 105.

Scheme 30

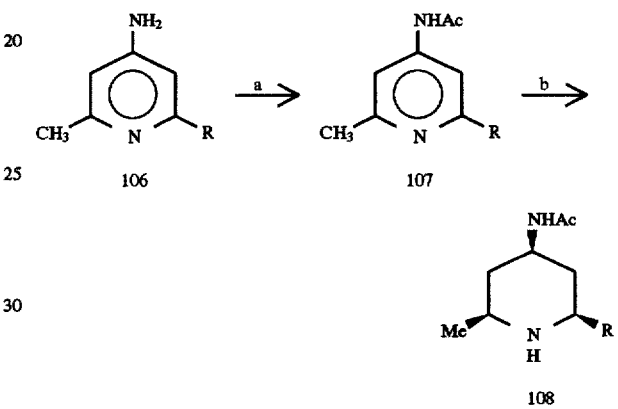

R is H or Me a) $Ac_2O$, pyridine
b) $H_2$/Ru, 60 psi, methanol

Scheme 30 shows methods for preparing 2-methyl 4-substituted piperidines and 2,6-dimethyl 4-substituted pip-

Scheme 29

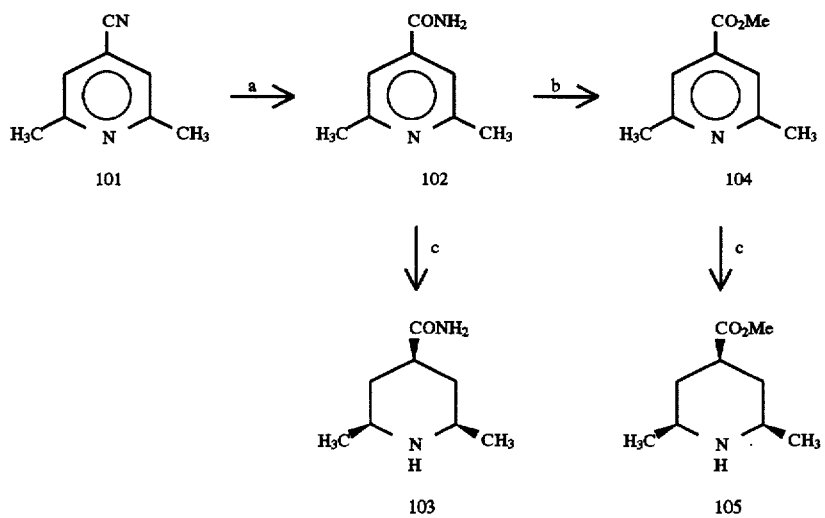

a) NaOH, EtOH, $H_2O_2$
b) HCl(g), MeOH
c) $H_2$/Ru, 60 psi, 140° C.

eridines 108 which can be coupled as described in Scheme 6 to afford compounds of the present invention. In Scheme 30, compound 106 may be prepared by the combination of the method of R. F. Evans et al., JOC 27, 1665 (1962), followed by the method of R. J. Martins et al., RECUEIL 86, 655 (1967). Compound 106 is acetylated using acetic anhydride and pyridine and the resultant acetamide 107 is hydrogenated under the conditions described in Scheme 28 to afford compound 108.

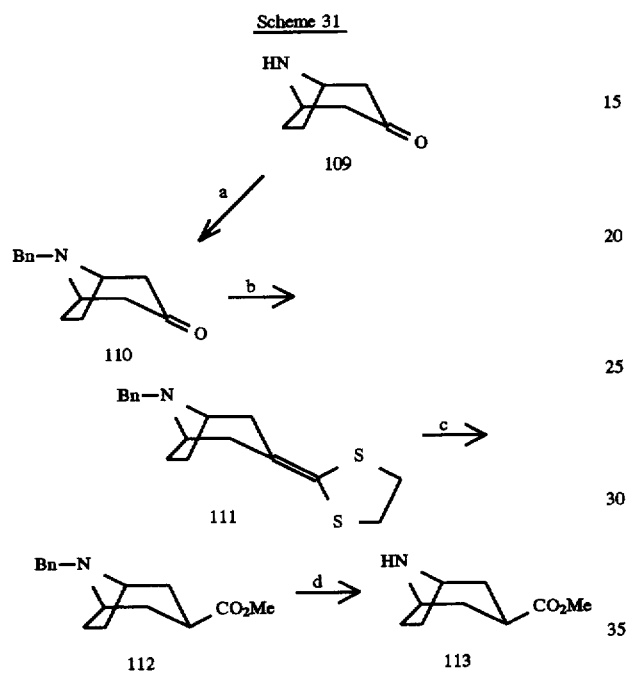

a) DMF, K₂CO₃, BnBr 0° C. ⎯→ r.t.
b) Trimethylsilyldithiane, THF, nBuLi, 0° C.
c) CH₃OH, 6N HCl, HgCl₂, TFA.
d) CH₃OH, conc. HCl, Pd(OH)₂/C, 60 psi.

Scheme 31 shows a method for preparing substituted tropones (referred to herein as "ZH") which tropones may be coupled in accordance with Scheme 6 to provide compounds of the present invention. In Scheme 28, tropone 109 (which may be derived from commercially available N-methyl tropone) is N-benzylated with benzylbromide in DMF in the presence of K₂CO₃ at 0° C. to provide 110 which is homologated with the lithium anion derived from dimethylsilyldithiane (THF, nBuLi, 0° C.) to give the dithiane adduct 111.

The dithiane adduct 111 is converted into the corresponding methyl ester using mercuric chloride-catalyzed hydrolysis in methanol to provide methyl ester 112 which is debenzylated via hydrogenation in methanol/concentrated hydrochloric acid over palladium hydroxide on carbon at 60 psi to afford carboxymethyl-substituted tropane 113. It should be understood that such carboxymethyl-substituted tropanes may be further modified in accordance with the method described in Schemes 20 and 21 to provide a wide variety of substituted tropones.

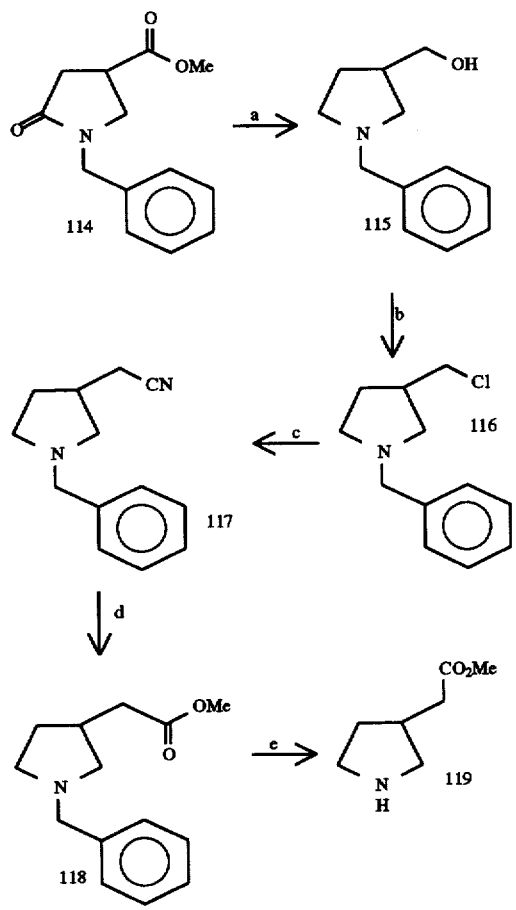

a) LAH, THF b) SOCl₂, △ c) NaCN, H₂O, 100° C., 48 hrs.
d) MeOH/AcCl, r.t. 12 hrs.

e) [cyclohexadiene], MeOH, 10% Pd/C

Scheme 32 shows the preparation of 3-substituted pyrrolidine 119 from methy-1-benzyl-5-oxo-3-pyrrolidine carboxylate 114 which is commercially available. In step (a) of Scheme 32 compound 114 is reduced with LAH in THF at room temperature to afford alcohol 115, which is then reacted with thionyl chloride at reflux to give to the corresponding chloride 116. Compound 116 is then treated with aqueous sodium cyanide at 100° C. for about 48 hours to yield the nitrile 117. Hydrolysis of nitrile 117 in methanolic HCl affords methyl ester 118, which may be debenzylated using hydrogen-transfer hydrogenation conditions (1,4 cyclohexadiene, methanol 10% Pd/C) to provide the 3-substituted pyrrolidine 119.

SCHEME 33

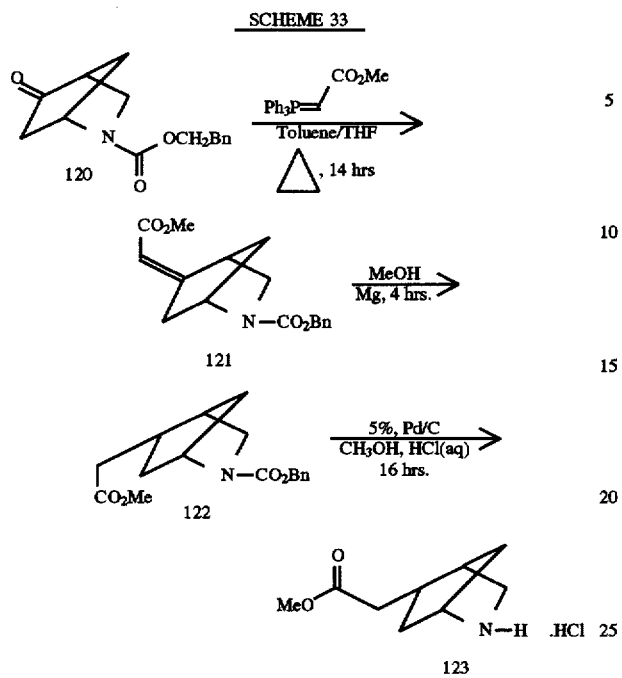

Scheme 33 shows a 3-step procedure for the preparation of [2.2.1]-2-aza-bicycloheptane 123 from 2-(carbobenzyloxy) 2-azabicyclo[2.2.1]heptan-5-one 120. Compound 120 is prepared as described by F. Ivy Carroll, et al., J. Med. Chem. 35, 2184 (1992). Compound 120 is condensed with methyl (triphenylphosphoranylidene) acetate in THF at 50°–70° C. to afford α,β unsaturated ester 121. Reduction of compound 121 with magnesium in methanol affords the corresponding saturated ester 122. Compound 122 is decarbobenzyloxylated [5% Pd/C, MeOH, aq, HCl] to afford the corresponding amine 123.

Dieis-Alder reaction in the presence of either cyclopentadiene or 1,3 cyclohexadiene [40% aqueous formaldehyde, in 1N HCl] to afford azabicyclic alkenes 127 which may be hydrogenated in ethanol over 4% palladium on carbon at 5 psi to afford compounds 128. Compounds 126, 127 and 128 are compounds of the present invention.

SCHEME 35

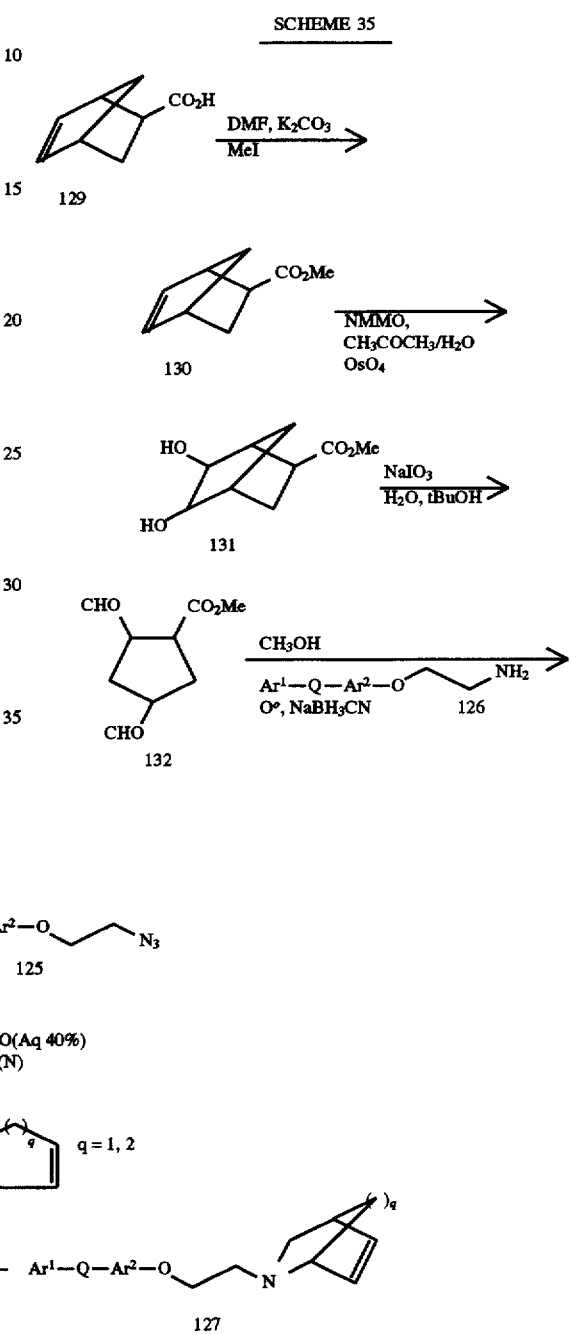

SCHEME 34

Scheme 34 shows the preparation of compounds of the present invention which are characterized as containing a 2-aza[2.2.1]bicyclo heptane or 2-aza[2.2.2]bicyclooctane moiety. Tosylate 124 is displaced with sodium azide in DMF to afford the corresponding azide 125. Azide 125 is reduced with LAH in THF to afford the corresponding primary amine 126. Primary amine 126 may be further condensed in an aza

SCHEME 35 (continued)

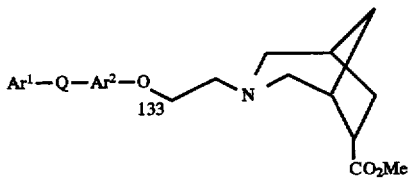

Scheme 35 describes preparation of compounds 133 of the invention having a 3-aza[3.2.1]bicyclo octane-7-methoxycarbonyl moiety. 5-norbornene-2-carboxylate is esterified in DMF containing methyl iodide and potassium carbonate. The resulting methyl ester 130 is dihydroxylated with catalytic osmium tetroxide in acetone/$H_2O$ using N-methylmorpholine oxide to recycle the catalyst. The resulting diol 131 is cleaved with aqueous sodium periodate in t-butanol to afford dialdehyde 132. Condensation of dialdehyde 132 with amine 126 in methanol followed by reduction with sodium cyanoborohydride affords compound 133 which is a compound of the invention.

EXAMPLE 1

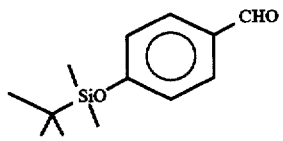

To a stirred solution of 4-hydroxybenzaldehyde (12.3 g, 0.1 mol, Aldrich) in DMF (50 mL) was added t-butyldimethylsilyl chloride (18.1 g, 0.12 mol) and imidazole (17 g, 0.25 mol). The mixture was stirred at room temperature for 16 hours, and diluted with pentane (200 mL). The organic layer was washed with water (3×) and brine, dried over $Na_2SO_4$ and concentrated in vacuo to give 25 g of the title compound as yellow oil. The resulting product had the following properties: $^1$H NMR: 300 MHz spectrum consistent with proposed structure. $M^+=236$.

EXAMPLE 2

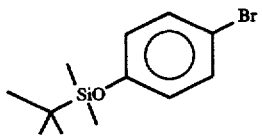

The compound of example 2 was prepared in the same manner as described in example 1, replacing 4-hydroxybenzaldehyde by 4-bromophenol. The resulting product had the following properties: $^1$H NMR: 300 MHz spectrum consistent with proposed structure.

Analysis Calcd for $C_{12}H_{19}OSiBr$ 0.4$H_2O$: C, 48.94; H, 6.78. Found: C, 48.82; H, 6.73. $M^+=287$.

EXAMPLE 3

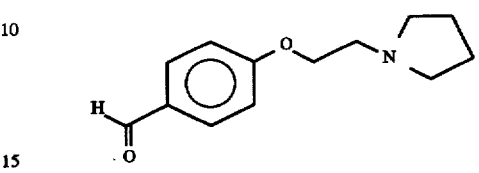

The title compound was prepared in the same manner as Example 44 sustituting 4-hydroxybenzaldehyde. The crude aldehyde was chromatographed (silica gel, methanol/methylene chloride/ammonium hydroxide 5/94/1) to afford an amber oil. The product had the following properties: H.R.M.S. $M^+$ calcd for $C_{13}H_{17}NO_2$: 219.1259. Found 219.1239.

EXAMPLE 4

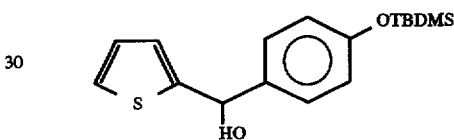

2-Bromothiophene (815 mg, 5 mmols, Aldrich) was dissolved in dry THF (20 mL) and cooled to −78° C. n-Butyllithium (3.4 mL of 1.6M solution) was added and the reaction was stirred for 2 hours under Argon. The aldehyde of Example 1 (1.18 g, 5 mmols) in THF (1 mL) was added and reaction mixture allowed to warm to room temperature over 1.5 hours. Water was added and the solution was extracted with ethyl acetate (3×30 mL). The combined organic layers were washed with brine, dried over $Na_2SO_4$, filtered and concentrated in vacuo. The residue was chromatographed on silica gel using EtOAc/Hep (20/80) as eluant to give 160 mg of compound as yellow oil. The resulting product had the following properties: $^1$H NMR: 300 MHz spectrum consistent with proposed structure.

The compounds exemplified in Table 1 were prepared essentially as described in Example 4 above except that 2-bromothiophene was replaced with the indicated aryl (halide)compound.

TABLE 1

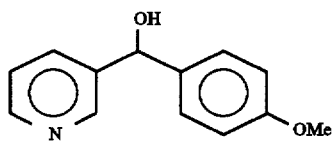

| Ex. No. | Compound | Aryl(halide)Ar¹ | Analysis |
|---|---|---|---|
| 5 | (OH, thiophene, phenyl-OTBDMS) | 3-bromothiophene | $C_{17}H_{24}O_2SSi$<br>Calc: C, 63.70; H, 7.55<br>Found: C, 63.85; H, 7.42 |
| 6 | (OH, thiazole, phenyl-OTBDMS) | thiazole | $C_{16}H_{23}NO_2SSi$<br>Calc: C, 58.78; H, 7.28; N, 4.28<br>Found: C, 63.85; H, 7.42; N, 4.14 |
| 7 | (MeO-phenyl, OH, phenyl-OTBDMS) | 4-bromoanisole | $C_{20}H_{28}O_3SSi$<br>Calc: C, 69.72; H, 8.19.<br>Found: C, 69.55; H, 8.29.<br>M⁺ 344. |
| 8 | (F-phenyl, OH, phenyl-OTBDMS) | Ex 2 + 3-fluorobenzaldehyde | $C_{19}H_{26}FO_2Si$:<br>Calc: C, 68.64; H, 7.58.<br>Found: C, 68.39; H, 7.69. |
| 9 | (MeO, F-phenyl, OH, phenyl-OTBDMS) | 3-fluoro-p-anisaldehyde Arylhalide (Ar¹) | Compound was fully characterized in the next step. See Example No. 314. |

EXAMPLE 10

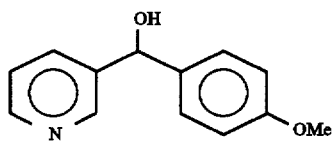

4-Bromoanisole (1.5 g, 8 mmol, Aldrich) was dissolved in dry THF (35 mL) and cooled to −78° C. n-Butyllithium (5 mL of 1.6M solution) was added and the reaction was stirred for 2 hours under Argon. 3-pyridinecarboxaldehyde (856 mg, 8 mmol) in THF (1 mL) was added and reaction mixture allowed to warm to room temperature over 1.5 hours. Water was added and the solution was extracted with ethyl acetate (3×30 mL). The combined organic layers were washed with brine, dried over $Na_2SO_4$, filtered and concentrated in vacuo. The residue was chromatographed on silica gel using EtOAc/Hep (20/80) as eluant to give 1 g of compound as white solid. The resulting product had the following properties: ¹H NMR: 300 MHz spectrum consistent with proposed structure. Analysis calcd for $C_{13}H_{13}NO_2$ 0.1 $H_2O$: C, 71.94; H, 6.13; N, 6.45. Found: C, 72.04; H, 6.19; N, 6.39.

EXAMPLE 11

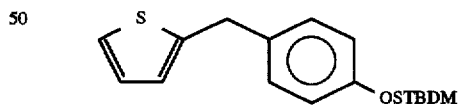

The product of example 4 (0.5 mmol) was mixed with $Et_3SiH$ (0.5 mL, Aldrich) and TFA (0.4mL) and stirred at room temperature for 6 hours under Argon. The reaction mixture was concentrated and the residue obtained was basified with 10% aqueous NaOH solution. The reaction solution was extracted with ether (3×10 mL). The combined organic layers were washed with brine, dried ($Na_2SO_4$) and filtered. The filtrate was concentrated to give 160 mg product. The resulting product was fully characterized in the next step. See Example No. 148.

The compounds exemplified in Table 2 were prepared essentially as described in Example 11, above, except that the precursor compounds of Examples 5-10 were substituted for the compound of Example 4.

TABLE 2

$$Ar^1CH(OH)Ar^2-OR \xrightarrow{HSiEt_3} Ar^1CH_2Ar^2-OR$$

| Ex. No. | Compound | $Ar^1CH(OH)Ar^2-OR$ | Analysis |
|---|---|---|---|
| 12 | (thiophene-CH2-phenyl-OTBDMS) | Ex. 5 | Compound was fully characterized in the next step. See Example No. 149. |
| 13 | (thiazole-CH2-phenyl-OTBDMS) | Ex. 6 | $C_{19}H_{23}NOSiS$<br>Calc: C, 62.90; H, 7.59; N, 4.58<br>Found: C, 62.60; H, 7.76; N, 4.36 |
| 14 | (MeO-phenyl-CH2-phenyl-OTBDMS) | Ex. 7 | $M^+ = 328$ |
| 15 | (F-phenyl-CH2-phenyl-OTBDMS) | Ex. 8 | Compound was fully characterized in the next step. See Example No. 22. |
| 16 | (MeO,F-phenyl-CH2-phenyl-OTBDMS) | Ex. 9 | Compound was fully characterized in the next step. See Example No. 314. |
| 17 | (pyridine-CH2-phenyl-OMe) | Ex. 10 | $M^+ = 199$ |

EXAMPLE 18

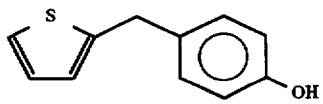

The product of example 11 was treated with tetrabutylammonium fluoride (2.5 mL of 1M solution, Aldrich) and the mixture was stirred at room temperature for 2 hours. The solvent was removed under reduced pressure, the residue obtained was treated with water and ether. The organic layer was separated and washed two times with water and brine, dried over $Na_2SO_4$ and concentrated in vacuo to give 90 mg of the title compound as yellow oil. The resulting product was fully characterized in the next step. See Example No. 148.

The compounds exemplified in Table 3 were prepared essentially as described in Example 18, above, except that the silylated precursor compounds indicated in Table 3 were substituted for the compound of Example 11.

TABLE 3

$$Ar^1CH_2Ar^2-OR \xrightarrow{TBAF} Ar^1CH_2Ar^2-OH$$

| Ex. No. | Compound | $Ar^1CH_2Ar^2-OR$ | Analysis |
|---|---|---|---|
| 19 | (thiophene-CH2-phenyl-OH) | Ex. 12 | Compound was fully characterized in the next step. See Example No. 149. |

TABLE 3-continued $$Ar^1CH_2Ar^2-OR \xrightarrow{TBAF} Ar^1CH_2Ar^2-OH$$

| Ex. No. | Compound | $Ar^1CH_2Ar^2$—OR | Analysis |
|---|---|---|---|
| 20 | (structure: thiazole-CH₂-C₆H₄-OH) | Ex. 13 | Compound was fully characterized in the next step. See Example No. 231. |
| 21 | (structure: MeO-C₆H₄-CH₂-C₆H₄-OH) | Ex. 14 | $M^+ = 214$ |
| 22 | (structure: F-C₆H₄-CH₂-C₆H₄-OH) | Ex. 15 | $C_{13}H_{11}OF \cdot 0.3H_2O$<br>Calc: C, 75.20; H, 5.63.<br>Found: C, 75.37; H, 5.61.<br>$M^+ = 202$ |
| 23 | (structure: MeO,F-C₆H₃-CH₂-C₆H₄-OH) | Ex. 16 | Compound was fully characterized in the next step. See Example No. 314. |

EXAMPLE 24

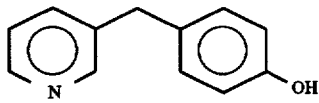

The product of example 17 (500 mg, 2.5 mmol) was dissolved in $CH_2Cl_2$ (10 mL) and cooled to −78° C. Boron tribromide (3 mL of 1M solution in $CH_2Cl_2$, Aldrich) was added and the reaction mixture allowed to warm to room temperature over 1 hour. The reaction mixture was continued to stir for 6 hours. Water was added and the reaction solution was extracted with $CH_2Cl_2$ (30 mL×3). The combined organic layers were washed with brine, dried over $Na_2SO_4$, filtered and concentrated in vacuo. The resulting product had the following properties: $^1H$ NMR: 300 MHz spectrum consistent with proposed structure. $M^+=185$.

EXAMPLE 25

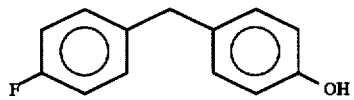

4-Fluoro-4'-hydroxybenzophenone (2 g, 9.3 mmol) was dissolved in EtOH (85 mL) and water (17 mL) and cooled to 0° C. Sodium borohydride (1.7 g, 46 mmol) was added and the mixture was stirred at room temperature for 16 hours. The mixture was treated with 1N NaOH and extracted with ethyl acetate. The organic phase was washed with brine, dried over $Na_2SO_4$ and concentrated. The residue was deoxygenated in the same manner as described in example 11. The resulting product had the following properties: $^1H$ NMR: 300 MHz spectrum consistent with proposed structure. Analysis calcd for $C_{13}H_{11}OF \cdot 0.1 \ H_2O$: C, 76.53; H, 5.53. Found: C, 76.49; H, 5.46. $M^+=202$.

EXAMPLE 26

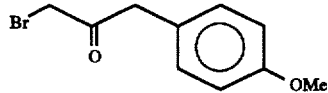

To a solution of 4-methoxyphenylacetic acid (3.32 g, 20 mmol) in benzene (30 mL) was added oxalyl chloride (2.0 mL, 23 mmol) followed by 1 drop of DMF. The mixture was stirred at 25° C. for 1.5 h and concentrated. To a solution of the crude acid chloride in ether (50 mL) at 0° C. was added ethereal diazomethane until $N_2$ evolution ceased. HBr gas was bubbled through the solution at 0° C. for 30 min (until $N_2$ no longer evolved). The solution was washed with water, dilute $NaHCO_3$ and brine and the ether layer dried over $Na_2SO_4$ and concentrated to provide a brown oil which was used without further purification.

EXAMPLE 27

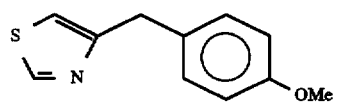

A solution of thioformamide in dioxane was prepared by refluxing formamide (1.5 mL, 43 mmol) and $P_2S_5$ (3.3 g, 7.3 mmol) in 70 mL dioxane for 2 h. The solution was added to a solution of the product from Example 26 (1.0 g, 4.1 mmol) and 2 g $MgCO_3$ in 10 mL dioxane and the mixture refluxed for 1 h. The mixture was cooled and poured into ether and 1N NaOH. The ether layer was separated and was washed with brine, dried over $Na_2SO_4$ and concentrated. Flash chromatography using a gradient of 10:1 to 5:1 hexane/EtOAc provided the title compound as a colorless oil.

EXAMPLE 28

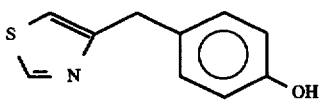

To a solution of the product from Example 27 (0.52 g, 2.53 mmol) in CH$_2$Cl$_2$ (10 mL) at −78° C. was added 8 mL of 1N BBr$_3$ in CH$_2$Cl$_2$ and the mixture stirred at −78° C. for 20 min and at 25° C. for 16 h. The mixture was poured into H$_2$O and the CH$_2$Cl$_2$ was separated, washed with brine, dried over Na$_2$SO$_4$ and concentrated to provide the product as a boronic acid complex. The product was dissolved in methanol and treated with concentrated HCl. After stirring at 25° C. for 25 h, the mixture was concentrated to give the title compound as an oil.

EXAMPLE 29

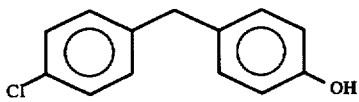

The compound of example 29 was prepared in the same manner as described in example 25, replacing 4-fluoro-4'-hydroxybenzophenone with 4-chloro-4'-hydroxybenzophenone. The resulting product had the following properties: $^1$H NMR: 300 MHz spectrum consistent with proposed structure.

Analysis Calcd for C$_{13}$H$_{11}$OCl 0.7H$_2$O: Calculated: C, 67.51; H, 5.40. Found: C, 67.46; H, 5.31. M$^+$ 218.

EXAMPLE 30

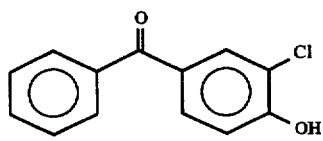

To a stirred solution of 2-chlorophenol (5 g, 38.9 mmol, Aldrich) and pyridine (3.2 mL, 40 mmol) in methylene chloride (100 mL) was added benzoyl chloride (0.1 mL) dropwise over 15 minutes. The solution was stirred 4 hours at room temperature and then poured onto crushed ice (100 mL), allowed to warm to room temperature and stirred 18 hours. The mixture was extracted with 100 mL of ethyl acetate and the ethyl acetate was washed with 10% aqueous HCl (25 mL), water (25 mL), 10% aqueous NaOH (25 mL) water (25 mL), saturated brine (25 mL) and dried over MgSO$_4$. After filtration, the volatile components were removed at reduced pressure on a rotary evaporator. The reaction was assumed to be quantitative (no 2-chlorophenol present upon TLC analysis). This crude benzoate (1.1 g) without further purification was treated with aluminum chloride (1 g, 7.5 mmol) in small portions over 5 minutes. This mixture was then heated to 160° C. (oil bath temperature) for 2 hours. The resulting brown mass was cooled to room temperature and treated with crushed ice/ concentrated HCl (1:1 by volume, total volume 100 mL) for 30 minutes. The aqueous mixture was then extracted with two 50 mL portions of ethyl acetate. The combined extracts were washed twice with 10% aqueous NaOH (25 mL). These base extracts were combined and washed with ethyl acetate (25 mL). The base extracts were then acidified by the dropwise addition of concentrated HCl. The resulting precipitate was filtered and washed with water This produced 0.63 g (59%) of the title compound.

HRMS (M+) for C$_{13}$H$_9$$^{35}$ClO$_2$ Calculated: 232.0291 Found: 232.0310

The compounds exemplified in Table 4 were prepared essentially as described in Example 30 with the exception of Example 39 which was prepared from 2-methoxyphenol, benzoic acid and polyphosphoric acid at 120° C. for 1 hour, with the disclosed substitutions being made for 2-chlorophenol.

TABLE 4

| Ex. No. | Compound | Ar$^2$OH | Analysis |
|---|---|---|---|
| 31 | (2-Cl, 4-OH benzophenone structure) | 3-chlorophenol | HRMS (M+) for C$_{13}$H$_9$$^{35}$ClO$_2$<br>Calc: 232.0291<br>Found: 232.0304 |

TABLE 4-continued

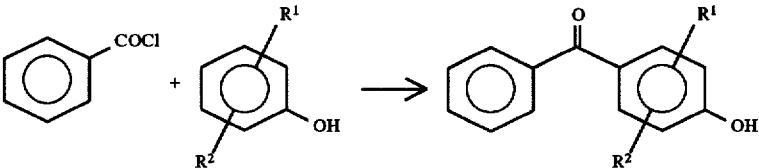

| Ex. No. | Compound | Ar²OH | Analysis |
|---|---|---|---|
| 32 | 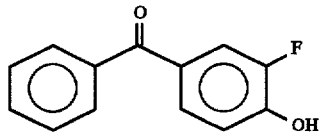 | 2-fluorophenol | HRMS (M+) for $C_{13}H_9FO_2$<br>Calc: 216.0587<br>Found: 216.0595 |
| 33 | 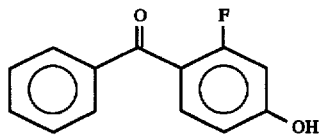 | 3-fluorophenol | HRMS (M+) for $C_{13}H_9FO_2$<br>Calc: 216.0587<br>Found: 216.0588 |
| 34 | 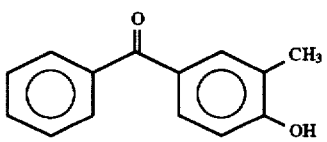 | 2-methylphenol | Melting point<br>Found: 173–175° C.<br>Literature: 173–174° C.<br>(J. Am. Chem. Soc., 49, 1029 (1927)) |
| 35 | 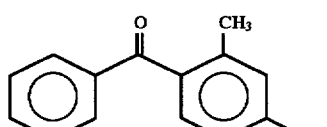 | 3-methylphenol | HRMS (MH+) for $C_{14}H_{13}O_2$<br>Calc: 213.0916<br>Found: 213.0913 |
| 36 | 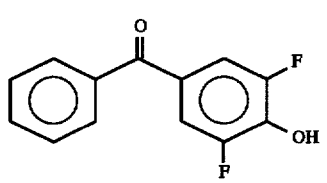 | 2,6-difluorophenol | HRMS (M+) for $C_{13}H_8F_2O_2$<br>Calc: 234.0492<br>Found: 234.0497 |
| 37 | 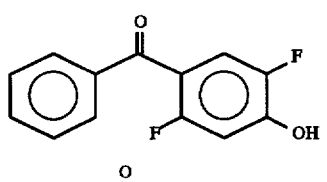 | 2,5-difluorophenol | HRMS (M+) for $C_{13}H_8F_2O_2$<br>Calc: 234.0492<br>Found: 234.0494 |
| 38 | 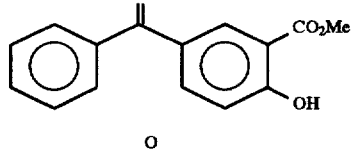 | 2-hydroxymethylbenzoate | HRMS (M+) for $C_{15}H_{12}O_4$<br>Calc: 256.0736<br>Found: 256.0741 |
| 39 | 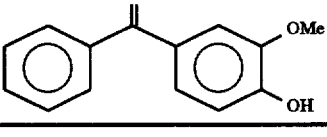 | 2-methoxyphenol | HRMS (M+) for $C_{14}H_{12}O_3$<br>Calc: 228.0786<br>Found: 228.0796 |

EXAMPLE 40

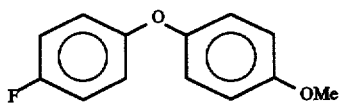

4-Fluorophenol (8.8 g, 78.5 mmol) and KOH (4 g, 71.3 mmol) were heated together in a round-bottom flask with a bunson burner until the KOH dissolved. A catalytic amount of activated Cu (~100 mg) was added, followed by 4-iodoanisole (15 g, 64 mmol). The mixture was heated at 160° C. for 1.75 hours and poured into cold dilute aqueous NaOH. The solution was extracted with 3 portions of ether and the combined extracts were washed with brine, dried over $Na_2SO_4$ and concentrated to provide the crude product. Flash chromatography on silica gel using 40:1 hexane/ EtOAc gave the product (3.7 g, 17 mmol) as a colorless oil:

Anal. calc'd for $C_{13}H_{11}FO_2$: Calculated: C, 71.55; H, 5.08. Found: C, 71.44; H, 5.13.

EXAMPLE 41

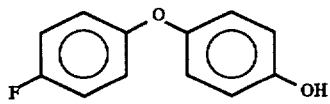

The product of Example 40 (1..45 g, 6.64 mmol) was stirred in 40 mL $CH_2Cl_2$ at –78° C. and 7 mL of 1N $BBr_3$ in $CH_2Cl_2$ was added. After stirring at 0° C. for 30 min and 25° C. for 20 h, the mixture was poured into $H_2O$. The $CH_2Cl_2$ was separated, washed with brine, dried over $Na_2SO_4$ and concentrated. Recrystallization from hexane/ $CH_2Cl_2$ provided the product as a white solid: mp 91°–94° C.;

Anal. calc'd for $C_{12}H_9FO_2 \cdot 0.1$ $H_2O$: Calculated: C, 69.97; H, 4.50. Found: C, 69.93; H, 4.54.

EXAMPLE 42

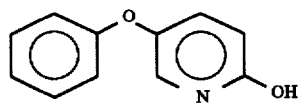

To an excess of phenol (4 g) in a round bottom flask was added $K_2CO_3$ (3.2 g, 23.2 mmol), CuI (110 mg, 0.58 mmol) and 2-amino-5-bromopyridine. The reaction mixture was stirred at 180° C. for 16 hours, cooled to room temperature and diluted with 50 ml of 10% NaOH. The aqueous layer was extracted with two 40 ml portions of ethyl acetate. The organic layers were combined, dried, concentrated and chromatographed on a 4 mm chromatotron plate (20% ethyl acetate/80% hexane). The product was identified by NMR and used in the next example.

EXAMPLE 43

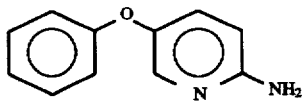

To the product of example 42 (1.5 g, 8.1 mmol) in 20 ml of 40N $H_2SO_4$ was added to $NaNO_3$ (685 mg, 8.1 mmol) at 0° C. The reaction was then stirred at room temperature for 0.5 hour followed by the addition of 50 ml of water. The reaction was extracted with 100 ml of ethyl acetate, the organic layer dried and the solvent removed in vacuo. Recrystallization of the crude solid from 50% $CH_2Cl_2$/50% hexane afforded the title compound.

EXAMPLE 44

1-[2-(4-phenoxyphenoxy)ethyl]pyrrolidine

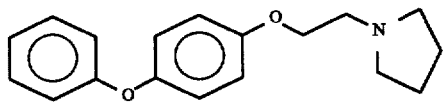

A solution of 4-phenoxyphenol (0.56 g, 3.0 mmol), 1-(2-chloroethyl)-pyrrolidine HCl (0.51 g, 3.0 mmol) and powdered $K_2CO_3$ (1.2 g, 8.7 mmol) in 30 mL DMF was stirred at 80°–90° C. for 15 hours. The solution was cooled, poured into $Et_2O$ and water and the ether layer washed with water and brine, dried over $Na_2SO_4$ and concentrated in vacuo to give 0.79 g of a brown oil. The crude product was flashed chromatographed on silica gel using a gradient of 2:1 hexane/EtOAc to 100% EtOAc to provide the title compound (0.65 g, 76.5%) as a light yellow oil:

Analysis calculated for $C_{18}N_{21}NO_2$: Calculated: C, 76.30; H, 7.47; N, 4.94. Found: C, 76.51; H, 7.50; N, 4.84.

The compounds exemplified in the following Table were prepared essentially as described in Example 44 with substitution of the indicated phenol for 4-phenoxyphenol.

TABLE 5

| Ex. No. | Compound | Starting Material | Analysis |
|---|---|---|---|
| 45 | ![structure] | 4-hydroxydiphenyl-methane | $C_{19}H_{23}NO$: Calc: C, 81.10; H, 8.24; N, 4.98. Found: C, 81.10; H, 8.36; N, 4.95. |

TABLE 5-continued $AR^1-Q-Ar^2-YH + Cl\text{-}CH_2CH_2\text{-}N(\text{pyrrolidine}) \longrightarrow AR^1-Q-Ar^2-Y-CH_2CH_2\text{-}N(\text{pyrrolidine})$

| Ex. No. | Compound | Starting Material | Analysis |
|---|---|---|---|
| 46 | [structure] | trans-4-hydroxy-stilbene | mp 104–104.5° C.; $C_{20}H_{23}NO$: Calc: C, 81.87; H, 7.90; N, 4.77. Found: C, 81.51; H, 8.02; N, 4.70. |
| 47 | [structure] | 4-hydroxybenzo-phenone | $C_{19}H_{21}NO_2 \cdot 0.1H_2O$: Calc: C, 76.79; H, 7.19; N, 4.71. Found: C, 76.73; H, 7.12; N, 4.66. |
| 48 | [structure] | Ex. 41 | $C_{18}H_{20}FNO_2$: Calc: C, 71.74; H, 6.69; N, 4.65. Found: C, 71.47; H, 6.88; N, 4.47. |
| 49 | [structure] | Ex. 28 | $^1$H NMR(CDCl$_3$)d 1.80(4H, m), 2.63(4H, m), 2.90(2H, t), 4.08(4H, m), 6.84(1H, d), 6.87(2H, d), 7.19(2H, d), 8.66(1H, d); HRMS, m/z 288.1286(calc'd for $C_{16}H_{20}SON_2$, 288.1296). |
| 50 | [structure] | 4-fluoro-4'-hydroxy-benzophenone | $C_{19}H_{20}FNO_2$: Calc: C, 72.82; H, 6.43; N, 4.47 Found: C, 72.68; H, 6.75; N, 4.35 |
| 51 | [structure] | 4-chloro-4'-hydroxy-benzophenone | $C_{19}H_{20}ClNO_2$: Calc: C, 69.19; H, 6.11; N, 4.25; Cl, 10.75 Found: C, 69.28; H, 6.10; N, 4.15; Cl, 10.49 |
| 52 | [structure] | Ex. 30 | HRMS (M+) for $C_{19}H_{20}^{35}ClNO_2$ Calc: 329.1183 Found: 329.1186 |
| 53 | [structure] | Ex. 31 | HRMS (MH+) for $C_{19}H_{21}^{35}ClNO_2$ Calc: 330.1261 Found: 330.1285 |
| 54 | [structure] | Ex. 32 | HRMS (M+) for $C_{19}H_{20}FNO_2$ Calc: 313.1478 Found: 313.1490 |

TABLE 5-continued

AR¹—Q—Ar²—YH + Cl—CH₂CH₂—N(pyrrolidine) ⟶ AR¹—Q—Ar²—Y—CH₂CH₂—N(pyrrolidine)

| Ex. No. | Compound | Starting Material | Analysis |
|---|---|---|---|
| 55 | [2-fluoro-4-(2-pyrrolidin-1-ylethoxy)phenyl] phenyl methanone | Ex. 33 | HRMS (M+) for C₁₉H₂₀FNO₂<br>Calc: 313.1478<br>Found: 313.1479 |
| 56 | [2-methyl-4-(2-pyrrolidin-1-ylethoxy)phenyl] phenyl methanone | Ex. 34 | HRMS (M+) for C₂₀H₂₃NO₂<br>Calc: 309.1729<br>Found: 309.1707 |
| 57 | [3-methyl-4-(2-pyrrolidin-1-ylethoxy)phenyl] phenyl methanone | Ex. 35 | HRMS (M+) for C₂₀H₂₃NO₂<br>Calc: 309.1729<br>Found: 309.1738 |
| 58 | [3,5-difluoro-4-(2-pyrrolidin-1-ylethoxy)phenyl] phenyl methanone | Ex. 36 | HRMS (MH+) for C₁₉H₂₀F₂NO₂<br>Calc: 332.1462<br>Found: 332.1491 |
| 59 | [2,5-difluoro-4-(2-pyrrolidin-1-ylethoxy)phenyl] phenyl methanone | Ex. 37 | HRMS (M+) for C₁₉H₁₉F₂NO₂<br>Calc: 331.1384<br>Found: 331.1371 |
| 60 | methyl 5-benzoyl-2-(2-pyrrolidin-1-ylethoxy)benzoate | Ex. 38 | HRMS (M+) for C₂₁H₂₃NO₄<br>Calc: 353.1627<br>Found: 353.1601 |
| 61 | [3-methoxy-4-(2-pyrrolidin-1-ylethoxy)phenyl] phenyl methanone | Ex. 39 | HRMS (M+) for C₂₃H₂₀NO₃<br>Calc: 325.1678<br>Found: 325.1689 |
| 62 | 1-benzyloxy-4-(2-pyrrolidin-1-ylethoxy)benzene<br>+0.10 H₂O | 4-[benzyloxy]phenol | C₁₉H₂₃NO₂·0.10 H₂O:<br>Calc: C, 76.27; H, 7.82; N, 4.68.<br>Found: C, 76.09; H, 7.80; N, 4.62. |
| 63 | 4'-(2-pyrrolidin-1-ylethoxy)biphenyl-4-carboxylic acid | 4'-hydroxy-4-biphenylcarboxylic acid | C₁₉H₂₂NO₃·1.1 H₂O:<br>Calc: C, 68.90; H, 7.06; N, 4.23.<br>Found: C, 68.87; H, 6.75; N, 3.99. |
| 64 | 4-[4-(2-pyrrolidin-1-ylethoxy)phenoxy]benzoic acid | 4'-hydroxy-4-phenoxybenzoic acid | C₁₉H₂₂NO₄·2.4 H₂O:<br>Calc: C, 61.57; H, 7.02; N, 3.78.<br>Found: C, 61.72; H, 7.10; N, 3.94.<br>H.R.M.S. M⁺ calcd: 328.1549.<br>Found: 328.1550. |

TABLE 5-continued

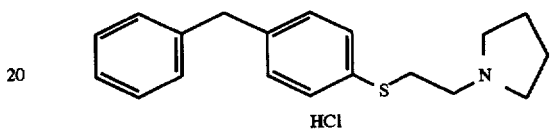

| Ex. No. | Compound | Starting Material | Analysis |
|---|---|---|---|
| 65 | 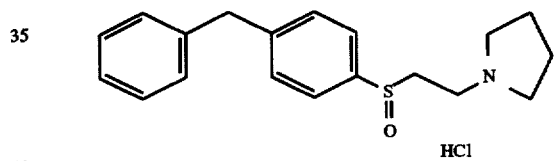 | Ex. 43 | $C_{17}H_{20}N_2O_2 \cdot 0.1 H_2O$:<br>Calc: C, 71.35; H, 7.12; N, 9.79.<br>Found: C, 71.28; H, 7.31; N, 9.51. |

EXAMPLE 66

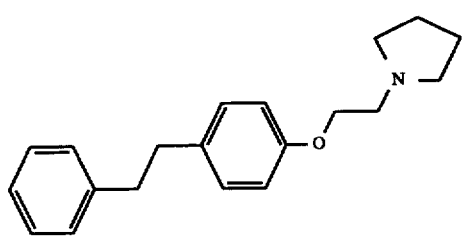

The product from Example 46 (0.103 g, 0.35 mmol) was hydrogenated in MeOH (20 mL) with catalytic 4% Pd/C under 5 psi $H_2$ pressure at 25° C. for 4 h. The solution was concentrated and filtered through a plug of silica gel using EtOAc to give the title compound (0.093 g, 0.315 mmol) as a colorless oil: $^1$H NMR (CDCl$_3$) δ 1.83 (4H, m), 2.62 (4H, m), 2.87 (6H, m), 4.09 (2H, t), 6.83 (2H, d), 7.08 (2H, d), 7.19 (3H, t), 7.28 (2H, t); HRMS, m/z 295.1928 (calc'd for $C_{20}H_{25}NO$, 295.1936).

EXAMPLE 67

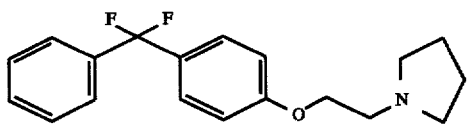

The product from Example 47 (0.5 g, 1.69 mmol), 1,2-ethanedithiol (0.28 mL, 3.38 mmol) and BF$_3$.2AcOH (0.47 mL, 3.38 mmol) were combined and stirred at 25° C. for 21 h. The mixture was poured into EtOAc and aqueous NaHCO$_3$ and the EtOAc washed with 15% NaOH and brine, dried over Na$_2$SO$_4$ and concentrated to give the crude thioketal. A solution of 1,3-dibromo-5,5-dimethylhydantoin (0.48 g, 1.69 mmol) in CH$_2$Cl$_2$ (5 mL) was cooled to −78° C. and hydrogen fluoride-pyridine (0.8 mL, 3.5 mmol) was added, followed by a solution of the thioketal in CH$_2$Cl$_2$ (3 mL). After stirring at −78° C. for 1 h, the mixture was poured into CH$_2$Cl$_2$ and aqueous NaHCO$_3$ and the CH$_2$Cl$_2$ separated, washed with brine, dried over Na$_2$SO$_4$ and concentrated to give the crude product. Flash chromatography on silica gel using a gradient of 2:1 hexane/EtOAc to 100% EtOAc provided the title compound (0.108 g, 20%) as a light yellow oil: $^1$H NMR (CDCl$_3$) d 1.82 (4H, m), 2.65 (4H, m), 2.82 (2H, t), 4.15 (2H, t), 6.94 (2H, d), 7.44 (7H, m); HRMS, m/z 317.1583 (calc'd for $C_{19}H_{21}NOF_2$, 317.1591).

EXAMPLE 68

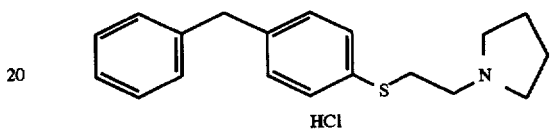

HCl

The title compound was prepared in the same manner as Example 44 using 4-benzylthiophenol as the starting material and stirring at 80° C. for 6.5 h. The crude product was treated with ethanolic HCl to give, after washing with ether, the HCl salt as a white solid: mp 137°–139° C.; Anal. calc'd for $C_{19}H_{23}NS$·HCl: C, 68.34; H, 7.24; N, 4.19; Cl, 10.62. Found: C, 68.33; H, 7.27; N, 4.15; Cl, 10.36.

EXAMPLE 69

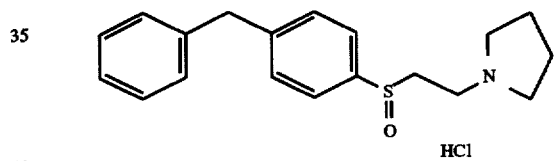

HCl

A solution of the product from Example 68 (0.5 g, 1.5 mmol) and 80–85% mCPBA (0.32 g, ~1.5 retool) in CH$_2$Cl$_2$ (20 mL) was stirred at 0° C. for 2 h. The mixture was concentrated and flash chromatographed on silica gel using a gradient of 100:1:1 to 100:4:1 CH$_2$Cl$_2$/MeOH/NH$_4$OH. The HCl salt was generated with ethanolic HCl to provide, after concentration, the title compound as a white solid: mp 180°–182° C. (d); Anal. calc'd for $C_{19}H_{23}NOS$·HCl: C, 65.22; H, 6.91; N, 4.00; Cl, 10.13. Found: C, 65.16; H, 7.20; N, 3.95; Cl, 9.84.

EXAMPLE 70

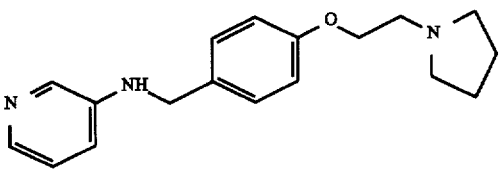

Aminopyridine (586 mg, 6.2 mmol) was dissolved in 2 mL methanol. To the pyridine was added 2 mL 5N HCl/CH$_3$OH followed by the aldehyde from Example 3. Sodium cyanoborohydride (60 mg) was added to the mixture which was stirred for 12 hours at RT. The reaction was quenched with 20 mL 10% sodium hydroxide and extracted with 3×50 mL ethyl acetate. The combined organic phases were dried (MgSO$_4$), filtered and concentrated to afford a brown oil. The crude product was chromatographed (silica gel, methanol/methylene chloride/ammonium hydroxide 2/97.5//0.5) to give yellow crystals. The product had the following properties: Anal. calcd for C$_{18}$H$_{24}$N$_3$O.0.25 H$_2$O: C, 71.61; H, 7.85; N, 13.92. Found C, 71.54; H, 7.84; N, 13.78.

EXAMPLE 71

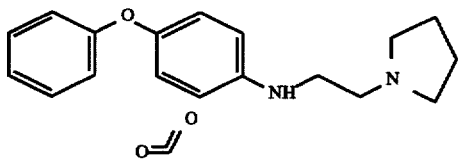

The title compound was prepared in the same manner as Example 44 using 4-phenoxyaniline as the starting material and stirring at 60° C. for 20 h, to provide a tan solid. This was dissolved in MeOH and treated with ethanolic HCl to provide, after concentration, the HCl salt. Recrystallization afforded a CO$_2$ complex of the product as white plates: mp 202°–202.5° C.; Anal. calc'd for C$_{18}$H$_{22}$N$_2$O.HCl.CO$_2$: C, 62.89; H, 6.39; N, 7.72; Cl, 9.77. Found: C, 62.64; H, 6.43; N, 7.59; Cl, 9.81.

EXAMPLE 72

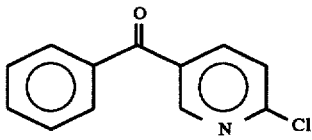

Oxalyl chloride (0.56 ml, 6.35 mmol) was added to a stirred solution of 6-Chloronicotinic acid (1 g, 6.35 mmol; Aldrich) in THF (10 ml). After the addition of a drop of DMF to initiate the reaction, the mixture was stirred at room temperature for another 10 minutes. The solvent was removed in vacuo and the acid chloride was then dissolved in benzene (20 ml). AlCl$_3$ (2.1 g, 15.9 mmol) was then added slowly and the reaction was stirred at reflux for 1.5 hours. The mixture was then concentrated and flash chromatographed through a pad of silica gel (10% EA\90% hexane) to afford 1.35 g. of a pale yellow solid. The resulting product had the following properties:

Analysis calculated for C$_{12}$H$_8$NOCl: Calculated: C, 66.22; H, 3.70; N, 6.44. Found: C, 66.11; H, 3.63; N, 6.32. m.p. 55°–56° C.

EXAMPLE 73

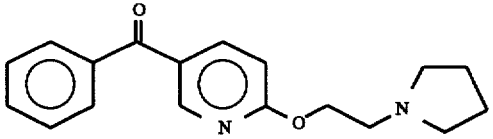

NaH (75 mg, 1.84 mmol; 60% dispersion) was added to a solution of pyrrolidinoethanol (450 mg, 1.84 mmol; Aldrich) in benzene (20 ml). The mixture was stirred at room temperature for 10 minutes and then the product from example 71 was added and the reaction was allowed to stir for 4 hours. The reaction was diluted with 50 ml of EA and the organic layer was washed with 100 ml of H$_2$O. The organic layer was dried, concentrated, and chromatographed on a 2 mm chromatotron plate (90 CH$_2$Cl$_2$\4 MeOH\1 NH$_4$OH) to afford 480 mg of pure product.

Analysis Calculated for C$_{18}$H$_{20}$N$_2$O$_2$ 0.2 H$_2$O: Calculated: C, 72.07; H, 6.85; N, 9.34. Found: C, 72.09; H, 6.89; N, 9.30.

EXAMPLE 74

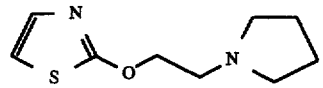

1-(2-hydroxyethyl)pyrrolidine (10 mL, 85.5 mmol, Aldrich) was treated with sodium hydride (50% dispersion in mineral oil, 0.5 g, 10.4 mmol) in small portions over 15 minutes and stirred 0.5 hour. To this solution was added 2-bromothiazole (1.6 g, 9.6 mmol, Aldrich) and the mixture was stirred 18 hours at room temperature. The mixture was poured into water (250 mL) and extracted with two 50 mL portions of ethyl acetate. The combined ethyl acetate extracts were washed with water (2×50 mL), saturated brine (50 mL) and dried over MgSO$_4$. After filtration, the volatile components were removed at reduced pressure on a rotary evaporator. The residue was chromatographed on silica gel gradient eluting with ether:hexane (1:1 to 100% ether) saturated with aqueous concentrated ammonium hydroxide. This produced 1.4 g (74%) of the title compound.

HRMS (MH+) for C$_9$H$_{15}$N$_2$OS. calculated: 199.0905 found: 199.0924

EXAMPLE 75

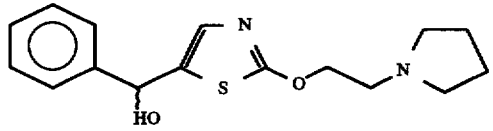

To a cooled (−40° C.) and stirred solution of the product of Example 74 (0.1 g, 0.5 mmol) in tetrahydrofuran (5 mL) was added n-butyllithium (1.6M in THF, 0.38 mL, 0.6 mmol) dropwise over one minute. The mixture was allowed to warm to 0° C. and stirred for 1 hour. The mixture was then treated with benzaldehyde (0.1 mL, 1.0 mmol) and stirred for 15 minutes. The mixture was poured into water (25 mL) and extracted with 25 mL of ethyl acetate. The ethyl acetate was washed 2 times with water (2×10 mL), saturated brine (10 mL) and dried over MgSO$_4$. After filtration, the volatile components were removed at reduced pressure on a rotary evaporator. This produced 0.1 g (66%) of the title compound.

HRMS (MH+) for C$_{18}$H$_{21}$N$_2$O$_2$S calculated: 305.1324 found: 305.1326

EXAMPLE 76

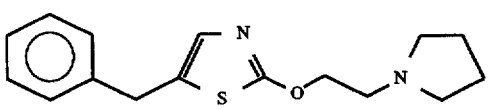

The product from Example 75 (0.1 g, 0.33 mmol) was subjected to the reaction conditions described for the preparation of Example 11. The crude product was chromatographed on silica gel eluting with ethyl acetate:hexane (1:1) saturated with aqueous concentrated ammonium hydroxide. This produced 0.07 g (74%) of the title compound.

HRMS (MH+) for calculated: 289.1375 found: 289.1373

EXAMPLE 77

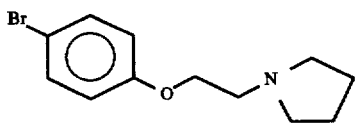

A mixture of 4-Bromophenol (20 g), $K_2CO_3$ (35 g), 1°(2-Chloroethyl)pyrrolidine•HCl (19.7g) in DMF was heated to 70° C. overnight. The mixture was cooled to room temperature and quenched with water, extracted with ethyl acetate. The organic phase was washed with water (3 times), dried over $MgSO_4$ and concentrated. The residue was chromatographed over silica gel using $EtOH/CH_2Cl_2/NH_4OH$ (4/95/1) as eluent to give 15 g of title product.

EXAMPLE 78

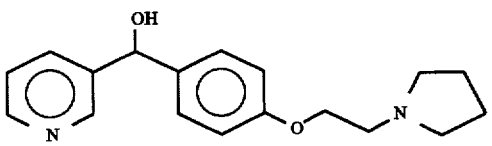

1-[2-(4-Bromophenoxy)ethyl]pyrrolidine (540.3 mg, 2 mmol, Aldrich) was dissolved in dry THF (6 mL) and cooled to −78° C. t-Butyllithium (2.4 mL of 1.8M solution) was added and the reaction was stirred for 4 h under Argon. 3-Pyridinecarboxaldehyde (214.2 mg, 2 mmol, Aldrich) in THF (0.5 mL) was added and reaction mixture allowed to warm to r.t. over 1 h. Water was added and the reaction solution was extracted with ethyl acetate (3×20 mL). The combined organic layers were washed with brine, dried over $Na_2SO_4$, filtered and concentrated in vacuo. The residue was chromatographed on silica gel using $CHCl_3/EtOH/NH_4OH$ (95/5/0.5) as eluant to give 220 mg of compound as yellow oil: $^1H$ NMR: 300 MHz spectrum consistent with proposed structure. Analysis Calcd for $C_{18}H_{22}N_2O_2$ $0.6H_2O$: C, 69.92; H, 7.56; N, 9.06. Found: c, 69.60; H, 7.31; N, 8.94.

The compounds exemplified in the following Table were prepared essentially as described in Example 78.

TABLE 6

$$Ar^1CHO + M-Ar^2-O\underset{M = Li, MgBr}{\longrightarrow} Ar^1CHOH-Ar^2-O$$

| Ex. No. | Compound | Ar¹ Precursor | Analysis |
|---|---|---|---|
| 79 | (pyrrolidinyl-ethoxy-phenyl)(pyridinyl)methanol | 4-pyridinecarboxaldehyde | $C_{18}H_{22}N_2O_2 \cdot 0.2H_2O$:<br>Calc: C, 71.59; H, 7.48; N, 9.28.<br>Found: C, 71.63; H, 7.40; N, 9.22. |
| 80 | (pyrrolidinyl-ethoxy-phenyl)(3-methoxyphenyl)methanol | 3-anisaldehyde | $C_{20}H_{26}NO_3 \cdot 0.4H_2O$:<br>Calc: C, 71.79; H, 7.77; N, 4.19.<br>Found: C, 71.64; H, 7.59; N, 4.19.<br>M⁺ = 327. |
| 81 | (pyrrolidinyl-ethoxy-phenyl)(4-methoxyphenyl)methanol | 4-anisaldehyde | $C_{20}H_{25}NO_3 \cdot 0.2H_2O$:<br>Calc: C, 72.57; H, 7.73; N, 4.23.<br>Found: C, 72.47; H, 7.70; N 4.51.<br>M⁺ = 327. |
| 82 | (pyrrolidinyl-ethoxy-phenyl)(2-methoxyphenyl)methanol | 2-anisaldehyde | $C_{20}H_{26}NO_3 \cdot 0.8H_2O$:<br>Calc: C, 70.27; H, 7.84; N, 4.10.<br>Found: C, 70.25; H, 7.72; N, 3.73.<br>M⁺ = 327. |
| 83 | (pyrrolidinyl-ethoxy-phenyl)(quinolinyl)methanol | 2-quinolinecarboxaldehyde | $C_{22}H_{24}N_2O_2 \cdot 0.4H_2O$:<br>Calc: C, 74.30; H, 7.03; N, 7.80.<br>Found: C, 74.23; H, 7.47; N, 7.69.<br>M⁺ = 348. |

TABLE 6-continued $$Ar^1CHO + M-A^2-O\underset{M = Li, MgBr}{\longrightarrow} Ar^1CHOH-Ar^2-O$$

| Ex. No. | Compound | Ar¹ Precursor | Analysis |
|---|---|---|---|
| 84 | [structure: OH-CH(3-quinolinyl)-C6H4-O-CH2CH2-pyrrolidine] | 3-quinolinecarboxaldehyde | $C_{22}H_{24}N_2O_2 \cdot 0.3H_2O$: Calc: C, 74.68; H, 7.01; N, 7.92. Found: C, 74.68; H, 7.08; N, 7.81. |
| 85 | [structure: OH-CH(2-thienyl)-C6H4-O-CH2CH2-pyrrolidine] | 2-thiophenecarboxaldehyde | $C_{17}H_{21}NOS_2$: Calc: C, 67.29; H, 6.98; N, 4.62. Found: C, 67.14; H, 6.92; N1 4.56. |
| 86 | [structure: OH-CH(3-thienyl)-C6H4-O-CH2CH2-pyrrolidine] | 3-thiophenecarboxaldehyde | $C_{17}H_{21}NO_2S1.2H_2O$: Calc: C, 62.82; H, 7.26; N, 4.31. Found: C, 62.81; H, 6.81; N, 4.36. $M^+ = 303$. |
| 87 | [structure: OH-CH(2-furyl)-C6H4-O-CH2CH2-pyrrolidine] | 2-furaldehyde | $C_{17}H_{21}NO_3 \cdot 0.2H_2O$: Calc: C, 70.18; H, 7.41 N, 4.81. Found: C, 69.99; H, 7.19; N, 4.77. $M^+ = 287$. |
| 88 | [structure: OH-CH(3-furyl)-C6H4-O-CH2CH2-pyrrolidine] | 3-furaldehyde | $C_{17}H_{21}NO_3 \cdot 0.3H_2O$: Calc: C, 69.74; H, 7.44 N, 4.78. Found: C, 69.68; H, 7.13; N, 4.79. $M^+ = 287$. |
| 89 | [structure: OH-CH(benzodioxolyl)-C6H4-O-CH2CH2-pyrrolidine] | piperonal | $C_{20}H_{23}NO_4 \cdot 0.2H_2O$: Calc: C, 69.83; H, 6.84; N, 4.06. Found: C, 69.75; H, 6.88; N, 4.09. $M^+ = 341$ |

TABLE 6-continued

Ar¹CHO + M—Ar²—O— → Ar¹CHOH—Ar²—O—

M = Li, MgBr

| Ex. No. | Compound | Ar¹ Precursor | Analysis |
|---|---|---|---|
| 90 | | | NMR spectrum consistent with proposed structure. |
| 91* | | | C₁₉H₂₂FNO₂·0.1H₂O. Calc: C, 71.95; H, 7.05; N, 4.41. Found: C, 71.78; H, 7.19; N, 4.43. |
| 92 | | 2-pyridinecarboxaldehyde | Fully characterized in example 138. |
| 93 | | 2-fluorobenzaldehyde | C₁₉H₂₂FNO₂·0.1H₂O Calc: C, 71.95; H, 7.05; N, 4.41 Found: C, 71.78; H, 7.19; N, 4.43 |
| 94 | | 3-fluorobenzaldehyde | Fully characterized in example 142. |

TABLE 6-continued $$Ar^1CHO + M-Ar^2-O-\overset{\displaystyle\bigcirc}{N} \longrightarrow Ar^1CHOH-Ar^2-O-\overset{\displaystyle\bigcirc}{N}$$

M = Li, MgBr

| Ex. No. | Compound | Ar¹ Precursor | Analysis |
|---|---|---|---|
| 95 | (structure: 3-chlorophenyl-CH(OH)-C₆H₄-O-CH₂CH₂-pyrrolidine) | 3-chlorobenzaldehyde | Fully characterized in example 143. |
| 96 | (structure: 3-fluoro-4-methoxyphenyl-CH(OH)-C₆H₄-O-CH₂CH₂-pyrrolidine) | 3-fluoro-p-anisaldehyde | Compound was fully characterized in the next step. See Example No. 144. |

*Compound of Example 91 was desilylated using the method described in Example 18

EXAMPLE 97

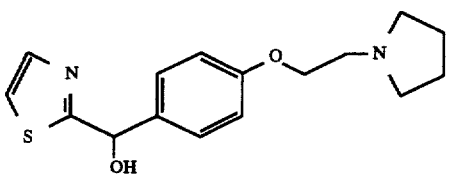

To a solution of thiazole (0.5 g, 5.87 mmol) in THF (15 mL) at 0° C. was added 1.6M nBuLi in hexanes (3.75 mL, 6 mmol) and the mixture stirred at 0° C. for 15 min. This solution was added to a solution of the product from Example 3 (1.1 g, 5.0 mmol) in THF (20 mL) at −78° C. and the mixture stirred for 45 min. The reaction mixture was quenched with saturated $NH_4Cl$ and poured into ether and water. The ether layer was separated, washed with brine, dried over $Na_2SO_4$ and concentrated. Flash chromatography on silica gel using a gradient of 100:1:0.5 to 100:2:0.5 $CH_2Cl_2$/MeOH/$NH_4OH$ gave the title compound (1.12 g, 74%) as a light brown solid: Anal. calc'd for $C_{16}H_{20}N_2O_2S \cdot 0.30\ H_2O$: C, 62.03; H, 6.70; N, 9.04. Found: C, 62.04; H, 6.64; N, 9.07.

EXAMPLE 98

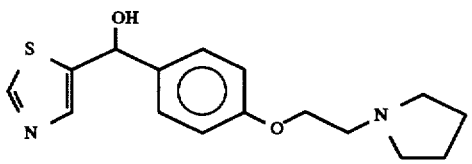

To a solution of 2-trimethylsilylthiazole (1.09 g, 6.9 mmol) in THF (25 mL) at −78° C. was added 1.6M n-BuLi in hexanes (4.5 mL, 7.2 mmol) and the mixture warmed to −50° C. for 1 min and cooled to −78° C. A solution of the product from Example 3 (1.4 g, 6.4 mmol) in THF (6 mL) was added and the mixture stirred at −78° C. for 45 min. The reaction mixture was quenched with saturated $NH_4Cl$ and poured into ether and water. The ether layer was separated, washed with brine, dried over $Na_2SO_4$ and concentrated. Flash chromatography on silica gel using a gradient of 100:2:0.5 to 100:3:0.5 $CH_2Cl_2$/MeOH/$NH_4OH$ gave the title compound (0.42 g).

EXAMPLE 99

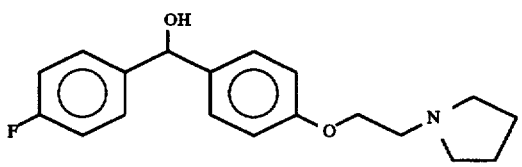

To a stirred solution of the ketone of example 50 (850 mg) in EtOH (25 ml) was added water (5 ml), then $NaBH_4$ (513 mg) was added pinch by pinch and the mixture stirred at room temperature for 2 hours. The reaction mixture was quenched with 1N NaOH, extracted with ethyl acetate, dried over $MgSO_4$ and concentrated. The residue was chromatographed over silica gel using 4/95/1 EtOH/$CH_2Cl_2$/$NH_4OH$ to give the title product (500 mg).

Analysis Calculated for $C_{19}H_{21}FNO_2$ Calculated: C, 72.35; H, 7.03; N, 4.44 Found: C, 72.01; H, 7.01; N, 4.38

TABLE 7

$Ar^1COAr^2$—O—CH₂CH₂—N(pyrrolidine) → $Ar^1CHOHAr^2$—O—CH₂CH₂—N(pyrrolidine)

| Ex. No. | Compound | Starting Ketone | Analysis |
|---|---|---|---|
| 100 | (4-chlorophenyl)(phenyl)methanol with OCH₂CH₂-pyrrolidine para to Cl | Ex. 52 | HRMS (MH+) for $C_{19}H_{23}{}^{35}ClNO_2$ Calc: 332.1417 Found: 332.1410 |
| 101 | (3-chloro-4-substituted-phenyl)(phenyl)methanol | Ex. 53 | HRMS (MH+) for $C_{19}H_{23}{}^{35}ClNO_2$ Calc: 332.1417 Found: 332.1426 |
| 102 | (3-fluoro-4-substituted-phenyl)(phenyl)methanol | Ex. 54 | HRMS (M+) for $C_{19}H_{22}FNO_2$ Calc: 315.1635 Found: 315.1639 |

TABLE 7-continued $$Ar^1COAr^2\text{—}O\text{—}\overset{}{\frown}\text{N}\overset{}{\frown} \longrightarrow Ar^1CHOHAr^2\text{—}O\text{—}\overset{}{\frown}\text{N}\overset{}{\frown}$$

| Ex. No. | Compound | Starting Ketone | Analysis |
|---|---|---|---|
| 103 | [structure: phenyl-CH(OH)-(2-F,4-OCH2CH2-pyrrolidinyl)phenyl] | Ex. 55 | HRMS (M+) for $C_{19}H_{22}FNO_2$<br>Calc: 315.1635<br>Found: 315.1628 |
| 104 | [structure: phenyl-CH(OH)-(3-CH3,4-OCH2CH2-pyrrolidinyl)phenyl] | Ex. 56 | HRMS (M+) for $C_{20}H_{25}NO_2$<br>Calc: 311.1885<br>Found: 311.1856 |
| 105 | [structure: phenyl-CH(OH)-(2-CH3,4-OCH2CH2-pyrrolidinyl)phenyl] | Ex. 57 | HRMS (M+) for $C_{20}H_{25}NO_2$<br>Calc: 311.1885<br>Found: 311.1882 |
| 106 | [structure: phenyl-CH(OH)-(3,5-diF,4-OCH2CH2-pyrrolidinyl)phenyl] | Ex. 58 | HRMS (M+) for $C_{19}H_{21}F_2NO_2$<br>Calc: 333.1540<br>Found: 333.1529 |
| 107 | [structure: phenyl-CH(OH)-(2,3-diF,4-OCH2CH2-pyrrolidinyl)phenyl] | Ex. 59 | HRMS (M+) for $C_{19}H_{21}F_2NO_2$<br>Calc: 333.1540<br>Found: 333.1548 |
| 108 | [structure: phenyl-CH(OH)-(3-CO2Me,4-OCH2CH2-pyrrolidinyl)phenyl] | Ex. 60 | HRMS (M+) for $C_{21}H_{25}NO_4$<br>Calc: 355.1784<br>Found: 355.1808 |
| 109 | [structure: phenyl-CH(OH)-(3-OMe,4-OCH2CH2-pyrrolidinyl)phenyl] | Ex. 61 | HRMS (M+) for $C_{20}H_{25}NO_3$<br>Calc: 327.1834<br>Found: 327.1807 |
| 110 | [structure: 4-Cl-phenyl-CH(OH)-(4-OCH2CH2-pyrrolidinyl)phenyl] | Ex. 51 | $C_{17}H_{22}ClNO_2$<br>Calc: C, 68.77; H, 6.68; N, 4.22; Cl, 10.68<br>Found: C, 68.48; H, 6.75; N, 4.17; Cl, 10.62 |
| 111 | [structure: phenyl-CH(OH)-(6-OCH2CH2-pyrrolidinyl)pyridin-3-yl] | Ex. 73 | $C_{18}H_{22}N_2O_2 \cdot 0.4H_2O$:<br>Calc: C, 70.75; H, 7.52; N, 9.17.<br>Found: C, 70.63; H, 7.52; N, 9.08. |

EXAMPLE 112

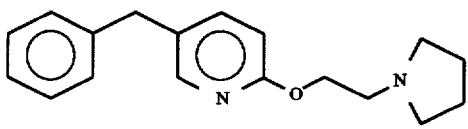

This example demonstrates the reduction of benzylic alcohols using hydrogenation in the presence of palladium.

The product of example 111 (250 mg, 0.84 mmol) was dissolved in 20 ml of 60% MeOH\40% acetic acid and transferred to a Parr shaker along with a catalytic amount of 4% Pd\C. The reaction was shaken for 5 hours at room temperature under a 5 psi pressure of $H_2$. The reaction mixture was filtered and basified with 10% NaOH. The mixture was extracted with 2 25 ml portions of EA which were combined. The organic layer was dried and the solvent removed in vacuo to afford pure product.

Analysis calculated for $C_{18}H_{22}N_2O$ 0.25 $H_2O$: Calculated: C, 75.36; H, 7.91; N, 9.76. Found: C, 75.43; H, 8.13; N, 9.45.

EXAMPLE 113

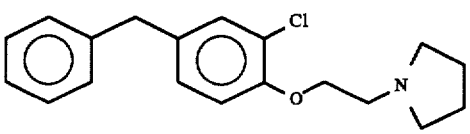

This example demonstrates reduction of benzylic alcohols using triethylsilane.

To a stirred solution of the product from Example 100 (0.26 g, 0.78 mmol) and triethylsilane (1 mL) in methylene chloride (5 mL) was added trifluoroacetic acid (0.1 mL) in one portion. This solution was stirred 10 minutes at room temperature. The mixture was poured into 5% aqueous $Na_2CO_3$ (25 mL) and extracted with 25 mL of ethyl acetate. The ethyl acetate was washed 2 times with water (2×10 mL), saturated brine (10 mL) and dried over $MgSO_4$. After filtration, the volatile components were removed at reduced pressure on a rotary evaporator. The crude product was chromatographed on silica gel gradient eluting with ethyl acetate:hexane (1:9 to 1:1) saturated with aqueous concentrated ammonium hydroxide. This produced 0.22 g (89%) of the title compound.

HRMS (M+) for $C_{19}H_{22}{}^{35}ClNO$ Calculated: 315.1390 Found: 315.1385

In the same manner as described in example 112 the compounds described in Table 8 were reduced.

TABLE 8

$Ar^1CH(OH)Ar^2$-O-CH₂CH₂-N(pyrrolidine) → $Ar^1CH_2Ar^2$-O-CH₂CH₂-N(pyrrolidine)

| Ex. No. | Compound | Starting Alcohol | Analysis |
|---------|----------|------------------|----------|
| 114 | (benzyl-Cl-phenyl-O-CH₂CH₂-pyrrolidine) | Ex. 101 | HRMS (M+) for $C_{19}H_{22}{}^{35}ClNO$ Calc: 315.1390 Found: 315.1388 |
| 115 | (benzyl-F-phenyl-O-CH₂CH₂-pyrrolidine) | Ex. 102 | HRMS (M+) for $C_{19}H_{22}FNO$ Calc: 299.1685 Found: 299.1678 |
| 116 | (benzyl-F-phenyl-O-CH₂CH₂-pyrrolidine) | Ex. 103 | HRMS (M+) for $C_{19}H_{22}FNO$ Calc: 299.1685 Found: 299.1681 |
| 117 | (benzyl-CH₃-phenyl-O-CH₂CH₂-pyrrolidine) | Ex. 104 | HRMS (M+) for $C_{20}H_{25}NO$ Calc: 295.1936 Found: 295.1945 |
| 118 | (benzyl-CH₃-phenyl-O-CH₂CH₂-pyrrolidine) | Ex. 105 | HRMS (M+) for $C_{20}H_{25}NO$ Calc: 295.1936 Found: 295.1914 |
| 119 | (benzyl-F,F-phenyl-O-CH₂CH₂-pyrrolidine) | Ex. 106 | HRMS (M+) for $C_{19}H_{21}F_2NO$ Calc: 317.1591 Found: 317.1593 |

TABLE 8-continued

Ar¹CH(OH)Ar²–O–CH₂CH₂–N(pyrrolidine)  →  Ar¹CH₂Ar²–O–CH₂CH₂–N(pyrrolidine)

| Ex. No. | Compound | Starting Alcohol | Analysis |
|---|---|---|---|
| 120 | [structure: benzyl-difluorophenyl-OCH₂CH₂-pyrrolidine] | Ex. 107 | HRMS (M+) for $C_{19}H_{21}F_2NO$<br>Calc: 317.1591<br>Found: 317.1598 |
| 121 | [structure: thiazole-CH₂-phenyl-OCH₂CH₂-pyrrolidine] | Ex. 97 | HRMS, m/z 288.1290 (calc'd for $C_{16}H_{20}SON_2$, 288.1297). |
| 122 | [structure: thiazole isomer-CH₂-phenyl-OCH₂CH₂-pyrrolidine] | Ex. 98 | HRMS, m/z 288.1299 (calc'd for $C_{16}H_{20}SON_2$, 288.1296). |
| 123 | [structure: benzyl-(CO₂Me)phenyl-OCH₂CH₂-pyrrolidine] | Ex. 108 | HRMS (MH+) for $C_{21}H_{26}NO_3$<br>Calc: 340.1913<br>Found: 340.1885 |
| 124 | [structure: benzyl-(OMe)phenyl-OCH₂CH₂-pyrrolidine] | Ex. 109 | HRMS (MH+) for $C_{20}H_{25}NO_2$<br>Calc: 311.1885<br>Found: 311.1875 |
| 125 | [structure: pyridyl-CH₂-phenyl-OCH₂CH₂-pyrrolidine] | Ex. 77 | $C_{18}H_{22}N_2O\cdot0.2H_2O$:<br>Calc: C, 75.60; H, 7.89; N, 9.80.<br>Found: C, 75.53; H, 7.69; N, 9.58.<br>M⁺ = 282. |
| 126 | [structure: pyridyl-CH₂-phenyl-OCH₂CH₂-pyrrolidine] | Ex. 78 | $C_{18}H_{22}N_2O\cdot0.3H_2O$:<br>Calc: C, 75.12; H, 7.92; N, 9.73.<br>Found: C, 74.96; H, 7.14; N, 9.47.<br>M⁺ = 282. |
| 127 | [structure: (m-OMe)benzyl-phenyl-OCH₂CH₂-pyrrolidine] | Ex. 79 | $C_{20}H_{25}NO_2\cdot0.4H_2O$:<br>Calc: C, 75.39; H, 8.16; N, 4.40.<br>Found: C, 75.20; H, 8.13; N, 4.43.<br>M⁺ = 311. |
| 128 | [structure: (p-MeO)benzyl-phenyl-OCH₂CH₂-pyrrolidine] | Ex. 80 | $C_{20}H_{25}NO_2\cdot0.2H_2O$:<br>Calc: C, 76.25; H, 8.13; N, 4.45.<br>Found: C, 76.11; H, 7.88; N, 4.41.<br>M⁺ = 311. |
| 129 | [structure: (o-OMe)benzyl-phenyl-OCH₂CH₂-pyrrolidine] | Ex. 88 | $C_{20}H_{25}NO_2$:<br>Calc: C, 77.14; H, 8.09; N, 4.50.<br>Found: C, 77.18; H, 7.61; N, 4.11.<br>M⁺ = 311. |
| 130 | [structure: methylenedioxybenzyl-phenyl-OCH₂CH₂-pyrrolidine] | Ex. 82 | $C_{20}H_{23}NO_4\cdot0.2H_2O$:<br>Calc: C, 69.63; H, 6.84; N, 4.06.<br>Found: C, 69.75; H, 6.88; N, 4.09.<br>M⁺ = 325. |
| 131 | [structure: quinolinyl-CH₂-phenyl-OCH₂CH₂-pyrrolidine] | Ex. 83 | M⁺ = 332. |

TABLE 8-continued

Ar¹CH(OH)Ar² —O—CH₂CH₂—N(pyrrolidine) → Ar¹CH₂Ar² —O—CH₂CH₂—N(pyrrolidine)

| Ex. No. | Compound | Starting Alcohol | Analysis |
|---|---|---|---|
| 132 | quinolin-3-yl-CH₂-C₆H₄-O-CH₂CH₂-N(pyrrolidine) | Ex. 84 | $C_{22}H_{24}N_2O\cdot0.5H_2O$:<br>Calc: C, 74.39; H, 7.38; N, 8.20.<br>Found: C, 77.42; H, 7.31; N, 8.26. |
| 133 | thien-2-yl-CH₂-C₆H₄-O-CH₂CH₂-N(pyrrolidine) | Ex. 84 | $C_{17}H_{21}NOS$:<br>Calc: C, 71.04; H, 7.34; N, 4.87.<br>Found: C, 70.57; H, 7.45; N, 4.77.<br>$M^+ = 287$. |
| 134 | thien-3-yl-CH₂-C₆H₄-O-CH₂CH₂-N(pyrrolidine) | Ex. 85 | $C_{17}H_{21}NOS\cdot0.2H_2O$:<br>Calc: C, 70.16; H, 7.41; N, 4.81.<br>Found: C, 70.15; H, 7.07; N, 4.83.<br>$M^+ = 287$. |
| 135 | furan-2-yl-CH₂-C₆H₄-O-CH₂CH₂-N(pyrrolidine) | Ex. 86 | $M^+ = 271$. |
| 136 | furan-3-yl-CH₂-C₆H₄-O-CH₂CH₂-N(pyrrolidine) | Ex. 87 | $M^+ = 271$. |
| 137 | 4-HO-C₆H₄-CH₂-C₆H₄-O-CH₂CH₂-N(pyrrolidine) | Ex. 90 | $C_{19}H_{23}NO_2\cdot0.3H_2O$:<br>Calc: C, 75.37; H, 7.86; N, 4.63.<br>Found: C, 75.23; H, 7.24; N, 4.14.<br>$M^+ = 297$. |
| 138 | pyridin-2-yl-CH₂-C₆H₄-O-CH₂CH₂-N(pyrrolidine) | Ex. 92* | HRMS for $C_{18}H_{22}N$<br>Calc: 282.1732<br>Found: 282.1726 |
| 139 | 4-F-C₆H₄-CH₂-C₆H₄-O-CH₂CH₂-N(pyrrolidine) | Ex. 99 | $C_{19}H_{22}FNO\cdot1/4H_2O$<br>Calc: C, 75.10; H, 7.46; N, 4.61<br>Found: C, 75.31; H, 7.32; N, 4.54 |
| 140 | 4-Cl-C₆H₄-CH₂-C₆H₄-O-CH₂CH₂-N(pyrrolidine) | Ex. 110 | $C_{19}H_{22}NClO$<br>Calc: C, 72.24; H, 7.02; N, 4.44<br>Found: C, 72.02; H, 7.34; N, 4.30 |
| 141 | 2-F-C₆H₄-CH₂-C₆H₄-O-CH₂CH₂-N(pyrrolidine) | Ex. 93 | $C_{19}H_{22}FNO$<br>Calc: C, 76.23; H, 7.41; N, 4.69<br>Found: C, 76.29; H, 7.34; N, 4.64 |
| 142 | 3-F-C₆H₄-CH₂-C₆H₄-O-CH₂CH₂-N(pyrrolidine) | Ex. 94 | $C_{19}H_{22}FNO$<br>Calc: C, 76.23; H, 7.41; N, 4.69<br>Found: C, 76.11; H, 7.67; N, 4.66 |
| 143 | 3-Cl-C₆H₄-CH₂-C₆H₄-O-CH₂CH₂-N(pyrrolidine) | Ex. 95 | $C_{19}H_{22}ClNO\cdot0.25H_2O$<br>Calc: C, 71.24; H 7.06; N, 4.37; Cl, 11.07<br>Found: C, 71.18; H, 7.18; N, 4.38; Cl, 10.95 |

TABLE 8-continued

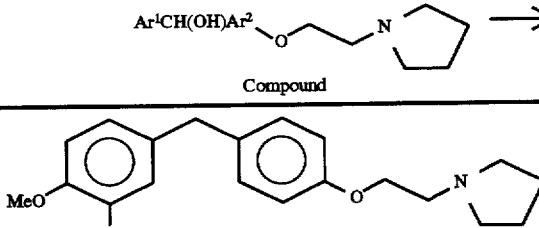

| Ex. No. | Compound | Starting Alcohol | Analysis |
|---|---|---|---|
| 144 | MeO- ... -F (structure) | Ex. 96 | C$_{20}$H$_{24}$FNO$_2$·0.1H$_2$O<br>Calc: C, 72.53; H, 7.36; N, 4.23<br>Found: C, 72.42; H, 7.64; N, 4.12<br>M$^+$ = 329 |

*The alcohol of Example 93 was converted to its corresponding acetate with Ac$_2$O and then hydrogenated

EXAMPLE 145

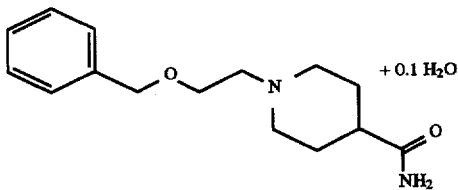

+ 0.1 H$_2$O

To a stirred solution of 15.2 g of 2-benzyloxyethanol in 100 ml of CH$_2$Cl$_2$ and 50 ml pyridine was added 20 g of p-toluenesulfonyl chloride and 20 mg of N,N-dimethylaminopyridine at 0° C. The mixture was stirred at 0° C. for 10 minutes, warmed up to 25° C. and stirred at 25° C. for 4 hrs, and concentrated in vacuo. The residue was extracted with ethyl acetate, washed with water, dried over Na$_2$SO$_4$ and concentrated in vacuo gave crude oily gum which was flash chromatographed on silica to give 6.5 g of corresponding tosylate which was reacted with isonipecotamide to provide the title compound following the procedure described in example 10.

Calcd for C$_{15}$H$_{22}$N$_2$O$_2$·0.1H$_2$O: C, 68.20; H, 8.47; N, 10.61 Found: C, 68.28; H, 8.31; N, 10.44

EXAMPLE 146

Preparation of 1-[2-[(5-benzoylpyridin-2-yl)oxy]ethyl]-4-piperidinecarboxamide

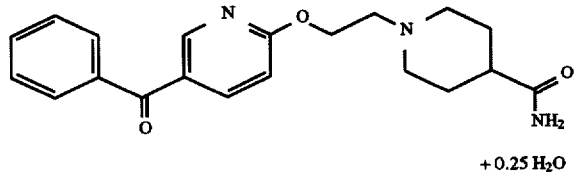

+ 0.25 H$_2$O

A solution of 1.5 g of the compound of example 145 in 25 ml of ethanol in a parr shaker was exposed to hydrogen gas at 25° C. at 60 psi pressure for 23 hrs. The catalyst was removed by filtration and the filtrate was concentrated in vacuo to afford an oily gum. To a stirred solution of 344 mg of the gum in 6 ml of DMF was added 200 mg of 50% NaH (in oil) and the mixture was stirred at 25° C. for 15 minutes under nitrogen atmosphere. 436 mg of the compound of example 73 was added to the mixture and was stirred at 25° C. for 4 hrs, quenched with water and the mixture was poured into water and was extracted with ethyl acetate. The organic extract was washed with water, dried over Na$_2$SO$_4$ and concentrated in vacuo to give 380 mg of oily residue, which was chromatographed on silica gel using 85% CHCl$_3$, 14% ethanol and 1% NH$_4$OH as eluant to provide 14 mg of title compound as white crystaline solid.

Calcd for C$_{20}$H$_{23}$N$_3$O$_3$·¼H$_2$O: C, 67.11; H, 6.62; N, 11.74 Found: C, 67.17; H, 6.94; N, 11.63

EXAMPLE 147

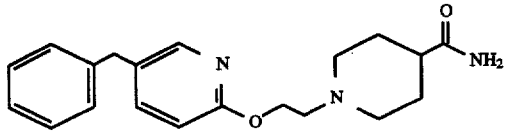

To a stirred solution of 365 mg of the compound prepared in example 146 in 5 ml of ethanol was added 365 mg of NaBH$_4$ and the mixture was stirred at room temperature for 1 hr. The mixture was poured into water and extracted with ethyl acetate. The organic phase was washed with water, dried over Na$_2$SO$_4$, concentrated in vacuo to yield crude residue. The crude residue was chromatographed on silica gel using 80% CHCl$_3$, 19% ethanol and 1% NH$_4$OH as eluant to provide 210 mg of an oily gum. To a solution of the oily gum in 10 ml of ethanol containing 1 ml of glacial acetic acid, in a parr shaker was exposed to hydrogen gas at 25° C. over 10% Pd/C catalyst at 5 psi pressure for 6 hrs. The catalyst was removed by filtration and the solvent was removed from the filtrate under reduced pressure to give an oily residue. The oily residue was extracted with ethyl acetate, washed with 10% K$_2$CO$_3$ solution and water, dried over Na$_2$SO$_4$, concentrated in vacuo to provide a residue which was chromatographed on silica gel using 85% CHCl$_3$, 14% ethanol and 1% NH$_4$OH as eluant to provide 110 mg of the title compound 57 as white solid.

Calcd for C$_{21}$H$_{25}$N$_3$O$_2$·¼ H$_2$O: C, 69.84; H, 7.47; N, 12.22 Found: C, 69.39; H, 7.78; N, 11.98

EXAMPLE 148

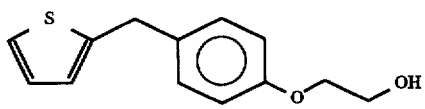

The phenol of example 18 (90 mg, 0.47 mmol) was dissolved in DMF (2 mL). To this was added tetrabutylammonium bromide (16 mg, 0.05 mmol) and ethylene carbonate (62 mg, 0.71 mmol). The mixture was heated at 140° C. under Argon for 4 hours. The reaction was cooled to room temperature and the solvent was removed under reduced pressure. The residue was dissolved in EtOAc and washed with brine, dried (Na$_2$SO$_4$) and concentrated to provide the title compound as yellow oil. The resulting product had the following properties: $^1$H NMR: 300 MHz spectrum consistent with proposed structure.

Analysis Calculated for C$_{13}$H$_{14}$O$_2$S 0.7H$_2$O: Calc: C, 63.23; H, 6.29. Found: C, 63.20; H, 5.83. M$^+$=234

The compounds exemplified in the following Table were prepared essentially as described in Example 148, except that the phenol of example 18 was replaced with the corresponding phenol designated in the Table.

To a solution of the product from Example 48 (2.04 g, 10 mmol) in 25 mL DMF was added t-butyl bromoacetate (1.9 mL, 11.8 mmol) and catalytic n-Bu$_4$NI, followed by 60% NaH dispersion in oil (0.48 g, 12 mmol). The mixture was heated at 60° C. for 3.5 hours and cooled. The mixture was poured into ether and water and the ether layer separated, washed with brine, dried over Na$_2$SO$_4$ and concentrated. Flash chromatography on silica using 20:1 hexane/EtOAc to provide the title compound (2.84 g, 89%) as a colorless oil.

Anal. calc'd for C$_{18}$H$_{19}$FO$_4$: Calculated: C, 67.91; H, 6.02. Found: C, 67.67; H, 6.18.

TABLE 9

| Ex. No. | Compound | Starting Phenol | Analysis |
|---|---|---|---|
| 149 |  | Ex. 19 | C$_{13}$H$_{14}$O$_2$S<br>Calc: C, 66.64; H, 6.02.<br>Found: C, 66.26; H, 6.16.<br>M$^+$ = 234 |
| 150 | 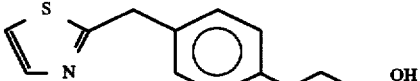 | Ex. 20 | Compound was fully characterized in the next step. See Example No. 231. |
| 151 | 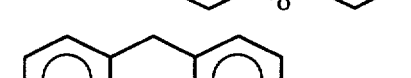 | Ex. 21 | C$_{16}$H$_{18}$O$_3$<br>Calc: C, 74.40; H, 7.02<br>Found: C, 73.97; H, 6.65<br>M$^+$ = 258 |
| 152 | 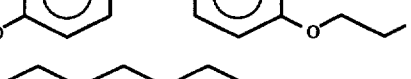 | Ex. 22 | Compound was fully characterized in the next step. See Example No. 233. |
| 153 |  | Ex. 24 | Compound was fully characterized in the next step. See Example No. 236. |
| 154 | 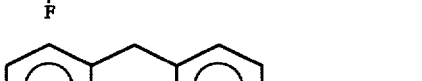 | Ex. 29 | Compound was fully characterized in the next step. See Example No. 234. |
| 155 |  | Ex. 25 | Compound was fully characterized in the next step. See Example No. 235. |
| 156 | 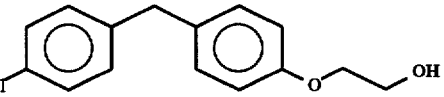 | Ex. 23 | Compound was fully characterized in the next step. See Example No. 314. |

EXAMPLE 157

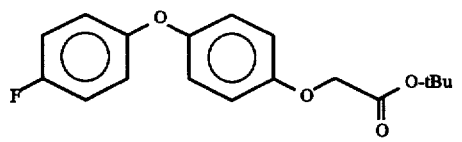

TABLE 10

| Ex. No. | Compound | Starting Phenol | Analysis |
|---|---|---|---|
| 158 | [structure: 4-benzyl-phenyl-O-CH2-C(=O)-O-tBu] | 4-hydroxy-diphenylmethane | NMR spectrum consistant with proposed structure. |
| 159 | [structure: phenyl-O-phenyl-O-CH2-C(=O)-OtBu] | 4-phenoxyphenol | NMR spectrum consistant with proposed structure. |
| 160 | [structure: benzyl-O-phenyl-O-CH2-C(=O)-OtBu] | 4-(benzyloxy)phenol | $C_{18}H_{20}O_4$: Calc: C, 72.59; H, 7.05. Found: C, 72.28; H, 7.18. |

EXAMPLE 161

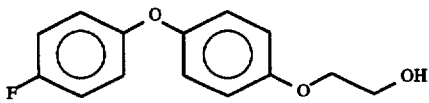

To a solution of the product from Example 157 (2.7 g, 8.48 mmol) in THF (50 mL) was added solid LAH (0.38 g, 10 mmol) in portions and the mixture stirred at 25° C. for 30 minutes. The mixture was poured into EtOAc and water and the EtOAc layer separated, washed with brine, dried over $Na_2SO_4$ and concentrated to provide the title compound (2.08 g, 99%) as a white solid: mp 78°–79° C.;

Anal. calc'd for $C_{14}H_{13}FO_3 \cdot 0.2\ H_2O$: Calculated: C, 66.77; H, 5.36. Found: C, 66.97; H, 5.38.

To a stirred solution of 4-hydroxy-diphenylmethane (20 g, Aldrich) in $CH_2Cl_2$ (100 mL) was added 50% aqueous solution of NaOH (50 mL) followed by allyl bromide (15 mL, Aldrich) and tetraethylammonium bromide (1 g), After 16 hours, the layers were separated. The aqueous phase was extracted with ether. The combined organic extract was dried over $MgSO_4$ and distilled to give 4-allyloxy-diphenylmethane (16 g). B.p. 130°–135° C./1 mm. This product (16 g) was heated to 230° C. for 8 hours. After cooling, the resulting product was taken-up in $CHCl_3$ (500 mL). The solution was stirred and cooled to 0° C. To this was added 3-chloroperoxybenzoic acid (16 g, 80–85%, Aldrich) suspended in $CHCl_3$ (100 mL). After 2 hours, the mixture was filtered through celite and the filtrate washed with saturated $NaHCO_3$ solution. The organic extract was dried over $MgSO_4$, and heated to reflux with 1-methyl-morpholine (10 mL) for 15 minutes. The mixture was concentrated and the residue chromatographed over silica gel using 30% ethyl acetate in hexane to give the title product (10 g) as a colourless thick oil.

TABLE 11

| Ex. No. | Compound | Starting tBu Ester | Analysis |
|---|---|---|---|
| 162 | [structure: benzyl-phenyl-O-CH2CH2-OH] | Ex. 158 | NMR spectrum consistent per the proposed structure |
| 163 | [structure: phenyl-O-phenyl-O-CH2CH2-OH] | Ex. 159 | NMR spectrum consistent per the proposed structure |
| 164 | [structure: benzyl-O-phenyl-O-CH2CH2-OH] | Ex. 160 | $C_{16}H_{10}O_3 \cdot 0.15\ H_2O$: Calc: C, 72.94; H, 6.65. Found: C, 72.92; H, 6.58. |

EXAMPLE 165

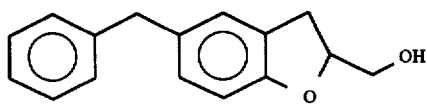

EXAMPLE 166

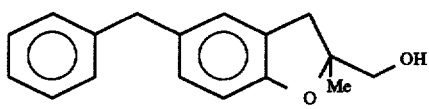

To a stirred solution of 4-hydroxy-diphenylmethane (25 g, Aldrich) in $CH_2Cl_2$ (200 mL) was added 50% aqueous solution of NaOH (50 mL) followed by 3-chloro-2-methylpropene (50 mL, Aldrich) and tetrabutylammonium bromide (1 g). After 16 hours, the layers were separated. The aqueous phase was extracted with ether. The combined organic extract was dried over $MgSO_4$ and distilled to give 4-methallyloxy-diphenylmethane (16 g). B.p. 135° C./1 mm.

The product (8.8 g) was heated to 215°–220° C. for 8 hours. After cooling, the resulting product was chromatgraphed over silica gel using 6% ethyl acetate in hexane to give the corresponding rearranged product (8 g). This material was taken-up in $CHCl_3$ (500 mL). The solution was stirred and cooled to 0° C. To this was added $Na_2CO_3$ (4 g) and 3-chloroperoxybenzoic acid (9 g, 80–85%, Aldrich) suspended in $CHCl_3$ (100 mL). After 4.5 hours, the mixture was filtered through celite and the filtrate washed with 5% aqueous $Na_2CO_3$ solution. The organic extract was dried over $MgSO_4$ and concentrated to 100 mL. To this solution was added para-toluenesulphonic acid (0.5 g) and the mixture let stand at room temperature for 16 hours. The solution was then concentrated and the residue chromatographed over silica gel using 30% ethyl acetate in hexane to give the title product (10 g) as a colorless thick oil.

EXAMPLE 167

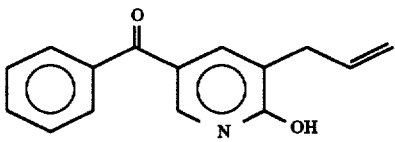

A 60% mineral oil suspension of sodium hydride (1.9 g) was washed with hexane and suspended in THF (200 mL) at −78° C. To this stirred solution was added allyl alcohol (3 mL). After 1 hour, the product of Example 73 was added in one lot and the mixture stirred for 16 hours. Then allyl alcohol (5 mL) was added and the mixture refluxed for 0.25 hours. The mixture was cooled, washed with water, dried over $MgSO_4$ and concentrated to give a thick liquid. A solution of this material in diphenylether (20 ml) was heated to reflux for 5 hours. The mixture was cooled and chromatographed over silica gel using 80–100% ethyl acetate in hexane to give the title product (1.8 g) as a white solid.

EXAMPLE 168

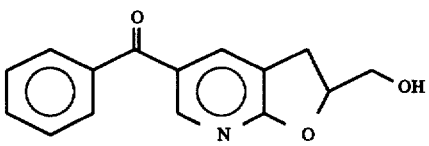

To a stirred solution of the product of Example-167 (1.1 g) in $CHCl_3$ (20 mL) at 0° C. was added 3-chloroperoxybenzoic acid (1.5 g, 50–60%, Aldrich) suspended in $CHCl_3$ (5 mL). After 2 hours, 3-chloroperoxybenzoic acid (0.5 g, 80–85%, Aldrich) was added to the reaction mixture. After 4 hours, the mixture was allowed to warm to room temperature over 1 hr. The mixture was washed with 5% aqueous $K_2CO_3$ solution, dried over $MgSO_4$ and concentrated. The residue was chromatographed over silica gel using 50% ethyl acetate in hexane as eluant to give a mixture of an epoxide and the title product. This mixture in ethyl acetate (20 mL) was allowed to stand at room temperature with para-toluenesulfonic acid (20 mg) for 16 hours. The solution was washed with water, dried over $MgSO_4$ and concentrated to give the title product as a white solid (0.85 g).

EXAMPLE 169

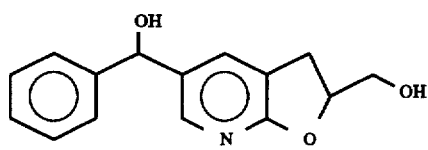

To a stirred solution of the product of Example 168 (0.8 g) in THF (50 mL) was added sodium borohydride (0.4 g) and the mixture refluxed for 1 hour. The mixture was treated with saturated aqueous $NH_4Cl$ with caution and extracted with ethyl acetate. The organic phase was washed with water, dried over $MgSO_4$ to give the title product as a colorless solid.

EXAMPLE 170

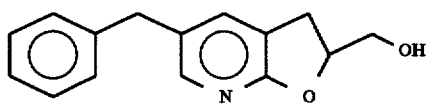

The product of Example 169 was hydrogenated in a parr apparatus in a mixture of ethyl acetate and acetic acid over 5% Pd on carbon under 5 psi hydrogen atmosphere at room temperature for 3 hours. The reaction mixture was filtered and the filtrate concentrated. The residue was chromatographed over silica gel using ethyl acetate as eluant to give the title product as a colorless solid (0.3 g).

EXAMPLE 171

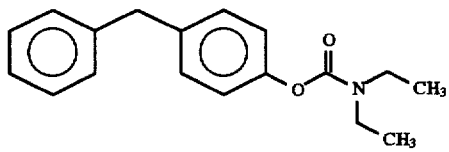

A 35% mineral oil suspension of potassium hydride (12 g) was washed with hexane and suspended in THF (150 mL) at −78° C. The mixture was stirred and 4-hydroxydiphenylmethane (18.5 g) was added as solid in several portions over 0.5 hours. The mixture was allowed to warm to 0° C. over 2 hours and cooled back to −78° C. To this was added diethylcarbamoylchloride (13.6 g, Aldrich) over 0.25 hours and the mixture allowed to warm to room temperature over 16 hours. The mixture was refluxed for 0.5 hours and cooled in ice. To this was added water and the organic phase was dried over $MgSO_4$ and distilled to give the title product as a colorless liquid. B.p. 170°–175° C./0.05 mm.

EXAMPLE 172

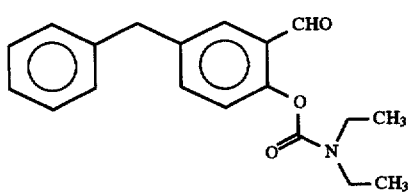

To a stirred solution the product of Example 171 (5.085 g) in ether (150 mL) and tetramethylethylene-diamine (3 mL) at −78° C. was added a 1.3 molar solution of sec.butyl lithium in cyclohexane (16 mL). After 1 hour, dimethylforamide (1.45 mL) was added. After 2 hours, saturated aqueous $NH_4Cl$ was added and the layers separated. The organic phase was dried over $MgSO_4$ and concentrated. The residue was chromatographed over silica gel using 20% ethyl acetate in hexane to to give the title product as thick oil (5.1 g).

EXAMPLE 173

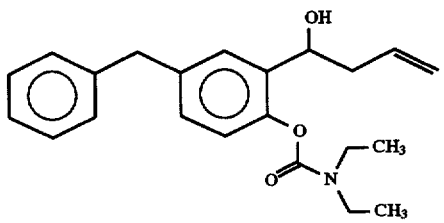

The product of Example 172 was taken-up in ether (125 mL) and the solution cooled to −78° C. To this stirred solution was added a 1N ether solution of allylmagnesium bromide (16 mL). After 10 minutes, the mixture was warmed to 0° C. and quenched carefully with saturated aqueous $NH_4Cl$. The layers were separated and the organic phase was dried over $MgSO_4$ and concentrated. The residue was chromatographed over silica gel using 20% to 30% ethyl acetate in hexane to give the title product as a thick gum (3.9 g).

EXAMPLE 174

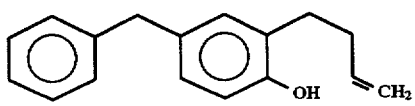

To a stirred solution of the product of Example 173 (1.24 g) in THF (30 mL) at 0° C. was added sulfur trioxide-pyridine complex (0.812 g, Aldrich). After 0.5 hours, the mixture was allowed to stand at 4° C. for 16 hours. Then the mixture was stirred at 0° C. for 4 hours and cooled to −78° C. To this mixture was added lithium aluminium hydride (1 g) in one lot. The mixture was allowed to warmed to 0° C. over 1 hour, then to room temperature over 3 hours. To this was added, carefully, water and then excess of 1N HCl. The mixture was extracted with ether. The combined organic extract was dried and concentrated to give the title product as a thick gum (0.38 g).

EXAMPLE 175

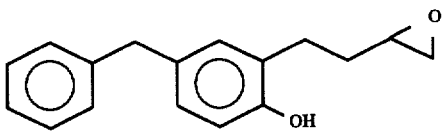

To a stirred solution of the product of Example-174 (0.38 g) in $CHCl_3$ (5 mL) at 0° C. was added 3-chloroperoxybenzoic acid (0.38 g, 80–85%, Aldrich) suspended in $CHCl_3$ (3 mL). After 1 hour 3-chloroperoxybenzoic acid (0.38 g, 80–85%, Aldrich) was added. After 1 hour, the mixture was washed with saturated $NaHCO_3$. The organic phase was dried by gravity filtration and concentrated. The residue was chromatographed over silica gel using 20% ethyl acetate in hexane to give the title product as a colorless gum (0.18 g).

EXAMPLE 176

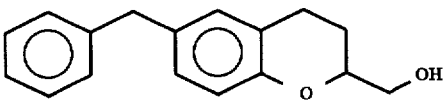

A solution of the product of Example 175 (0.18 g) and para-toluenesulphonic acid (5 mg) in $CHCl_3$ (5 mL) was allowed to stand at room temperature for 16 hours. The solution was washed with water and dried over $MgSO_4$ to give the title product as a thick gum.

EXAMPLE 177

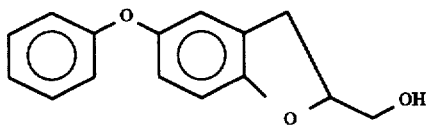

The procedure of Example 166 was repeated using 4-phenoxyphenol (Aldrich) and allyl bromide in the place of 4-hydroxy-diphenylmethane and 3-chloro-2-methylpropane respectively to obtain the title compound as a thick liquid.

EXAMPLE 178

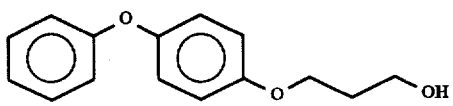

4-Phenoxyphenol (4.66 g, 25 mmol), 3-chloro-1-propanol (2.51 g, 26.5 mmol), and tetrabutylammonium iodide (82 mg, 0.22 mmol) were dissolved in 50 mL DMF. Sodium hydride (1.33 g, 33.2 mmol, 60% dispersion in mineral oil) was added slowly to the reaction mixture which was stirred at 60° C. for 12 hours. The reaction was poured into 400 mL water and extracted with 4×150 mL ethyl acetate. The combined organic phases were dried ($MgSO_4$), filtered and concentrated to afford a brown oil. The crude oil was chromatographed (silica gel, 20% ethyl acetate/hexane) to give the pure product as white crystals (3.58 g, 59%). The product had the following properties: Anal. calcd for $C_{15}H_{16}O_3$: C, 73.75; H, 6.60. Found C, 73.36: H, 6.65.

EXAMPLE 179

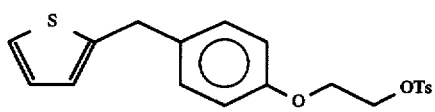

The alcohol of example 148 (90 mg, 0.38 mmols) was dissolved in a mixture of CH$_2$Cl$_2$ (2 mL) and pyridine. The solution was cooled to 0° under Argon, and then p-toluenesulfonyl chloride (87 mg, 0.46 mmol) followed by DMAP (3 mg) were added to the mixture. The reaction mixture was stirred at 0° C. for 0.5 hours, and then warmed up to room temperature and stirred for 16 hours. The solvent was removed under reduced pressure. The residue was dissolved in ether, washed with saturated KHSO$_4$ and brine, dried (Na$_2$SO$_4$) and filtered. The filtrate was concentrated to give 120 mg of the title compound as yellow oil.

The compounds in Table 12 were made in an analogous manner. The resulting product was fully characterized in the next step. See Example No. 229.

TABLE 12

| Ex. No. | Compound | Starting Alcohol | Analysis |
|---|---|---|---|
| 180 | 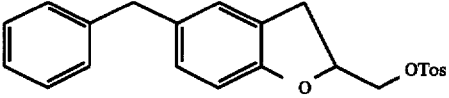 | Ex. 165 | Compound was characterized by NMR and structure confirmed by the analysis of compound of Example 282 |
| 181 | 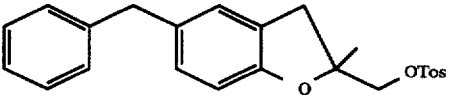 | Ex. 166 | Compound was characterized by NMR and structure confirmed by the analysis of compound of Example 285 |
| 182 | 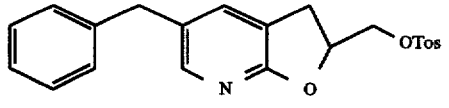 | Ex. 170 | Compound was characterized by NMR and structure confirmed by the analysis of compound of Example 287 |
| 183 | 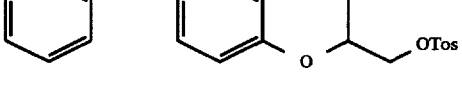 | Ex. 176 | Compound was characterized by NMR and structure confirmed by the analysis of compound of Example 293 |
| 184 | 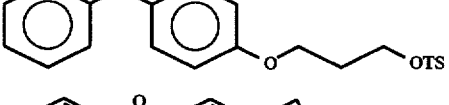 | Ex. 178 | Compound was characterized by NMR and structure confirmed by the analysis of compound of Example 350 |
| 185 | 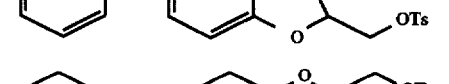 | Ex. 177 | Compound was characterized by NMR and structure confirmed by the analysis of compound of Example 291 |
| 186 | 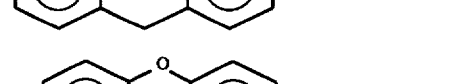 | Ex. 162 | Compound was fully characterized in the next step. See Example No. 238. |
| 187 | 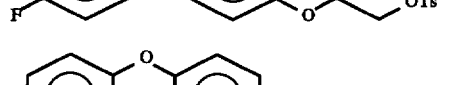 | Ex. 161 | C$_{21}$H$_{19}$SFO$_6$: Calc: C, 62.68; H, 4.76. Found: C, 62.73; H, 4.85. |
| 188 | 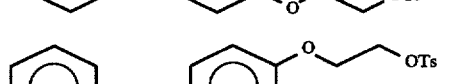 | Ex. 163 | Compound was fully characterized in the next step. See Example No. 252. |
| 189 | 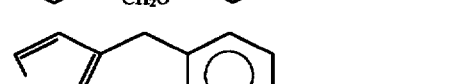 | Ex. 164 | Compound was fully characterized in the next step. See Example No. 198. |
| 190 |  | Ex. 149 | Compound was fully characterized in the next step. See Example No. 230. |

TABLE 12-continued

| Ex. No. | Compound | Starting Alcohol | Analysis |
|---|---|---|---|
| 191 | (thiazole-CH2-C6H4-O-CH2CH2-OTs) | Ex. 150 | Compound was fully characterized in the next step. See Example No. 231. |
| 192 | (4-MeO-C6H4-CH2-C6H4-O-CH2CH2-OTs) | Ex. 151 | Compound was fully characterized in the next step. See Example No. 232. |
| 193 | (3-F-C6H4-CH2-C6H4-O-CH2CH2-OTs) | Ex. 152 | Compound was fully characterized in the next step. See Example No. 233. |
| 194 | (4-Cl-C6H4-CH2-C6H4-O-CH2CH2-OTs) | Ex. 154 | $C_{21}H_{19}SFO_5$: Calc: C, 62.68; H, 4.76. Found: C, 62.73; H, 4.85. |
| 195 | (4-F-C6H4-CH2-C6H4-O-CH2CH2-OTs) | Ex. 163 | Compound was fully characterized in the next step. See Example No. 235. |
| 196 | (pyridyl-CH2-C6H4-O-CH2CH2-OTs) | Ex. 153 | Compound was fully characterized in the next step. See Example No. 236. |
| 197 | (3-F-4-MeO-C6H3-CH2-C6H4-O-CH2CH2-OTs) | Ex. 88 | Compound was fully characterized in the next step. See Example No. 314. |

EXAMPLE 198

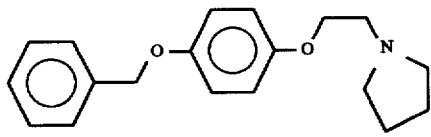

4-(Benzyloxy)phenol (0.41 g, 2.05 mmol), 1-(2-chloroethyl)pyrrolidine hydrochloride (0.36 g, 2.1 mmol) and powdered potassium carbonate (1.09g, 7.9 mmol) were stirred in 23 mL of N,N-dimethylformamide at 80° C. for 12 hours. The reaction was cooled to room temperature and poured into 300 mL water. The aqueous phase was extracted with 4×50 mL ethyl acetate. The combined organic washes were dried (NaSO4), filtered, and concentrated to afford 0.43 g amber oil. The crude product was chromatographed (silica gel, 20% methanol/heptane) to give the pure product (0.39 g, 64%) as a pale yellow solid. The product had the following properties:

Analysis calculated for $C_{19}H_{23}NO_2 \cdot 0.10 \; H_2O$: Calc: C, 76.27; H, 7.82; N, 4.68. Found: C, 76.09; H, 7.80; N, 4.62.

EXAMPLE 199

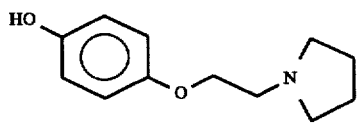

The product from Example 198 (2.78 g, 9.3 mmol) was dissolved in 35 mL THF in a Parr Shaker apparatus. A catalytic amount of 4% Pd/C was added, and the reaction was run under 60 p.s.i. of $H_2$ at room temperature for 23 hours. The reaction was filtered through Celite and concentrated to afford the product (1.49 g, 78%) as yellow crystals. The product had the following properties: mp 113°–115°.

Analysis calculated for $C_{12}H_{17}NO_2 \cdot 0.25H_2O$: Calc: C, 68.06; H, 8.33; N, 6.61. Found: C, 68.16; H, 8.06; N, 6.55.

EXAMPLE 200

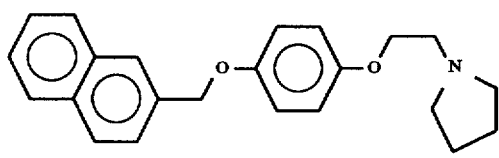

2-(Bromomethyl)naphthalene (0.36g, 1.6 mmol), the phenol from Example 199 (0.33 g, 1.6 mmol) and powdered potassium carbonate (0.52, 3.8 mmol) were stirred in 15 mL DMF at 80° for 12 hours. The reaction was cooled to room temperature and poured into 200 mL water. The aqueous phase was extracted with 4×30 mL ethyl acetate. The combined organic washes were dried (NaSO$_4$), filtered, and concentrated to afford a tan solid which was recrystallized from ethyl acetate/hexane to give the pure product (67 mg, 12%). The product had the following properties:

H.R.M.S. M$^+$ calculated for $C_{23}H_{25}NO_2$: Calc: 347.1886. Found: 347.1856.

The compounds exemplified in the following Table were prepared essentially as described in Example 200 except that 2-(Bromoethyl)naphthalene was replaced by the designated Ar$^1$ Precursor.

TABLE 13

| Ex. No. | Compound | Ar$^1$ Precursor | Chrom. | Analysis |
|---|---|---|---|---|
| 201 | | 2-(chloromethyl)-quinoline monohydrochloride | silica gel, methanol/ methylene chloride/ ammonium hydroxide 2/97/1 | $C_{22}H_{24}N_2O_2 \cdot 0.75\,H_2O$: Calc: C, 73.00; H, 7.10; N, 7.74. Found: C, 73.08; H. 7.12; N, 7.56. |
| 202 | | 4-(chloromethyl)-2-methylthiazole hydrochloride | silica gel, methanol/ methylene chloride/ ammonium hydroxide 2/97/1 | $C_{17}H_{22}N_2O_2S \cdot 0.30\,H_2O$: Calc: C, 63.05; H, 7.03; N, 8.65. Found: C, 63.09; H, 7.12; N, 8.63. |
| 203 | | 4-bromobenzyl bromide | 80% ethyl acetate/hexane/ trace triethylamine | $C_{19}H_{22}NO_2Br \cdot 0.25\,H_2O$: Calc: C, 59.92; H, 5.96; N, 3.68. Found: C, 59.92; H, 5.76; N, 3.68. |
| 204 | | 2,6-dichlorobenzyl bromide | 5% methanol/ ethyl acetate/ trace triethylamine | $C_{19}H_{21}NO_2Cl_2$: Calc: C, 62.30; H, 5.78; N, 3.82. Found: C, 61.99; H, 5.57; N, 3.79. |
| 205 | | 4-Fluorobenzyl chloride | 5% methanol/ ethyl acetate/ trace triethylamine | $C_{19}H_{22}NO_2F \cdot 0.10\,H2O$: Calc: C, 71.74; H, 7.07; N, 4.40. Found: C, 71.70; H, 7.01; N, 4.35. |
| 206 | | 3-Chlorobenzyl chloride | silica gel, 70% ethyl acetate/ hexane/trace triethylamine | $C_{19}H_{22}NO_2Cl$: Calc: C, 68.77; H, 6.68; N, 4.22. Found: C, 68.57; H, 6.60; N, 4.15. |
| 207 | | 2-Fluorobenzyl chloride | 5% methanol/ ethyl acetate/ trace triethylamine | $C_{19}H_{22}NO_2F \cdot 0.60\,H_2O$: Calc: C, 69.96; H, 7.17; N, 4.29. Found: C, 69.98; H, 6.97; N, 4.23. |

TABLE 13-continued

| Ex. No. | Compound | Ar¹ Precursor | Chrom. | Analysis |
|---|---|---|---|---|
| 208 | | 2-Chlorobenzyl chloride | 5% methanol/ ethyl acetate/ trace triethyl- amine | $C_{19}H_{22}NO_2Cl.0.25\ H_2O$: Calc: C, 67.85; H, 6.74; N, 4.16. Found: C, 67.98; H, 6.68; N, 4.16. |
| 209 | | α'-Chloro-α,α,α- trifluoro-m-xylene | 10% methanol/ ethyl acetate/ trace triethyl- amine | $C_{20}H_{22}NO_2F_3$: Calc: C, 65.74; H, 6.07; N, 3.83. Found: C, 65.45; H, 6.04; N, 3.56. |
| 210 | | α-bromo-o-xylene | 5% methanol/ ethyl acetate/ trace triethyl- amine | $C_{20}H_{26}NO_2.0.60\ H_2O$: Calc: C, 74.55; H, 8.20; N, 4.35. Found: C, 74.51; H, 8.18; N, 4.87. |
| 211 | | 3-Fluorobenzyl chloride | ethanol/methyl- ene chloride/ ammonium hy- droxide 5/94/1 | $C_{19}H_{23}NO_2F.0.20\ H_2O$: Calc: C, 71.54; H, 7.08; N, 4.39. Found: C, 71.63; H, 7.19; N, 4.34. |
| 212 | | α-chloro-p-xylene | ethanol/methyl- ene chloride/ ammonium hy- droxide 1/98/1 | $C_{20}H_{26}NO_2.0.15\ H_2O$: Calc: C, 76.47; H, 8.12; N, 4.46. Found: C, 76.48; H, 8.22; N, 4.38. |
| 213 | | 4-Methoxybenzyl chloride | ethanol/methyl- ene chloride/ ammonium hy- droxide 2.5/97/ 0.5) | $C_{20}H_{25}NO_3.0.85\ H_2O$: Calc: C, 70.09; H, 7.85; N, 4.09. Found: C, 70.07; H, 7.47; N, 4.04. |
| 214 | | 1-(chloromethyl)- naphthalene | ethanol/methyl- ene chloride/ ammonium hy- droxide 5/94/1) | $C_{23}H_{26}NO_2.0.15\ H_2O$: Calc: C, 78.89; H, 7.28; N, 4.00. Found: C, 78.89; H, 7.37; N, 3.90. |

EXAMPLE 215

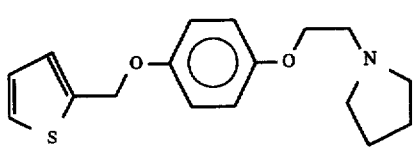

2-Thiophenemethanol (4.18 g, 36.6 mmol), tosyl chloride (7.09 g, 37.2 mmol) and pyridine (3 mL, 37.1 mmol) were stirred in 100 mL methylene chloride at RT for 12 hours. The reaction was poured into 200 mL water. The phases were separated, and the organic phase was washed with 2×200 mL 10% HCl, 2×200 mL water, and dried ($Na_2SO_4$). The resultant crude tosylate (1.05 g, 3.9 mmol) was reacted with the phenol from Example 199 (0.34 g, 1.7 mmol) and sodium hydride (0.11 g, 2.8 mmol, 60% dispersion in mineral oil) in 25 mL DMF at RT overnight. The reaction was poured into 100 mL water and washed with 4×50 mL ethyl acetate. The organic phases were dried ($Na_2SO_4$) and concentrated to afford an amber oil. The crude product was chromatographed (silica gel, ethanol/methylene chloride/ammonium hydroxide 5/94/1) to give an amber oil. The product had the following properties:

Analysis calculated for $C_{17}H_{21}NO_2S \cdot 0.15\ H_2O$: Calc: C, 66.70; H, 7.01; N, 4.58. Found: C, 66.72; H, 6.94; N, 4.47.

EXAMPLE 216

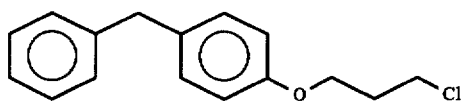

4-Hydroxydiphenyl methane (Aldrich) 1.84 g in 50 ml dimethylformamide (DMF) was added sodium hydride (60% dispersion in mineral oil) 0.5 g (Aldrich) portionwise at R.T. during 15 min. The reaction mixture was stirred for ½ hr and 1.57 g of 1-bromo-3-chloro propane (Aldrich) in 10 ml of DMF was added dropwise during 10 min and the mixture was stirred at room temperature overnight.

Diethyl ether 100 ml and 3 ml of water was added to the reaction mixture and the organic phase was further washed with $H_2O$ (10 ml×2), dried, filtered, the solvent removed in vacuo, and the organic material was chromatographed over silica gel using 5% EtOAc in hexane and gave the title compound as colorless thick oil 2.1 g.

TABLE 14

X' = Br, OH.   X = OTs, Cl.

| Ex. No. | Compound | Starting Phenol | Analysis |
|---|---|---|---|
| 217 | | 4-hydroxydiphenyl methane | ¹H NMR: 400 MHz<br>Compound was fully characterized in the next step. See Example No. 226. |
| 218 | | 4-phenoxyphenol | ¹H NMR: 300 MHz<br>Compound was fully characterized in the next step. See Example No. 250. |
| 219 | | 4-phenoxyphenol | ¹H NMR: 300 MHz |
| 220 | | Ex. 19 | M⁺ = 266. |
| 221 | | Ex. 18 | Compound was fully characterized in the next step. See Example No. 327. |
| 222 | | Ex. 25 | M⁺ = 278. |
| 223 | | Ex. 24 | M⁺ = 261. |
| 224 | | Ex. 41 | NMR spectrum consistent with proposed structure. |

EXAMPLE 225 (METHOD A)

Methyl 1-[2-[4-(phenylmethyl)phenoxy]ethyl]-2S-pyrrolidine-2-carboxylate, monohydrochloride, hydrate

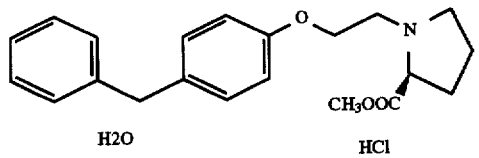

H2O      HCl

To a stirred solution of 165 mg of L-proline methyl ester hydrochloride in 5 ml of N,N-dimethylformamide was added 500 mg of powdered potassium carbonate and the mixture was stirred under a nitrogen atmosphere at room temperature for 10 minutes. 382 mg of the compound of example 186 was added to the mixture and was heated to 65° and stirred under a nitrogen atmosphere for 4 hrs. The mixture was cooled to room temperature and the solvent was removed by evaporation under reduced pressure to give crude oily gum, which was extracted with ethyl acetate and was washed with water, dried over sodium sulfate and concentrated in vacuo to give crude product which was chromatographed on silica using 75% toluene, 25% ethyl acetate as mobile phase to yield 180 mg of oily gum which was converted into its HCl salt using 6N HCl: Dioxane and crystallization from ether gave 158 mg of the title compound as white crystalline solid.

Analysis Calculated for $C_{21}H_{25}NO_3HCl \cdot H_2O$: Calculated: C, 64.03; H, 7.16; N, 3.56. Found: C, 63.76; H, 7.14; N, 3.51.

EXAMPLE 226 (METHOD B)

Preparation of 1-[3-[4-(phenylmethyl)phenoxy]propyl]-4-piperidinecarboxamide

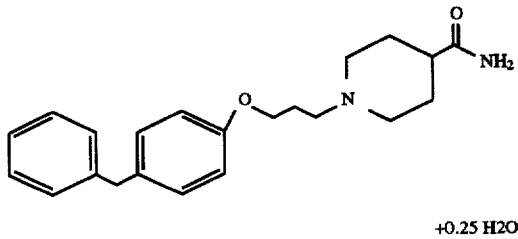

+0.25 H2O

To a stirred solution of 260.5 mg of the compound of example 216 in 5 ml of N,N-dimethylformamide was added 300 mg of powdered $K_2CO_3$ and was stirred under nitrogen atmosphere for 10 minutes. 150 mg of isonipecotamide was added to the mixture and it was heated to 65° C. and was stirred at 65° C. under nitrogen atmosphere for 4 hours. The mixture was cooled to room temperature and solvent was removed by evaporation under reduced pressure to give crude oily gum which was dissolved in ethyl acetate and was washed with water, dried over sodium sulfate and concentrated in vacuo to give crude product, which upon crystallization from diethyl ether gave the title compound.

Analysis Calculated $C_{22}H_{28}N_2O_2 \cdot ¼ H_2O$: Calculated: C, 74.02; H, 8.05; N, 7.85 Found: C, 73.98; H, 8.19; N, 7.72

EXAMPLE 227 (METHOD C)

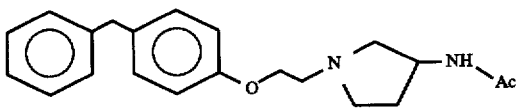

To a stirred suspension of 3-acetamido pyrrolidine (260 mg,) and potassium carbonate (700 mg, finely divided) in DMF (15 ml), Tosylate of example 186 (700 mg) was added. The reaction mixture was heated at 60° C. for 10 hours, evaporated and the residue partitioned between ethyl acetate and sat potassium carbonate solution. The ethyl acetate layer was separated, dried ($Na_2SO_4$) and evaporated to afford a yellow oil that was further purified by radial chromatography on silica (eluant; methylene chloride/ethanol, 97/3) to yield a clear oil (400 mg).

The resulting oil was further purified by crystallization as its HCl salt (ethanol/diethyl ether) to afford the title compound (400 mg).

Analysis Calculated for $C_{21}H_{26}N_2O_2 \cdot 1HCl$: Calculated: C, 67.28; H, 7.26; N, 7.47. Found: C, 67.47; H, 7.97; N, 6.88.

EXAMPLE 228 (METHOD D)

Phenylmethyl 1-[3-[4-(phenylmethyl)phenoxy]propyl]-L-prolinate

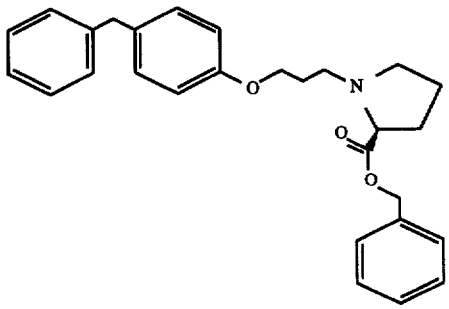

To product of example 216 (0.27 g) and 240 mg L-proline benzyl ester hydrochloride in 5 ml DMF was added powdered $K_2CO_3$ 280 mg, sodium iodide 50 mg. The reaction mixture was heated at 80° overnight under nitrogen.

It was then cooled to room temperature and 50 ml of ether and 3 ml of water were added. The organic phase was further washed with water (10 ml×2) and dried. It was filtered and solvent was removed under vacuo. The residue was chromatographed over silica gel using 10:90:1 EtOAc: hexane: $Et_3N$ to give the title compound as colorless oil. 0.32 g was obtained.

Analysis for $C_{28}H_3NO_3$: Calculated: C, 78.29; H, 7.27; N, 3.26. Found: C, 78.42; H, 7.15; N, 3.10.

REACTION

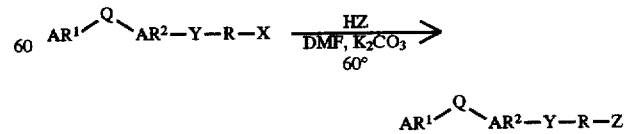

X = OTs, Cl or Br

TABLE 15

| Ex. No. | AR¹ Q AR² Y R Z | ZH | Method/ Prep | Isol'n/ Chrom. | Analysis |
|---|---|---|---|---|---|
| 229 | 4-(2-(thiophen-2-ylmethyl)phenoxy)ethyl-piperidine-4-carboxamide | 4-CONH₂-piperidine-NH | A | A | $C_{19}H_{24}N_2O_2S \cdot 0.3H_2O$: Calc: C, 65.22; H, 7.09; N, 8.01. Found: C, 65.30; H, 6.99; N, 7.92. |
| 230 | 4-(2-(thiophen-3-ylmethyl)phenoxy)ethyl-piperidine-4-carboxamide | 4-CONH₂-piperidine-NH | A | A | $C_{19}H_{24}N_2O_2S$: Calc: C, 66.25; H, 7.02; N, 8.13. Found: C, 65.91; H, 7.04; N, 8.03. |
| 231 | 4-(2-(thiazol-2-ylmethyl)phenoxy)ethyl-piperidine-4-carboxamide | 4-CONH₂-piperidine-NH | A | A | $C_{18}H_{23}N_3O_2S \cdot 1.2H_2O$: Calc: C, 58.90; H, 6.97; N, 11.45. Found: C, 58.78; H, 6.87; N, 11.38. |
| 232 | 4-(2-(4-methoxybenzyl)phenoxy)ethyl-piperidine-4-carboxamide | 4-CONH₂-piperidine-NH | A | A | $C_{22}H_{28}N_2O_3 \cdot 0.3H_2O$: Calc: C, 70.68; H, 7.71; N, 7.49. Found: C, 70.70; H, 7.16; N, 7.34. |
| 233 | 4-(2-(3-fluorobenzyl)phenoxy)ethyl-piperidine-4-carboxamide | 4-CONH₂-piperidine-NH | A | A | $C_{21}H_{25}FN_2O_2$: Calc: C, 70.76; H, 7.07; N, 7.86. Found: C, 70.52; H, 6.96; N, 7.66. M⁺ = 356. |

TABLE 15-continued

| Ex. No. | AR¹ Q AR² Y R Z | ZH | Method/ Prep | Isol'n/ Chrom. | Analysis |
|---|---|---|---|---|---|
| 234 | 4-Cl-C₆H₄-CH₂-C₆H₄-O-(CH₂)₂-N(piperidine-4-CONH₂) | CONH₂-piperidine(NH) | A | A | C₂₁H₂₅ClN₂O₂·0.2H₂O: Calc: C, 66.99; H, 6.80; N, 7.44. Found: C, 66.77; H, 6.61; N, 7.33. M⁺ = 372. |
| 235 | 4-F-C₆H₄-CH₂-C₆H₄-O-(CH₂)₂-N(piperidine-4-CONH₂) | CONH₂-piperidine(NH) | A | A | C₂₁H₂₅FN₂O₂·0.2H₂O: Calc: C, 70.06; H, 7.11; N, 7.78. Found: C, 70.17; H, 7.35; N, 7.78. M⁺ = 356. |
| 236 | pyridyl-CH₂-C₆H₄-O-(CH₂)₂-N(piperidine-4-CONH₂) | CONH₂-piperidine(NH) | A | A | C₂₀H₂₅N₃O₂·0.2H₂O: Calc: C, 70.03; H, 7.46; N, 12.25. Found: C, 69.82; H, 7.43; N, 12.18. M⁺ = 339. |
| 237 | C₆H₅-CH₂-C₆H₄-O-(CH₂)₂-N(pyrrolidine-2-CO₂Me) | CO₂Me-pyrrolidine(NH) | A | B | C₂₁H₂₅NO₃·HCl·H₂O: Calc: C, 64.03; H, 7.16; N, 3.56. Found: C, 63.76; H, 7.14; N, 3.51. |
| 238 | C₆H₅-CH₂-C₆H₄-O-(CH₂)₂-N(piperidine-4-NHAc) | NHAc-piperidine(NH) | A | B | C₂₂H₂₈N₂O₂: Calc: C, 74.97; H, 8.01; N, 7.95. Found: C, 74.66; H, 7.66; N, 7.82. |
| 239 | pyridyl-CH₂-C₆H₄-O-(CH₂)₂-N(piperidine-4-CONH₂) | CONH₂-piperidine(NH) | A | B | C₂₁H₂₆N₂O₂: Calc: C, 74.53; H, 7.74; N, 8.28. Found: C, 74.18; H, 7.88; N, 8.25. |

TABLE 15-continued

| Ex. No. | AR¹ Q AR² Y R Z | ZH | Method/ Prep | Isol'n/ Chrom. | Analysis |
|---|---|---|---|---|---|
| 240 | Ph-CH₂-C₆H₄-O-(CH₂)₂-NH-cyclohexyl | NH₂-cyclohexyl | A | B | $C_{21}H_{31}NO\cdot HCl$: Calc: C, 72.91; H, 8.16; N, 4.05. Found: C, 72.60; H, 8.30; N, 4.07. |
| 241 | Ph-CH₂-C₆H₄-O-(CH₂)₂-NH-cyclopentyl | NH₂-cyclopentyl | A | B | $C_{20}H_{29}NO\cdot HCl$: Calc: C, 72.38; H, 7.98; N, 4.22. Found: C, 72.31; H, 7.94; N, 4.17. |
| 242 | Ph-CH₂-C₆H₄-O-(CH₂)₂-N(4-CONH₂-piperidine) | 4-CONH₂-piperidine | B | C | $C_{22}H_{28}N_2O_2\cdot \frac{1}{4}H_2O$: Calc: C, 74.02; H, 8.05; N, 7.85. Found: C, 73.98; H, 8.19; N, 7.72. |
| 243 | Ph-CH₂-C₆H₄-O-(CH₂)₂-N(3-CONH₂-piperidine) | 3-CONH₂-piperidine | A | B | $C_{21}H_{26}N_2O_2$: Calc: C, 73.74; H, 7.78; N, 8.19. Found: C, 73.91; H, 7.87; N, 8.16. |
| 244 | Ph-CH₂-C₆H₄-O-(CH₂)₂-N(3-CONH₂-piperidine) | 3-CONH₂-piperidine | B | C | $C_{22}H_{28}N_2O_2$: Calc: C, 74.97; H, 8.01; N, 7.95. Found: C, 74.66; H, 8.41; N, 7.89. |
| 245 | Ph-CH₂-C₆H₄-O-(CH₂)₂-N(4-CO₂Et-piperidine) | 4-CO₂Et-piperidine | A | B | $C_{23}H_{29}NO_3\cdot HCl$: Calc: C, 68.39; H, 7.49; N, 3.47. Found: C, 68.20; H, 7.56; N, 3.49. |

TABLE 15-continued

| Ex. No. | AR¹ Q AR² Y R Z | ZH | Method/ Prep | Isol'n/ Chrom. | Analysis |
|---|---|---|---|---|---|
| 246 | (4-benzylphenoxy)(CH₂)₂-N-piperidine-4,4-dioxolane spiro | 1,4-dioxa-8-azaspiro[4.5]decane | A | B | $C_{22}H_{27}NO_3 \cdot HCl$: Calc: C, 67.77; H, 7.25; N, 3.59. Found: C, 67.52; H, 7.20; N, 3.55. |
| 247 | (4-benzylphenoxy)(CH₂)₂-N-(4-hydroxypiperidine) | 4-hydroxypiperidine | A | B | $C_{20}H_{25}NO_2 \cdot HCl$: Calc: C, 69.05; H, 7.53; N, 4.03 Found: C, 68.97; H, 7.47; N, 3.96 |
| 248 | benzofuran-2-carboxamido-piperidine-N-(CH₂)₂-O-(4-benzylphenyl) | 2-(1H-inden-2-yl)carboxamido-piperidine | A | B | $C_{29}H_{30}N_2O_3 \cdot 1/4 H_2O$: Calc: C, 75.87; H, 6.70; N, 6.10 Found: C, 75.83; H, 6.99; N, 6.14 |
| 249 | 4-(ethoxycarbonylethylcarbamoyl)piperidine-N-(CH₂)₂-O-(4-benzylphenyl) | Ex. 482 | A | B | $C_{26}H_{34}N_2O_4 \cdot 1/4 H_2O$: Calc: C, 70.48; H, 7.85; N, 6.32 Found: C, 70.39; H, 7.81; N, 6.25 |
| 250 | 3-carbamoylpiperidine-N-(CH₂)₃-O-(3-phenoxyphenyl) | 3-carbamoylpiperidine | A | B | $C_{21}H_{26}N_2O_3$: Calc: C, 71.16; H, 7.39; N, 7.9 Found: C, 70.86; H, 7.65; N, 7.73 |

TABLE 15-continued

| Ex. No. | AR¹ Q AR² Y R Z | ZH | Method/ Prep | Isol'n/ Chrom. | Analysis |
|---|---|---|---|---|---|
| 251 | 4-(4-phenoxyphenoxyethyl)-piperidine with 4-CONH₂ | piperidine-4-CONH₂ (NH) | B | C | $C_{22}H_{28}N_2O_2$; Calc: C, 74.97; H, 8.01; N, 7.95 Found: C, 74.66; H, 8.41; N, 7.89 |
| 252 | 3-(4-phenoxyphenoxyethyl)-piperidine with CONH₂ | piperidine-CONH₂ (NH) | B | C | $C_{20}H_{26}N_2O_3$; Calc: C, 70.57; H, 7.11; N, 8.23 Found: C, 70.40; H, 6.93; N, 8.17 |
| 253 | 3-(4-phenoxyphenoxyethyl)-piperidine with CONH₂ | piperidine-3-CONH₂ (HN) | B | C | $C_{20}H_{24}N_2O_3·1/4H_2O$; Calc: C, 69.64; H, 7.16; N, 8.12 Found: C, 69.53; H, 7.29; N, 7.95 |
| 254 | 4-(4-phenoxyphenoxyethyl)-piperidine with CO₂Et | piperidine-4-CO₂Et (NH) | B | C | $C_{22}H_{27}NO_4·HCl$; Calc: C, 65.10; H, 6.95; N, 3.45 Found: C, 64.78; H, 6.64; N, 3.42 |
| 255 | 4-(4-phenoxyphenoxyethyl)-piperidine with CONHMe | piperidine-4-CONHMe (NH) | B | C | $C_{21}H_{26}N_2O_3$; Calc: C, 71.16; H, 7.39; N, 7.90 Found: C, 70.88; H, 7.69; N, 7.87 |
| 256 | 3-(4-benzylphenoxyethyl)-pyrrolidine with NHAc | pyrrolidine-3-NHAc (NH) | C | D | $C_{21}H_{26}N_2O_2·1HCl$; Calc: C, 67.28; H, 7.26; N, 7.47. Found: C, 67.47; H, 7.97; N, 6.88. |

TABLE 15-continued

| Ex. No. | AR¹ Q AR² Y R Z | ZH | Method/ Prep | Isol'n/ Chrom. | Analysis |
|---|---|---|---|---|---|
| 257 | 4-benzylphenyl-O-(CH₂)₂-morpholine | morpholine (NH) | C | D | C₁₉H₂₃NO₂·1HCl·0.25H₂O: Calc: C, 67.45; H, 7.30; N, 4.14. Found: C, 67.42; H, 7.28; N, 4.05. |
| 258 | 4-benzylphenyl-O-(CH₂)₃-pyrrolidine-2-CO₂Bn | pyrrolidine-2-CO₂Bn (NH) | D | E | C₂₈H₃NO₃: Calc: C, 78.29; H, 7.27; N, 3.26 Found: C, 78.42; H, 7.15; N, 3.10 |
| 259 | 4-benzylphenyl-O-(CH₂)₃-pyrrolidine | pyrrolidine (NH) | D | F | C₂₀H₂₅NO: Calc: C, 81.31; H, 8.53; N, 4.74 Found: C, 81.33; H, 8.84; N, 4.57 |
| 260 | 4-benzylphenyl-O-(CH₂)₃-pyrrolidine-2-CO₂Bu | pyrrolidine-2-CO₂Bu (NH) | D | G | C₂₅H₃₂NO₃·0.2H₂O: Calc: C, 75.42; H, 8.20; N, 3.52 Found: C, 75.12; H, 8.49; N, 3.44 |
| 261 | 4-benzylphenyl-O-(CH₂)₃-NH-CH₂-CO₂Bn | H₂N-CH₂-CO₂Bn | D | E | C₂₆H₂₉NO₃: Calc: C, 77.58; H, 7.01; N, 3.48 Found: C, 77.26; H 7.23; N, 3.46 |
| 262 | 4-benzylphenyl-O-(CH₂)₃-(3-CO₂Me-4-oxo-piperidine) | 3-CO₂Me-4-oxo-piperidine (NH) | D | H | C₂₃H₂₇NO₄: Calc: C, 72.42; H, 7.13; N, 3.67 Found: C, 71.95; H, 6.86; N, 4.16 |

TABLE 15-continued

| Ex. No. | AR¹ Q AR² Y R Z | ZH | Method/ Prep | Isol'n/ Chrom. | Analysis |
|---|---|---|---|---|---|
| 263 | Ph-CH₂-C₆H₄-O-(CH₂)₃-piperidine-4-CO₂tBu | CO₂tBu piperidine-4 NH | D | I | $C_{26}H_{35}NO_3$:<br>Calc: C, 76.25; H, 8.61; N, 3.42<br>Found: C, 76.04; H, 8.76; N, 3.37 |
| 264 | Ph-CH₂-C₆H₄-O-(CH₂)₃-NH-CH(CO₂Et) | H₂N-CH(CO₂Et) | D | F | $C_{20}H_{25}NO_3$:<br>Calc: C, 73.37; H, 7.70; N, 4.28<br>Found: C, 73.33; H, 7.83; N, 4.25 |
| 265 | Ph-CH₂-C₆H₄-O-(CH₂)₃-NH-(CH₂)-CO₂Et | H₂N-(CH₂)-CO₂Et | D | J | $C_{21}H_{27}NO_3 \cdot 0.0 H_2O$:<br>Calc: C, 73.10; H, 8.00; N, 4.06<br>Found: C, 72.91; H, 7.97; N, 4.20 |
| 266 | Ph-CH₂-C₆H₄-O-(CH₂)₃-NH-(CH₂)-CO₂Bn | H₂N-(CH₂)-CO₂Bn | D | I | $C_{25}H_{27}NO_3 \cdot 0.2 H_2O$:<br>Calc: C, 76.39; H, 7.03; N, 3.56<br>Found: C, 76.10; H, 7.05; N, 3.48 |
| 267 | Ph-CH₂-C₆H₄-O-(CH₂)₃-NH-(CH₂)-CO₂Me | H₂N-(CH₂)-CO₂Me | D | J | $C_{20}H_{25}NO_3 \cdot 0.2 H_2O$:<br>Calc: C, 72.57; H, 7.73; N, 4.23<br>Found: C, 72.67; H, 7.73; N, 4.19 |
| 268 | Ph-CH₂-C₆H₄-O-(CH₂)₃-NH-(CH₂)-CO₂tBu | H₂N-(CH₂)-CO₂tBu | D | A | $C_{23}H_{31}NO_3 \cdot 0.3 H_2O$:<br>Calc: C, 73.69; H, 8.50; N, 3.74<br>Found: C, 73.62; H, 8.61; N, 3.70 |
| 269 | Ph-CH₂-C₆H₄-O-(CH₂)₃-piperidine-CO₂Et | piperidine-CO₂Et NH | D | E | $C_{24}H_{31}NO_3$:<br>Calc: C, 15.56; H, 8.19; N, 3.67<br>Found: C, 75.32; H, 8.38; N, 3.63 |
| 270 | Ph-CH₂-C₆H₄-O-(CH₂)₂-piperidine-CO₂Et | piperidine-CO₂Et HN | D | E | $C_{23}H_{29}NO_3 \cdot 0.1 H_2O$:<br>Calc: C, 74.81; H, 7.97; N, 3.79<br>Found: C, 74.60; H, 8.00; N, 3.77 |

TABLE 15-continued

| Ex. No. | AR¹ Q AR² Y R Z | ZH | Method/ Prep | Isol'n/ Chrom. | Analysis |
|---|---|---|---|---|---|
| 271 | [structure: CH₂-phenyl-phenyl-O-(CH₂)₂-NH-CH(pyridyl)-CH₂-CO₂Et] | H₂N-CH₂CH₂-CO₂Et | B | E | C₂₆H₂₈N₂O₅, M⁺ 448 from Mass spectrometry NMR consistant with the structure. |
| 272 | [structure: CH₂-phenyl-phenyl-O-(CH₂)₄-NH-CH₂CH₂-CO₂Et] | H₂N-CH₂CH₂-CO₂Et | D | E | C₂₂H₂₉NO₂: Calc: C, 74.33; H, 8.22; N, 3.94 Found: C, 74.21; H, 8.23; N, 3.86 |
| 273 | [structure: CH₂-phenyl-phenyl-O-(CH₂)₄-NH-CH₂CH₂-CO₂Bn] | H₂N-CH₂CH₂-CO₂Bn | D | E | C₂₇H₃₁NO₃·0.2H₂O: Calc: C, 77.70; H, 7.51; N, 3.33 Found: C, 76.47; H, 7.77; N, 3.16 |
| 274 | [structure: CH₂-phenyl-phenyl-O-(CH₂)₅-NH-CH₂CH₂-CO₂Et] | H₂N-CH₂CH₂-CO₂Et | D | F | C₂₃H₃₁NO₃·0.1H₂O: Calc: C, 74.40; H, 8.47; N, 3.77 Found: C, 74.19; H, 8.55; N, 3.72 |
| 275 | [structure: CH₂-phenyl-phenyl-O-(CH₂)₂-N(pyrrolidine)-CH₂-CO₂Me] | Ex. 479 | B | L | C₂₂H₂₇NO₃·0.50H₂O: Calc: C, 72.90; H, 7.79; N, 3.86. Found: C, 72.97; H, 7.95; N, 3.92. |
| 276 | [structure: CH₂-phenyl-phenyl-O-(CH₂)₂-N(pyrrolidine)-CO₂Me] | Ex. 481 | B | M | ¹H NMR (CDCl₃) d 2.12 (2H, q), 2.61 (1H, q), 2.71–2.97 (4H, m), 3.04 (2H, m), 3.69 (3H, s), 3.92 (2H, s), 4.06 (2H, t), 6.83 (2H, d), 7.09 (2H, d), 7.18 (3H, m), 7.27 (2H, t); HRMS; m/z 339.1831 (calc'd for C₂₁H₂₅NO₃, 339.1834). |

TABLE 15-continued

| Ex. No. | AR¹ Q AR² Y R Z | ZH | Method/ Prep | Isol'n/ Chrom. | Analysis |
|---|---|---|---|---|---|
| 277 | (structure: PhCH₂-C₆H₄-O-(CH₂)₂- with piperazine N-Ac) | Ac-N(piperazine)NH | B | N | $C_{21}H_{25}N\cdot HCl\cdot 0.25H_2O$: Calc: C, 75.88; H, 8.04; N, 4.21; Cl, 10.67. Found: C, 76.06; H, 8.28; N, 4.29; Cl, 10.53. |
| 278 | (structure: bicyclic with CO₂Me, PhCH₂-C₆H₄-O-(CH₂)₂-) | Ex. 474 | B | N | $C_{21}H_{25}N\cdot HCl\cdot 0.30H_2O$: Calc: C, 75.68; H, 8.04; N, 4.20; Cl, 10.64. Found: C, 75.88; H, 8.19; N, 4.28; Cl, 10.35. |
| 279 | (structure: piperidine-CN, PhCH₂-C₆H₄-O-(CH₂)₂-) | Ex. 443 | B | N | $C_{21}H_{28}N_2O_2\cdot 1.1HCl\cdot 0.1H_2O$: Calc: C, 66.31; H, 7.23; N, 7.37; Cl, 10.25. Found: C, 66.17; H, 7.51; N, 7.31; Cl, 10.21. |
| 280 | (structure: benzofuran-CH₂-pyrrolidine, PhCH₂-) | (pyrrolidine NH) | B | N | $C_{20}H_{23}NO\cdot 1.1HCl\cdot 0.5H_2O$: Calc: C, 69.76; H, 7.36; N, 4.07; Cl, 11.84. Found: C, 69.97; H, 7.38; N, 4.01; Cl, 11.95. |
| 281 | (structure: benzofuran-CH₂-piperidine-CONH₂, PhCH₂-) | CONH₂-piperidine-NH | B | N | $C_{22}H_{26}N_2O_2\cdot 0.25H_2O$: Calc: C, 74.44; H, 7.53; N, 7.89. Found: C, 74.59; H, 7.41; N, 7.78. |
| 282 | (structure: benzofuran-CH₂-piperidine-CO₂Et, PhCH₂-) | CO₂Et-piperidine-NH | B | N | $C_{24}H_{29}NO_3\cdot HCl$: Calc: C, 69.30; H, 7.27; N, 3.37; Cl, 8.52. Found: C, 69.20; H, 7.28; N, 3.27; Cl, 8.81. |

TABLE 15-continued

| Ex. No. | AR¹ Q AR² Y R Z | ZH | Method/ Prep | Isol'n/ Chrom. | Analysis |
|---|---|---|---|---|---|
| 283 | [structure: benzyl-phenyl-benzofuran-CH₂-N-bicyclic-CO₂Me] | Ex. 474 | B | N | $C_{25}H_{29}NO_3 \cdot HCl \cdot H_2O$: Calc: C, 67.35; H, 7.23; N, 3.14; Cl, 7.95 Found: C, 67.38; H, 6.86; N, 3.14; Cl, 7.98 |
| 284 | [structure: benzyl-phenyl-benzofuran-CH₂-N-piperidine-CN] | Ex. 443 | B | N | |
| 285 | [structure: benzyl-phenyl-benzofuran(diMe)-CH₂-N-pyrrolidine] | [pyrrolidine NH] | B | N | $C_{22}H_{26}N_2O_2 \cdot HCl \cdot H_2O$: Calc: C, 65.25; H, 7.22; N, 6.92; Cl, 8.76 Found: C, 65.50; H, 7.13; N, 6.61; Cl, 8.87 |
| 286 | [structure: benzyl-phenyl-benzofuran(diMe)-CH₂-N-piperidine-CONH₂] | [piperidine-4-CONH₂ NH] | B | N | $C_{23}H_{28}N_2O_2 \cdot 1.25H_2O$: Calc: C, 71.38; H, 7.94; N, 7.24 Found: C, 71.68; H, 7.81; N, 7.26 |
| 287 | [structure: benzyl-phenyl-pyridofuran-CH₂-N-pyrrolidine] | [pyrrolidine NH] | B | N | $C_{19}H_{22}N_2O \cdot 1.9HCl \cdot 0.5H_2O$: Calc: C, 61.23; H, 6.73; N, 7.52; Cl, 18.07 Found: C, 61.60; H, 6.50; N, 7.60; Cl, 18.37 |
| 288 | [structure: benzyl-phenyl-pyridofuran-CH₂-N-piperidine-CONH₂] | [piperidine-4-CONH₂ NH] | B | N | $C_{21}H_{25}N_3O_2$: Calc: C, 71.77; H, 7.17; N, 11.96 Found: C, 72.14; H, 7.11; N, 11.98 |

TABLE 15-continued

| Ex. No. | AR¹ Q AR² Y R Z | ZH | Method/ Prep | Isol'n/ Chrom. | Analysis |
|---|---|---|---|---|---|
| 289 | pyrrolidine-CH₂-(2,3-dihydrobenzofuran with 5-OPh) | pyrrolidine-NH | B | N | $C_{19}H_{21}NO_2 \cdot 1HCl$: Calc: C, 68.77; H, 6.68; N, 4.22; Cl, 10.67 Found: C, 68.32; H, 7.08; N, 4.08; Cl, 10.72 |
| 290 | 4-CONH₂-piperidine-N-CH₂-(2,3-dihydrobenzofuran with 5-OPh) | 4-CONH₂-piperidine-NH | B | N | $C_{19}H_{21}NO_2 \cdot 1HCl$: Calc: C, 71.57; H, 6.86; N, 7.95 Found: C, 71.32; H, 7.20; N, 7.83 |
| 291 | 4-CO₂Et-piperidine-N-CH₂-(2,3-dihydrobenzofuran with 5-OPh) | 4-CO₂Et-piperidine-NH | B | N | $C_{23}H_{27}NO_4 \cdot 1HCl$: Calc: C, 66.10; H, 6.75; N, 3.35; Cl, 8.48 Found: C, 68.23; H, 7.02; N, 3.25; Cl, 8.43 |
| 292 | pyrrolidine-CH₂-(chroman with 6-CH₂Ph) | pyrrolidine-NH | B | N | $C_{21}H_{25}NO \cdot 1HCl$: Calc: C, 73.34; H, 7.62; N, 4.07; Cl, 10.31 Found: C, 73.08; H, 7.98; N, 4.15; Cl, 10.23 |
| 293 | 4-CONH₂-piperidine-N-CH₂-(chroman with 6-CH₂Ph) | 4-CONH₂-piperidine-NH | B | N | $C_{23}H_{28}N_2O_2 \cdot HCl \cdot 0.25H_2O$: Calc: C, 68.13; H, 7.33; N, 6.91; Cl, 8.74 Found: C, 68.12; H, 7.23; N, 6.77; Cl, 8.76 |
| 294 | 4-Ac-piperazine-N-CH₂-(chroman with 6-CH₂Ph) | 4-Ac-piperazine-NH | B | N | $C_{22}H_{26}N_2O_2 \cdot HCl \cdot H_2O$: Calc: C, 65.25; H, 7.22; N, 6.92; Cl, 8.76 Found: C, 65.50; H, 7.13; N, 6.61; Cl, 8.87 |

TABLE 15-continued

| Ex. No. | AR¹ Q AR² Y R Z | ZH | Method/ Prep | Isol'n/ Chrom. | Analysis |
|---|---|---|---|---|---|
| 295 | [structure: benzyl-phenyl-dihydrobenzofuran-CH₂-N-cyclobutyl-CONHCH₃] +0.25 H2O | CONHMe, 4-piperidine-NH | A | N | $C_{23}H_{28}N_2O_2 \cdot 0.25H_2O$<br>Calc: C, 74.87; H, 7.79; N, 7.95<br>Found: C, 74.49; H, 7.98; N, 7.46 |
| 296 | [structure: phenoxy-phenyl-dihydrobenzofuran-CH₂-N-cyclobutyl-CONHCH₃] +0.25 H2O | CONHMe, 4-piperidine-NH | A | N | $C_{22}H_{26}N_2O_3 \cdot 0.25H_2O$<br>Calc: C, 71.23; H, 7.20; N, 7.55.<br>Found: C, 71.00; H, 7.17; N, 7.47. |
| 297 | [structure: benzyl-phenoxyethyl-piperidine-CONH₂ with 2-CH₃] | Ex. 468 | A | L | $C_{22}H_{28}N_2O_2 \cdot 0.25H_2O$<br>Calc: C, 74.02; H, 8.05; N, 7.85.<br>Found: C, 74.29; H, 7.99; N, 7.45. |
| 298 | [structure: benzyl-phenoxyethyl-piperidine-CO₂Et with 2-CH₃] | Ex. 469 | A | A | $C_{24}H_{31}NO_3$;<br>Calc: C, 75.66; H, 8.19; N, 3.67.<br>Found: C, 75.23; H, 7.99; N, 3.65. |
| 299 | [structure: benzyl-phenoxyethyl-piperidine-CONHCH₃] | Ex. 470 | A | A | $C_{23}H_{30}N_2O_2 \cdot 0.6H_2O$:<br>Calc: C, 73.22; H, 8.33; N, 7.42.<br>Found: C, 73.05; H, 8.25; N, 7.41. |
| 300 | [structure: phenoxy-phenoxyethyl-piperidine] ·HCl | CO₂Et-CH₂-4-piperidine-NH | A | A | $C_{23}H_{29}NO_4 \cdot HCl \cdot 0.25H_2O$:<br>Calc: C, 65.08; H, 7.24; N, 3.30.<br>Found: C, 65.28; H, 7.07; N, 3.53. |

TABLE 15-continued

| Ex. No. | AR¹ Q AR² Y R Z | ZH | Method/ Prep | Isol'n/ Chrom. | Analysis |
|---|---|---|---|---|---|
| 301 | 4-benzylphenoxy-ethyl-N-piperidine-4-CH₂-CO₂Et | piperidine-4-CH₂-CO₂Et (NH) | A | A | $C_{24}H_{31}NO_3 \cdot HCl$: Calc: C, 68.97; H, 7.72; N, 3.35. Found: C, 69.52; H, 7.81; N, 3.46. |
| 302 | 4-benzylphenoxy-propyl-N-piperidine-4-CH₂-CO₂Et · HCl | piperidine-4-CH₂-CO₂Et (NH) | B | A | $C_{25}H_{33}NO_3 \cdot HCl \cdot 0.25H_2O$: Calc: C, 68.79; H, 7.97; N, 3.21. Found: C, 69.00; H, 8.12; N, 3.26. |
| 303 | 4-benzylphenoxy-ethyl-N-(spiro ketone) | spiro ketone (HN) | A | K | $C_{23}H_{27}NO_2$: Calc: C, 79.05; H, 7.79; N, 4.01. Found: C, 78.80; H, 7.61; N, 3.98. |
| 304 | bicyclic-CH₂CO₂CH₃ N-CH₂CH₂-O-C₆H₄-C₆H₅ (endo) | Ex. 489 | A | K | $C_{24}H_{29}NO_3$: Calc: C, 75.96; H, 7.70; N, 3.69. Found: C, 75.68; H, 8.08; N, 3.63. |

TABLE 15-continued

| Ex. No. | AR¹ Q AR² Y R Z | ZH | Method/ Prep | Isol'n/ Chrom. | Analysis |
|---|---|---|---|---|---|
| 305 | ![structure: 4-benzylphenoxy-ethyl-N-piperidine with CO₂CH₃ and OH] | Ex. 494 | A | K | $C_{22}H_{27}NO_4$: Calc: C, 71.52; H, 7.37; N, 3.79. Found: C, 71.44; H, 7.66; N, 3.77. |
| 306 | ![structure: chromane-methyl-N-piperidine with CO₂CH₃ and OH, HCl salt] | Ex. 494 | B | K | $C_{22}H_{25}NO_5 \cdot HCl \cdot 0.25H_2O$: Calc: C, 62.26; H, 6.29; N, 3.30; Cl, 8.35. Found: C, 62.00; H, 6.44; N, 3.23; Cl, 8.66. |
| 307 | ![structure: 4-phenoxyphenoxy-ethyl-N-bicyclic with CH₂CO₂H, endo] | Ex. 492 | A | K | $C_{24}H_{29}NO_3$: Calc: C, 75.96; H, 7.70; N, 3.69. Found: C, 75.57; H, 7.80; N, 3.68. |
| 308 | ![structure: 4-phenoxyphenoxy-ethyl-N-bicyclic with NC] | Ex. 506 | A | K | ¹H NMR 300 MHz Compound was fully characterized in the next step. See Example No. 440. |

TABLE 15-continued

| Ex. No. | AR¹ Q AR² Y R Z | ZH | Method/ Prep | Isol'n/ Chrom. | Analysis |
|---|---|---|---|---|---|
| 309 | 3-F-C6H4-CH2-C6H4-O-CH2CH2-N(piperidine-4-CO2Et) | piperidine-4-CO2Et, NH | A | A | $C_{23}H_{28}O_3NF$: Calc: C, 71.66; H, 7.32; N, 3.63. Found: C, 71.63; H, 7.58; N, 3.65. $M^+ = 385$ |
| 310 | thiophene-CH2-C6H4-O-CH2CH2-N(piperidine-4-CO2Et) | piperidine-4-CO2Et, NH | A | A | $C_{21}H_{27}SNO_3$: Calc: C, 67.53; H, 7.29; N, 3.75. Found: C, 61.47; H, 7.35; N, 3.62. $M^+ = 373$ |
| 311 | pyridine-CH2-C6H4-O-CH2CH2-N(piperidine-4-CO2Et) | piperidine-4-CO2Et, NH | A | A | $C_{22}H_{28}O_3N_2 \cdot 0.25H_2O$: Calc: C, 70.85; H, 7.70; N, 7.51. Found: C, 70.86; H, 7.59; N, 7.13. $M^+ = 368$ |
| 312 | 4-F-C6H4-CH2-C6H4-O-CH2CH2-N(piperidine-4-CO2Et) | piperidine-4-CO2Et, NH | A | A | $C_{23}H_{28}NFO_3 \cdot 0.1H_2O$: Calc: C, 71.33; H, 7.34; N, 3.62. Found: C, 71.19; H, 7.34; N, 3.52. $M^+ = 386$ |
| 313 | thiophene-CH2-C6H4-O-CH2CH2-N(piperidine-4-CO2Et) | piperidine-4-CO2Et, NH | A | A | $C_{21}H_{27}SNO_3$: Calc: C, 67.53; H, 7.29; N, 3.75. Found: C, 67.22; H, 7.05; N, 3.65. $M^+ = 373$ |
| 314 | 3-F-4-MeO-C6H3-CH2-C6H4-O-CH2CH2-N(piperidine-4-CONH2) | piperidine-4-CONH2, NH | A | A | $C_{22}H_{27}N_2O_3F \cdot 0.3H_2O$: Calc: C, 67.43; H, 7.10; N, 7.15. Found: C, 67.41; H, 7.23; N, 7.07. $M^+ = 386$ |

TABLE 15-continued

| Ex. No. | AR¹ Q AR² Y R Z | ZH | Method/ Prep | Isol'n/ Chrom. | Analysis |
|---|---|---|---|---|---|
| 315 | (piperidine with NHAc, CH₃, H₃C, N-CH₂CH₂-O-phenyl-CH₂-phenyl) | Ex. 512 | A | A | $C_{24}H_{32}N_2O$: Calc: C, 75.25; H, 8.48; N, 7.36. Found: C, 75.41; H, 8.48; N, 7.18. |
| 316 | (piperidine with CONH₂, CH₃, H₃C, N-CH₂CH₂-O-phenyl-CH₂-phenyl) | Ex. 508 | A | A | $C_{23}H_{30}N_2O_2 \cdot 0.5H_2O$: Calc: C, 73.57; H, 8.32; N, 7.46. Found: C, 73.30; H, 8.02; N, 7.31. |
| 317 | (piperidine with CO₂Me, CH₃, H₃C, N-CH₂CH₂-O-phenyl-CH₂-phenyl) | Ex. 510 | A | A | $C_{24}H_{31}NO_3 \cdot 1HCl \cdot 0.5H_2O$: Calc: C, 67.51; H, 7.79; N, 3.28. Found: C, 67.54; H, 7.72; N, 3.17. |
| 318 | (NH-CH₂CH₂-N(CO₂Me)-, O-phenyl-CH₂-phenyl) | H₂N-CO₂Me | D | F | $C_{19}H_{23}NO_3$: Calc: C, 72.82; H, 7.40; N, 4.47. Found: C, 72.56; H, 7.79; N, 4.38. |
| 319 | (N-CH₂CH₂-N(CO₂Bn)H-, O-phenyl-CH₂-phenyl) | H₂N-CO₂Bn | D | F | $C_{25}H_{27}NO_3$: Calc: C, 76.78; H, 6.71; N, 3.73. Found: C, 76.38; H, 6.34; N, 3.77. |
| 320 | (N-CH₂CH₂-N(CO₂Et)H-, O-phenyl-CH₂-phenyl) | H₂N-CO₂Et | D | F | $C_{21}H_{27}NO_3$: Calc: C, 73.87; H, 7.97; N, 4.10. Found: C, 73.71; H, 8.21; N, 4.01. |
| 321 | (N-CH₂CH₂-N(H)(CO₂Et)-, O-phenyl-CH₂-phenyl) | H₂N-CO₂Et | A | G | $C_{22}H_{29}NO_3 \cdot 0.5H_2O$: Calc: C, 72.50; H, 8.30; N, 3.84. Found: C, 72.46; H, 8.14; N, 3.80. |
| 322 | (NH-CH₂CH₂CH₂-CO₂Bn, O-phenyl-CH₂-phenyl) | H₂N-CO₂Bn | A | G | $C_{27}H_{31}NO_3 \cdot 0.2H_2O$: Calc: C, 77.00; H, 7.51; N, 3.33. Found: C, 76.47; H, 7.77; N, 3.16. |

TABLE 15-continued

| Ex. No. | AR¹ Q AR² Y R Z | ZH | Method/ Prep | Isol'n/ Chrom. | Analysis |
|---|---|---|---|---|---|
| 323 | ![structure with benzyl-phenoxy-O-(CH2)-NH-(CH2)-CO2Et] | H2N~~CO2Et | A | G | $C_{22}H_{27}N_2O_3F\cdot0.3H_2O$:<br>Calc: C, 67.43; H, 7.10; N, 7.15.<br>Found: C, 67.41; H, 7.23; N, 7.07. |
| 324 | ![structure with benzyl-phenoxy-O-(CH2)-NH-(CH2)-CO2Me] | H2N~~CO2Me | A | G | $C_{19}H_{23}NO_3$:<br>Calc: C, 72.82; H, 7.40; N, 4.47.<br>Found: C, 73.04; H, 7.64; N, 4.45. |
| 325 | ![cyclopropyl CO2Et with N-CH2CH2-O-phenyl-CH2-phenyl·HCl] | Ex. 486 | A | | $C_{23}H_{27}NO_3\cdot HCl$:<br>Calc: C, 68.73; H, 7.02; N, 3.48.<br>Found: C, 68.88; H, 7.16; N, 3.39. |

ISOLATION/PURIFICATION PROCEDURES
A. 84/15/1 CHCl₃/EtOH/NH₄OH
B. 75/25 Toluene/Ethyl Acetate
C. Crystallization from Et₂O
D. 97/3 Toluene/Ethyl Acetate
E. 109/1 EtOAc:Hexane:NEt₃
F. 99/1 EtOAc/NEt₃
G. 20/80/1 EtOAc/Toluene/TEA
H. 1/1 EtOAc/Heptane
I. 50:50:1 EtOAc/Toluene/TEA
J. 10:1:1 EtOH/EtOAc/TEA
K. 1/98.5/0.5 MeOH/CH₂Cl₂/NH₄OH
L. 3/97/trace EtOH/EtOAc/NH₄OH
M. 100:0.5:0.5 CH₂Cl₂/MeOH/NH₄OH
N. 85/14/1 CHCl₃/EtOH/NH₄OH

EXAMPLE 326

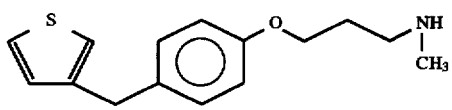

To a stirred solution of methylamine (40% solution in H₂O, Aldrich) (13.7 mL, 180 mmol) was added a solution of example 220 (0.47 g, 1.8 mmol, in CH₃CN 5 mL). The resulting mixture was heated to 45°–50° C. for 4–5 hours and then allowed to stir at r.t. for 15 hours. The reaction was concentrated in vacuo and the aqueous residue extracted with EtOAc (2×15 mL). The organic layers were combined and acidified with 1N HCl to PH 1 at 0° C. A white precipitate was formed, and the solid was collected by vacuum filtration. The solid was washed with 1N HCl, followed by hexane to afford 0.35 g salt. The solid was dissolved in 10% NaOH (30 mL) and extracted with Et₂O (2×20 mL). The organic layers were combined, dried over Na₂SO₄, and concentrated in vacuo to give the free amine as a clear colorless oil (0.3 g). The resulting product was fully characterized in the next step. See Example No. 330.

EXAMPLE 330

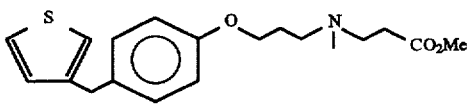

To a stirred solution of example 326 (0.30 g, 1.1 mmol in CH₂Cl₂ (6 mL) was added methyl acrylate (Aldrich, 0.13 mL, 1.5 mmol) at r.t. The reaction was allowed to stir at r.t. for 17 hours, and then concentrated under a stream of nitrogen gas. The residue was purified by column chromatography using 10% MeOH/CH₂Cl₂ as eluant to afford 0.32 g of the title compound as a clear colorless oil. The resulting product had the following properties: Analysis calcd for C₁₉H₂₅NO₃S: C, 65.58; H, 7.25; N, 4.03. Found: C, 65.38; H, 7.30; N, 3.95.

TABLE 16

| Ex. No. | Compound | Starting Material | Analysis |
|---|---|---|---|
| 327 | (structure with thiophene-CH₂-phenyl-O-(CH₂)₃-NH-CH₃) | Ex. 221 | M⁺ = 261 |
| 328 | (structure with F-phenyl-CH₂-phenyl-O-(CH₂)₃-NH-CH₃) · HCl | Ex. 222 | M⁺ = 273 |
| 329 | (structure with pyridyl-CH₂-phenyl-O-(CH₂)₃-NH-CH₃) | Ex. 223 | M⁺ = 256 |

TABLE 17

| Ex. No. | Compound | Starting Material | Analysis |
|---|---|---|---|
| 331 | 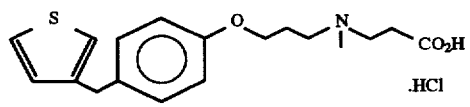 | Ex. 327 | $C_{19}H_{25}NO_3S \cdot 2H_2O$:<br>Calc: C, 65.00; H, 7.29; N, 3.99.<br>Found: C, 64.94; H, 7.19; N, 3.90.<br>$M^+ = 347$ |
| 332 | | Ex. 328 | $C_{21}H_{26}O_3NF \cdot 0.25H_2O$:<br>Calc: C, 69.30; H, 7.34; N, 3.85.<br>Found: C, 69.26; H, 7.41; N, 3.77.<br>$M^+ = 359$ |
| 333 | | Ex. 329 | $C_{20}H_{26}N_2O_3$:<br>Calc: C, 10.15; H, 1.65; N, 8.18.<br>Found: C, 69.82; H, 7.47; N, 7.99.<br>$M^+ = 342$ |

EXAMPLE 334

To a stirred solution of example 330 (80 mg, 0.23 mmol) was added 6N HCl (1 mL). The reaction was heated to 70° C. for 4 hours, then concentrated in vacuo to give a white solid. The solid was slurried with Et2O and collected by vacuum filtration to give 110 mg of the title compound. The resulting product had the following properties: Analysis calcd for $C_{19}H_{24}NO_3SCl \cdot 1.3 H_2O$: C, 56.30; H, 6.01; N, 3.46. Found: C, 56.05; H, 6.22; N, 3.37.

EXAMPLE 337

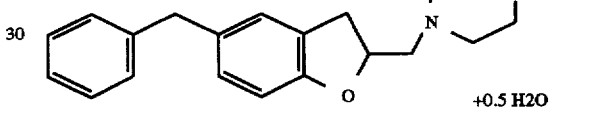

A mixture of the product of Example 180 (0.48 g), N-benzylpiperazine (1 mL), $K_2CO_3$ (0.7 g) in DMF (4 mL) was heated to 80° C. for 16 hr. The volatiles were removed in vacuo and the residue was extracted with ethyl acetate and water. The organic phase was washed with water (3 times), dried over $MgSO_4$ and concentrated. The residue was chromatographed over silica gel using CHCl3/EtOH/aqueous NH3 (85/14/1) as eluant to give a N-benzyl piperazine derivative. This product in 30 mL of ethanol was hydrogenated over 20% Pd(OH)2 on carbon at 60 psi hydrogen atmosphere for 18.4 h. The mixture was filtered and the filtrate concentrated. The residue (Sample A) was heated to reflux with toluene (4 mL) and trimethylsilylisocyanate (2.5

TABLE 18

| Ex. No. | Compound | Starting Material | Analysis |
|---|---|---|---|
| 335 | | Ex. 331 | $C_{18}H_{24}NO_3SCl$:<br>Calc: C, 58.45; H, 6.54; N, 3.79.<br>Found: C, 58.12; H, 6.30; N, 3.65.<br>$M^+ = 333$ |
| 336 | | Ex. 332 | $C_{20}H_{25}FNO_3Cl$:<br>Calc: C, 62.90; H, 6.60; N, 3.67.<br>Found: C, 62.43; H, 6.72; N, 3.58.<br>$M^+ = 345$ | mL) for 3h. The mixture was cooled and chromatographed over silica gel using CHCl3/EtOH/aqueous NH3 (85/14/1) as eluant to give the title product as a white solid.

Anal. for $C_{21}H_{25}N_3O_2 \cdot 0.5\ H_2O$

| Calculated | | Found |
|---|---|---|
| 69.98 | C | 69.78 |
| 7.27 | H | 6.82 |
| 11.66 | N | 11.53 |

EXAMPLE 338 A, B AND C

A.
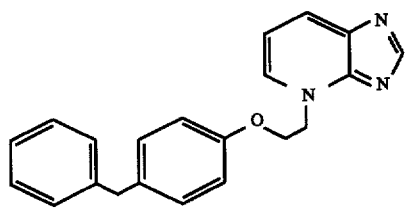

B.
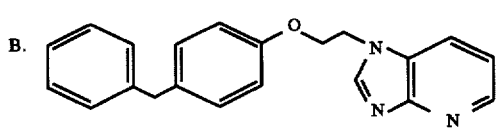

C.
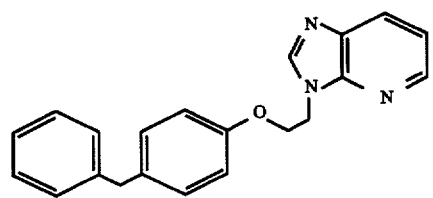

+0.25 H2O

To a stirred solution of 1.5 g of tosylate prepared in example 186 in 20 ml of N,N-dimethylformamide was added 1.5 g of $K_2CO_3$ and 480 mg of 4-azabenzimidazole. The mixture was heated to 65° C. for 4 hours, the mixture was cooled to room temperature and extracted with ethyl acetate. The organic extract was washed with water, dried over $Na_2SO_4$ and concentrated in vacuo to give crude oily gum which was chromatographed over silica gel to yield the title compounds 338A, 338B and 338C (in order of elution).

A: Calcd for $C_{21}H_{19}N_3O \cdot \frac{1}{2}H_2O$: Calculated: C, 74.53; H, 5.96; N, 12.42 Found: C, 74.30; H, 5.81; N, 12.45

B: Calcd for $C_{21}H_{19}N_3O$: Calculated: C, 76.57; H, 5.89; N, 12.76 Found: C, 76.48; H, 5.76; N, 12.81

C: Calcd for $C_{21}H_{19}N_3O \cdot \frac{1}{4}H_2O$: Calculated: C, 75.54; H, 5.89; N, 12.59 Found: C, 75.80; H, 5.75; N, 12.64

TABLE 19

$$Ar^1-Q-Ar^2-Y-R-X \xrightarrow{ZH} Ar^1-Q-Ar^2-Y-R-Z$$

| Ex. # | Starting Tosylate or Starting Chloride | ZH | Product | Isolation Chromatography | Analysis |
|---|---|---|---|---|---|
| 339 | Ex. 186 | 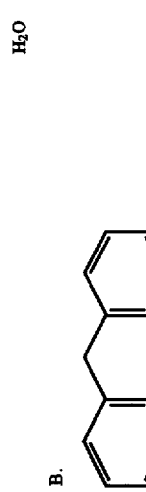 | 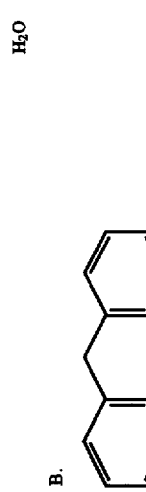 | Silica, chloroform/ ethanol/NH₄OH; 92.5/7/0.5 | C₂₂H₂₀N₂O: Calc: C, 80.46; H, 6.14; N, 8.53 Found: C, 79.90; H, 6.23; N, 8.40 |
| 340 | Ex. 186 | 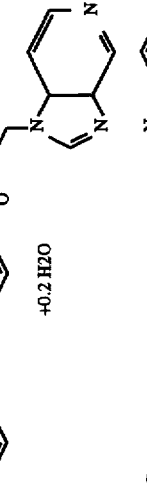 | A. 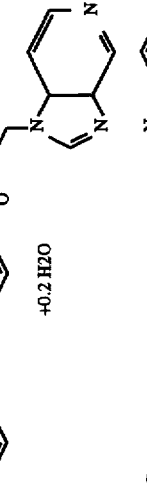 H₂O<br><br>B. 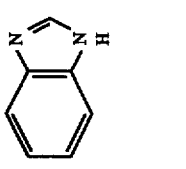 +0.2 H₂O<br><br>C. 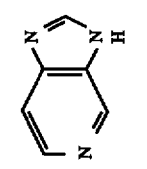 +0.25 H₂O | Silica, ethanol/ methylene chloride; 10/90 | C₂₁H₁₉N₃O.H₂O: Calc: C, 72.60; H, 6.09; N, 12.10 Found: C, 72.94; H, 5.68; N, 12.25<br><br>C₂₁H₁₉N₃O.0.2H₂O: Calc: C, 75.74; H, 5.87; N, 12.62 Found: C, 76.03; H, 5.90; N, 12.66<br><br>C₂₁H₁₉N₃O.1/4H₂O: Calc: C, 75.54; H, 5.89; N, 12.59 Found: C, 75.90; H, 5.92; N, 12.60 |

TABLE 19-continued $$Ar^1-Q-A^2-Y-R-X \xrightarrow{ZH} Ar^1-Q-A^2-Y-R-Z$$

| Ex. # | Starting Tosylate or Starting Chloride | ZH | Product | Isolation Chromatography | Analysis |
|---|---|---|---|---|---|
| 341 | Ex. 216 | [imidazopyridine NH] | A. [imidazo[4,5-b]pyridine-propoxy-phenyl-benzyl structure] | Silica, methylene chloride/ethanol/ NH4OH; 90/9/1 | $C_{22}H_{21}N_3O$: Calc: C, 76.94; H, 6.16; N, 12.24 Found: C, 76.78; H, 6.35; N, 12.20 |
|  |  |  | B. [isomeric imidazopyridine structure] |  | $C_{22}H_{21}N_3O$: Calc: C, 76.94; H, 6.16; N, 12.24 Found: C, 76.58; H, 6.37; N, 12.14 |
| 342 | Ex. 186 | [pyrrolopyridine NH] | [pyrrolo[2,3-b]pyridine-ethoxy-phenyl-benzyl structure] +0.4 H2O | Silica, 75/25; ethylacetate/toluene | $C_{22}H_{20}N_2O \cdot 0.4H_2O$: Calc: C, 78.73; H, 6.25; N, 8.35 Found: C, 78.81; H, 6.33; N, 8.04 |
| 343 | Ex. 184 | [benzimidazole NH] | [benzimidazole-propoxy-phenoxy-phenyl structure] | silica, methanol/ methylene chloride/ ammonium hydroxide 1/98.5/0.5 | $C_{22}H_{20}N_2O_2 \cdot 0.25 H_2O$: Calc: C, 75.73; H, 5.92; N, 8.03. Found: C, 75.72; H, 5.95; N, 7.96. |
| 344 | Ex. 188 | [benzimidazole NH] | [benzimidazole-ethoxy-phenoxy-phenyl structure] | silica gel, methanol/ methylene chloride/ ammonium hydroxide 5/94/1 | $C_{21}H_{18}N_2O_2 \cdot 0.15 H_2O$: Calc: C, 75.73; H, 5.54; N, 8.42. Found: C, 75.77; H, 5.62; N, 8.46. |

TABLE 19-continued $$Ar^1-Q-Ar^2-Y-R-X \xrightarrow{ZH} Ar^1-Q-Ar^2-Y-R-Z$$

| Ex. # | Starting Tosylate or Starting Chloride | ZH | Product | Isolation Chromatography | Analysis |
|---|---|---|---|---|---|
| 345 | Ex. 189 | benzimidazole | | silica gel, methanol/ methylene chloride/ ammonium hydroxide 1/98.5/0.5. | $C_{22}H_{20}N_2O_2$: Calc: C, 76.72; H, 5.85; N, 8.13. Found: C, 76.44; H, 5.98; N, 8.05. |
| 346 | Ex. 189 | imidazo[4,5-b]pyridine | A. | silica gel, methanol/ methylene chloride/ ammonium hydroxide 1/98.5/0.5. | $C_{21}H_{19}N_3O_2 \cdot 0.2 H_2O$: Calc: C, 72.27; H, 5.60; N, 12.04. Found: C, 72.34; H, 5.58; N, 11.54. H.R.M.S. M+ calc: 345.1477. Found: 345.1473. |
|  |  |  | B. |  | $C_{21}H_{19}N_3O_2$: Calc: C, 73.03; H, 5.54; N, 12.17. Found: C, 73.12; H, 5.59; N, 12.15. |
|  |  |  | C. |  | $C_{21}H_{19}N_3O_2 \cdot 0.20 H_2O$: Calc: C, 72.26; H, 5.60; N, 12.04. Found: C, 72.30; H, 5.62; N, 11.77. |

TABLE 19-continued $$Ar^1-Q-Ar^2-Y-R-X \xrightarrow{ZH} Ar^1-Q-Ar^2-Y-R-Z$$

| Ex. # | Starting Tosylate or Starting Chloride | ZH | Product | Isolation Chromatography | Analysis |
|---|---|---|---|---|---|
| 347 | Ex. 189 | (imidazopyridine NH) | A. (product structure) | methanol/methylene chloride/ammonium hydroxide 1/98.5/0.5. | $C_{21}H_{19}N_3O_2 \cdot 0.40\ H_2O$: Calc: C, 71.53; H, 5.66; N, 11.92. Found: C, 71.71; H, 5.68; N, 11.42. H.R.M.S. M+ calc: 345.1477. Found: 345.1479. |
|   |   |   | B. | | $C_{21}H_{19}N_3O_2 \cdot 0.40\ H_2O$: Calc: C, 71.53; H, 5.66; N, 11.92. Found: C, 71.21; H, 5.29; N, 11.57. |
|   |   |   | C. | | $C_{21}H_{19}N_3O_2 \cdot 0.70\ H_2O$: Calc: C, 70.45; H, 5.74; N, 11.74. Found: C, 70.58; H, 5.44; N, 11.41. |
| 348 | Ex. 188 | (imidazopyridine NH) | A. | methanol/methylene chloride/ammonium hydroxide 5/94/1 | $C_{20}H_{17}N_3O_2 \cdot 0.25\ H_2O$: Calc: C, 71.52; H, 5.25; N, 12.51. Found: C, 71.43; H, 5.17; N, 12.50. |

TABLE 19-continued $Ar^1-Q-Ar^2-Y-R-X \xrightarrow{ZH} Ar^1-Q-Ar^2-Y-R-Z$

| Ex. # | Starting Tosylate or Starting Chloride | ZH | Product | Isolation Chromatography | Analysis |
|---|---|---|---|---|---|
| 349 | Ex. 188 | [imidazo-pyridine structure] | B. [structure] | | $C_{20}H_{17}N_3O_2 \cdot 0.50 H_2O$: Calc: C, 70.57; H, 5.33; N, 12.34. Found: C, 70.68; H, 5.34; N, 12.38. |
| | | | C. [structure] | | H.R.M.S. M$^+$ calc: 331.1321. Found: 331.1296. |
| | | | A. [structure] | methanol/methylene chloride/ammonium hydroxide 1/98.5/0.5. | $C_{20}H_{17}N_3O$: Calc: C, 72.49; H, 5.17; N, 12.68. Found: C, 72.19; H, 5.23; N, 12.61. |
| | | | B. [structure] | | $C_{20}H_{17}N_3O \cdot 0.15 H_2O$: Calc: C, 71.91; H, 5.22; N, 12.58. Found: C, 71.87; H, 5.22; N, 12.41. |
| | | | C. [structure] | | $C_{20}H_{17}N_3O_2 \cdot 1.75 H_2O$: Calc: C, 66.19; H, 5.69; N, 11.58. Found: C, 66.00; H, 5.29; N, 11.68 |

TABLE 19-continued $$Ar^1-Q-Ar^2-Y-R-X \xrightarrow{ZH} Ar^1-Q-Ar^2-Y-R-Z$$

| Ex. # | Starting Tosylate or Starting Chloride | ZH | Product | Isolation Chromatography | Analysis |
|---|---|---|---|---|---|
| 350 | Ex. 184 | 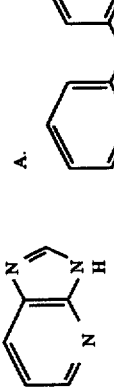 | A. 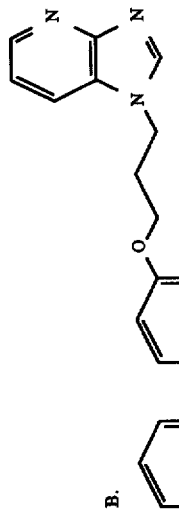 <br><br> B. 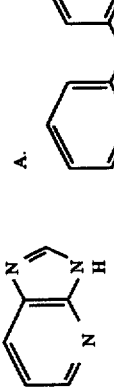 <br><br> C. 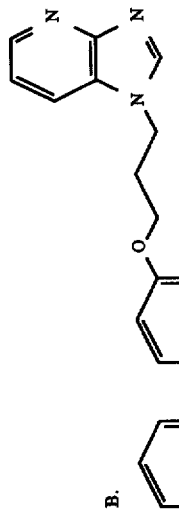 | methanol/methylene chloride/ammonium hydroxide 5/94/1. | $C_{21}H_{19}N_3O_2 \cdot 0.15\ H_2O$: Calc: C, 72.46; H, 5.59; N, 12.07. Found: C, 72.48; H, 5.65; N, 11.97. <br><br> $C_{21}H_{19}N_3O_2 \cdot 0.50\ H_2O$: Calc: C, 71.17; H, 5.69; N, 11.86. Found: C, 71.15; H, 5.26; N, 11.54. <br><br> H.R.M.S. M$^+$ calc: 345.1478. Found: 345.1493. |
| 351 | Ex. 184 | 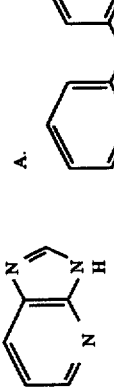 | A. 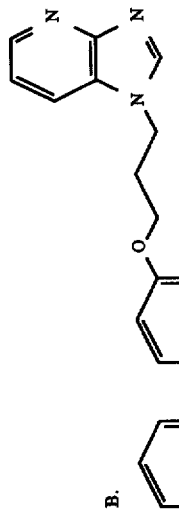 | methanol/methylene chloride/ammonium hydroxide 5/94/1. | $C_{21}H_{19}N_3O_2 \cdot 0.50\ H_2O$: Calc: C, 71.17; H, 5.69; N, 11.86. Found: C, 71.16; H, 5.46; N, 11.46. |

TABLE 19-continued $Ar^1-Q-Ar^2-Y-R-X \xrightarrow{ZH} Ar^1-Q-Ar^2-Y-R-Z$

| Ex. # | Starting Tosylate or Starting Chloride | Product | Isolation Chromatography | Analysis |
|---|---|---|---|---|
| | | B. | | $C_{21}H_{19}N_3O_2 \cdot 0.50\ H_2O$: Calc: C, 71.17; H, 5.69; N, 11.86. Found: C, 71.14; H, 5.39; N, 11.94. |
| | | C. | | $C_{21}H_{19}N_3O_2 \cdot 0.50\ H_2O$: Calc: C, 71.17; H, 5.69; N, 11.86. Found: C, 71.25; H, 5.42; N, 11.61. |
| 352 | Ex. 186 | | Silica, chloroform/ ethanol/NH$_4$OH; 92.5/7/0.5 | $C_{18}H_{18}N_2O \cdot HCl$ Calc: C, 68.67; H, 6.08; N, 8.9. Found: C, 68.54; H, 6.07; N, 8.79. |
| 353 | Ex. 186 | | Silica, EtOAc | $C_{22}H_{22}N_4O_3$: Calc: C, 67.35; H, 5.84; N, 14.35. Found: C, 67.68; H, 5.68; N, 14.35. |
| 354 | Ex. 161 | A. | 100:1:1 CH$_2$Cl$_2$/MeOH/ NH$_4$OH | $C_{20}H_{16}FN_3O_2$: Calc: C, 68.76; H, 4.62; N, 12.03. Found: C, 68.66; H, 4.63; N, 11.78. |

TABLE 19-continued
Ar¹—Q—A²—Y—R—X $\xrightarrow{\text{ZH}}$ Ar¹—Q—A²—Y—R—Z
| Ex. # | Starting Tosylate or Starting Chloride | ZH | Product | Isolation Chromatography | Analysis |
|---|---|---|---|---|---|
| 355 | Ex. 161 | 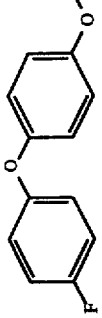 | B.  | | $C_{20}H_{16}FN_3O_2$:<br>Calc: C, 68.76; H, 4.62; N, 12.03.<br>Found: C, 68.40; H, 4.70; N, 11.86. |
| | | | C.  | | HRMS, m/z 349.1222 calc: $C_{20}H_{16}FN_3O_2$, 349.1227. |
| | | | A. 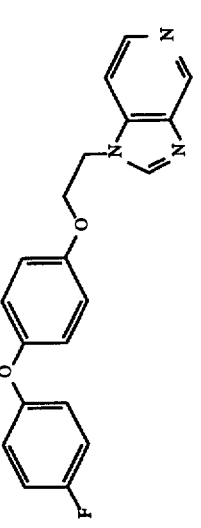 | 100:1:1 $CH_2Cl_2$/MeOH/ $NH_4OH$ | $C_{20}H_{16}FN_3O_2 \cdot 0.2\,H_2O$:<br>Calc: C, 68.06; H, 4.68; N, 11.90.<br>Found: C, 68.28; H, 4.72; N, 11.72. |
| | | | B. 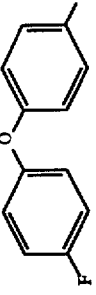 | | HRMS, m/z 349.1244 calc: $C_{20}H_{16}FN_3O_2$, 349.1227. |

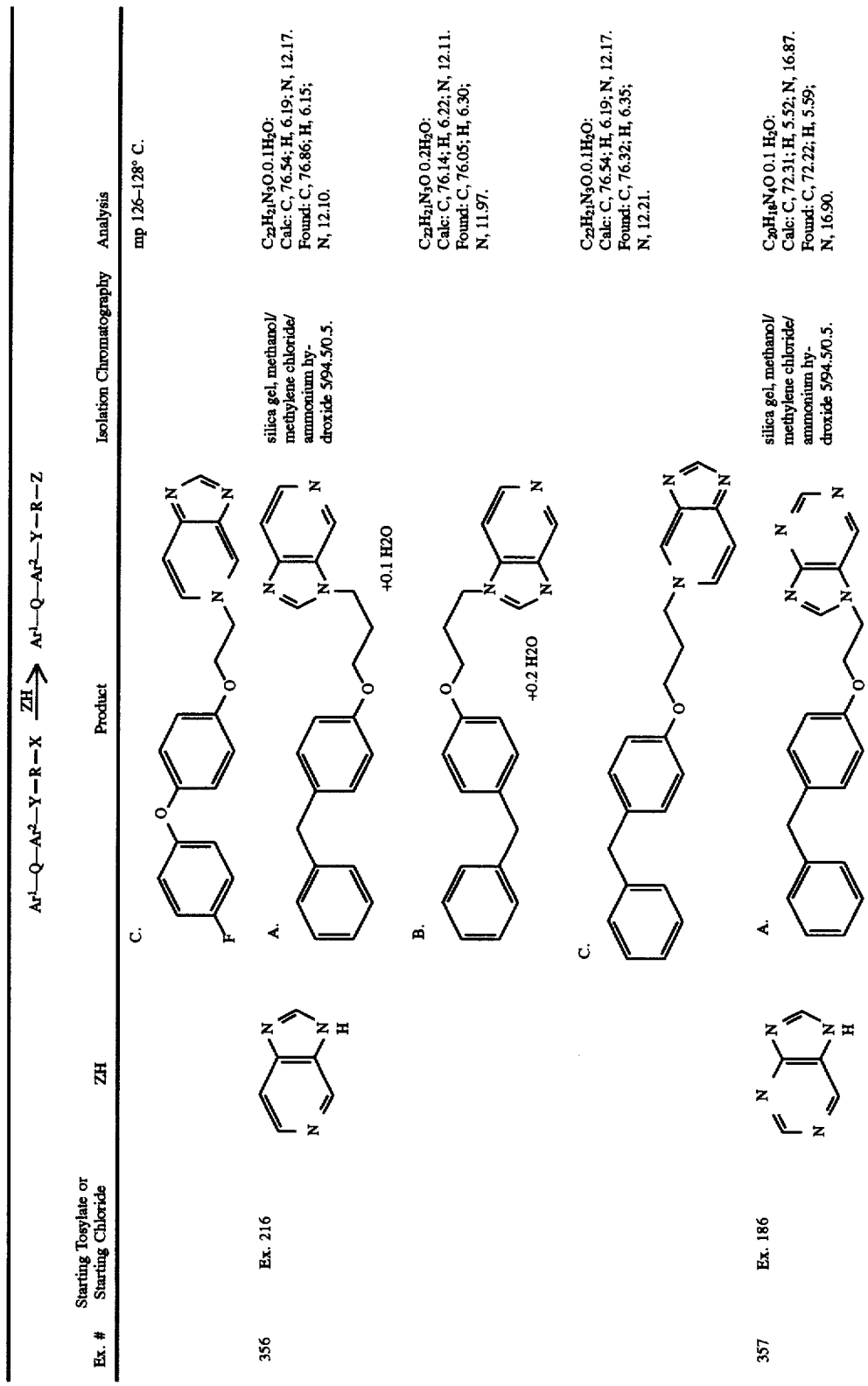

TABLE 19-continued

Ar¹—Q—A²—Y—R—X $\xrightarrow{ZH}$ Ar¹—Q—A²—Y—R—Z

| Ex. # | Starting Tosylate or Starting Chloride | Product | Isolation Chromatography | Analysis |
|---|---|---|---|---|
| 358 | Ex. 180 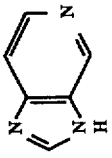 | B. 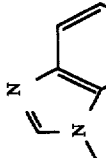 | | $C_{20}H_{18}N_4O$ 0.1 $H_2O$: Calc: C, 72.31; H, 5.52; N, 16.87. Found: C, 72.18; H, 5.53; N, 16.83. |
| | | C. 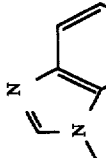 | | $C_{20}H_{18}N_4O$ 0.5 $H_2O$: Calc: C, 70.78; H, 5.64; N, 16.51. Found: C, 70.61; H, 5.44; N, 16.52. |
| | | D. 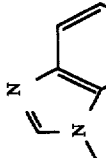 | | $C_{20}H_{18}N_4O$, 1 HCl, 1.3 $H_2O$: Calc: C, 61.55; H, 5.58; N, 14.36. Found: C, 61.24; H, 5.18; N, 15.03. |
| | | A. 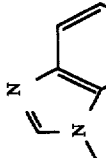 | Ethanol/methylene chloride/aq. NH₃ 10/90/1 | $C_{22}H_{19}N_3O$. 2HCl. Calc: C, 63.77; H, 5.11; N, 10.14; Cl, 17.11. Found: C, 63.43; H, 5.32; N, 10.11; Cl, 16.95. |
| | | B. 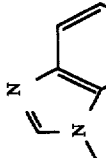 | | $C_{22}H_{19}N_3O$. 1.5HCl. 0.5 $H_2O$ Calc: C, 65.23; H, 5.35; N, 10.37; Cl, 13.13 Found: C, 64.95; H, 5.32; N, 10.37; Cl, 13.50 |

TABLE 19-continued $$Ar^1-Q-Ar^2-Y-R-X \xrightarrow{ZH} Ar^1-Q-Ar^2-Y-R-Z$$

| Ex. # | Starting Tosylate or Starting Chloride | ZH | Product | Isolation Chromatography | Analysis |
|---|---|---|---|---|---|
| | | | C. 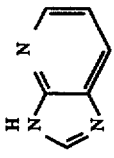 HCl | | $C_{22}H_{19}N_3O \cdot 1.9$ HCl $\cdot 0.75$ H$_2$O<br>Calc: C, 62.29; H, 5.32; N, 9.91; Cl, 15.88.<br>Found: C, 62.66; H, 5.33; N, 10.05; Cl, 15.88. |
| 359 | Ex. 180 | 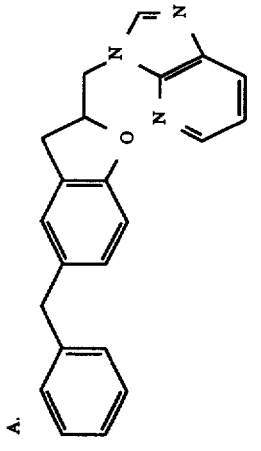 | A. 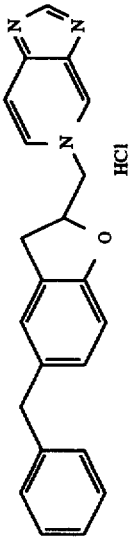 | Ethanol/methylene chloride/aq. NH$_3$ 10/90/1 | $C_{22}H_{19}N_3O \cdot$ HCl $\cdot 0.25$ H$_2$O<br>Calc: C, 69.10; H, 5.40; N, 10.99; Cl, 9.27.<br>Found: C, 69.11; H, 5.50; N, 11.48; Cl, 9.48. |
| | | | B. 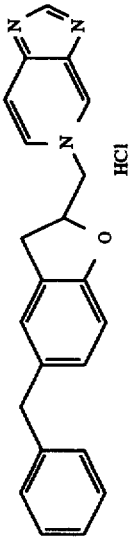 +0.5 H2O | | $C_{22}H_{19}N_3O \cdot 0.5$ H$_2$O<br>Calc: C, 75.41; H, 5.75; N, 11.99.<br>Found: C, 74.92; H, 5.61; N, 11.95. |
| | | | C. 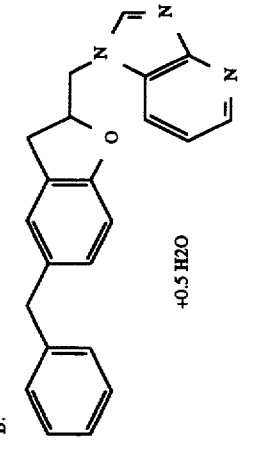 +0.5 H2O 1.05 HCL | | $C_{22}H_{19}N_3O \cdot 1.05$ HCl $\cdot 0.5$ H$_2$O<br>Calc: C, 67.98; H, 5.46; N, 10.81; Cl, 9.58.<br>Found: C, 67.46; H, 5.48; N, 10.51; Cl, 9.57. |

TABLE 19-continued $$Ar^1-Q-A^2-Y-R-X \xrightarrow{ZH} Ar^1-Q-Ar^2-Y-R-Z$$

| Ex. # | Starting Tosylate or Starting Chloride | ZH | Product | Isolation Chromatography | Analysis |
|---|---|---|---|---|---|
| 360 | Ex. 180 | (1H-pyrazolo[3,4-b]pyridine) | (benzyl-dihydrobenzofuran with triazolopyridine substituents, 3 isomers shown) | Ethylacetate/toluene linear gradient 5/95 to 11/89 | $C_{21}H_{18}N_4O \cdot 0.05 H_2O$ Calc: C, 73.47; H, 5.31; N, 16.32. Found: C, 73.07; H, 5.40; N, 16.01.<br><br>$C_{21}H_{18}N_4O$ Calc: C, 73.67; H, 5.30; N, 16.36. Found: C, 73.58; H, 5.38; N, 16.32.<br><br>$C_{21}H_{18}N_4O$ Calc: C, 73.67; H, 5.30; N, 16.36. Found: C, 73.77; H, 5.45; N, 16.30. |
| 361 | Ex. 180 | (1H-pyrazolo[3,4-b]pyridine) | (benzyl-dihydrobenzofuran with triazolopyridine substituent) HCl | Ethanol/methylene chloride/aq. NH₃ 10/90/1 | $C_{21}H_{18}N_4O \cdot HCl$ Calc: C, 66.58; H, 5.06; N, 14.79; Cl, 9.36 Found: C, 66.39; H, 5.04; N, 14.73; Cl, 9.32 |

TABLE 19-continued

Ar¹—Q—Ar²—Y—R—X $\xrightarrow{ZH}$ Ar¹—Q—Ar²—Y—R—Z

| Ex. # | Starting Tosylate or Starting Chloride | ZH | Product | Isolation Chromatography | Analysis |
|---|---|---|---|---|---|
| | | | (structure shown) + 0.25 H2O HCl | | $C_{21}H_{18}N_4O \cdot 0.25 H_2O$ Calc: C, 72.72; H, 5.38; N, 16.15. Found: C, 73.00; H, 5.49; N, 16.36. |

EXAMPLE 362 A AND B

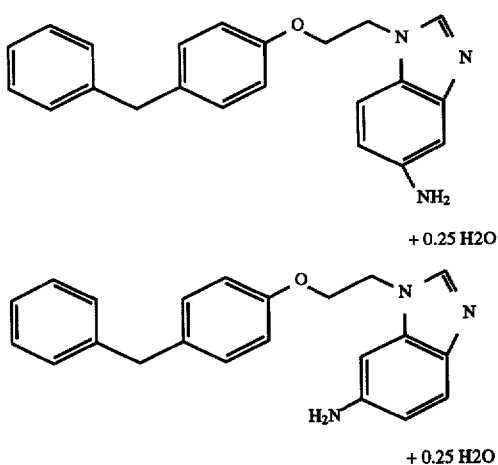

+ 0.25 H2O

+ 0.25 H2O

To a stirred solution of 764 mg of the tosylate prepared according to example 186 in 10 ml of DMF was placed 1 g of $K_2CO_3$ and 326 mg of 5-nitrobenzimidazole. The reaction mixture was heated to 65° C. and was stirred at 65° C. under nitrogen atmosphere for 4 hours. The reaction mixture was cooled to room temperature, poured into water and extracted with ethyl acetate. The organic extract was washed with water, dried over $Na_2SO_4$ and concentrated in vacuo to afford a residue which was taken up in 8 ml of 1:1 mixture of ethanol and HCl. The mixture was treated with 800 mg of $SnCl_2.2H_2O$ in 1 ml of concentrated HCl. The mixture was heated on the steam bath for 45 minutes, cooled to room temperature and neutralized 10% NaOH solution. The basic solution was extracted with ethyl acetate. The organic extract was washed with water, dried over $Na_2SO_4$, concentrated in vacuo to yield an oily residue which was chromatographed on silica gel using 92.5% $CHCl_3$, 7% ethanol, and 0.5% $NH_4OH$ as eluant to provide the title compounds.

A: Calcd for $C_{22}N_{21}N_3O.¼H_2O$: Calc: C, 75.91; H, 6.23; N, 12.08 Found: C, 75.96; H, 6.10; N, 12.03

B: Calcd for $C_{22}H_{21}N_3O.¼ H_2O$: Calc: C, 75.95; H, 6.23; N, 12.08 Found: C, 75.73; H, 6.05; N, 11.94

EXAMPLE 363

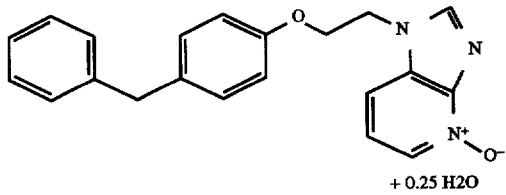

+ 0.25 H2O

To a stirred solution of 200 mg of the compound prepared in example 338B in 5 ml of $CHCl_3$ was added 200 mg of 80–85% m-chloroperoxybenzoic acid and the mixture was stirred at room temperature for 1 hr. The mixture was diluted with 10 ml of $CHCl_3$ and was washed with 10% $K_2CO_3$ solution and water, dried over $Na_2SO_4$ and concentrated. The residue was chromatographed over silica gel using 85% $CHCl_3$, 14% ethanol and 1% aqueous NaOH as eluant to yield the title compound as white solid (example 49).

Calcd for $C_{21}H_{19}N_3O_2.¼H_2O$: Calc: C, 72.09: H, 5.62; N, 12.01 Found: C, 71.71; H, 5.50; N, 11.81

EXAMPLE 364

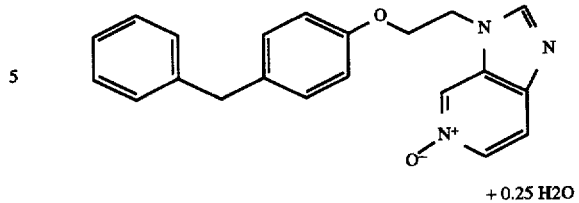

+ 0.25 H2O

Following the procedure described in example 363 and replacing the compound of example 338B with the compound of example 340C provided the title compound as white solid.

Calcd for $C_{21}H_{19}N_3O2.¼H_2O$: Calc: C, 72.09; H, 5.02; N, 12.01 Found: C, 72.16; H, 5.62; N, 11.96

EXAMPLE 365

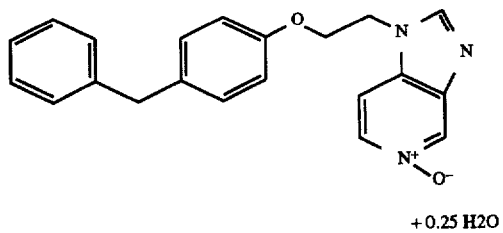

+ 0.25 H2O

Following the procedure described in example 363 and replacing the compound of example 338B with the compound of example 340B provided the title compound as white solid.

Calcd for $C_{21}H_{19}N_3O_2.¼H_2O$: Calc: C, 72.09; H, 5.62; N, 12.01 Found: C, 72.31; H, 5.82; N, 12.05

EXAMPLE 366

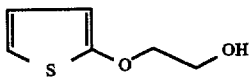

To stirred ethylene glycol (200 mL) was added sodium pellets (5.75 g, 250 mmol, Aldrich). After the sodium was dissolved the solution was cooled to room temperature. To this solution was added copper (II) oxide (4.8 g, 60 mmol), and 2-iodothiophene (25 g, 119 mmol). This mixture was then heated at 120° C. for 40 hours. The mixture was cooled to room temperature and poured into water (1000 mL). The aqueous mixture was then extracted with two 250 mL portions of ether. The combined ether extracts were washed 3 times with water (2×100 mL), saturated brine (100 mL) and dried over $MgSO_4$. After filtration, the volatile components were removed at reduced pressure on a rotary evaporator. The residue was chromatographed on silica gel gradient eluting with ethyl acetate:hexane (100% hexane to 1:5). This produced 15.9 g (30.3%) of the title compound as an oil.

HRMS (M+) for $C_6H_8O_2S$ Calculated: 144.0245 Found: 144.0245

EXAMPLE 367

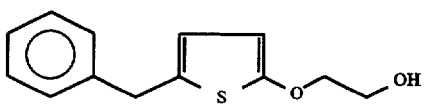

To a stirred solution of the product of Example 366 (1 g, 7 mmol) in tetrahydrofuran (20 mL) at −50° C. was added n-butyllithium (1.6M in THF, 10 mL, 16 mmol) dropwise over one minute. The mixture was slowly warmed over one hour to −20° C. and then cooled to −50° C. The mixture was then treated with benzyl bromide (0.9 mL, 7.6 mmol) and warmed to room temperature over one hour. The mixture was poured into water (50 mL), saturated brine (25 mL) and dried over $MgSO_4$. After filtration, the volatile components were removed at reduced pressure on a rotary evaporator. The crude product was used in Example 368 without further purification.

EXAMPLE 368

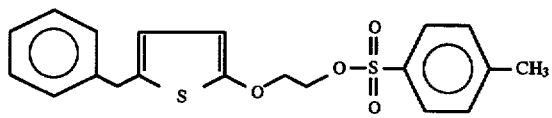

To a cooled (0° C.) and stirred solution of the product of Example 367 (1.6 g, 7 mmol) in methylene chloride (25 mL) was added pyridine (2.2 mL, 28 mmol) and p-toluenesulfonyl chloride (2.7 g, 14 mmol). The mixture was allowed to warm to room temperature and stirred for 18 hours. The mixture was poured into water (100 mL) and extracted with two 50 mL portions of ethyl acetate. The combined ethyl acetate extracts were washed 2 times with water (2×25 mL), saturated brine (25 mL) and dried over $MgSO_4$. After filtration, the volatile components were removed at reduced pressure on a rotary evaporator. The residue was chromatographed on a reverse phase column gradient eluting with methanol-water. This produced 0.64 g (24%) of the title compound.

HRMS (M+) for $C_{20}H_{20}S_2O_4$ Calculated: 388.0803 Found: 388.0803

EXAMPLE 369

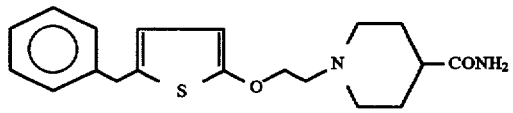

To a stirred solution of the product of Example 368 (0.1 g, 0.26 mmol) and isonipecotamide (0.06 g, 0.5 mmol, Aldrich) in N,N-dimethylformamide (5 mL) was added anhydrous potassium carbonate (0.25 g) in one portion. This mixture was heated at 80° C. for 18 hours. The mixture was poured into water (100 mL) and extracted with 25 mL of ethyl acetate. The ethyl acetate was washed 2 times with water (2×25 mL), saturated brine (25 mL) and dried over $MgSO_4$. After filtration, the volatile components were removed at reduced pressure on a rotary evaporator. The residue was chromatographed on silica gel gradient eluting with hexane:ethyl acetate (1:1 to 100% ethyl acetate) saturated with aqueous concentrated ammonium hydroxide. The solid produced was triturated with ether. This produced 0.02 g (22.3%) of the title compound.

HRMS (M+) for $C_{19}H_{24}N_2SO_2$: Calculated: 344.1558 Found: 344.1566.

EXAMPLE 370

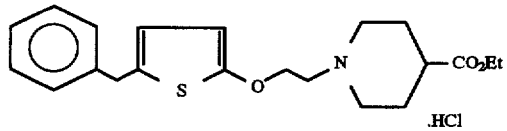

The product from Example 368 (0.1 g, 0.26 mmol) and ethyl isonipecotate (0.08 g, 0.5 mmol, Aldrich) was subjected to the reaction conditions described for the preparation of Example 369. The crude product was chromatographed on silica gel eluting with ethyl acetate:hexane (1:1) saturated with aqueous concentrated ammonium hydroxide. The product was taken up in ether (5 mL) and treated with hydrogen chloride and the resulting solid was triturated with ether. This produced 0.06 g (56%) of the title compound.

HRMS (M+) for $C_{21}H_{27}NO_3S$: Calculated: 373.1712 Found: 373.1715

EXAMPLE 371

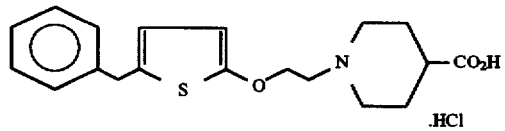

To a stirred solution of the product of Example 370 (0.04 g, 0.1 mmol) in tetrahydrofuran (2 mL) was added 6N HCl (5 drops). This solution was heated at 60° C. for 5 hours. The volatile components were removed at reduced pressure on a rotary evaporator and the residue was triturated with ether to give the title compound.

HRMS (MH+) for $C_{19}H_{23}NO_3S$: Calculated: 346.1477 Found: 346.1479.

EXAMPLE 372

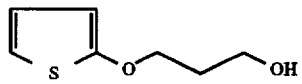

1,3-Propanediol (200 mL, Aldrich) was subjected to the reaction conditions described for the preparation of Example 366. This produced 13.2 g (70%) of the title compound.

HRMS (M+) for $C_7H_{10}O_2S$: Calculated: 158.0402 Found: 158.0397.

EXAMPLE 373

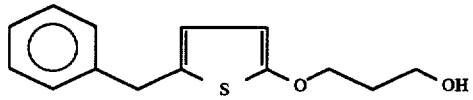

The product from Example 372 (6 g, 37.9 mmol) was subjected to the reaction conditions described for the preparation of Example 362. The residue was chromatographed on a reverse phase column gradient eluting with methanol-water. This produced 0.76 g (7.9%) of the title compound.

HRMS (M+) for $C_{14}H_{16}O_2S$: Calculated: 248.0871 Found: 248.0874.

EXAMPLE 374

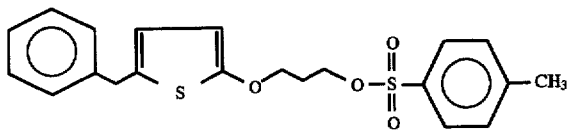

The product from Example 373 (0.5 g, 2.01 mmol) was subjected to the reaction conditions described for the preparation of Example 368. The crude product was chromatographed on silica gel gradient eluting with ethyl acetate:hexane (1:19 to 1:9). This produced 0.53 g (65%) of the title compound.

NMR (CDCl₃): 7.76 (d, 2H), 7.35–7.19 (complex, 7H), 6.37 (d, 1H), 5.90 (d, 1H), 4.16 (T, 2H), 3.98 (S, 2H), 3.95 (T, 2H), 2.39 (S, 3H), 2.06 (Pent., 2H).

EXAMPLE 375

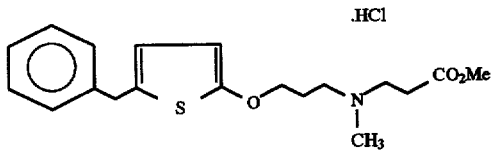

The product from Example 374 (0.2 g, 0.5 mmol) and N-methyl-β-alanine was subjected to the reaction conditions described for the preparation of Example 369. The crude product was chromatographed on silica gel eluting with ethyl acetate:hexane (1:4). The product was taken up in ether (5 mL) and treated with hydrogen chloride and the resulting solid was triturated with ether. This produced 0.08 g (42%) of the title compound.

HRMS (MH+) for $C_{19}H_{25}SNO_3$: Calculated: 348.1633 Found: 348.1651.

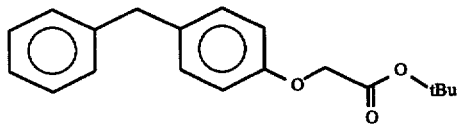

To a stirred suspension of sodium hydride (prewashed with hexane) (3.2 g, 50% oil dispersion) in DMF (100 ml) 4-hydroxydiphenylmethane (10 g, 54 mmol) was added. The reaction mixture stirred at room temperature for 30 minutes, cooled to 0° C. and tetra-n-butylammonium iodide (cat) followed by tert butylbromo acetate (9.6 ml, 1.1 eq) were added. After 30 minutes the reaction mixture was quenched into a mixture of 2N hydrochloric acid/ice and the resulting solution extracted into diethyl ether. The organic extracts were separated, washed with saturated potassium hydrogen sulfate, followed by saturated potassium carbonate, dried ($Na_2SO_4$) and evaporated to afford the title compound as a yellow oil.

The resulting yellow oil was further purified by chromatography on silica (eluant: diethyl ether/hexane 10/90) to afford the title compound as a colorless oil (15.02 g). NMR spectrum of this oil was consistent with the proposed structure.

EXAMPLE 377

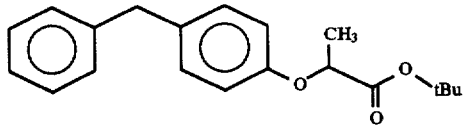

To a stirred solution of the t-butyl ester from example 376 (2.78 g,10 mmol) in THF(100 ml) at -78° C., lithium diisopropylamide (6 ml, 2M solution (Aldrich), 1.2 eq) was added. The reaction mixture was stirred at -78° C. for 40 min, quenched with methyl iodide (1 ml, excess) and allowed to attain room temperature. The reaction mixture was evaporated, and partitioned between diethyl ether and saturated potassium hydrogen sulfate solution. The organic extracts were separated, dried ($Na_2SO_4$) and evaporated to afford a yellow oil (3.2 g). The crude product was purified by chromatography on silica (eluant; hexane/diethyl ether, 80/20) to afford the title compound (2.76 g,).

This compound was characterized by NMR and fully authenticated at the next step (Example 381).

TABLE 20

| Ex. No. | Compound | Alkylating Agent | Analysis |
|---|---|---|---|
| 378 |  | EtI | $C_{21}H_{26}O_3$:<br>Calc: C, 77.27; H, 8.03.<br>Found: C, 76.95; H, 8.32. |

TABLE 20-continued

| Ex. No. | Compound | Alkylating Agent | Analysis |
|---|---|---|---|
| 379 | 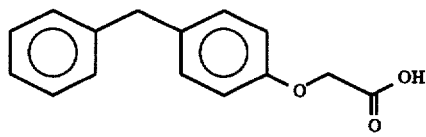 | BnBr | $C_{26}H_{28}O_3$:<br>Calc: C, 79.46; H, 7.31.<br>Found: C, 79.31; H, 7.32. |

EXAMPLE 380

To a stirred solution of t-butyl ester from example 376 (9.60 g, 34.5 mmol) in methylene chloride (50 ml) and methanol (5 ml) at 0° C. trifluoroacetic acid (50 ml, prechilled in ice) was added. The reaction mixture was stirred at 0° C. for 20 minutes, then allowed to attain room temperature overnight. The reaction mixture was evaporated to afford an off white solid which was recrystallized from diethyl ether/hexane to yield the title compound (6.12 g).

Analysis Calculated for $C_{15}H_{14}O_3 0.1H_2O$: Calculated: C, 73.82; H, 5.86. Found: C, 73.77; H, 5.76.

Following examples were carried out (i.e. examples 381, 382, 383) as described in Example 380.

EXAMPLE 384

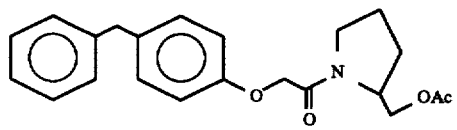

To a stirred solution of the acid from example 380 (800 mg, 3.31 mmol) in dimethylformamide (10 ml) and pyridine (2 ml), disuccinyl carbonate (842 mg) and 4-dimethylaminopyridine (cat) were added. The reaction mixture was stirred at room temperature for 50 minutes and then D-prolinol (500 mg) was added. The reaction mixture was stirred overnight, evaporated, and partitioned between ethyl acetate and saturated potassium hydrogen sulfate solution. The organic extracts were separated, dried ($Na_2SO_4$) and evaporated to afford an off white solid (crude yield=1.20 g). The crude solid was dissolved in acetic anhydride, to which pyridine (2-drops) were added. The reaction mixture was stirred for 4 hours, quenched with saturated sodium hydrogen carbonate solution and extracted into ethyl acetate. The organic extracts were separated, dried ($Na_2SO_4$) and evaporated to afford an off white solid. This crude product was further purified by chromatography on silica (eluant; diethyl ether) to afford the title compound (920 mg).

Analysis calculated for $C_{22}H_{25}NO_4 0.15H_2O$: Calc: C, 71.39; H, 6.89; N, 3.78. Found: C, 71.37; H, 6.82; N, 3.70.

TABLE 21

| Ex. No. | Compound | Starting Ester | Analysis |
|---|---|---|---|
| 381 | ![structure] 4-benzylphenoxy-CH(Me)-COOH | Ex. 377 | $C_{16}H_{16}O_3$:<br>Calc: C, 73.69; H, 6.38.<br>Found: C, 73.63; H, 6.24. |
| 382 | ![structure] 4-benzylphenoxy-CH(CH3)-COOH | Ex. 378 | $C_{17}H_{18}O_3$:<br>Calc: C, 74.30; H, 6.78.<br>Found: C, 74.21; H, 6.69. |
| 383 | ![structure] 4-benzylphenoxy-CH(CH2Ph)-COOH | Ex. 379 | $C_{22}H_{20}O_3 0.6H_2O$:<br>Calc: C, 76.99; H, 6.23.<br>Found: C, 76.90; H, 5.88. |

EXAMPLE 385

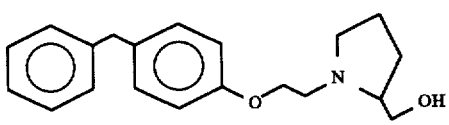

The title compound was prepared from the amide described in example 384 (650 mg) in a manner identical to that described in example 397. This afforded the title compound (360 mg).

Analysis calculated for $C_{20}NO_{2.5}NO_1 \cdot 1HCl \cdot 0.8H_2O$: Calc: C, 66.30; H, 7.68; N, 3.87. Found: C, 66.13; H, 7.71; N, 4.21.

EXAMPLE 386

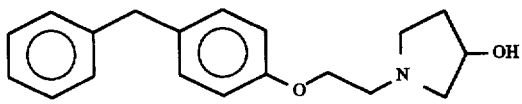

The title compound was prepared as described in examples 384 and 385 above, replacing D-prolinol with 3-hydroxy pyrrolidine, to afford the title compound (100 mg).

Analysis calculated for $C_{19}H_{23}NO_2 \cdot 1HCl \cdot 0.5H_2O$: Calc: C, 66.56; H, 7.35; N, 4.09. Found: C, 66.42; H, 7.06; N, 4.53.

EXAMPLE 387

1-(1-piperidinyl)-2-[4-(phenylmethyl)phenoxy]ethanone

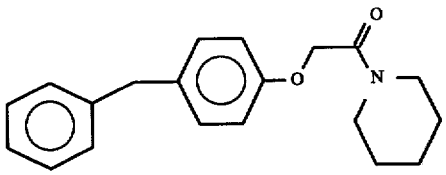

245 mg of sodium hydride (50% in oil) washed with hexane to remove the oil, was added to the solution of 920 mg of 4-hydroxydiphenylmethane in 10 ml of N,N-dimethylformamide. The mixture was stirred at room temperature under nitrogen atmosphere for 10 minutes, and then 806 mg of 1-(chloroacetyl)piperidine was added to the mixture. The reaction mixture was poured into water and was extracted with ether. The ether extract was washed with water, followed by 10% NaOH solution, dried over $Na_2SO_4$. The solvent was removed by evaporation under reduced pressure to provide crude product which was crystallized from ether/hexane to provide 656 mg of the title compound as white crystalline solid.

Analysis calculated for $C_{20}H_{23}NO_2$: Calc: C, 77.64; H, 7.49; N, 4.53. Found: C, 77.83; H, 7.49; N, 4.49.

EXAMPLE 388

1-(2,6-dimethylpiperidin-1-yl)-2-[4-(phenylmethyl)phenoxy]ethanone

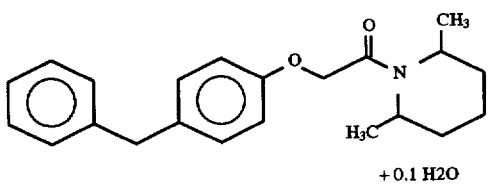

+0.1 H2O

Following the procedure described in example 387 and replacing 1-(chloroacetyl)piperidine with 1-(chloroacetyl)-2,6-dimethylpiperidine yielded the title compound.

Analysis calculated for $C_{22}H_{27}N_2O \cdot 0.1H_2O$: Calc: C, 77.89; H, 8.08, N, 4.13. Found: C, 77.84, H, 8.16; N, 4.13.

EXAMPLE 389

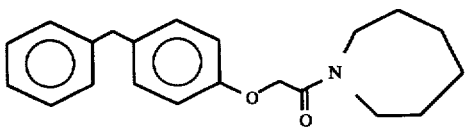

To stirred solution of the acid from example 380 (800 mg, 3.31 mmol) in dimethylformamide (10 ml) and pyridine (2 ml), disuccinyl carbonate (842 mg) and 4-dimethylaminopyridine (cat) were added. The reaction mixture was stirred at room temperature for 50 minutes and then hexamethyleneimine (330 mg) was added. The reaction mixture was stirred overnight, evaporated, and partitioned between ethyl acetate and saturated potassium hydrogen sulfate solution. The organic extracts were separated, dried ($Na_2SO_4$) and evaporated to afford an off white solid (crude yield=1.1 g). The crude product was purified by chromatography on silica (eluant; diethyl ether/hexane, 70/30) to afford the title compound (800 mg).

Analysis calculated for $C_{21}H_{25}NO_2 \cdot 0.15\ H_2O$: Calc: C, 77.34; H, 7.82; N, 4.29. Found: C, 77.40; H, 7.84; N, 4.30.

TABLE 22

| Ex. No. | Compound | Starting Amine and Acid | Analysis |
|---|---|---|---|
| 390 | | Azacycloheptane and Ex. 381 | $C_{22}H_{27}NO_2$: Calc: C, 78.30; H, 8.06; N, 4.15. Found: C, 78.15; H, 7.85; N, 4.12. |

TABLE 22-continued

| Ex. No. | Compound | Starting Amine and Acid | Analysis |
|---|---|---|---|
| 391 | | 2,5 Dimethyl pyrrolidine and Ex. 380 | $C_{21}H_{25}NO_2.0.1H_2O$: Calc: C, 77.50; H, 7.81; N, 4.31. Found: C, 77.48; H, 7.83; N, 4.36. |
| 392 | | S-(+)-2-(methoxymethyl)-pyrrolidine and Ex. 380 | NMR spectrum was consistent with the proposed structure. Compound was fully characterized in the next step. See Example No. 400. |
| 393 | | piperidine and Ex. 381 | $C_{21}H_{25}NO_2.0.1H_2O$: Calc: C, 77.55; H, 7.81; N, 4.31. Found: C, 77.56; H, 7.79; N, 4.36. |
| 394 | | hexahydroazepine and Ex. 381 | Compound was fully characterized in the next step. See Example No. 397. |
| 395 | | pyrrolidine and Ex. 382 | $C_{20}H_{23}NO_2.0.6H_2O$: Calc: C, 75.46; H, 7.90; N, 4.19. Found: C, 75.44; H, 8.14; N, 4.03. |
| 396 | | pyrrolidine and Ex. 383 | $C_{26}H_{27}NO_2.1.3H_2O$: Calc: C, 75.70; H, 7.33; N, 3.40. Found: C, 75.64; H, 7.02; N, 3.24. |

EXAMPLE 397

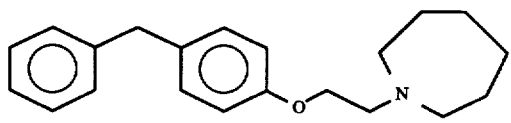

To a stirred suspension of Lithium aluminum hydride (400 mg, excess) in THF (10 ml) at room temperature, the amide for example 389 (700 mg) was added. The reaction mixture was stirred at room temperature for 3 hours, quenched with water (1 ml) and then diluted with ethyl acetate (50 ml). The reaction mixture was filtered and the mother liquors evaporated to afford a colorless oil. The free amine was converted to its HCl salt and crystallized from ethanol/diethyl ether to afford the title compound (545 mg).

Analysis calculated for $C_{21}H_{27}NO1HCl0.2\ H_2O$: Calc: C, 72.17; H. 8.19; N, 4.01. Found: C, 72.21; H, 8.21; N, 4.07.

TABLE 23

| Ex. No. | Compound | Starting Material | Analysis |
|---|---|---|---|
| 398 | (structure) | Ex. 390 | $C_{21}H_{29}NO.1HCl$:<br>Calc: C, 73.41; H, 8.40; N, 3.89.<br>Found: C, 73.04; H, 8.58; N, 3.99. |
| 399 | (structure) HCl | Ex. 391 | Calcd for $C_{21}H_{27}NO.HCl$:<br>Calc: C, 72.92; H, 8.10; N, 4.05.<br>Found: C, 72.70; H, 8.47; N, 3.99. |
| 400 | (structure) | Ex. 392 | $C_{21}H_{27}NO_2HCl.1/2H_2O$:<br>Calc: C, 68.00; H, 7.88; N, 3.78.<br>Found: C, 67.91; H, 7.75; N, 4.06. |
| 401 | (structure) HCl | Ex. 387 | $C_{20}H_{26}NO.HCl$:<br>Calc: C, 72.38; H, 7.90; N, 4.22.<br>Found: C, 72.23; H, 7.93; N, 4.21. |
| 402 | (structure) HCl | Ex. 388 | $C_{22}H_{29}NO.HCl$:<br>Calc: C, 73.41; H, 8.40; N, 3.89.<br>Found: C, 73.43; H, 8.49; N, 3.59. |
| 403 | (structure) | Ex. 393 | $C_{20}H_{25}NO.1HCl0.2H_2O$:<br>Calc: C, 72.17; H, 8.19; N, 4.01.<br>Found: C, 72.26; H, 8.12; N, 4.10. |
| 404 | (structure) | Ex. 394 | $C_{22}H_{29}NO.1HCl0.15H_2O$:<br>Calc: C, 72.87; H, 8.42; N, 3.86.<br>Found: C, 72.85; H, 8.49; N, 4.00. |
| 405 | (structure) | Ex. 395 | $C_{21}H_{27}NO.1HCl0.2H_2O$:<br>Calc: C, 72.17; H, 8.19; N, 4.01.<br>Found: C, 72.21; H, 8.19; N, 3.96. |
| 406 | (structure) | Ex. 396 | $C_{26}H_{29}NO.1HCl0.1H_2O$:<br>Calc: C, 76.21; H, 7.43; N, 3.42.<br>Found: C, 76.10; H, 7.45; N, 3.31. |

EXAMPLE 407

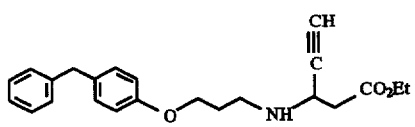

1) 3-Bromo propionaldehyde dimethyl acetal was reacted with 4-hydroxy diphenyl methane as in example 216 and was purified through column chromatography to afford intermediate A.

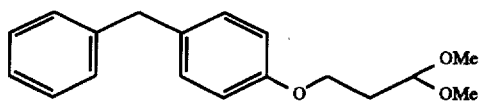

A 2) 1 g of intermediate A in 10 ml of THF was added 0.5 ml of H₂O. P-toluenesulfonic acid 50 mg was added and heated to 70.° overnight. The solvent was removed and the organic material was extracted with 30 ml ether. The etherial extracts were dried (Na₂SO₄) and evaporated to afford to intermediate aldehyde B.

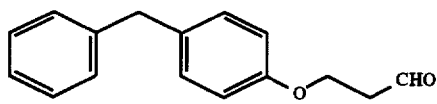

B

3) The intermediate B 240 mg in 3 ml of EtOH was added 177 mg of ethyl 3-amino pentyn-1-carboxylate (The NutraSweet Company)and 1 mmole of KOH (56 mg) and was stirred for ½ hr. 63 mg of NaBH₃CN was then added and the reaction was worked up as example 12 and after chromatography to provide 20 mg of the title compound as a colorless oil.

Analysis for $C_{23}H_{27}NO_3 \cdot 0.1H_2O$

|   | Theory | Found |
|---|---|---|
| C | 74.18 | 74.17 |
| H | 7.36 | 7.66 |
| N | 3.75 | 3.77 |

EXAMPLE 408

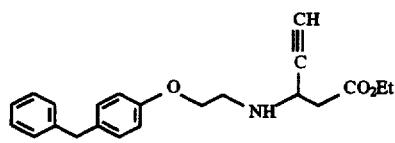

The title compound was prepared in accordance with example 407 except that bromoacetaldehyde diethyl acetal was used instead of 3-bromopropionaldehyde dimethyl acetal.

Analysis for $C_{22}H_{25}NO_3$

|   | Theory | Found |
|---|---|---|
| C | 75.19 | 69.79 |
| H | 7.17 | 7.11 |
| N | 3.98 | 4.21 |

EXAMPLE 409

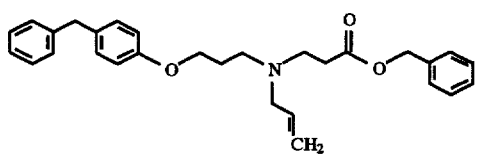

To a stirred solution 100 mg of the compound of example 261 in 5 DMF was added NaH 12 mg (60% dispersion, Aldrich). After 10 minutes of stirring, 30 mg benzyl bromide (Aldrich) in 2 ml DMF was added dropwise stirred at room temperature for 1 hr. Organic material was extracted with 30 ml ether and was washed with H₂O(5 ml×3), dried, and purified by column chromatography to provide 60 mg of the title compound as a colorless oil.

Analysis for $C_{29}H_{33}NO_3$

|   | Theory | Found |
|---|---|---|
| C | 78.52 | 78.18 |
| H | 7.50 | 7.50 |
| N | 3.16 | 3.06 |

EXAMPLE 410

Preparation of ethyl [[4-[4-(phenylmethyl)phenoxy]-butyl](2-propenyl)amino]propanoate

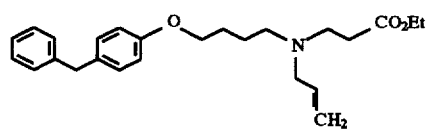

150 mg of the compound of example 271 was reacted in accordance with the method of example 409 to provide 100 mg of the title compound as a colorless oil.

Analysis for $C_{25}H_{33}NO_3$

|   | Theory | Found |
|---|---|---|
| C | 75.92 | 75.94 |
| H | 8.41 | 8.59 |
| N | 3.54 | 3.43 |

EXAMPLE 411

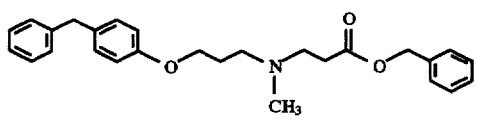

To 100 mg of the compound of example 261 and 0.1 ml of 37% aq HCHO in 2 ml of CH₃CN was added 25 mg of NaBH₃CN and the reaction mixture stirred for 15 min. Two drops of glacial acetic acid was added and the reaction mixture was stirred for another 30 min. Solvent was removed in vacuo and the remaining mixture was basicified with 15% KOH to pH 8 and the organic material was extracted with 20 ml ether. The organic phase was washed with H₂O (10 ml×3) and was dried. It was filtered and the resulting oily substance was purified by silica gel chromatography using 50:50:1-EtOAc:tol:TEA as eluant to provide 90 mg of the title compound.

Analysis for $C_{25}H_{27}NO_3 \cdot 0.2H_2O$

|   | Theory | Found |
|---|---|---|
| C | 76.39 | 76.10 |
| H | 7.03 | 7.05 |
| N | 3.56 | 3.48 |

EXAMPLE 412

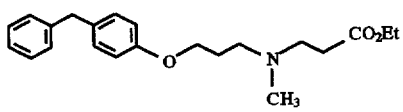

170 mg of the compound of example 265 was converted to 100 mg of the title compound using the procedure described in example 411.

Analysis for $C_{22}H_{29}NO_3$

|   | Theory | Found |
|---|--------|-------|
| C | 74.33  | 74.28 |
| H | 8.22   | 8.44  |
| N | 3.94   | 4.00  |

EXAMPLE 413

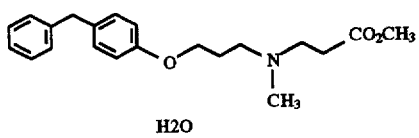

H2O 160 mg of the compound of example 267 was converted to 37.4 mg of the title compound following the procedure of example 411.

Analysis for $C_{21}H_{27}NO_3H_2O$

|   | Theory | Found |
|---|--------|-------|
| C | 70.17  | 69.85 |
| H | 8.13   | 8.04  |
| N | 3.90   | 3.92  |

EXAMPLE 414

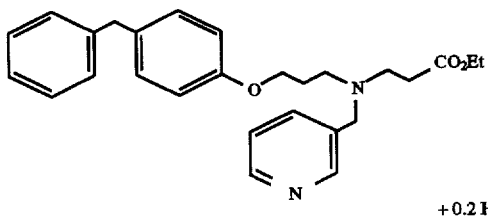

+ 0.2 H2O 770 mg of the compound of example 265 was reacted with 3-pyridine carboxaldehyde (Aldrich) 0.12 g following the procedure of example 411. Silica gel chromatography afforded 0.7 g of the title compound.

Analysis for $C_{27}H_{32}N_2O_3.0.2H_2O$

|   | Theory | Found |
|---|--------|-------|
| C | 74.70  | 74.31 |
| H | 7.06   | 7.49  |
| N | 6.45   | 6.28  |

EXAMPLE 415

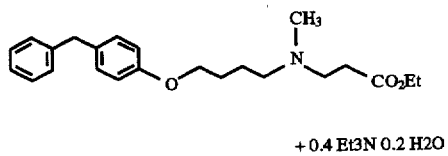

+ 0.4 Et3N 0.2 H2O 640 mg of the compound of example 272 was reacted in accordance with the method described in example 411 to obtain 350 mg of the title compound as a colorless oil.

Analysis for $C_{23}H_{31}NO_3.0.4Et_3N.0.2H_2O$

|   | Theory | Found |
|---|--------|-------|
| C | 73.76  | 73.43 |
| H | 9.11   | 8.66  |
| N | 4.74   | 4.33  |

EXAMPLE 416

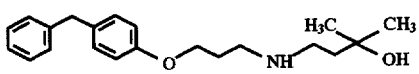

+ 0.5 H2O

The compound of example 265 (267 mg) in anhyd. THF was cooled to 0° C. and 2 mmol of MeMgCl in THF was added during ½ hr and stirred at room temperature for ½ hr. 2 ml of aqueous NH$_4$Cl solution was added dropwise at 0° C. and the solvent was removed in vacuo. The organic material was extracted with 30 ml ether and was chromatographed in a silica gel column using 20:80:1-EtOH:EtOAc-TEA as eluant to provide 75 mg of the title compound as a colorless oil.

Analysis for $C_{21}H_{29}NO_2.0.5H_2O$

|   | Theory | Found |
|---|--------|-------|
| C | 74.96  | 74.80 |
| H | 8.99   | 8.35  |
| N | 4.16   | 4.65  |

EXAMPLE 417

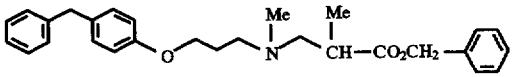

1.13 g of the compound of example 411 in THF was added dropwise to 3 mmol of LDA in 20 ml of THF at −78° during ½ hr. After ½ hr at −78°, 5 mmol of methyl iodide was added and reaction mixture was warmed to room temperature. Solvent was removed in vacuo and organic material was extracted with 50 ml ether and was dried. The desired product, 590 mg of the title compound, was obtained from column chromatography as a colorless oil.

Analysis for $C_{28}H_{33}NO_3.0.2H_2O$

|   | Theory | Found |
|---|--------|-------|
| C | 77.28  | 77.00 |
| H | 7.74   | 7.86  |
| N | 3.22   | 3.07  |

EXAMPLE 418

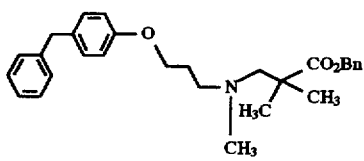

Product of example 417, (290 mg) was subjected to conditions described in example 417 and after chromatography on silica gel, a colorless oil was obtained, 21.4 mg.

Analysis for $C_{29}H_{35}NO_3$·EtOAc

|   | Theory | Found |
|---|--------|-------|
| C | 74.27  | 74.54 |
| H | 8.12   | 7.76  |
| N | 2.62   | 2.66  |

EXAMPLE 419

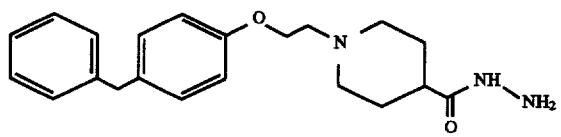

To a stirred solution of 350 mg of the ester of example 245 in 3 ml of n-butanol was added 1 g of hydrazine hydrate and the mixture was heated to reflux and was allowed to reflux under nitrogen atmosphere for 6 hours. The mixture was cooled to room temperature. The solvent was removed by evaporation under reduced pressure to give the crude oily gum, which upon crystallization from diethyl ether provided the title compound as white solid.

Calcd for $C_{21}H_{27}N_3C_2 \cdot 0.2H_2O$: C, 70.64; H, 7.73; N, 11.77. Found: C, 70.62; H, 7.88; N, 11.71.

EXAMPLE 420

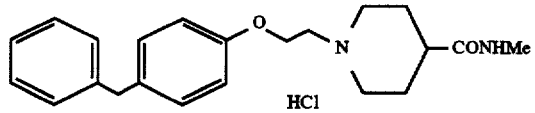

Following the procedure described in example 419 and replacing hydrazine hydrate with 40% methyl amine provided the title compound.

Calcd for $C_{22}H_{28}N_2O_2$: C, 74.97; H, 8.01; N, 7.95. Found: C, 74.67; H, 8.48; N, 7.88.

EXAMPLE 421

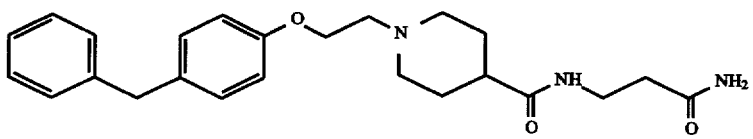

To a stirred solution of 600 mg of the compound of example 249 in 10 ml of ethanol was condensed 1 ml of liquid ammonia and the mixture was heated in a pressure vessel to 85° C. under 200 psi for 4 hours. The mixture was cooled and filtered. The filtrate was concentrated under vacuo to give an oily gum which was chromatographed on silica using 85% $CHCl_3$: 14% ethanol: 1% $NH_{40}H$ as mobile phase to provide 180 mg of the title compound.

Calcd for $C_{24}H_{31}N_3O_3$: C, 70.39; H, 7.63; N, 10.26.

Found: C, 70.17; H, 7.92; N, 10.19.

EXAMPLE 422

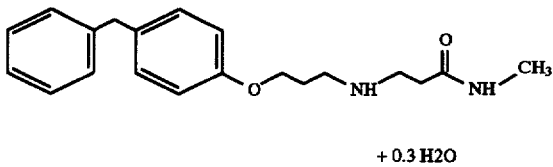

150 mg (0.44 mmol) of the compound of example 265 were dissolved in 10 ml of 40% methylamine (wt. % solution in water). A catalytic amount of NaCN was added and the reaction was stirred at 50° C. for 2 hours. The reaction was cooled and the mixture was diluted with 50 ml of $H_2O$ and then extracted with two 25 ml portions of EA. The organic layers were combined, dried and concentrated. Chromatography was carried out on a 1 mm chromatotron plate (90% EA\9% MeOH\1% triethylamine) to afford 100 mg of pure product.

Calcd for $C_{20}H_{26}N_2O_2 \cdot 0.3H_2O$: Calculated: C, 72.39; H, 8.08; N, 8.44. Found: C, 72.36; H, 8.09; N, 8.22.

EXAMPLE 423

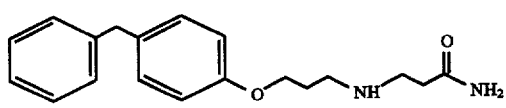

+ 0.3 H2O

The title compound was prepared essentially as described in Example 422 except that ammonium hydroxide was used instead of methylamine.

Analysis Cald. for $C_{19}H_{24}N_2O_2 \cdot 0.3H_2O$: Calc: C, 71.81; H, 7.80; N, 8.81. Found: C, 72.10; H, 7.94; N, 8.55.

EXAMPLE 424

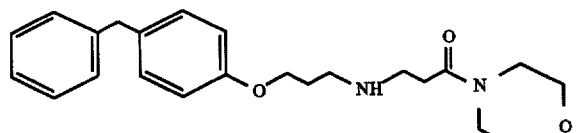

+0.6 H2O

The title compound was prepared essentially as described in Example 422 except that morpholine was used instead of methylamine.

Calc: C, 70.24; H, 8.00; N, 7.12. Found: C, 70.09; H, 8.13; N, 7.46.

EXAMPLE 425

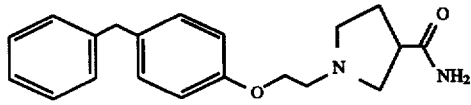

The product from Example 276 (0.20 g) was stirred in concentrated NH$_4$OH (3 mL) with catalytic NaCN at reflux in a sealed vial for 23 h. The mixture was cooled and poured into EtOAc and water. The EtOAc layer was separated, washed with brine, dried over Na$_2$SO$_4$ and concentrated. Flash chromatography on silica gel using a gradient of 99:1:0.5 to 97:3:0.5 CH$_2$Cl$_2$/MeOH/NH$_4$OH gave the title compound (0.052 g) as a colorless oil: Anal. calc'd for $C_{20}H_{24}N_2O_2$: C, 74.05; H, 7.46; N, 8.63. Found: C, 74.12; H, 7.76; N, 8.44.

EXAMPLE 426

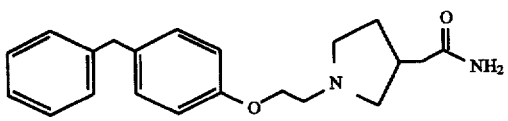

The product from Example 275 (254 mg, 0.72 mmol) and a catalytic amount of sodium cyanide were dissolved in 10 mL ammonium hydroxide. The reaction was refluxed for 12 hours. After cooling to RT, the reaction was neutralized with 10% HCl. The aqueous phases was extracted with 4×30 mL ethyl acetate. The combined organic extracts were dried (Na$_2$SO$_4$), filtered, and concentrated to afford the crude product as a white solid. The product was chromatographed (silica gel, methanol/methylene chloride/ammonium hydroxide 2/97.5/0.5) to afford the pure product as a white solid. The product had the following properties: mp 106°–107° C. Anal. calcd for $C_{22}H_{27}NO_3$: C, 74.53; H, 7.74; N, 8.28. Found C, 74.36; H, 7.66; N, 8.12.

EXAMPLE 427

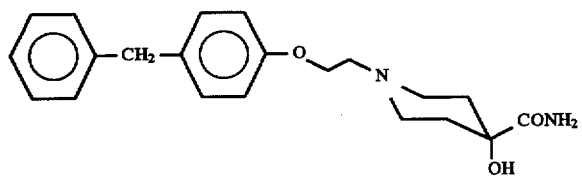

A solution of 153 mg of the product from example 305 in 5 mL of ethanol and 5 mL of concentrated ammonium hydroxide solution was prepared and placed in a Parr bottle. The vessel was stoppered and stirred at room temperature for 48 hours. The reaction mixture was concentrated and the residue was purified on prep plates eluting with 89.5% CHCl$_3$—10.0% ethanol—0.5% NH$_4$OH to yield 59 mg of white powder.

Analysis for $C_{21}H_{26}N_2O_3 \cdot 1.0H_2O$

| Calculated | | Found |
|---|---|---|
| 67.72 | C | 67.82 |
| 7.58 | H | 7.17 |
| 7.52 | N | 7.35 |

EXAMPLE 428

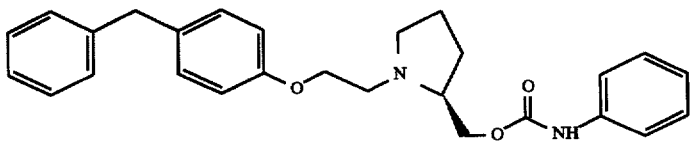

To a stirred solution of the alcohol from example 385 (100 mg, 0.29 mmol) in methylene chloride (5 ml) and triethy-

EXAMPLE 429

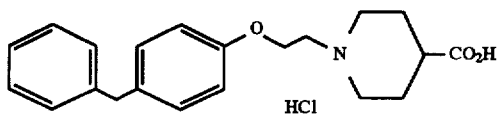

To a stirred solution of the ester of example 245 in 8.0 ml of methanol was added 2 ml of 1N NaOH solution. The mixture was heated and allowed to reflux for 1 hour. The reaction mixture was cooled to room temperature and the solvent removed by evaporation under reduced pressure to give a solid residue which was taken up in 10 ml of water and neutralized with 2N HCl until it turned cloudy (pH= 4.65). The solution was extracted with ethyl acetate and washed with water and dried over $Na_2SO_4$. The solvent was removed by evaporation under reduced pressure to give an oily gum which was converted to HCl salt with ethanolic HCl to give 33 mg of the title compound as a white solid.

Calcd for $C_{21}H_{25}NO_3 \cdot HCl \cdot H_2O$: Calculated: C, 64.03; H, 7.16; N, 3.56. Found: C, 63.53; H, 6.70; N, 3.59.

EXAMPLE 430

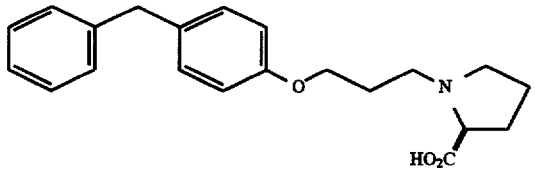

The compound of example 228 (0.2 g) was hydrogenated over 4% Pd/C in 10 ml 3A EtOH, 5 psi for 1.6 hrs. Concentration of the EtOH sol. gave 0.12 g of the title product as white precipitate. The title compound was recrystallized from toluene (m.p. 165-169).

Analysis for $C_{21}H_{24}NO_3 \cdot 0.5H_2O$

|   | Theory | Found |
|---|--------|-------|
| C | 72.60  | 72.88 |
| H | 7.25   | 7.51  |
| N | 4.03   | 3.96  |

EXAMPLE 431

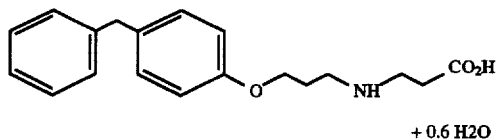

+ 0.6 H2O 800 mg of the compound of example 261 was hydrogenated over 4% Pd/C in 3A EtOH 20 ml at 5 psi for 2 hr, filtered and recrystallized from 3A EtOH to provide 120 mg of the title compound (m.p. 165°-167°).

Analysis for $C_{19}H_{23}NO_3 \cdot 0.6H_2O$

|   | Theory | Found |
|---|--------|-------|
| C | 70.39  | 70.15 |
| H | 7.52   | 7.29  |
| N | 4.32   | 4.24  |

EXAMPLE 432

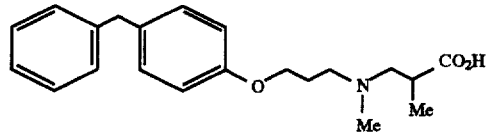

0.1 g of the compound of example 417 was hydrogenated over 4% Pd/C in EtOH as described in example 431. Removal of the solvent in vacuo followed by silica gel chromatography provided 80 mg of the title compounds as yellow oil.

Analysis for $C_{21}H_{27}NO_3 \cdot 0.2C_7H_8$

|   | Theory | Found |
|---|--------|-------|
| C | 74.76  | 74.28 |
| H | 8.01   | 7.95  |
| N | 3.89   | 3.34  |

EXAMPLE 433

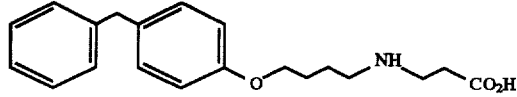

The compound of example 273 was hydrogenated as was described for example 431 to afford 70 mg of the title compound, m.p. 140-141.

Analysis for $C_{20}H_{25}NO_3$

|   | Theory | Found |
|---|--------|-------|
| C | 73.37  | 73.36 |
| H | 7.70   | 7.64  |
| N | 4.28   | 4.20  |

EXAMPLE 434

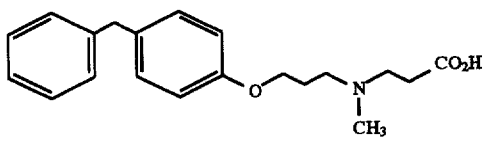

The compound of example 411 was hydrogenated as example 431 to afford 30 mg of the title compound as white needles (m.p. 113–116).

Analysis for $C_{20}H_{25}NO_3 \cdot 0.2EtoAc$

|   | Theory | Found |
|---|---|---|
| C | 72.40 | 72.10 |
| H | 7.77  | 8.00  |
| N | 4.06  | 4.41  |

EXAMPLE 436

To a stirred solution of example 309 (30 mg, 0.08 mmols) in THF (2.5 mL) was added 6 N HCl (1 mL) at r.t. The resulting solution was heated to 85° C. for 5 hours. The reaction was concentrated in vacuo to give a sticky gum. The residue was washed with $Et_2O$ and then slurried in EtOAc. The solid was collected by vacuum filtration to give 19 mg off-white solid. The resulting product had the following properties: Analysis calcd for $C_{21}H_{25}NO_3FCl0.8H_2O$: C, 61.78; H, 6.57; N, 3.43. Found: C, 61.41; H, 6.09; N, 3.26. $M^+=357$.

TABLE 16a

| Ex. No. | Compound | Starting Material | Analysis |
|---|---|---|---|
| 437 | | Ex. 310 | $C_{19}H_{24}NO_3SCl0.8H_2O$:<br>Calc: C, 57.58; H, 6.51; N, 3.53.<br>Found: C, 57.61; H, 6.32; N, 3.30.<br>$M^+ = 345$ |
| 438 | | Ex. 312 | $C_{21}H_{25}NO_3FCl1H_2O$:<br>Calc: C, 61.24; H, 6.61; N, 3.40.<br>Found: C, 61.27; H, 4.47; N, 3.40.<br>$M^+ = 357$ |
| 439 | | Ex. 313 | $C_{19}H_{24}NO_3SCl1.3H_2O$:<br>Calc: C, 56.30; H, 6.61; N, 3.46.<br>Found: C, 56.05; H, 6.22; N, 3.37.<br>$M^+ = 345$ |

EXAMPLE 435

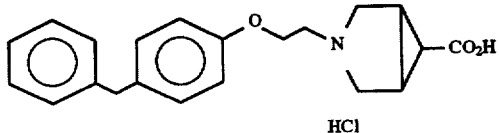

The product from Example 325 (100 mg) was dissolved in 5 ml of freshly distilled THF and was treated with 0.5 mL of 6N HCl and the mixture was refluxed for 4 hours. The reaction mixture was cooled to room temperature and was concentrated in vacuo to yield solid residue, which upon crystallization from ether yielded 78 mg of title compound.

Calculated for $C_{21}H_{23}NO_3 \cdot HCl$: Calc: C, 65.88; H, 6.58; N, 3.66. Found: C, 66.06; H, 6.83; N, 3.36.

EXAMPLE 440

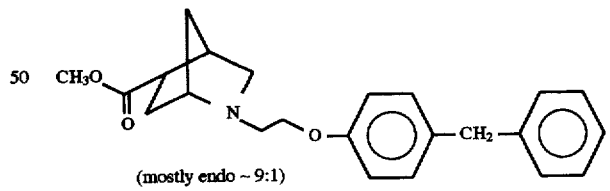

(mostly endo ~ 9:1)

A solution of 20 mL of 3:1 concentrated hydrochloric acid-water and 725 mg of the product from example 308 was refluxed for 12 hours. The reaction mixture was concentrated and the residue repeatedly azeotroped with toluene and then the residue was dried in vacuo. This material was dissolved in 50 mL of anhydrous methanol and saturated with anhydrous HCl gas with chilling in an ice bath for 1 hour. The reaction mixture was then degassed and concentrated to a small volume and partitioned between 10% $K_2CO_3$ solution and ethyl acetate. The aqueous portion was extracted with additional ethyl acetate and the combined organic extracts washed with saturated NaCl solution, dried over MgSO₄ and concentrated. The product was purified on a silica gel column eluting with 94.5% CH₂Cl₂—5.0% CH₃OH—0.5% NH₄OH to afford 333 mg of viscous oil.

Anal. for $C_{23}H_{27}NO_3 \cdot 0.25H_2O$:

| Calculated | | Found |
|---|---|---|
| 74.67 | C | 74.60 |
| 7.49 | H | 7.66 |
| 3.79 | N | 3.76 |

EXAMPLE 441

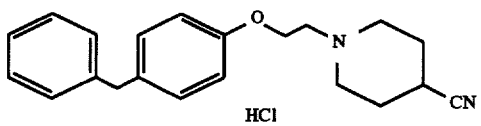

To a stirred solution of 300 mg of the amide of example 242 in 5 ml of THF containing 0.3 ml of pyridine was added 0.2 ml of trifluoroacetic anhydride at 0° C. and the mixture was stirred at 0° to 5° C. for 30 minutes. The reaction was warmed up to room temperature and was allowed to stir at room temperature for 16 hours. The solvent was removed by evaporation under reduced pressure to give an oily gum which was chromatographed on silica gel using 92.5% CHCl₃: 7% ethanol and 0.5% NH₄OH as a mobile phase to give oily gum which was converted into HCl salt followed by crystallization from ether to provide the title compound.

Calcd for $C_{21}H_{24}N_2OHCl \cdot 0.3H_2O$: Calculated: C, 69.82; H, 7.12; N, 7.73. Found: C, 69.36; H, 6.89; N, 7.66.

EXAMPLE 442

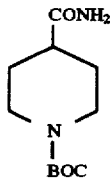

To a stirred suspension of isonipecotamide (35 g, Aldrich) in triethyamine (36 mL) and CHCL3 (400 mL) at 0° C. was added ditertiary butyldicarbonate (55 g, Aldrich). The mixture was allowed to warm to room temperature over 3 hr. The volatiles were removed and the residue was taken up in a mixture of CH₂Cl₂ and ether. The organic solution was washed with water, dried over MgSO₄ and concentrated in vacuo to give the title compound, as a white solid (51 g).

EXAMPLE 443

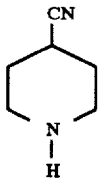

To a stirred solution of the product of Example 442 (51 g) in pyridine (175 mL) at 0° C. was added trifluoroacetic anhydride (38 mL) over 45 min. The mixture was allowed to warm to room temperature over 16 hr. The mixture was concentrarted in vacuo to ⅓rd its original volume and poured into ice-cold water. The mixture was extracted with CHCl₃. The organic phase was washed with water (2 times), dried over MgSO₄ and distilled in vacuo to give the title compound (32 g, Bp=110°–115° C./0.01 mm).

EXAMPLE 444

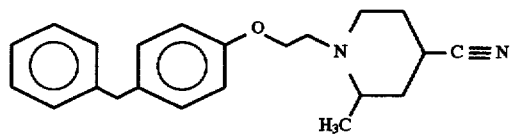

Following the procedure described in example: 441 and replacing the compound of example 242 with the compound of example 297 yields the title compound as HCl salt. Calcd. for $C_{22}H_{26}N_2O \cdot HCl \cdot 0.25H_2O$: Calc: C, 70.38; H, 7.38; N, 7.46. Found: C, 70.10; H, 7.00; N, 7.35.

EXAMPLE 445

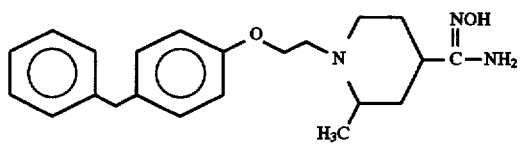

To a stirred solution of 250 mg of the compound of example 444 in 10 ml of absolute ethanol containing 500 mg of triethylamine is added 250 mg of NH₂OH.HCl and the mixture is heated to reflux and is allowed to reflux for 2½% hours. The mixture is cooled to room temperature and is concentrated in vacuo to provide a crude oily gum, which is extracted with ethyl acetate. The organic extract is washed with water, dried over Na₂SO₄ and concentrated in vacuo to give a residue which is chromatographed on silica gel using 85% CHCl₃, 14% ethanol, and 1% NHaOH as eluant to provide 166 mg of the title compound, as white solid. Calcd. for $C_{22}H_{29}N_3O_2 \cdot \frac{1}{4}H_2O$: Calc: C, 71.03; H, 7.99; N, 11.30. Found: C, 71.28; H, 7.92; N, 11.16.

EXAMPLE 446

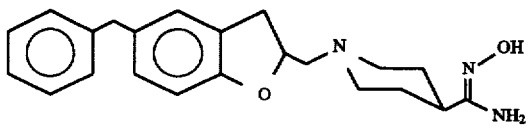

To a stirred solution of the product of Example 284 (1.5 g) and hydroxylamine hydrochloride (0.38 g, Aldrich) in ethanol (10 mL) was added sodium ethoxide (0.38 g) and the mixture heated to reflux for 4h and allowed to stand at room temperature for 2 days. The volatiles were removed and the residue chromatographed over silica gel using CHCl₃/Ethanol/Aqueous NH₃ 85/14/1, to give the title product as a colorless solid.

Anal. for $C_{22}H_{27}N_3O_2$

| Calculated | | Found |
|---|---|---|
| 72.30 | C | 72.03 |
| 7.45 | H | 7.54 |
| 11.50 | N | 11.21 |

EXAMPLE 447

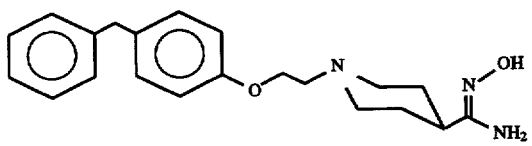

The procedure of Example 446 was repeated using the product of Example 441 in the place of the product of Example 284 to give the title product as a colorless solid.

Anal. for $C_{24}H_{31}N_3O_4 \cdot 0.25H_2O$

| Calculated | | Found |
|---|---|---|
| 67.03 | C | 67.01 |
| 7.38 | H | 6.98 |
| 9.77 | N | 9.43 |

EXAMPLE 448

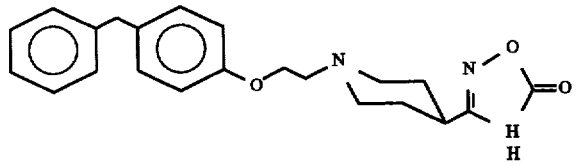

To a stirred solution of the product of Example 447 (0.45 g) in THF (10 mL at −60° C. was added a toluene solution of phosgene (0.931M, 3.3 mL, Fluka). The mixture was allowed to warm to room temperature over 16 hr. The volatiles were removed and the residue chromatographed over silica gel using CHCl3/Ethanol/Aqueous NH3 25/10/1, to give the title product as a colorless hygroscopic solid.

Anal. for $C_{22}H_{25}N_3O_3 \cdot 0.5H_2O$

| Calculated | | Found |
|---|---|---|
| 68.02 | C | 68.00 |
| 6.75 | H | 6.54 |
| 10.82 | N | 10.89 |

EXAMPLE 449

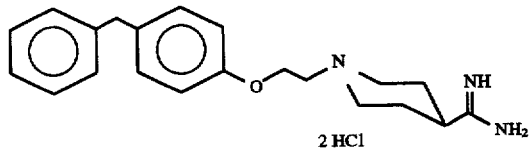

A solution of the product of Example 447 (0.576 g) in ethanol (15 mL) and acetic acid (3 mL) was hydrogenated in a parr hydrogenation apparatus over 4% Pd/C under 60 psi of hydrogen pressure for 24 hr. The solution was filtered and the filtrate concentrated. The residue was chromatographed over reverse phase silica gel using methanol/water as eluant of provide the free base of the title product. This material was taken in a small volume of ethanol and saturated ethanol HCl was added. The mixture was concentrated. The residue was dried at 78° C./0.5 mm to give the title compound as a sticky solid.

Anal. for $C_{21}H_{27}N_3O \cdot 1.9HCl \cdot 0.75H_2O$:

| Calculated | | Found |
|---|---|---|
| 60.02 | C | 59.99 |
| 7.29 | H | 7.18 |
| 10.00 | N | 9.50 |
| 16.03 | Cl | 16.12 |

EXAMPLE 450

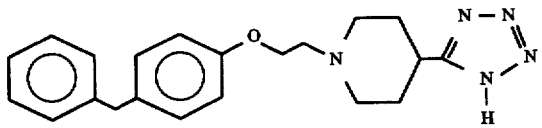

The product from Example 441 (350 mg) was dissolved in xylene (15 ml) and was treated with NaN3 (220 mg), tributyltin chloride (0.38 ml) and LiCl (140 mg), and the mixture was heated to reflux under nitrogen atm. and was allowed to reflux for 20 hours. The mixture was cooled to room temperature and concentrated in vacuo to afford an oily gum which was taken up in methanol (~20 ml) and filtered. The filtrate was concentrated in vacuo to provide an oily gum which upon reverse phase column chromatography yielded 182 mg of the title compound as white solid.

Calculated for $C_{21}H_{25}N_5O \cdot 0.6 H_2O$: Calc: C, 67.39; H, 7.06; N, 18.71. Found: C, 66.97; H, 6.87; N, 19.10.

EXAMPLE 451

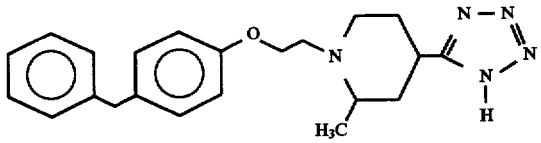

Following the procedure described in Example 450, and replacing the product of Example 441, with the product of Example 444, provided the title compound as white solid.

Calculated for $C_{22}H_{27}N_5O \cdot H_2O$: Calc: C, 66.81; H, 7.39; N, 17.71. Found: C, 67.12; H, 7.10; N, 17.63.

EXAMPLE 452

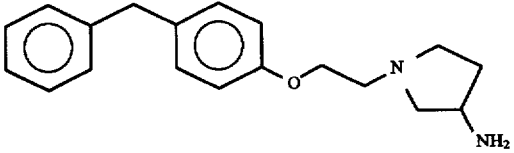

The product from Example 256 (1.12g, 3.3 mmol) was dissolved in 50 mL 1.2N HCl and stirred at 100° C. for 12 hours. The reaction was cooled to RT and made basic with 10% NaOH. The aqueous phases was extracted with 5×40 mL ethyl acetate. The combined organic extracts were dried (Na$_2$SO$_4$), filtered, and concentrated to afford a brown oil. The product had the following properties: Anal. calcd for C$_{19}$H$_{24}$N$_2$O.0.70H$_2$O: Calculated: C, 73.85; H, 8.28; N, 9.07. Found: C, 73.79; H, 8.09; N, 8.84.

EXAMPLE 453

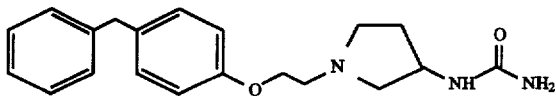

The product from Example 452 (645 mg, 2.16 mmol) and trimethylsilylisocyanate (364 mg, 3.16 mmol) were dissolved in 10 mL THF. The reaction was stirred for 12 hours at RT under argon. The reaction was quenched with 10 mL methanol. The solvent was concentrated in vacuo and the residue was dissolved in 20 mL methylene chloride. The organic phases was washed with 3×20 mL water and dried (Na$_2$SO$_4$) to afford the crude product as a tan solid. The solid was recrystallized from methanol/diethyl ether to give the pure product as a tan solid. The product had the following properties: mp 132°–134° C. Anal. calcd for C$_{20}$H$_{25}$N$_3$O$_2$.0.10H$_2$O: C, 70.40; H, 7.44; N, 12.31. Found C, 70.36; H, 7.47; N, 12.22.

EXAMPLE 454

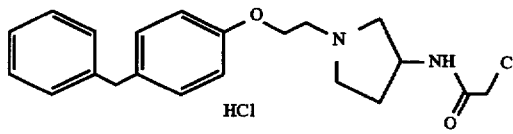

To a stirred solution of the amine from example 452 (100 mg, 0.34 mmol) in methylene chloride (1 ml) at room temperature, chloroacetyl chloride (30 µmol, 1.1 eq) was added. The reaction mixture was stirred at room temperature for 10 min, evaporated and the residue crystallized from diethyl ether to afford the title compound (111 mg)

Anal. calc. C$_{21}$H$_{25}$N$_2$O$_2$Cl.1HCl0.25H$_2$O: Calc: C, 60.80; H, 6.68; N, 6.75. Found: C, 60.72; H, 6.38; N, 6.53.

EXAMPLE 455

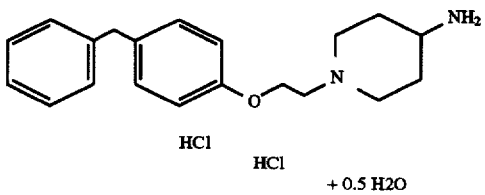

The title compound was prepared from the compound of example 238 (500 mg) in a manner identical to that described in example 452. This afforded the title compound as a white solid (401 mg)

Anal. calc. C$_{20}$H$_{26}$N$_2$O$_2$HCl0.5H$_2$O: Calc: C, 61.22; H, 7.45; N, 7.14. Found: C, 61.20; H, 7.50; N, 7.07.

EXAMPLE 456

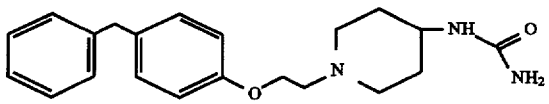

To a stirred solution of the amine from example 455 (180 mg, 0.47 mmol) and triethylamine (1 ml) in THF (4 ml) trimethylsilyl isocyanate (70 µl, 1.5 eq) was added. The reaction mixture was stirred at room temperature for 3 h, evaporated and the crude product precipitated from diethyl ether to afford the title compound (175 mg)

Anal. calc. C$_{21}$H$_{27}$N$_3$O$_2$.0.4H$_2$O: Calc: C, 69.93; H, 7.77; N, 11.65. Found: C, 69.80; H, 7.69; N, 11.78.

EXAMPLE 457

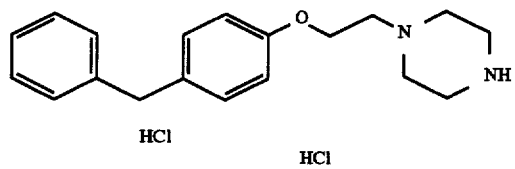

A mixture of the product of Example 277 and excess of 3N HCl was heated on a steam-bath for 16 hr. The volatiles were removed in vacuo to provide the title compound as a white solid.

Anal. calc. for C$_{19}$H$_{24}$N$_2$O.2HCl

| Calculated | | Found |
|---|---|---|
| 61.79 | C | 61.31 |
| 7.10 | H | 7.32 |
| 7.58 | N | 7.49 |
| 19.20 | Cl | 18.94 |

EXAMPLE 458

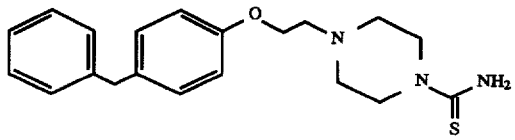

+0.25 H2O

A mixture of the free base of the product of Example 457 (0.23 g), trimethylsilylisothiocyanate (0.81 mL, Aldrich), K2CO3 (100 mg) and toluene (5 mL) was heated to reflux for 16 hours. The mixture was concentrated and the residue chromatographed on silica gel using CHCl3/ethanol/ aqueous NH$_3$, 85/14/1, to give the title product as a solid.

Anal. for C$_{20}$H$_{25}$N$_3$OS.0.25H$_2$O:

| Calculated | | Found |
|---|---|---|
| 66.73 | C | 66.87 |
| 7.14 | H | 6.91 |
| 11.67 | N | 11.65 |
| 8.91 | S | 8.88 |

EXAMPLE 459

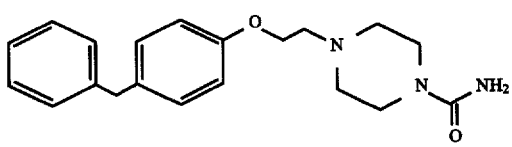

The procedure of Example 458 was repeated using trimethylsilyl isocyanate in the place of trimethylsilyl isothiocynate to provide the title product as a solid.

Anal. for $C_{20}H_{25}N_3O_2$

| Calculated | | Found |
|---|---|---|
| 70.77 | C | 70.54 |
| 7.42 | H | 7.75 |
| 12.38 | N | 12.31 |

EXAMPLE 460

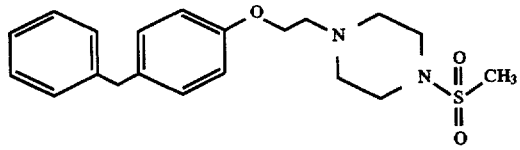

To a stirred solution of the free base of the product of Example 457 (0.33 g), and diisopropylethylamine (0.22 mL) in $CH_2C_2$ (5 mL) at $-78°$ C. was added methane sulfonylchloride (0.09 mL). The mixture was allowed to warm to room temperature over 1 hr. To the reaction mixture was added saturated aqueous $NaHCO_3$ and extracted with ethyl acetate. The organic extract was washed with water, dried over $MgSO_4$ and concentrated in vacuo. The residue was crystallized from $CH_2Cl_2$ to give the title product as a white solid as carbondioxide adduct.

Anal. calc. for $C_{20}H_{25}N_3OS.CO_2$

| Calculated | | Found |
|---|---|---|
| 60.27 | C | 60.18 |
| 6.26 | H | 6.62 |
| 6.69 | N | 6.65 |
| 7.66 | S | 7.80 |

EXAMPLE 461

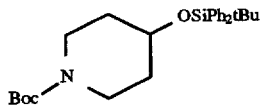

To a stirred solution of N-t-butyloxycarbonyl-4-hydroxypiperidine (3.00 g) and imidazole (2.7 g) in DMF (5 ml) at room temperature, t-butyldiphenylsilyl chloride (4.5 g) was added. The reaction mixture was stirred at room temperature overnight, quenched into water and the aqueous solution extracted into diethyl ether. The organic extracts were combined, dried ($Na_2SO_4$) and evaporated to afford a clear oil. The crude product was purified by chromatography on silica (eluant, hexane/diethyl ether, 90/10) to afford the title compound (6.30 g)

Anal. calc. $C_{26}H_{37}NO_3Si$: Calc: C, 71.03; H, 8.48; N, 3.19. Found C, 71.26; H, 8.39; N, 2.76.

EXAMPLE 462

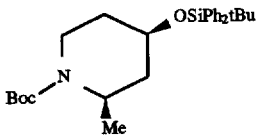

To a stirred solution of the product from example 461 (800 mg) in diethyl ether (5 ml) and TMEDA (1 ml) at $-78°$, sec butyl lithium was added. The reaction mixture was stirred at $-78°$ for 3 hr and then quenched with methyl iodide (1 ml) The reaction mixture was allowed to attain room temperature and then partitioned between diethyl ether and water. The organic layer was separated, dried ($Na_2SO_4$) and evaporated. The crude product was purified by chromatography on silica (eluant, hexane/diethyl ether, 75/25) to yield the title compound (650 mg).

EXAMPLE 463

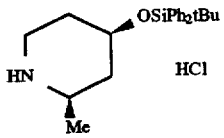

To a stirred solution of the product from example 462 (110 mg) in methylene chloride (1 ml) at room temperature, trifluoroacetic acid (2 ml) was added. The reaction mixture was stirred at room temperature for 10 mins, evaporated and the residue partitioned between diethyl ether and saturated potassium hydrogen carbonate solution. The organic layer was separated, dried ($Na_2SO_4$) and evaporated to afford a clear oil. The crude product was converted into its hydrochloride and crystallized from ethanol/diethyl ether to afford the title compound (40 mg)

Anal. calc. $C_{22}H_{31}NOSi1HCl.1H_2O$: Calc: C, 64.76; H, 8.40; N, 3.43. Found: C, 64.60; H, 7.97; N, 3.47.

EXAMPLE 464

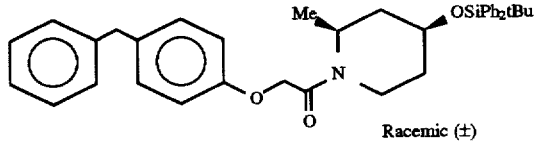

The title compound was prepared from the acid described in example 380 (1.89 mg) and the product from example 463 (2.3 g) in a manner analogous to that described in example 389. This afforded the title compound (2.55 g).

EXAMPLE 465

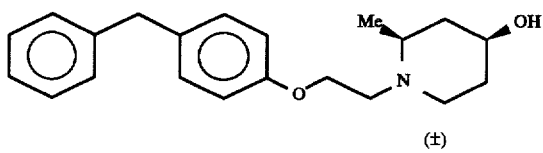

(±)

The title compound was prepared from the product of example 464 (2.5 g) in a manner identical to that described in example 397. This afforded the title compound (920 mg, 66%)

Anal. calc. $C_{21}H_{27}NO_2 \cdot 1HCl \cdot 0.4H_2O$: Calc: C, 68.33; H, 7.86; N, 3.79. Found: C, 68.45; H, 8.12; N, 3.74.

EXAMPLE 466

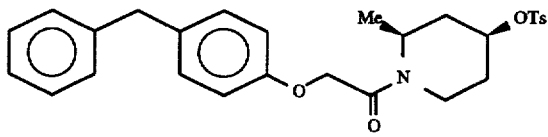

To a stirred solution of the product from example 464 (2.0 g) in THF (10 ml) at room temperature, TBAF (5 ml) was added. The reaction mixture was stirred at room temperature overnight, evaporated and the crude residue partitioned between ethyl acetate and saturated potassium hydrogen carbonate solution. The organic extracts were separated, dried ($Na_2SO_4$) and evaporated to afford the crude intermediate alcohol as a clear oil (1.80 g).

To a stirred solution of the above alcohol (1.8 g) in pyridine (10 ml) at 0°, toluene-4-sulfonyl chloride (800 mg) was added. The reaction mixture was stirred at room temperature for 24 h, evaporated and the residue partitioned between ethyl acetate and saturated potassium hydrogen carbonate solution. The organic extracts were separated, dried ($Na_2SO_4$) and evaporated to afford a yellow oil. The crude product was purified by chromatography on silica (eluant, diethyl ether) to afford the title compound (500 mg).

EXAMPLE 467

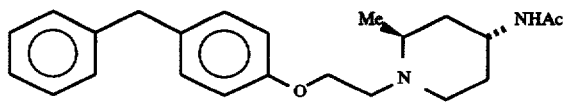

To a stirred solution of the product from example 466 (400 mg 0.81 mmol) in DMF (5 ml) at 60°, sodium azide was added. The reaction mixture was stirred at 60° for 10 hr, evaporated and the residue partitioned between diethyl ether and water. The organic extracts were dried ($Na_2SO_4$), and evaporated to afford the crude intermediate azide (210 mg). To a stirred solution of the above azide (210 mg.) in methanol (5 ml) over a hydrogen atmosphere, 5% Pd/C was added. The reaction mixture stirred at room temperature for 1 hr, evaporated and the residue suspended/dissolved in ethyl acetate. The organic solution was filtered (to remove the catalyst) and evaporated to afford the intermediate amine (150 mg). To a stirred suspension of lithium aluminum hydride (50 mg) in THF (4 ml) at room temperature the above amine was added. The reaction mixture was stirred at room temperature for 30 mins, quenched with water (200 mg) and then diluted with ethyl acetate (20 ml). The reaction mixture was filtered and the filtrate evaporated to afford the intermediate diamine (80 mg). To a stirred solution of the above diamine (70 mg) in acetic anhydride (1 ml) at room temperature, pyridine (3 drops) was added. The reaction mixture was stirred at room temperature for 15 mins, quenched with saturated sodium hydrogen carbonate solution and extracted into ethyl acetate. The organic extracts were dried ($Na_2SO_4$), evaporated, and the crude product was precipitated from diethyl ether to afford the title compound (62 mg).

Anal. calc. $C_{23}H_{30}N_2O_2$. Calculated: C, 75.38; H, 8.25; N, 7.64. Found: C, 76.05; H, 8.89; N, 6.70.

EXAMPLE 468

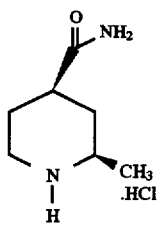

To a stirred solution of 100 ml of $CH_2Cl_2$ and 100 ml of 15M $NH_4OH$ solution is added 10.0 g of 2-chloro-6-methyl-4-pyridinecarbonyl chloride, and the mixture is stirred at room temperature for 30 minutes, during which time white solid is precipitated out of the mixture which is filtered and dried to provide 7.8 g of white solid. A solution of 5.5 g of the white solid in 55 ml of ethanol is exposed to hydrogen gas in parr bomb at 140° C. at 1000 psi pressure for 18 hours. The mixture is cooled to room temperature. The catalyst is removed by filtration and the filtrate is concentrated in vacuo to provide 5.4 g of title compound as white crystaline solid.

EXAMPLE 469

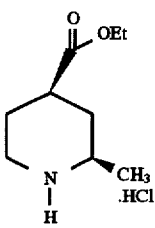

Following the procedure described in example: 468 and replacing $NH_4OH$ with ethanol provides the title compound.

EXAMPLE 470

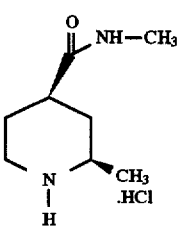

Following the procedure described in example: 468 and replacing $NH_4OH$ with 40% $CH_3NH_2$ provides the title compound.

EXAMPLE 471

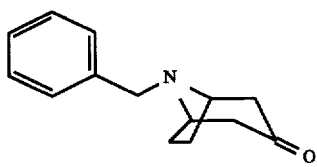

To a stirred suspension of nor-tropinone hydrochloride (REF) (9.2 g) in DMF (100 mL) at 0° C. was added $K_2CO_3$ (10 g). After 5 min., benzyl bromide (7 mL) was added and the mixture allowed to warm to room temperature over 16 hr. The mixture was extracted with ethyl acetate and water. The organic phase was washed four times with water, dried over $MgSO_4$ and concentrated. The residue was chromatographed over silica gel using $CHCl_3$ containing 0.5% ethanol and a trace of aqueous $NH_3$ to give the title product as a colorless thick liquid (12.8 g).

EXAMPLE 472

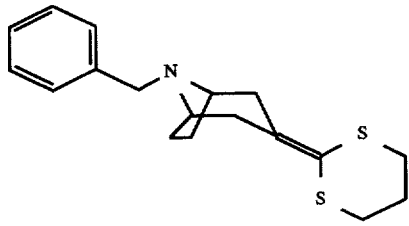

To a stirred solution of trimethylsilyldithiane (9.2 mL, Aldrich) in THF (175 mL) at 0° C. was added in drops, n-butyl lithium (30.3 mL, 1.6M cyclohexane solution). After 45 min., the product of Example 471 (12.8 g) in THF (20 mL) was added in drops. After 20 min., water and ether were added to the reaction mixture. The organic phase was dried over $MgSO_4$ and concentrated to give the title compound as a thick foul smelling liquid (15.52 g).

EXAMPLE 473

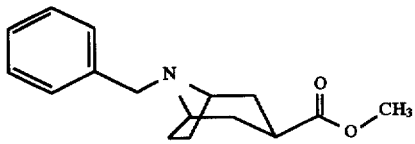

To a stirred solution of the product of Example 472 (15.52 g) in methanol (480 mL) was added aqueous HCl (6N, 20.4 mL), $HgCl_2$ (28 g) and trifluoro acetic acid (9.5 mL). The mixture was heated to reflux for 3 hr. The mixture was filtered through celite. The filtrate was concentrated and the residue chromatographed using $CHCl_3$/Ethanol/aqueous $NH_3$, 100/5/0.1, as eluant to provide the title compound as a thick liquid.

EXAMPLE 474

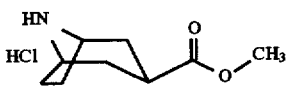

A solution of the product of Example 473 in methanol and Conc. HCl (2 mL) was shaken in a parr hydrogenation apparatus over 40% Pd(OH)2/C under 60 psi hydrogen pressure at room temperature. After the uptake of hydrogen ceased, the solution was filtered and the filtrate concentrated in vacuo to give the title product.

EXAMPLE 475

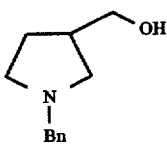

Methyl-1-benzyl-5-oxo-3-pyrrolidine carboxylate (25 g, 0.11 mol) was dissolved in 200 mL THF under argon. Lithium aluminum hydride (6.5 g, 0.17 mol) was added slowly to the THF. After the addition was complete, the reaction was refluxed for 3½ hours. The reaction was cooled to RT and quenched with water/diethyl ether. After filtering and concentrating in vacuo, the crude product was obtained as a yellow oil. The oil was chromatographed (silica gel, methanol/methylene chloride/ammonium hydroxide 5/94/1) to afford the pure product as a yellow oil. The product had the following properties: Anal. calcd for $C_{12}H_{17}NO.0.10H_2O$: C, 74.75; H, 8.98; N, 7.25. Found C, 74.66; H, 9.35; N, 7.20.

EXAMPLE 476

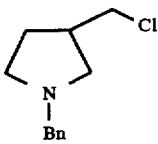

The product from Example 475 (0.46 g, 2.4 mmol) and thionyl chloride (1.5 mL, 20.6 mmol) were refluxed in 5 mL chloroform for 2 hours. The reaction was concentrated in vacuo, and the residue was dissolved in 20 mL water. 10% NaOH was added until the pH was ~8. The aqueous phase was extracted with 5×30 mL ethyl acetate. The combined organic phases were dried ($Na_2SO_4$), filtered and concentrated in vacuo to afford the chloride as an amber oil. The product had the following properties: Anal. calcd for $C_{12}H_{16}NCl.0.20H_2O$: C, 67.57; H, 7.75; N, 6.57; Cl, 16.62. Found C, 67.57; H, 7.44; N, 6.48; Cl, 16.47.

EXAMPLE 477

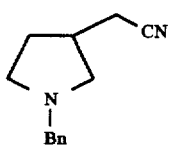

The product from Example 476 (2.52 g, 12 mmol), sodium cyanide (3 g, 61 mmol) and aliquot 336 (156 mg, 0.38 mmol) were stirred in 5 mL water at 100° C. for 48 hours. The reaction was cooled to RT and poured into 50 mL water. The aqueous phase was extracted with 4×40 mL ethyl acetate. The combined organic extracts were dried ($Na_2SO_4$), filtered and concentrated to afford the crude product as a dark yellow oil. The oil was chromatographed (silica gel, methanol/methylene chloride/ammonium hydroxide 1/98.5/0.5) to give the pure product as a yellow oil. The product had the following properties: Anal. calcd for $C_{13}H_{16}N_2 \cdot 0.08H_2O$: C, 77.40; H, 8.07; N, 13.89. Found C, 77.46; H, 8.37; N, 13.84.

EXAMPLE 478

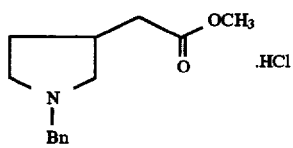

The product from Example 477 (1.08 g, 5.4 mmol) was dissolved in 50 mL methanol and cooled to 0° C. Acetyl chloride (25 mL, 35 mmol) was added slowly to the methanol. The reaction was stirred at RT for 12 hours. The solvent was concentrated in vacuo, and the residue was dissolved in 10 mL water. To the water was added 25 mL saturated sodium bicarbonate. The aqueous phase was extracted with 4×50 mL ethyl acetate. The combined organic extracts were dried ($Na_2SO_4$), filtered and concentrated to afford the crude ester as a yellow oil. The HCl salt was prepared by dissolving the ester in 5 mL diethyl ether and adding 3M ethanolic HCl dropwise. The pure HCl salt was obtained as a yellow oil. The product had the following properties: Anal. calcd for $C_{14}H_{20}NO_2Cl \cdot 0.65H_2O$: C, 59.74; H, 7.63; N, 4.98. Found C, 59.68; H, 7.75; N, 5.05.

EXAMPLE 479

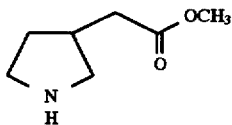

The product from Example 478 (1.04 g, 3.8 mmol) and 1,4-cyclohexadiene (5 mL, 52 mmol) were dissolved in 20 mL methanol. The reaction flask was flushed with argon and 10% Pd/C (1.02 g) was added portionwise. The reaction was refluxed for 12 hours under argon. The reaction war filtered through Celite/silica gel. The solvent was concentrated in vacuo to afford the product as a yellow waxy solid. The product had the following properties: H.R.M.S. M+1 calcd for $C_7H_{13}NO_2$: 144.1025. Found 144.1011.

EXAMPLE 480

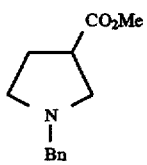

To a solution of N-benzyl-N-(trimethylsilylmethyl)-aminoacetonitrile (7.6 g, 32.7 mmol) and methyl acrylate (3.0 mL, 33.3 mmol) in $CH_3CN$ (60 mL) was added AgF (4.5 g, 35.5 mmol) and the mixture stirred in the dark at 25° C. for 19 h. The mixture was filtered and concentrated. Flash chromatography using a gradient of 10:1 to 3:1 hexane/EtOAc provided the title compound (3.3 g, 46%) as a colorless oil.

EXAMPLE 481

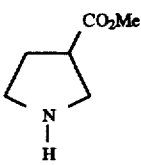

The product from Example 480 (3.3 g, 15 mmol) was submitted to 60 psi $H_2$ in a Parr shaker in EtOH with catalytic $Pd(OH)_2$ at 25° C. for 3 h. The solution was filtered and concentrated to provide the title compound.

EXAMPLE 482

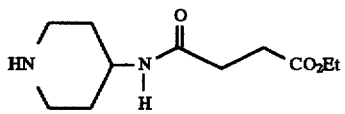

To a stirred solution of 2.28 g of BOC-isonipecotic acid in 10 ml of N,N-dimethylformamide was placed 2.56 g of N,N-disuccinimidyl carbonate and 2 ml of pyridine. The mixture was treated with 20 mg of N,N-4-dimethylamino pyridine and 1.0 g of triethylamine. The reaction mixture was stirred at room temperature under nitrogen atmosphere for 40 minutes. 1.53 g of β-alanine ethyl ester hydrochloride was added to the mixture. The mixture was stirred at room temperature for 16 hrs. The mixture was poured into water and extracted with ethyl acetate. The organic extract was washed with a saturated solution of $KHCO_3$, and water and saturated solution of $KHSO_4$ ($KHCO_3$ or $KHSO_4$) and dried over $Na_2SO_4$. The solvent was removed by evaporation under reduced pressure to give crude oily gum which was taken up in 10 ml of 90% trifluoroacetic acid and was allowed to stir at room temperature for 30 minutes. The solvent was removed by evaporation under reduced pressure to give 1.6 g of title compound which was used in Example 249 without further purification.

EXAMPLE 483

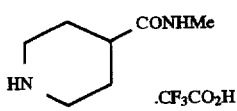

Following the procedure described in example 482 and replacing β-alanine-ethyl ester hydrochloride with 40% methylamine provided the title compound as TFA salt which was taken up to the next step without further purification.

EXAMPLE 484

3-Pyrroline (6.91 g, 100 mmoles) was dissolved in 150 ml of 80:20 mixture of dioxane:H$_2$O and was treated with 25 ml of Et$_3$N and the mixture was stirred at room temperature for 10 minutes. Di-tert-butyl dicarbonate (18.6 g, 100 mmoles) was added and the mixture was stirred at 25° C. for 6 hours. The mixture was concentrated in vacuo to yield oily residue, which was dissolved in ethyl acetate (~100 ml), and was washed with water, dried over Na=SO$_4$, filtered and the filtrate was concentrated in vacuo to provide 8.6 g. The title compound whose H$^1$ NMR 300 MHz spectrum was consistent with proposed structure.

EXAMPLE 485

The compound was prepared following the methodology described in European patent EP 0 413 455 A2 and replacing 1-benzyloxycarbonyl-3-pyrroline with the product from Example 484. H$^1$ NMR 300 MHz spectrum was consistent with proposed structure.

EXAMPLE 486

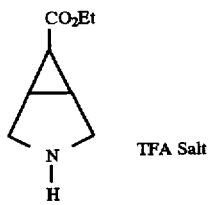

The product from Example 485 (1 g) was taken up in 20 ml of CH$_2$Cl$_2$ and was treated with 2 ml of TFA and the mixture was stirred at room temperature for 3 hours. The mixture was concentrated in vacuo to provide 1.15 g of title compound as oil whose H$^1$NMR 300 MHz spectrum was consistent with proposed structure.

EXAMPLE 487

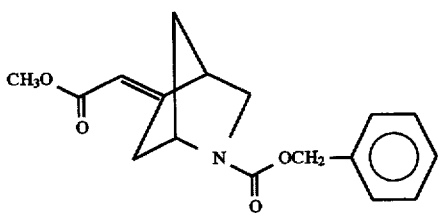

A solution of 2.4 g of 2-(carbobenzyloxy) 2-azabicyclo[2.2.1]heptan-5-one (J. Med. Chem. 1992, 35, 2184–2191), 6.7 g of methyl (triphenylphosphoranylidene) acetate (Aldrich), 25 mL toluene and 10 mL THF was refluxed for 14 hours under N$_2$. The reaction mixture was cooled, concentrated and purified on a silica gel column eluting with 30% ethyl acetate in hexane to yield 2.31 g of a tinted liquid. The NMR spectra was consistent for the proposed structure.

EXAMPLE 488

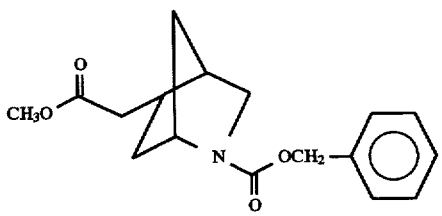

A mixture of 2.3 g of the product from example 487, 1.8 g of magnesium turnings, and 80 mL of anhydrous methanol was stirred under N$_2$ with cooling in a water bath until all of the metal had dissolved (~4 h). A 100 mL portion of 3N HCl was added and stirred for 5 minutes and then concentrated to a volume of approximately 50 mL. The aqueous residue was extracted thoroughly with ether, the organic extracts concentrated and the residue purified on a silica gel column eluting with 40% ethyl acetate in hexane to yield 1.4 g of colorless liquid. The NMR spectra was consistent for the proposed structure.

EXAMPLE 489

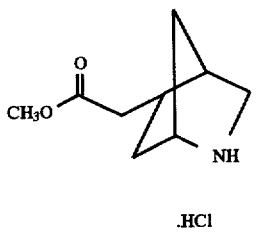

A solution of 1.3 g of the product from example 488 and 4.5 mL of 1N HCl in 50 mL of methanol was decarbobenzyloxylated under an atmosphere of hydrogen using 50 mg of 5% palladium on carbon catalyst at room temperature for 16 hours. The reaction mixture was filtered through a pad of celite and the filtrate concentrated. The residue, 700 mg, was used directly in the next step without further purification. The NMR spectra was consistent for the proposed structure.

EXAMPLE 490

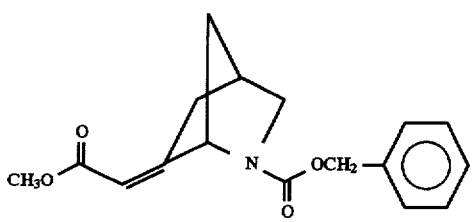

A solution of 4.9 g of 2-(carbobenzyloxy)-2-azabicyclo[2.2.1]heptan-6-one (J. Med. Chem. 1992, 35, 2184–2191) in 75 mL of toluene was reacted with 10.0 g of methyl (triphenylphosphoranylidene) acetate (Aldrich) as described in Example 487. The reaction was worked up and purified in the same manner to produce 6.9 g of colorless oil. The NMR spectra was consistent for the proposed structure.

EXAMPLE 491

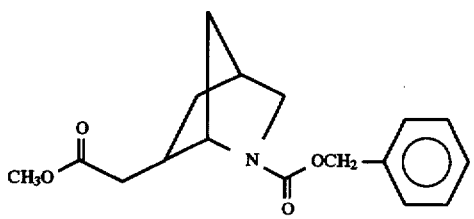

A mixture of 6.7 g of the product from example 490, 5.4 g of magnesium turning and 500 mL of anhydrous methanol was reacted as described in Example 488. The product was isolated as previously described to afford 5.0 g of viscous oil. The NMR spectra was consistent for the proposed structure.

EXAMPLE 492

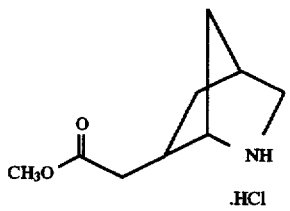

A 1.4 g quantity of product from example 491 was decarbobenzyloxylated as described in Example 489. The product was isolated as previously described to yield 1.0 g of white solid. The NMR spectra was consistent for the proposed structure.

EXAMPLE 493

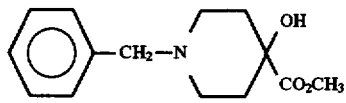

A mixture of 3.0 g of N-benzyl-4-piperidone (Aldrich), 2.0 g of trimethylsilylcyanide (Aldrich), 64 mg of zinc iodide and 20 mL of CH$_2$Cl$_2$ was refluxed for 18 hours under N$_2$. The reaction mixture was cooled and blown down under N$_2$ and then concentrated in vacuo. The residue was dissolved in 7 mL of concentrated hydrochloric acid and stirred at room temperature for 30 hours. The reaction mixture was then concentrated to dryness and the residue repeatedly azeotroped with toluene and then dried in vacuo. The residue was dissolved in 75 mL of methanol and anhydrous HCl gas was bubbled into the solution for 1 hour with chilling in an ice bath. The excess HCl was removed by bubbling N$_2$ through the solution and then the reaction mixture was concentrated and partitioned between 10% K$_2$CO$_3$ solution and ethyl acetate. The aqueous portion was extracted several times with ethyl acetate and the combined organic extracts were concentrated and purified on a silica get column eluting with 97.5% CHCl$_3$—2.0% CH$_3$OH—0.5% NH$_4$OH to afford 1.5 g of white solid. The NMR spectra was consistent for the proposed structure.

EXAMPLE 494

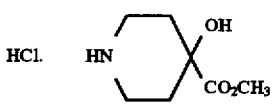

A mixture of 1.5 g of the product from example 493 in methanol containing excess dilute HCl solution was debenzylated using 20% palladium hydroxide on carbon at 5 psi for 20.6 hours at room temperature. The reaction mixture was filtered through a pad of celite and the filtrate was concentrated. The residue was azeotroped several times with toluene and then dried in vacuo. The NMR spectra was consistent for the proposed structure.

EXAMPLE 495

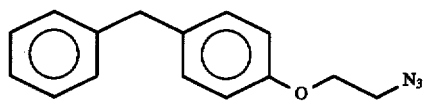

A mixture of 12.0 g (31.4 mmol) of tosylate described in example 186, 3.2 g (50.1 mmol) of sodium azide and 100 mL of DMF were heated at 60° C. for 5 hours under N$_2$. The reaction mixture was cooled and partitioned between water and ether. The aqueous portion was extracted several times with ethyl acetate and the combined organic extracts were washed with saturated sodium chloride solution and dried over sodium sulfate, filtered and the filtrate concentrated to afford 8.5 g of golden liquid which was used without further purification.

NMR (CDCl$_3$) S 3.47 (t, 2H), 3.89 (S, 2H), 4.03 (t, 2H), 6.8–7.3 (complex band, 9H).

EXAMPLE 496

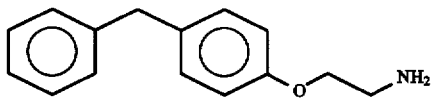

In a flame dried flask under N$_2$ was made a suspension of 2.30 g (60.6 mmol) of lithium aluminum hydride in 100 mL of anhydrous ether. The mixture was stirred and chilled to −70° C. while a solution of 8.5 g (33.6 mmol) of the azide from example 495 in 50 mL of anhydrous ether was added dropwise. The reaction mixture was allowed to warm to room temperature and stirred for 3 hours. The reaction was then quenched by careful addition of 2.3 mL water, 2.3 mL of 15% aqueous sodium hydroxide solution, and 6.9 mL of water. The white suspension was stirred for 30 minutes, filtered, and the filtrate concentrated to produce 6.40 g of viscous oil which solidified upon chilling.

NMR (CDCl₃) S 3.92 (t, 2H), 3.90 (S, 2H), 3.04 (t, 2H), 1.48 (broad band, 2H), 6.8–7.3 (complex band, 9H).

EXAMPLE 497

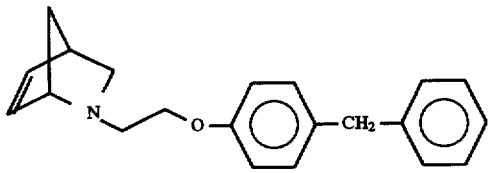

In a Parr bottle was placed 568 mg of 1,3 cyclopentadiene, 704 mg of 37% aqueous formaldehyde solution, 1.5 g of amine from example 496 and 6.6 mL of 1N HCl. The bottle was stoppered and the contents vigorously stirred at room temperature for 18 hours. The reaction mixture was partitioned between 2N NaOH solution and ethyl acetate. The aqueous portion was extracted several times with ethyl acetate and the combined organic extracts were washed with water, saturated NaCl solution, dried over Na₂SO₄ and concentrated. The residue was purified on a silica gel column eluting with 97.0% CH₂Cl₂—2.5% CH₃OH—0.5% NH₄OH to afford 817 mg of product. m.p. 37°–38°.

Anal. for $C_{21}H_{23}NO \cdot 0.05H_2O$:

| Calculated | | Found |
|---|---|---|
| 82.34 | C | 82.02 |
| 7.60 | H | 8.01 |
| 4.57 | N | 4.54 |

EXAMPLE 498

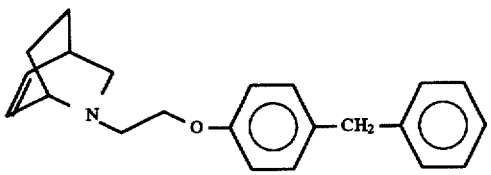

In a Parr bottle was placed 801 mg of 1,3 cyclohexadiene, 819 mg of 37% aqueous formaldehyde solution, 2.0 g of amine from example 496 and 8.8 mL of 1N HCl. The bottle was stoppered and the contents vigorously stirred at 55° for 48 hours. The reaction was worked up and purified as described in Example 497 to yield 375 mg of a light brown viscous oil.

Anal. for $C_{22}H_{25}NO \cdot 0.2H_2O$:

| Calculated | | Found |
|---|---|---|
| 81.80 | C | 81.57 |
| 7.93 | H | 8.10 |
| 4.34 | N | 4.51 |

EXAMPLE 499

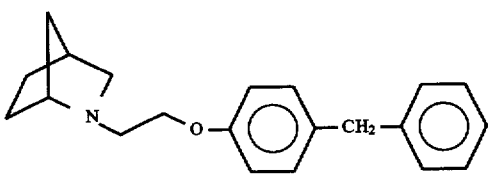

A solution of 171 mg of product from example 497 in ethanol was hydrogenated in a Parr shaker at room temperature and 5 psi for 1 hour using 4% palladium on carbon catalyst. The reaction mixture was filtered through a pad of celite, concentrated, and purified on a silica gel column eluting with 97.0% CH₂Cl₂—2.5% CH₃OH—0.5% NH₄OH to yield 130 mg of viscous oil.

Anal. for $C_{21}H_{25}NO \cdot 0.2H_2O$:

| Calculated | | Found |
|---|---|---|
| 81.09 | C | 80.89 |
| 8.23 | H | 8.42 |
| 4.50 | N | 4.53 |

EXAMPLE 500

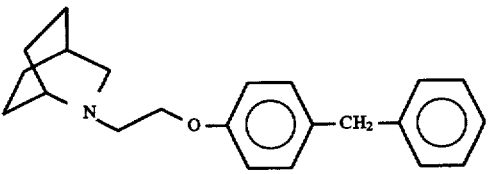

A solution of 133 mg of product from example 498 in ethanol was hydrogenated and purified as described in example 499 to afford 88 mg of oil.

Anal. for $C_{22}H_{27}NO \cdot 0.25H_2O$:

| Calculated | | Found |
|---|---|---|
| 81.06 | C | 80.77 |
| 8.50 | H | 8.46 |
| 4.30 | N | 4.21 |

EXAMPLE 501

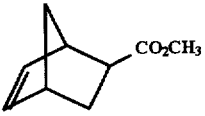

A mixture of 10 g of 5-norbornene-2-carboxylic acid (Pfaltz & Bauer), 11.1 g of K₂CO₃, 12.1 g of methyl iodide (Aldrich) and 75 mL of DMF was stirred at room temperature for 18 hours. The reaction mixture was partitioned between ether and water and then the aqueous portion was extracted with ethyl acetate several times. The combined organic extracts were washed twice with saturated NaCl solution, dried over Na₂SO₄, concentrated and the residue purified on a silica gel column eluting with 2.5% ethyl acetate in hexane to yield 6.2 g of a colorless sweet smelling liquid. The NMR spectra was consistent for the proposed structure.

EXAMPLE 502

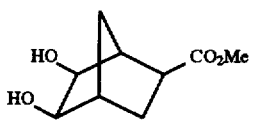

A mixture of 4.0 g of the product from example 501, 2.5 g of 4-methyl morpholine-N-oxide (Aldrich), 2 mL of a 2% solution of osmium tetroxide in isopropanol (Aldrich), 50 mL of water, and 50 mL of acetone was stirred under $N_2$ at room temperature for 18 hours. The reaction mixture was then partitioned between ethyl acetate and saturated NaCl solution and the aqueous portion was then extracted four times with additional ethyl acetate. The combined organic extracts were concentrated and the residue was purified on a silica gel column eluting with ethyl acetate to afford 4.6 g of a tan solid. The NMR spectra was consistent for the proposed structure.

EXAMPLE 503

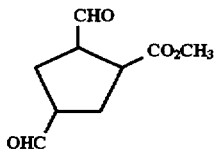

To a solution of 4.5 g of the product from example 502 in 100 mL of tert-butanol was added dropwise at room temperature a solution of 6.9 g of sodium periodate (Aldrich) in 25 mL of water. The resulting white suspension was stirred for 30 minutes and then filtered through a pad of celite. The filtrate was concentrated and the residue was purified on a silica gel column eluting with 80% ethyl acetate and 20% hexane to produce 1.6 g of a colorless liquid. The NMR spectra was consistent for the proposed structure.

EXAMPLE 504

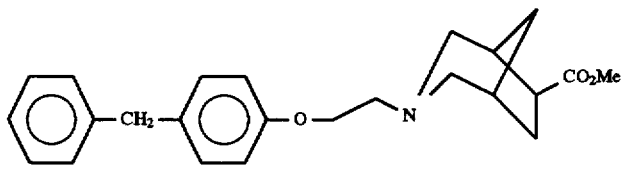

To a solution of 300 mg of amine hydrochloride from example 496 in 5 mL of methanol at 0° under $N_2$ was added 221 mg of the product from example 503 in 1 mL of methanol. The reaction was stirred for 5 minutes and then 126 mg of sodium cyanoborohydride (Aldrich) was added as a solid in portions over 10 minutes. The reaction was allowed to warm to room temperature, stirred overnight and then partitioned between 10% $K_2CO_3$ solution and ethyl acetate. The aqueous portion was extracted several additional times with ethyl acetate and the combined organic extracts were concentrated and purified on silica gel-column eluting with 40% ethyl acetate in hexane to afford 190 mg of a colorless oil.

Anal. for $C_{24}H_{29}NO_3$:

| Calculated | | Found |
|---|---|---|
| 75.96 | C | 75.62 |
| 7.70 | H | 7.60 |
| 3.69 | N | 3.59 |

EXAMPLE 505

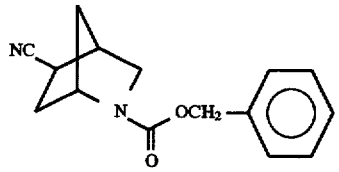

A solution of 3.0 g of 2-(carbobenzyloxy)-2-azabicyclo [2.2.1]heptan-5-one (J. Med. Chem. 1992, 35, 2184–2191) and 1.2 g of lithium cyanide (Johnson & Matthey) in 40 mL of dry THF was stirred at room temperature under $N_2$. A solution of 6.0 g of diethylcyanophosphonate (Aldrich) in 10 mL of dry THF was then added in one portion and the reaction stirred for 30 minutes. The reaction was quenched with 100 mL of water and extracted with ethyl acetate several times. The combined organic extracts were washed with saturated NaCl solution, dried over $Na_2SO_4$ and concentrated. The residue was azeotroped several times with toluene. This material was dissolved in 25 mL of dry THF and 1.2 mL of tert-butanol and added to 367 mL of a 0.1M solution of samarium diiodide in THF (Aldrich) in one portion under $N_2$ at room temperature. The reaction was stirred for 1 hour and then quenched with 250 mL of 1N HCl and stirred for 15 minutes. The reaction was extracted several times with ethyl acetate and the combined organic extracts were washed with 5% aqueous $Na_2S_2O_3$ solution and then saturated NaCl solution, dried over $Na_2SO_4$ and concentrated. The residue was purified on a silica gel column eluting with 40% ethyl acetate in hexane to afford 1.53 g of white solid. The NMR spectra was consistent for the proposed structure.

EXAMPLE 506

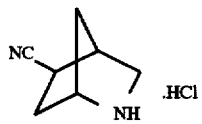

A 1.5 g quantity of the product from example 505 was decarbobenzyloxylated as described in example 489 to yield 1.0 g of salt. The NMR spectra was consistent for the proposed structure.

EXAMPLE 507

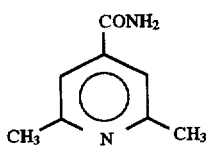

To a stirred solution of 2,6-dimethyl-4-cyanopyridine, (3.0 g 22.5 mmol) (JACS, 81, 4004, (1959) in ethanol at 0° C. (12 ml), 30% hydrogen peroxide (9 ml, 87.3 mmol) followed by NaOH (2.16 g, 54 mmol) were added. The reaction mixture was stirred at 0° C. for 30 minutes, diluted with water (50 ml) and extracted into $CHCl_3$ (3×50 ml). The organic extracts were separated, dried ($Na_2SO_4$) and evaporated to afford the title compound (1.7 g, 50%).

EXAMPLE 508

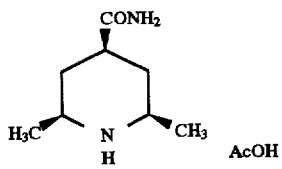

The compound of example 487 (950 mg)) was hydrogenated in a Parr shaker in EtOH (10 ml)/AcOH (½ ml) at 1200 psi and 140° C. over 5% Ru/C catalyst for 24 hours. The reaction mixture was filtered, evaporated and the resulting solid precipitated from diethyl ether/ethanol to afford the title compound (480 mg) which was used as is in Example 316.

EXAMPLE 509

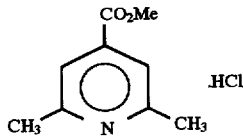

To a stirred solution of the compound from Example 507 (800 mg, 5.3 mmol) in methanol (35 ml), HCl gas was introduced through a gas inlet tube for 35 minutes. The reaction mixture was evaporated in vacuo, to afford the title compound (1.38 g) as a white solid.

EXAMPLE 510

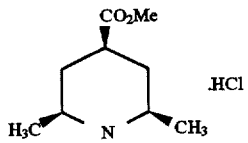

The title compound was prepared as described in Example 508, substituting the compound of Example 507 with that of 509.

The title compound was used as is in Example 317.

EXAMPLE 511

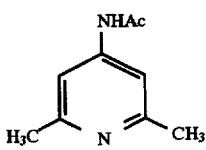

To a mixture of acetic anhydride (6 ml) and pyridine (½ ml), 4-amino-2,6-dimethylpyridine (1.0 g, 8.2 mmol) (Recucil 86, 655, (1967)) was added. The reaction mixture was stirred overnight, quenched with aqueous $NaHCO_3$ and extracted into $CHCl_3$ (2×50 ml). The organic extracts were dried ($Na_2SO_4$) and evaporated to afford an off white solid. The crude product was purified by chromatography on silica (eluant, $CHCl_3/CH_3OH/NH_4OH$, 85:14:1) to afford the title compound, (520 mg).

EXAMPLE 512

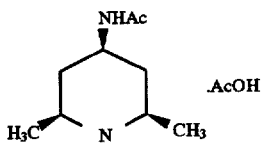

The title compound was prepared as described in Example 508, substituting the compound of Example 507 with that of Example 511.

The title compound was used as is in Example 315.

$LTA_4$ Hydrolase Methods

The following Table presents data demonstrating the pharmacological activity of the $LTA_4$ hydrolase inhibitors of the present invention having the formula I, $Ar^1$—Q—$Ar^2$—Y—R—Z, as defined herein. One or more of three different assays, (1) an in vitro $LTA_4$hydrolase enzyme assay, (2) a human whole blood assay utilizing calcium ionophore stimulation, and (3) a murine ex vivo assay utilizing calcium ionophore stimulation were employed to determine the level of $LTA_4$ hydrolase inhibitor activity.

Recombinant Human $LTA_4$Hydrolase Assay for $LTA_4$ Hydrolase Inhibitor Activity Compounds of the present invention were tested for $LTA_4$ hydrolase inhibitor activity against recombinant human $LTA_4$ hydrolase (rh$LTA_4$H). Recombinant human $LTA_4$ hydrolase-encoding vectors were prepared and used to express rh$LTA_4$H essentially as described by J. Gierse, et al., Protein Expression and Purification, 4, 358–366 (1993). Briefly, $LTA_4$ hydrolase encoding DNA was amplified by polymerase chain reaction using a pair of oligonucleotide primers based on the nucleotide sequence from the 5'-end, and the complement of the 3'-end, of the coding region of the $LTA_4$ hydrolase gene, the nucleotide sequence of which gene is known. (See, C. Funk, et al., Proc. Natl. Acad. Sci. USA 84, 6677–6681 (1987)). A λgt11 human placental cDNA library (Clonetech, Palo Alto, Calif.) provided the nucleic acid template. The $LTA_4$ hydrolase encoding region had a length of about 1.9 kb. The amplified 1.9 kb DNA was isolated and cloned into the genomic baculovirus, Autographa californica nuclear polyderosis virus (AcNPV) DNA, and the baculovirus expression vector was transfected into Spodoptera frugiperda Sf-9 cells employing the calcium phosphase co-preciipitation method (see, M. Summers, et al., Tex. Agric. Exp. Stn. Bull. 1555, 1–57 (1987). Recombinant LTA$_4$ hydrolase enzyme was purified from the transfected Sf-9 cells essentially as described by J. Gierse, et al., supra.

One or more predetermined amounts of a compound of the invention were incubated in assay buffer (0.1M potassium phosphate, 5 mg/ml fatty acid free BSA, 10% DMSO, pH 7.4) for 10 minutes at room temperature with 250 ng of recombinant hLTA$_4$H to allow binding, if any, between the enzyme and inhibitor. The stock enzyme solution was 1 mg/ml LTA$_4$ hydrolase, 50 mM Tris, pH 8.0, 150 mM NaCl, 2.5 mM beta-mercaptoethanol, 50% glycerol. The specific activity of the enzyme was about 650 nMoles/min/mg. LTA$_4$ (i.e., substrate) was prepared from the methyl ester of LTA$_4$ (Biomol, Inc., Plymouth Meeting, Pa.) by treating the methyl ester with 30 molar equivalents of LiOH at room temperature for 18 hours. The LTA$_4$ substrate in its free acid form was kept frozen at –80° C. until needed. LTA$_4$ (free acid) was thawed and diluted in assay buffer (minus DMSO) to a concentration of 350 ng/ml and 25 µl (8 ng) of LTA$_4$ substrate was added to the reaction mixture (total volume of reaction mixture=200 µl) at time zero. Each reaction was carried out at room temperature for 10 minutes. The reaction was stopped by diluting 25 µl of the reaction mixture with 500 µl of the assay buffer without DMSO. LTB$_4$ was quantified in the diluted sample by a commercially available enzyme-linked immunoassay [Caymen Chemical Co., Ann Arbor, Mich.] using the method recommended in the manufacturer's instructions and compared to the amount of LTB$_4$ produced in a negative control (i.e., essentially identical conditions except without addition of an inhibitor compound). The IC$_{50}$ was routinely calculated from the data produced.

LTB$_4$ and Thromboxane Production by Calcium Ionophore Stimulated Human Blood for LTA$_4$ Hydrolase Inhibitor Activity Human blood, collected in heparin-containing Vacutainer tubes, was diluted 1:4 with RPMI-1640 media and 200 µl of the diluted blood was added into each of the wells of a 96-well microtiter plate. One or more concert[rations of the leukotriene A$_4$ hydrolase inhibitor compounds being tested were prepared (diluted in DMSO) and 2 µl added and gently mixed with the diluted whole blood. After incubating for 15 minutes at 37° C. in a humidified incubator, calcium ionophore A23187 (Sigma Chemical Co., St. Louis, Mo.) was added to a final concentration of 20 mcg/ml and the incubation continued under the same conditions for an additional 10 minutes to allow LTB$_4$ formation. The reaction was terminated by centrifugation (833 g, 10 minutes at 4° C.) and supernatant were analyzed for LTB$_4$ and thromboxane by commercially available enzyme-linked immunoassays (Caymen Chemical Co., Ann Arbor, Mich.) according to the manufacturer's instructions. The IC$_{50}$ of each test compound was determined from the amount of inhibition of LTB$_4$ production as compared to an essentially identical assay in which no inhibitor compound was present.

Ex Vivo LTB$_4$ and Thromboxane Production by Calcium Ionophore Stimulated Mouse Blood for LTA$_4$ Hydrolase Inhibitor Activity Leukotriene A$_4$ hydrolase inhibitor compounds of the present invention were diluted to a predetermined concentration in phosphate buffered saline containing 2% DMSO and 1% Tween 80. The compounds were administered by oral gavage to adult male outbred mice weighing approximately 20–30 gm at a dose of 10 mg/kg body weight. (Compounds given at a dose of 50 mg/kg body weight are designrated in following Table by the symbol, *.) Sixty (60) minutes after administration of an LTA$_4$ inhibitor compound of the invention, blood was collected (into heparin-containing tubes) from the retroorbital sinus. The heparinized blood was added to the wells of a microtiter plate along with an equal volume of RPMI-1640 media, and calcium ionophore A23187 was added to a final concentration of 20 mcg/ml. The mixture was incubated for 10 minutes at 37° C. in a humidified incubator. The reaction was terminated by centrifugation (833 g, 10 minutes at 4° C.). Supernatants were analyzed for LTB$_4$ and thromboxane by commercially available enzyme-linked immunoassays [Caymen Chemical Co., Ann Arbor, Mich.] in accordance with the manufacturer's instructions. The percent inhibition was determined by comparison to animals treated identically except that the solution administered by oral gavage was devoid of inhibitor compound.

LTA$_4$ HYDROLASE INHIBITOR ACTIVITY

| Ex. # | Recombinant Human LTA$_4$ Hydrolase Assay IC$_{50}$ LTA$_4$H | Inhibition of Calcium Ionophore-Induced LTB$_4$ Production in Human Blood IC$_{50}$ HWB | Murine Ex Vivo LTB$_4$ Inhibition % I LTB$_4$/at 1 hour after administration of 10 mg/kg (* indicates administration of 50 mg/kg) |
|---|---|---|---|
| 44 | 30 nM | 79 nM | 25% |
| 45 | 26 nM | 116 nM | 35% |
| 46 | 1.35 µM | 1.5 µM | — |
| 48 | 150 nM | 390 nM | — |
| 49 | 190 nM | 490 nM | 46% |
| 62 | 30 nM | 310 nM | — |
| 63 | 40% at 25 µM | — | — |
| 64 | 52% at 25 µM | — | — |
| 65 | 110 nM | 510 nM | — |
| 66 | 220 nM | 220 nM | — |
| 67 | 11 nM | 170 nM | 0 |
| 68 | 480 nM | 940 nM | — |
| 69 | 6.52 µM | 11.8 µM | — |
| 70 | 35 nM | 2.78 µM | — |
| 71 | 6.5 µM | 4.26 µM | — |
| 76 | 2.9 µM | 3.5 µM | — |
| 112 | 7 nM | 82 nM | 82%* |
| 113 | 1.23 µM | 2.01 µM | — |
| 114 | 3 µM | 16 µM | — |
| 115 | 60 nM | 190 nM | — |
| 116 | 53 nM | 1.09 µM | 18% |
| 117 | 3.9 µM | 4.15 µM | — |
| 118 | 9 µM | — | — |
| 119 | 4 µM | — | — |
| 120 | 8 µM | — | — |
| 121 | 69 nM | 360 nM | 48% |
| 122 | 77 nM | 219 nM | 57% |
| 123 | 7 µM | — | — |
| 124 | 25 µM | — | — |
| 125 | 87 nM | 260 nM | 46% |
| 126 | 630 nM | 1.56 µM | — |
| 127 | 840 nM | 2.48 µM | — |
| 128 | 70 nM | 890 nM | 74% |
| 129 | 16 µM | — | — |
| 130 | 170 nM | 1.01 µM | — |
| 131 | 4.3 µM | 25 µM | — |
| 132 | 84 nM | 500 nM | 83% |
| 133 | 10 nM | 43 nM | 49% |
| 134 | 33 nM | 103 nM | 63% |
| 135 | 47 nM | 91 nM | ? |
| 136 | 77 nM | 72 nM | ? |
| 137 | 30 nM | 80 nM | 38% |
| 138 | 420 nM | 520 nM | 21% |
| 139 | 110 nM | 580 nM | 9% |
| 140 | 60 nM | 1.01 µM | 15% |
| 141 | 13 nM | 280 nM | — |
| 142 | 37 nM | 100 nM | 32% |
| 143 | 56 nM | 290 nM | — |
| 144 | 80 nM | 900 nM | — |

LTA₄ HYDROLASE INHIBITOR ACTIVITY

| Ex. # | Recombinant Human LTA₄ Hydrolase Assay IC$_{50}$ LTA₄H | Inhibition of Calcium Ionophore-Induced LTB₄ Production in Human Blood IC$_{50}$ HWB | Murine Ex Vivo LTB₄ Inhibition % I LTB₄/at 1 hour after administration of 10 mg/kg (* indicates administration of 50 mg/kg) |
|---|---|---|---|
| 147 | 1.06 μM | 730 nM | 94% |
| 198 | 30 nM | 310 nM | — |
| 200 | 350 nM | 1.9 μM | — |
| 201 | 330 nM | 1.75 μM | — |
| 202 | 44% at 3 μM | — | — |
| 203 | 380 nM | 3.3 μM | — |
| 204 | 49% at 25 μM | — | — |
| 205 | 900 nM | 1.15 μM | — |
| 206 | 200 nM | 1.65 μM | 0 |
| 207 | 220 nM | 640 nM | — |
| 208 | 4 μM | 2.15 μM | 13% |
| 209 | 3 μM | 2.34 μM | 0 |
| 210 | 4% at 25 μM | — | — |
| 211 | 120 nM | 620 nM | 47%* |
| 212 | 3 μM | 3.28 μM | — |
| 213 | 1.3 μM | 4.65 μM | — |
| 214 | 2.8 μM | 10 μM | — |
| 215 | 85 nM | 190 nM | 33%* |
| 225 | 450 nM | 1.86 μM | — |
| 226 | 4% at 100 μM | — | — |
| 227 | 210 nM | 420 nM | 23% |
| 228 | 28% at 3 μM | — | — |
| 229 | 240 nM | 220 nM | 70% |
| 230 | 390 nM | 284 nM | 53% |
| 231 | 5 μM | — | — |
| 232 | 2.1 μM | 10 μM | — |
| 233 | 370 nM | 490 nM | 98% |
| 234 | 8 μM | — | — |
| 235 | 10 μM | — | — |
| 236 | 20 μM | — | — |
| 237 | 450 nM | 1.86 μM | — |
| 238 | 50 nM | 180 nM | 49% |
| 239 | 9 μM | — | — |
| 240 | 1.07 μM | 2.45 μM | 33% |
| 241 | 600 nM | 630 nM | 33% |
| 242 | 132 nM | 608 nM | 95% |
| 243 | 70 nM | 650 nM | — |
| 244 | 15% at 100 μM | — | — |
| 245 | 1.77 μM | 147 nM | 97% |
| 246 | 7 μM | — | — |
| 247 | 100 nM | 200 nM | 70% |
| 248 | 200 nM | 70 nM | 56% |
| 249 | 3.2 μM | 605 nM 429 nM | — |
| 250 | 4.9 μM | 1.77 μM | — |
| 251 | 330 nM | 733 nM | 87% |
| 252 | 160 nM | 127 nM | 94% |
| 253 | 910 nM | 490 nM | 73% |
| 254 | 6 μM | 1.26 μM | 87% |
| 255 | 280 nM | 608 nM | — |
| 256 | 210 nM | 420 nM | 23% |
| 257 | 230 nM | 1.32 μM | 28%* |
| 258 | 1.25 μM | 1.44 μM | 81%* |
| 259 | 100 nM | 440 nM | 35%* |
| 260 | 14% at 3 μM | — | — |
| 261 | 1.25 μM | — | — |
| 262 | 220 nM | 2.48 μM | 52% |
| 263 | 4.5 μM | 8.76 μM | 60% |
| 264 | 3 μM | 1.10 μM | 87%* |
| 265 | 77 nM | 450 nM | 54% |
| 266 | 6.5 μM | 2.64 μM | 29% |
| 267 | 170 nM | 580 nM | 100%* |
| 268 | 53% at 3 μM | 7.98 μM | — |
| 269 | 2.77 μM | 1.18 μM | 50% |
| 270 | 50 μM | — | — |
| 271 | 11 μM | 7.98 μM | — |
| 272 | 7 μM | 76 nM | 97% |
| 273 | 610 nM | 154 nM | 100% |
| 274 | 800 nM | 1.25 μM | — |
| 275 | 390 nM | 146 nM | 75% |
| 276 | 4.1 μM | 232 nM | 75% |
| 277 | 520 nM | 546 nM | 42% |
| 278 | 22 nM | 247 nM | 95% |
| 279 | 470 nM | 410 nM | 57% |
| 280 | 11 nM | 21 nM | 33% |
| 281 | 93 nM | 167 nM | 83% |
| 282 | 3.7 μM | 1.37 μM | 57% |
| 283 | 19 nM | 90 nM | 90% |
| 285 | 130 nM | 1.73 μM | — |
| 286 | 41% at 100 μM | — | — |
| 287 | 330 nM | 2.39 μM | — |
| 288 | 700 nM | 960 nM | 0 |
| 289 | 43 nM | 316 nM | — |
| 290 | 450 nM | 528 nM | 94% |
| 291 | 8 μM | 1.85 μM | 67% |
| 292 | 7 nM | 52 nM | — |
| 293 | 480 nM | 3.2 μM | 93% |
| 294 | 110 nM | 340 nM | 57% |
| 295 | 440 nM | 604 nM | 80% |
| 296 | 710 nM | 512 nM | 72% |
| 297 | 120 nM | 359 nM | 63% |
| 298 | 2.5 μM | 758 nM | — |
| 299 | 57 nM | 133 nM | 93% |
| 300 | 5 μM | 2.51 μM | — |
| 301 | 4.5 μM | 828 nM | 81% |
| 302 | 3 μM | 2.40 μM | — |
| 303 | 97 nM | 1.65 μM | — |
| 304 | 15 nM | 112 nM | 80% |
| 305 | 10 nM | 1.23 μM | 42% |
| 306 | 5 nM | 177 nM | 11% |
| 307 | 440 nM | — | — |
| 309 | 2.5 μM | 1.77 μM | 96% |
| 310 | 930 nM | 1.35 μM | 96% |
| 311 | 44% at 100 μM | — | — |
| 312 | 46% at 100 μM | — | — |
| 313 | 25 μM | — | — |
| 314 | 1.5 μM | — | — |
| 315 | 163 nM | 648 nM | 53% |
| 316 | 50 nM | 131 nM | 85% |
| 317 | | | |
| 318 | 2.5 μM 4.2 μM | — | — |
| 319 | 47% at 100 μM | | |
| 320 | 14 nM | 354 nM | 85% |
| 321 | 250 nM | 421 nM | 87% |
| 322 | 610 nM | 154 nM | 100% |
| 323 | 800 nM | 1.2 μM | — |
| 324 | 220 nM | 586 nM | 62% |
| 325 | 20 μM | 2.4 μM | — |
| 330 | 900 nM | 90 nM | 95% |
| 331 | 16 nM | 95 nM | 97% |
| 332 | 14 μM | — | — |
| 333 | 0.5 μM 1.8 μM | — | — |
| 334 | 1 nM | N5Y | — |
| 335 | 2 nM | 115 nM | 98% |
| 336 | 31 nM | 187 nM | 99% |
| 337 | 360 nM | 628 nM | 82% |
| 338 | 140 nM | 690 nM | 22% |
| 338 A | | | |
| 338 B | 8 nM | 330 nM | 92%* |
| 338 C | 34% at 3 μM | 9.15 μM | — |
| 339 | 2.0 μM | 13.1 μM | 47% |
| 340 | 11 nM | 74 nM | 61% |

LTA$_4$ HYDROLASE INHIBITOR ACTIVITY

| Ex. # | Recombinant Human LTA$_4$ Hydrolase Assay IC$_{50}$ LTA$_4$H | Inhibition of Calcium Ionophore-Induced LTB$_4$ Production in Human Blood IC$_{50}$ HWB | Murine Ex Vivo LTB$_4$ Inhibition % I LTB$_4$/at 1 hour after administration of 10 mg/kg (* indicates administration of 50 mg/kg) |
|---|---|---|---|
| 340 A | 120 nM | 330 nM | 64% |
| 340 B | 550 nM | 730 nM | 39% |
| 340 C | 5.7 μM | 8.9 μM | — |
| 341 A | 140 nM | 930 nM | 29% |
| 341 B | 970 nM | 2.12 μM | — |
| 342 | 40% at 3 μM | — | — |
| 343 | ? 11.1 μM | 13.5 μM | — |
| 344 | 35% at 3 μM | — | — |
| 345 | 31% at 3 μM | — | — |
| 346 A | 1.9 μM | 3.57 μM | 23% |
| 346 B | 2.2 μM | 6.69 μM | — |
| 346 C | 1.8 μM | 7.05 μM | 34% |
| 347 A | 1.9 μM | 5.7 μM | 43% |
| 347 B | 5 nM | 380 nM | 52% |
| 347 C | 4.6 μM | 5.7 μM | 42% |
| 348 A | 440 nM | 560 nM | 22% |
| 348 B | 290 nM | 540 nM | 77% |
| 348 C | 480 nM | 790 nM | 78.5% |
| 349 A | 300 nM | 320 nM | 48% |
| 349 B | 13 nM | 200 nM | 52% |
| 349 C | 19 μM | 13.6 μM | — |
| 350 A | 550 nM | 950 nM | 38% |
| 350 B | 620 nM | 1.67 μM | 35% |
| 350 C | 1.08 μM | 2.72 μM | — |
| 351 A | 290 nM | 2.05 μM | 71% |
| 351 B | 43 nM | 360 nM | 42% |
| 351 C | 120 nM | 1.34 μM | 29%* |
| 352 | 73 nM | 260 nM | 0 |
| 353 | 51% at 3 μM | — | — |
| 354 A | 280 nM | 600 nM | 32% |
| 354 B | 480 nM | 1.18 μM | 6% |
| 354 C | 1.37 μM | 2.23 μM | 44% |
| 355 A | 870 nM | 910 nM | 37% |
| 355 B | 28 nM | 210 nM | 48% |
| 355 C | 350 nM | 1.28 μM | 14% |
| 356 A | 170 nM | 750 nM | 33% |
| 356 B | 100 nM | 340 nM | 48% |
| 357 A | 47 nM | 790 nM | 57% |
| 357 B | 730 nM | 140 nM | 60% |
| 357 C | 210 nM | 420 nM | 72% |
| 357 D | 40 nM | 140 nM | — |
| 358 A | 1.55 μM | 152 nM | — |
| 358 B | 410 nM | 640 nM | 33% |
| 358 C | 87 nM | 590 nM | 13% |
| 359 A | 100 μM | — | — |
| 359 B | 10 μM | — | — |
| 359 C | 3.5 μM | 4.2 μM | — |
| 360 A | 36% at 100 μM | — | — |
| 360 B | 19% at 100 μM | — | — |
| 360 C | 5 μM | — | — |
| 361 A | 24% at 100 μM | — | — |
| 361 B | 7 μM | — | — |
| 362 A | 5.07 μM | 3.35 μM | 28% |
| 362 B | 1.32 μM | 4.58 μM | — |
| 363 | 17 nM | 57 nM | 62% |
| 364 | 36 nM | 22 nM | 77% |
| 365 | 82 nM | 336 nM | 72% |
| 369 | 42 μM | 1.53 μM | 100% |
| 370 | 59 μM | 680 nM | 96% |
| 371 | 860 nM | 650 nM | |
| 375 | 900 nM | 240 nM | 67% |
| 385 | 140 nM | 210 nM | 32% |
| 386 | 32 nM | 190 nM | 51% |
| 397 | 37 nM | 120 nM | — |
| 398 | 220 nM | 470 nM | 0 |
| 399 | 100 nM | 220 nM | 30% |
| 400 | 60 nM | 380 nM | — |
| 401 | 55 nM | 170 nM | 23% |
| 402 | 20 nM | 180 nM | 58% |
| 403 | 750 nM | 3.8 μM | — |
| 404 | 1.75 μM | 2.75 μM | 52% |
| 405 | 420 nM | 2.01 μM | 49% |
| 406 | 500 nM | 4.0 μM | 46% |
| 407 | 20 μM | 707 nM | 0 |
| 408 | 76% at 100 μM | — | — |
| 409 | 12 μM | — | — |
| 410 | 33 μM | — | — |
| 411 | 2.4 μM | — | — |
| 412 | 190 nM | 240 nM | 72% |
| 413 | 43 nM | 42 nM | 86% |
| 414 | 11 μM | 830 nM | — |
| 415 | 5 μM | — | — |
| 416 | 410 nM | 1.97 μM | 31% |
| 417 | 4.3 μM | — | — |
| 418 | 12 μM | — | — |
| 419 | 47 nM | 120 nM | 90% |
| 420 | 57 nM | 133 nM | 93% |

LTA₄ HYDROLASE INHIBITOR ACTIVITY

| Ex. # | Recombinant Human LTA₄ Hydrolase Assay IC₅₀ LTA₄H | Inhibition of Calcium Ionophore-Induced LTB₄ Production in Human Blood IC₅₀ HWB | Murine Ex Vivo LTB₄ Inhibition % I LTB₄/at 1 hour after administration of 10 mg/kg (* indicates administration of 50 mg/kg) |
|---|---|---|---|
| 421 | 410 nM | 800 nM | — |
| 422 | 100 nM | 660 nM | 37% |
| 423 | 330 nM | 700 nM | — |
| 424 | 370 nM | 850 nM | — |
| 425 | 16 nM | 360 nM | 60% |
| 426 | 210 nM | 403 nM | 40% |
| 427 | 350 nM | 532 nM | 68% |
| 428 | 500 nM | 6.6 μM | 2% |
| 429 | 250 nM | 288 nM | 80% |
| 430 | 110 nM | 290 nM | 37% |
| 431 | 140 nM | 280 nM | 71% |
| 432 | 140 nM | 630 nM | 85% |
| 433 | 18 nM | 49 nM | 71% |
| 434 | 10 nM | 63 nM | 100% |
| 435 | 225 nM | 86 nM | — |
| 436 | 720 nM | 550 nM | — |
| 437 | 113 nM | 693 nM | — |
| 438 | 3.2 μM | — | — |
| 439 | 18 μM | — | — |
| 440 | 30 nM | — | — |
| 441 | 470 nM | 410 nM | 57% |
| 444 | 300 nM | 900 nM | — |
| 445 | 330 nM | 367 nM | — |
| 446 | 35 nM | 160 nM | 70% |
| 447 | 15 nM | 292 nM | 43% |
| 448 | 820 nM | 825 nM | — |
| 449 | 140 nM | 913 nM | — |
| 450 | 240 nM | 304 nM | 91% |
| 451 | 6 nM | ? | 90% |
| 452 | 20 nM | 290 nM | 57% |
| 455 | 11 nM | 180 nM | 67% |
| 456 | 87 nM | 440 nM | 72% |
| 457 | 150 nM | 620 nM | 22% |
| 458 | 560 nM | 1.39 μM | — |
| 459 | 1.11 μM | 2.4 μM | 44% |
| 460 | 84 μM | — | — |
| 465 | 300 nM | 470 nM | 38% |
| 467 | 60 nM | 226 nM | 71% |
| 496 | 10 nM | 280 nM | 54% |
| 497 | 200 nM | 216 nM | 45% |
| 498 | 56 nM | 206 nM | 22% |
| 499 | 240 nM | 220 nM | 60% |
| 500 | 140 nM | 142 nM | 53% |
| 504 | 29 nM | 7.7 μM | — |

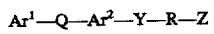 means Not Determined

We claim:

1. A compound of the Formula I:

$$Ar^1-Q-Ar^2-Y-R-Z \qquad (I)$$

or a pharmaceutically acceptable salt thereof, wherein:

Ar¹ is selected from the group consisting of phenyl, mono-, di-, or tri-substituted phenyl with the substituents selected from the group consisting of Cl, Br, F, CF₃, lower alkyl, lower alkoxy, NH₂, NO₂ and OH;

Ar² is phenyl optionally substituted with $R^7$, $R^8$ and $R^9$ wherein $R^7$, $R^8$, and $R^9$ are H, lower alkyl, lower alkoxy, hydroxy, halogen, —NH₂, and —NO₂;

Q is —O—, —CH₂—, —CH₂—CH₂—, —CH₂—CH₂—CH₂—, —CF₂—, and —CH₂O—;

Y is —O— and —S—;

R is linear or branched C₂-C₆ alkenyl; and

Z is

wherein $R^1$ is H, lower alkyl, or allyl, and $R^2$ is —(CH₂)ₐCOOR¹⁶, wherein $R^{16}$ is H, lower alkyl and benzyl, and a is an integer of from 0 to 5.

2. A compound according to claim 1, wherein Ar¹ is mono-substituted phenyl with the substituent selected from the group consisting of H, lower alkyl, lower alkoxy, halogen, NH₂ and NO₂; Q is —O—, —CH₂—, —CF₂—, or CH₂O—; Ar² is phenyl substituted with $R^8$, wherein $R^8$ is a substituent selected from the group consisting of H, lower alkyl, lower alkoxy, halogen, NH₂ and NO₂; and Y is —O—.

3. A compound according to claim 1 which is selected from the group consisting of:
3-[[3-[4-(phenylmethyl)phenoxy]propyl]amino]-propanoic acid;
3-[methyl[3-[4-(phenylmethyl)phenoxy]propyl]amino] propanoic acid;
3-[[4 -[4-(phenylmethyl)phenoxy]butyl]amino]-propanoic acid;
3-[[3-(4-phenoxyphenoxy)propyl]amino]-propanoic acid;
3-[methyl[3-(4-phenoxyphenoxy)propyl]amino]-propanoic acid;
3-[[4-(4-phenoxyphenoxy)butyl]amino]propanoic acid;
3-[[3-[4-[(4-fluorophenyl) methyl]phenoxy]-propyl]-methylamino]propanoic acid, monohydrochloride.

4. A compound according to claim 1 which is selected from the group consisting of:
ethyl 3-[[3-[4-(phenylmethyl)phenoxy]propyl]amino] propanoate;
phenylmethyl 3 [methyl[3-[4-(phenylmethyl)phenoxy] propyl]amino]propanoate;
ethyl 3-[[3-(4-phenoxyphenoxy)propyl]amino]propanoate;
ethyl 3-[methyl-[3-[4-(phenylmethyl)phenoxy]propyl] amino]propanoate;
methyl 3-[methyl[3-[4-(phenylmethyl)phenoxy]propyl] amino]propanoate, hydrate;
ethyl 3-[4-[4-(phenylmethyl)phenoxy]butyl]amino] propanoate;
phenylmethyl 3-[[4-[4-(phenylmethyl)phenoxy]butyl] amino]propanoate;
phenylmethyl 3-[[3-(4-phenoxyphenoxy)propyl]amino] propanoate;
phenylmethyl 3-[methyl[3-[4-(phenoxyphenoxy)propyl] amino]propanoate;
phenylmethyl 3-[[4-(4-phenoxyphenoxy)butyl]amino] propanoate;
methyl 3-[3-[4-[(4-fluorophenyl)methyl]phenoxy]propyl] methylamino]propanoate;
ethyl 3-[[4-[4-phenoxyphenoxy]butyl]amino]propanoate; and
methyl 3-[[3-[4-[(4-fluorophenyl)phenoxy)phenoxy]propyl] methylamino]propanoate.

5. A compound according to claim 1 wherein $R^1$ is H or lower alkyl.

6. A compound according to claim 5 wherein a is 1, 2 or 3.

7. A compound according to claim 1 wherein $R^{16}$ is H.

8. A compound according to claim 1 wherein $R^{16}$ is methyl, ethyl or benzyl.

9. A compound of the Formula I:

$$Ar^1-Q-Ar^2-Y-R-Z \qquad (I)$$

or a pharmaceutically acceptable salt thereof, wherein $Ar^1$ and $Ar^2$ are phenyl, Q is —CH$_2$—, Y is —O—, R is —CH$_2$—CH$_2$—CH$_2$— and Z is

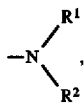

wherein $R^1$ is H and $R^2$ is —(CH$_2$)$_2$COOH.

* * * * *

UNITED STATES PATENT AND TRADEMARK OFFICE
CERTIFICATE OF CORRECTION

PATENT NO.    : 5,719,306

DATED         : February 17, 1998

INVENTOR(S)   : CHANDRAKUMAR, ET AL.                    Page 1 of 11

It is certified that error appears in the above-identified patent and that said Letters Patent is hereby corrected as shown below:

COLUMN 1
   Line 31, "coliris" should read --colitis--.

COLUMN 2
   Line 16, "(i)" should be deleted.

COLUMN 5
   Line 54 "(X)" should read --(x)--;
   Line 56, "of" should read --of:--.

COLUMN 14
   Line 23, "methyl] should read -- -methyl]--.

COLUMN 15
   Line 49, "-3H-imidazo" should read -- -3H-imidazo- --;
   Line 51, "-1H-imidazo" should read -- -1H-imidazo- --;
   Line 53, "-3H-imidazo" should read -- -3H-imidazo- --;
   Line 55, "-1H-imidazo" should read -- -1H-imidazo- --.

COLUMN 20
   Line 5, "TSC1" should read --TsCl--;
   Scheme 1, under Scheme 1: "5" should read --6--.

COLUMN 25
   Scheme 7, under Scheme 7: "OTS" should read --OTS--.

COLUMN 29
   Line 58, close up right margin;
   Line 60, close up left margin.

COLUMN 30
   Line 65, under Scheme 11: "38" should read --36--.

COLUMN 31
   Line 37, "define" should read --defined--.

UNITED STATES PATENT AND TRADEMARK OFFICE
CERTIFICATE OF CORRECTION

PATENT NO. : 5,719,306

DATED : February 17, 1998

INVENTOR(S) : CHANDRAKUMAR, ET AL.

It is certified that error appears in the above-identified patent and that said Letters Patent is hereby corrected as shown below:

COLUMN 32
  Line 42, "Et$_2$O" should read --Et$_2$O.--;
  Line 45, "CH$_2$Cl$_3$," should read --CHCl$_3$,--.

COLUMN 36

Scheme 17, under Scheme 17: 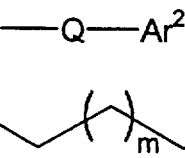 should read .

COLUMN 37

Line 42, under Scheme 18: "-R-" should read --$\genfrac{}{}{0pt}{}{-R-}{67}$--.

COLUMN 39
  Scheme 20, under Scheme 20: "-N" (both occurrences) should read ---N-- and "where-" should read --where---;

Scheme 20, under Scheme 20 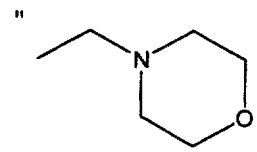 should read

-- 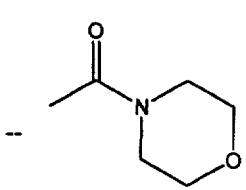 --.

COLUMN 41
  Line 17, under Scheme 21: "Ar$^{12}$-" should read --Ar$^1$- --.

COLUMN 44
  Line 63, "furthers" should read --further--.

UNITED STATES PATENT AND TRADEMARK OFFICE
CERTIFICATE OF CORRECTION

PATENT NO.   : 5,719,306

DATED        : February 17, 1998

INVENTOR(S)  : CHANDRAKUMAR, ET AL.

It is certified that error appears in the above-identified patent and that said Letters Patent is hereby corrected as shown below:

<u>COLUMN 52</u>
  Line 54, "methy-1-" should read --methyl-1- --.

<u>COLUMN 53</u>
  Scheme 34, under Scheme 34: "(Aq 40%)" should read --(aq 40%)--.

<u>COLUMN 54</u>
  Line 1, "Dieis-Alder" should read --Diels-Alder--;
  Line 25, "NaIO$_3$" should read --NaIO$_4$--.

<u>COLUMN 56</u>
  Line 23, "Found" should read --Found:--.

<u>COLUMN 64</u>
  Line 29, "water" should read --water.--.

<u>COLUMN 68</u>
  Line 42, "flashed" should read --flash--.

<u>COLUMN 74</u>
  Line 43, "(0.32g.-1.5 retool)" should read --(0.32g,-1.5 mmol)--.

<u>COLUMN 75</u>
  Line 15, under Example 71: " 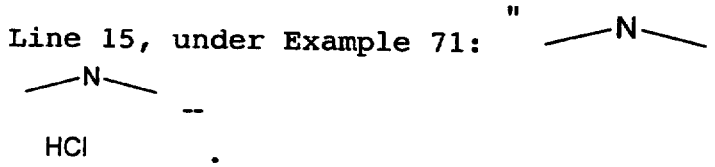 " should read
-- 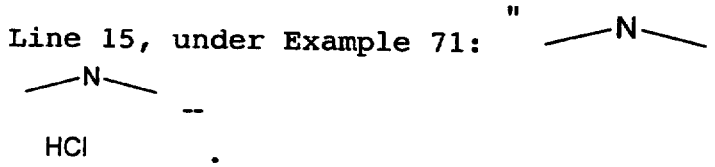 --
  HCl             .

<u>COLUMN 76</u>
  Line 38, "C$_9$H$_{15}$N$_2$OS." should read --"C$_9$H$_{15}$N$_2$OS--.

UNITED STATES PATENT AND TRADEMARK OFFICE
CERTIFICATE OF CORRECTION

PATENT NO. : 5,719,306

DATED : February 17, 1998

INVENTOR(S) : CHANDRAKUMAR, ET AL.

Page 4 of 11

It is certified that error appears in the above-identified patent and that said Letters Patent is hereby corrected as shown below:

COLUMN 77
Line 14, after "for" insert -- "$C_{16}H_{21}N_2OS$--.

COLUMN 78
Line 27, "Found: c," should read --Found: C,--.

COLUMN 81
Exhibit No. 90, "N1 4.56." should read --N, 4.56.--.

COLUMN 82
Exhibit No. 90, "Calc: C,69.83;" should read --Calc: C,69.63;--.

COLUMN 84
Exhibit No. 93, "$C_{19}H_{22}FNO_2.0.1H_2O$" should read --$C_{19}H_{22}FNO_2.0.1H_2O$:--

COLUMN 101
Line 32, "THE" should read --THF--.

COLUMN 102
Line 26, "(1g)," should read --(1g).--;
Line 66, "colourless" should read --colorless--.

COLUMN 103
Line 12, "(1g)," should read --(1g).--;
Line 65, "Example-167" should read --Example 167--.

COLUMN 105
Line 20, "to" (first occurrence) should be deleted.--;
Line 60, "aluminium" should read --aluminum--;
Line 61, "to warmed" should read --to be warmed--.

COLUMN 106
Line 9, "Example-174" should read --Example 174--;
Line 66, "calc d" should read --calc'd--.

UNITED STATES PATENT AND TRADEMARK OFFICE
CERTIFICATE OF CORRECTION

PATENT NO.  : 5,719,306

DATED       : February 17, 1998

INVENTOR(S) : CHANDRAKUMAR, ET AL.

It is certified that error appears in the above-identified patent and that said Letters Patent is hereby corrected as shown below:

COLUMN 107

Table 12, after Ex. No. 185: "∖∕OTs" should read -- ∖∕OTos --;

Table 12, after Ex. No. 187: "$C_{21}H_{19}SFO_6$:" should read --$C_{21}H_{19}SFO_5$:--.

COLUMN 113

Table 13, after Ex. No. 212: "$C_{20}H_{26}NO_2 0.15H_2O$:" should read $C_{20}H_{25}NO_2 0.15H_2O$:--.

Table 13, after Ex. No. 214: "$C_{23}H_{26}NO_2 0.15H_2O$:" should read --$C_{23}H_{25}NO_2 0.15H_2O$:--.

COLUMN 118

Line 10, "mg,)" should read --mg)--;
Line 13 "sat" should read --sat.--;
Line 27, "phenoxy]" should read --phenoxy]- --;
Line 43, "product" should read --the product--.

COLUMN 119

Table 15, after Ex. No. 229: "$C_{19}H_{24}N_2O_2S.03H_2O$" should read --$C_{19}H_{24}N_2O_2S.03H_2O$:--

Table 15, after Ex. No. 230: "N.8.13" should read --N,8.13.--;

Table 15, after Ex. No. 231: "Found: C, 58.78; H1 6.87; N, 11.38." should read --Found: C, 58.78; H,6.87; N,11.38. M+=345.--

COLUMN 121

Table 15 cont'd., after Ex. No. 235: "Nn 7.78." should read --N, 7.78.--

Table 15 cont'd., after Ex. No. 236: "$C_{20}H_{26}N_3O_2 0.2H_2O$:" should read --$C_{20}H_{25}N_3O_2 0.2H_2O$:--.

UNITED STATES PATENT AND TRADEMARK OFFICE
CERTIFICATE OF CORRECTION

| | | |
|---|---|---|
| PATENT NO. | : | 5,719,306 |
| DATED | : | February 17, 1998 |
| INVENTOR(S) | : | CHANDRAKUMAR, ET AL. |

Page 6 of 11

It is certified that error appears in the above-identified patent and that said Letters Patent is hereby corrected as shown below:

COLUMN 123

Table 15 cont'd., after Ex. No. 240: "$C_{21}H_{21}NOHCl$:" should read --$C_{21}H_{27}NOHCl$:--;

Table 15 cont'd., after Ex. No. 242: "N, 7.85" should read --N, 7.85.-- and "N, 7.72" should --N, 7.72.--;

Table 15 cont'd., after Ex. No. 244: "―(CH₂)₂―" should read -- ―(CH₂)₃― --.

COLUMN 129

Table 15 cont'd., after Ex. No. 261: "H97.23;" should --H, 7.23;--.

COLUMN 131

Table 15 cont'd., after Ex. No. 265: "$C_{21}H_{27}NO3.O.H_2O$:" should read --$C_{21}H_{27}NO3.O.2H_2O$:--.

COLUMN 132

Table 15 cont'd., after Ex. No. 269: "C, 15.56;" should read --C, 75.56;--.

COLUMN 133

Table 15, cont'd., after Ex. No. 276: "HRMS;" should read --HRMS,--.

COLUMN 135

Table 15 cont'd., after Ex. No. 279: "$C_{21}H_{28}N_2O_2.1.1HCl.0.1H_2O$:" should read --$C_{21}H_{26}N_2O_2.1.1HCl.0.1H_2O$:--;

Table 15 cont'd., after Ex. No. 281: "$C_{22}H_{28}N_2O_2.0.25H_2O$:" should read --$C_{22}H_{26}N_2O_2.0.25H_2O$:--.

COLUMN 139

Table 15 cont'd., after Ex. No. 291: "C, 68.23;" should read --C, 66.23;--.

UNITED STATES PATENT AND TRADEMARK OFFICE
CERTIFICATE OF CORRECTION

PATENT NO. : 5,719,306

DATED : February 17, 1998

INVENTOR(S) : CHANDRAKUMAR, ET AL.

It is certified that error appears in the above-identified patent and that said Letters Patent is hereby corrected as shown below:

COLUMN 147
Table 15 cont'd., after Ex. No. 310: "C, 61.47;" should read --C, 67.47;--.

COLUMN 151
Table 15 cont'd., "Toluene/Etnyl" should read --Toluene/Ethyl--;
Table 15 cont'd., "Et$_3$O" should read --Et$_2$O--.

COLUMN 155
Table 17, after Ex. No. 333: "C, 10.15; H, 1.65;" should read --C, 70.15; H, 7.65;--.

COLUMN 163
Table 19, after Ex. No. 346 C.: "C$_{21}$H$_{18}$N$_3$O$_2$.0.20H$_2$O:" should read --C$_{21}$H$_{19}$N$_3$O$_2$.0.20H$_2$O:--.

COLUMN 179
Table 19 cont'd., after Ex. No. 359A.: "C$_{22}$H$_{18}$N$_3$O.HCl.0.25H$_2$O" should read --C$_{22}$H$_{19}$N$_3$O.HCl.0.25H$_2$O--;
Table 19 cont'd., after Ex. No. 359B.: "C$_{22}$H$_{18}$N$_3$O.0.5H$_2$O" should read --C$_{22}$H$_{19}$N$_3$O.0.5H$_2$O--;
Table 19 cont'd., after Ex. No. 359C.: "C$_{22}$H$_{18}$N$_3$O.1.05HCl.0.5H$_2$O" should read --C$_{22}$H$_{19}$N$_3$O.105HCl1.0.5H$_2$O--.

COLUMN 181
Table 19, after Ex. No. 360, under product insert: --+0.05H20+--;
Table 19, after Ex. No. 360: "H, 545;" should read --H, 5.45;--.

COLUMN 189
Table 40, "Found: 348.1651." should read --Found: 348.1651.--
EXAMPLE 376

COLUMN 193
Line 13, "C$_{20}$NO$_{25}$NO$_1$.1HCl.0.8H$_2$O:" should read --C$_{20}$H$_{25}$NO$_2$.1HCl.0.8H$_2$O:--.

UNITED STATES PATENT AND TRADEMARK OFFICE
CERTIFICATE OF CORRECTION

PATENT NO. : 5,719,306

DATED : February 17, 1998

INVENTOR(S) : CHANDRAKUMAR, ET AL.

Page 8 of 11

It is certified that error appears in the above-identified patent and that said Letters Patent is hereby corrected as shown below:

COLUMN 194
Line 27, "H, 8.08," should read --H, 8.08;-- and "C, 77.84," should read-- C, 77.84;--;
Line 55, "N, 4.30." should read --N, 4.30. The compounds described in the following table were prepared essentially as described in Example 384.--.

COLUMN 197
Table 23, after Ex. No. 401 "$C_{20}H_{26}NO.HCl$: "should read --$C_{20}H_{25}NO.HCl$:--.

COLUMN 199
Line 8, "70.°" should read --70°C--;
Line 10, "afford to" should read --afford--;
Line 17, "The" should read --To--;
Line 65, "5" should read --5 ml--;
Line 67, "stirred" should read --and stirred--.

COLUMN 201
Line 33, $C_{21}H_{27}NO_3H_2O$" should read --$C_{21}H_{27}NO_3.H_2O$--.

COLUMN 204
Line 34, "1% $NH_{40}H$" should read -- 1% $NH_4OH$--.

COLUMN 207
Line 9, "(45 mg)" should read --(45 mg).--.

COLUMN 212
Line 38, "2½%" should read --2½--.

UNITED STATES PATENT AND TRADEMARK OFFICE
CERTIFICATE OF CORRECTION

PATENT NO. : 5,719,306

DATED : February 17, 1998

INVENTOR(S) : CHANDRAKUMAR, ET AL.

It is certified that error appears in the above-identified patent and that said Letters Patent is hereby corrected as shown below:

COLUMN 213

Example 448, under EXAMPLE 448: 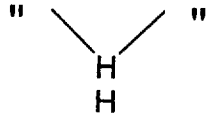 should read 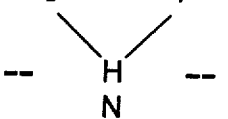 .

COLUMN 214
  Line 5, "of provide" should read --to provide--.

COLUMN 215
  Line 2, "was" should read --were--;

Line 10, under EXAMPLE 453: 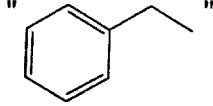 should read 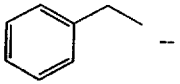 SC-57244 ;
  Line 22, "was" should read --were--;
  Line 45, "(111 mg)" should read --(111 mg).--
  Line 64, "(401 mg)" should read --(401 mg).--

COLUMN 216
  Line 13, "(175 mg)" should read --(175 mg).--

COLUMN 217
  Line 34, "CH$_2$C$_2$" should read --CH$_2$Cl$_2$--.

UNITED STATES PATENT AND TRADEMARK OFFICE
CERTIFICATE OF CORRECTION

PATENT NO. : 5,719,306

DATED : February 17, 1998

INVENTOR(S) : CHANDRAKUMAR, ET AL.

It is certified that error appears in the above-identified patent and that said Letters Patent is hereby corrected as shown below:

COLUMN 218
  Line 2, "(6.30g)" should read --(6.30g).--;
  Line 4, "$C_{26}H37NO_3Si$:" should read --$C_{26}H_{37}NO_3Si$:--;
  Line 21, "(1 ml)" should read --(1 ml).--;
  Line 48, "(40 mg)" should read --(40 mg).--

COLUMN 219
  Line 13, "66%)" should read --66%).--.

COLUMN 220
  Line 50, "example:" should read --example--;
  Line 65, "example:" should read --example--.

COLUMN 223
  Line 62, "war" should read --was--.

COLUMN 225
  Line 9, "β-alanine-ethyl" should read --β-alanine ethyl--.
  Line 28, "$Na-SO_4$," should read --$Na_2SO_4$--.

COLUMN 231
  Line 65, "gel-column" should read --gel column--.

COLUMN 234
  Line 66, "co-preciipitation" should read --co-precipitation--.

UNITED STATES PATENT AND TRADEMARK OFFICE
CERTIFICATE OF CORRECTION

PATENT NO.    : 5,719,306

DATED         : February 17, 1998

INVENTOR(S)   : CHANDRAKUMAR, ET AL.

It is certified that error appears in the above-identified patent and that said Letters Patent is hereby corrected as shown below:

COLUMN 235
  Line 38, "concert[rations" should read --concentrations--;
  Line 66, "designrated" should read --designated--;
  Line 66, "symbol,*.)" should read --symbol,*).--.

Signed and Sealed this

Sixteenth Day of January, 2001

Attest:

Q. TODD DICKINSON

Attesting Officer

Commissioner of Patents and Trademarks